US010806782B2

(12) United States Patent
Das et al.

(10) Patent No.: US 10,806,782 B2
(45) Date of Patent: Oct. 20, 2020

(54) HAND, FOOT, AND MOUTH VACCINES AND METHODS OF MANUFACTURE AND USE THEREOF

(71) Applicant: Takeda Vaccines, Inc., Deerfield, IL (US)

(72) Inventors: Subash Chandra Das, Middleton, WI (US); Joseph David Santangelo, Helios (SG); Dan Thomas Stinchcomb, Fort Collins, CO (US); Jorge E. Osorio, Mount Horeb, WI (US)

(73) Assignee: Takeda Vaccines, Inc., Deerfield, IL (US)

( * ) Notice: Subject to any disclaimer, the term of this patent is extended or adjusted under 35 U.S.C. 154(b) by 0 days.

(21) Appl. No.: 15/524,939

(22) PCT Filed: Nov. 6, 2015

(86) PCT No.: PCT/US2015/059587
§ 371 (c)(1),
(2) Date: May 5, 2017

(87) PCT Pub. No.: WO2016/073929
PCT Pub. Date: May 12, 2016

(65) Prior Publication Data
US 2018/0125965 A1    May 10, 2018

Related U.S. Application Data

(60) Provisional application No. 62/077,139, filed on Nov. 7, 2014.

(51) Int. Cl.
| *A61K 39/135* | (2006.01) |
| *C12N 7/06* | (2006.01) |
| *A61K 39/125* | (2006.01) |
| *A61K 39/12* | (2006.01) |
| *C12N 7/00* | (2006.01) |
| *A61K 39/00* | (2006.01) |

(52) U.S. Cl.
CPC ........... *A61K 39/125* (2013.01); *A61K 39/12* (2013.01); *C12N 7/00* (2013.01); *A61K 2039/5252* (2013.01); *A61K 2039/545* (2013.01); *A61K 2039/55505* (2013.01); *A61K 2039/575* (2013.01); *A61K 2039/70* (2013.01); *C12N 2770/00052* (2013.01); *C12N 2770/32134* (2013.01); *C12N 2770/32152* (2013.01); *C12N 2770/32171* (2013.01); *C12N 2770/32334* (2013.01); *C12N 2770/32363* (2013.01); *C12N 2770/32371* (2013.01); *Y02A 50/466* (2018.01)

(58) Field of Classification Search
None
See application file for complete search history.

(56) References Cited

U.S. PATENT DOCUMENTS

| 3,238,190 | A | 3/1966 | Erbring et al. |
| 4,522,809 | A | 6/1985 | Adamowicz et al. |
| 4,596,556 | A | 6/1986 | Morrow et al. |
| 5,057,540 | A | 10/1991 | Kensil et al. |
| 5,278,302 | A | 1/1994 | Caruthers et al. |
| 5,422,109 | A | 6/1995 | Brancq et al. |
| 5,424,067 | A | 6/1995 | Brancq et al. |
| 5,666,153 | A | 9/1997 | Copeland |
| 5,856,462 | A | 1/1999 | Agrawal |
| 5,993,412 | A | 11/1999 | Deily et al. |
| 6,113,918 | A | 9/2000 | Johnson et al. |
| 6,355,257 | B1 | 3/2002 | Johnson et al. |
| 6,500,419 | B1 | 12/2002 | Hone et al. |
| 9,834,757 | B2 | 12/2017 | Das et al. |
| 10,233,429 | B2 | 3/2019 | Das et al. |
| 2004/0001864 | A1 | 1/2004 | King et al. |
| 2009/0181050 | A1 | 7/2009 | Kim et al. |
| 2016/0129104 | A1 | 5/2016 | Das et al. |
| 2018/0187165 | A1 | 7/2018 | Das et al. |

FOREIGN PATENT DOCUMENTS

| CN | 101575593 A | 11/2009 |
| CN | 101897963 A | 12/2010 |
| CN | 102220288 A | 10/2011 |
| CN | 103834618 A | 6/2014 |
| EP | 0468520 A2 | 1/1992 |
| EP | 0480981 B1 | 10/1993 |
| EP | 0399843 B1 | 7/1994 |
| EP | 0382271 B1 | 12/1994 |
| EP | 0362279 B1 | 1/1995 |
| EP | 0689454 B1 | 9/1997 |
| EP | 0480982 B2 | 11/1997 |
| EP | 1294400 A1 | 3/2003 |

(Continued)

OTHER PUBLICATIONS

Huang et al. Mutations in VP2 and VP1 capsid proteins increase infectivity and mouse lethality of enterovirus 71 by virus binding and RNA accumulation enhancement. Virology 422 (2012) 132-143.*
Lin et al. Characterization of a vero cell-adapted virulent strain of enterovirus 71 suitable for use as a vaccine candidate. Vaccine 20 (2002) 2485-2493.*
Chou et al. (2012) Pilot Scale Production of Highly Efficacious and Stable Enterovirus 71 Vaccine Candidates. PLoS ONE 7(4): e34834.*
Uittenbogaard et al. Reactions of beta-propiolactone with nucleobase analogues, nucleosides, and peptides: implications for the inactivation of viruses. J Biol Chem. Oct. 21, 2011;286(42):36198-214. Epub Aug. 25, 2011.*
Hwa et al. Preclinical Evaluation of the Immunogenicity and Safety of an Inactivated Enterovirus 71 Candidate Vaccine. PLoS Negl Trop Dis, 2013, 7(11): e2538.*

(Continued)

*Primary Examiner* — Nianxiang Zou
(74) *Attorney, Agent, or Firm* — Morrison & Foerster LLP

(57) ABSTRACT

The present disclosure relates to hand, foot, and mouth disease vaccines and immunogenic compositions having one or more antigens from at least one virus that causes hand, foot, and mouth disease in humans, and methods of manufacture, formulation, and testing, and uses thereof.

14 Claims, 30 Drawing Sheets

Specification includes a Sequence Listing.

(56) References Cited

FOREIGN PATENT DOCUMENTS

| WO | 1995/17210 A1 | 6/1995 |
|---|---|---|
| WO | 1995/26204 A1 | 10/1995 |
| WO | 1996/02555 A1 | 2/1996 |
| WO | 1997/37000 A1 | 10/1997 |
| WO | 1997/37001 A1 | 10/1997 |
| WO | 1997/48440 A1 | 12/1997 |
| WO | 1998/20734 A1 | 5/1998 |
| WO | 1998/28037 A1 | 7/1998 |
| WO | 1998/56414 A1 | 12/1998 |
| WO | 1999/11241 A1 | 3/1999 |
| WO | 1999/12565 A1 | 3/1999 |
| WO | 1999/27961 A1 | 6/1999 |
| WO | 1999/33488 A2 | 7/1999 |
| WO | 1999/52549 A1 | 10/1999 |
| WO | 2000/09159 A1 | 2/2000 |
| WO | 2000/32047 A1 | 6/2000 |
| WO | 2001/38362 A2 | 5/2001 |
| WO | 2002/40665 A2 | 5/2002 |
| WO | 2002/083890 A2 | 10/2002 |
| WO | 2006/027698 A1 | 3/2006 |
| WO | 2010/139193 A1 | 12/2010 |
| WO | 2013/142809 A1 | 9/2013 |
| WO | 2014/112945 A1 | 7/2014 |
| WO | WO-2014145951 A2 | 9/2014 |
| WO | 2016/073929 A1 | 5/2016 |

OTHER PUBLICATIONS

GenBank: BAJ78248.1. polyprotein [Enterovirus A71]. Dated Feb. 22, 2011.*
Chong et al. Production of EV71 vaccine candidates. Human Vaccines & Immunotherapeutics 8:12, 1775-1783; Dec. 2012.*
GenBank: ACO89616.1. polyprotein [Enterovirus A71]. Dated Nov. 8, 2009.*
GenBank: AVD69557.1. polyprotein [Enterovirus A71]. Dated Feb. 19, 2018.*
"Antigen-Vaccine Preparation", Detergents by Applications, Available online at <https://web.archive.org/web/20130802090606/https://www.sigmaaldrich.com/life-science/biochemicals/biochemical-products.html?TablePage=104863014>, Aug. 2, 2013, 4 pages.
"Binary Ethylenimine", Wikipedia, Available online at <https://web.archive.org/web/20130720135631/https://en.wikipedia.org/wiki/Binary_ethylenimine>, Jul. 20, 2013, 1 page.
Das et al., U.S. Appl. No. 15/796,403, filed Oct. 27, 2017, titled "Hand, Foot, and Mouth Vaccines and Methods of Manufacture and Use Thereof".
"GenBank: BAJ05594.1", Available at <https://www.ncbi.nlm.nih.gov/protein/294774274?sat=43&satkey=3023031>, Apr. 16, 2010, pp. 1-2.
Lee et al., "Development of Enterovirus 71 Vaccines", Expert Review of Vaccines, vol. 9, No. 2, 2010, pp. 149-156.
Partial Supplementary European Search Report received for European Patent Application No. 15857562.1, dated Feb. 22, 2018, 12 pages.
Perrin et al., "Inactivation of DNA by β-Propiolactone", Biologicals, vol. 23, 1995, pp. 207-211.
Rweyemamu et al., "Effect of Formaldehyde and Binary Ethyleneimine (BEI) on the Integrity of Foot and Mouth Disease Virus Capsid", Rev. Sci. Tech. Off. Int. Epiz., vol. 8, No. 3, 1989, pp. 747-764.
Sanden et al., "Evolutionary Trajectory of the VP1 Gene of Human Enterovirus 71 Genogroup B and C Viruses", Journal of General Virology, vol. 91, 2010, pp. 1949-1958.
Search Report and Written Opinion received for Singapore Patent Application No. 10201509203P, dated Mar. 20, 2018, 11 pages.
Yang et al., "The Present and Future of Rabies Vaccine in Animals", Clinical and Experimental Vaccine Research, vol. 2, 2013, pp. 19-25.
An et al., "The Immunogenicity and Protection Effect of the BPL-Inactivated CA16 Vaccine in Different Animal Systems", Human Vaccines & Immunotherapeutics, vol. 10, No. 3, Mar. 2014, pp. 628-639.
Arita et al., "An Attenuated Strain of Enterovirus 71 Belonging to Genotype A Showed a Broad Spectrum of Antigenicity with Attenuated Neurovirulence in Cynomolgus Monkeys", Journal of Virology, vol. 81, No. 17, Sep. 2007, 9386-9395.
Bahnemann, Hans G., "Inactivation of Viral Antigens for Vaccine Preparation with Particular Reference to the Application of Binary Ethylenimine", Vaccine, vol. 8, Aug. 1990, 299-303.
Barr et al., "ISCOMS (Immunostimulating Complexes): The First Decade", Immunology and Cell Biology, vol. 74, 1996, pp. 8-25.
Bergelson et al., "Picornavirus Entry", Chapter 2, Advances in Experimental Medicine and Biology, vol. 790, 2013, pp. 24-41.
Brown et al., "Molecular Epidemiology and Evolution of Enterovirus 71 Strains Isolated from 1970 to 1998", Journal of Virology, vol. 73, No. 12, Dec. 1999, pp. 9969-9975.
Caine et al., "Adaptation of Enterovirus 71 to Adult Interferon Deficient Mice", Plos One, vol. 8, No. 3, Mar. 2013, pp. 1-11.
Chan et al., "Phylogenetic Designation of Enterovirus 71 Genotypes and Subgenotypes using Complete Genome Sequences", Infection, Genetics and Evolution, vol. 10, 2010, pp. 404-412.
Chang et al., "Fulminant Neurogenic Pulmonary Oedema with Hand, Foot, and Mouth Disease", The Lancet, vol. 352, Aug. 1, 1998, pp. 367-368.
Chen et al., "Antigenic Analysis of Divergent Genotypes Human Enterovirus 71 Viruses by a Panel of Neutralizing Monoclonal Antibodies: Current Genotyping of EV71 does not Reflect their Antigenicity", Vaccine, vol. 31, 2013, pp. 425-430.
Chen et al., "Oral Immunization of Mice using Transgenic Tomato Fruit Expressing VP1 Protein from Enterovirus 71", Vaccine, vol. 24, 2006, pp. 2944-2951.
Cheng et al., "A Phase I, Randomized, Open Label Study to Evaluate the Safety and Immunogenicity of an Enterovirus 71 Vaccine", Vaccine, vol. 31, 2013, pp. 2471-2476.
Chiu et al., "Protection of Neonatal Mice from Lethal Enterovirus 71 Infection by Maternal Immunization with Attenuated *Salmonella enterica* Serovar Typhimurium Expressing VP1 of Enterovirus 71", Microbes and Infection, vol. 8, 2006, pp. 1671-1678.
Chong et al., "Production of EV71 Vaccine Candidates", Human Vaccines & Immunotherapeutics, vol. 8, No. 12, Dec. 2012, pp. 1775-1783.
Chou et al., "Immunological Evaluation and Comparison of Different EV71 Vaccine Candidates", Clinical and Developmental Immunology, vol. 2012, Article ID 831282, 2012, pp. 1-8.
Chung et al., "Immunization with Virus-like Particles of Enterovirus 71 Elicits Potent Immune Responses and Protects Mice against Lethal Challenge", Vaccine, vol. 26, 2008, pp. 1855-1862.
Curry et al., "The Poliovirus 135S Particle is Infectious", Journal of Virology, vol. 70, No. 10, Oct. 1996, pp. 7125-7131.
Eckels et al., "Chikungunya Virus Vaccine Prepared by Tween-Ether Extraction", Applied Microbiology, vol. 19, No. 2, Feb. 1970, pp. 321-325.
Granoff et al., "MF59 Adjuvant Enhances Antibody Responses of Infant Baboons Immunized With Haemophilus Influenzae Type B and Neisseria Meningitidis Group C Oligosaccharide-$CRM_{197}$ Conjugate Vaccine", Infection and Immunity, vol. 65, No. 5, May 1997, pp. 1710-1715.
Huang et al., "Cross-Reactive Neutralizing Antibody Responses to Enterovirus 71 Infections in Young Children: Implications for Vaccine Development", Plos Neglected Tropical Diseases, vol. 7, No. 2, Feb. 2013, pp. 1-9.
Huang et al., "Mutations in VP2 and VP1 Capsid Proteins Increase Infectivity and Mouse Lethality of Enterovirus 71 by Virus Binding and RNA Accumulation Enhancement", Virology, vol. 422, 2012, pp. 132-143.
Huang et al., "Neurologic Complications in Children with Enterovirus 71 Infection", The New England Journal of Medicine, vol. 341, No. 13, Sep. 23, 1999, pp. 936-942.
Hwa et al., "Preclinical Evaluation of the Immunogenicity and Safety of an Inactivated Enterovirus 71 Candidate Vaccine", Plos Neglected Tropical Diseases, vol. 7, No. 11, Nov. 2013, pp. 1-7.
International Preliminary Report on Patentability received for PCT Patent Application No. PCT/US2015/059587, dated May 18, 2017, 14 pages.

(56) References Cited

OTHER PUBLICATIONS

International Search Report and Written Opinion received for PCT Patent Application No. PCT/US2015/059587, dated Feb. 4, 2016, 18 pages.

Khong et al., "A Non-Mouse-Adapted Enterovirus 71 (EV71) Strain Exhibits Neurotropism, Causing Neurological Manifestations in a Novel Mouse Model of EV71 Infection", Journal of Virology, vol. 86, No. 4, Feb. 2012, pp. 2121-2131.

Kobayashi et al., "Clinical Manifestations of Coxsackievirus A6 Infection Associated with a Major Outbreak of Hand, Foot, and Mouth Disease in Japan", Jpn. J. Infect. Dis., vol. 66, 2013, pp. 260-261.

Kung et al., "Genetic and Antigenic Analyses of Enterovirus 71 Isolates in Taiwan during 1998-2005", Clinical Microbiology and Infection, vol. 13, No. 8, Aug. 2007, pp. 782-787.

Lee et al., "Challenges to Licensure of Enterovirus 71 Vaccines", Plos Neglected Tropical Diseases, vol. 6, No. 8, Aug. 2012, pp. 1-7.

Lee et al., "Forecasting the Economic Value of an Enterovirus 71 (EV71) Vaccine", Vaccine, vol. 28, No. 49, Nov. 16, 2010, pp. 7731-7736.

Li et al., "Safety and Immunogenicity of a Novel Human Enterovirus 71 (EV71) Vaccine: A Randomized, Placebo-Controlled, Double-Blind, Phase I Clinical Trial", Vaccine, vol. 30, 2012, pp. 3295-3303.

Lin et al., "Characterization of a Vero Cell-Adapted Virulent Strain of Enterovirus 71 Suitable for Use as a Vaccine Candidate", Vaccine, vol. 20, 2002, pp. 2485-2493.

Liu et al., "Combined Peptides of Human Enterovirus 71 Protect against Virus Infection in Mice", Vaccine, vol. 28, 2010, pp. 7444-7451.

Liu et al., "Purification and Characterization of Enterovirus 71 Viral Particles Produced from Vero Cells Grown in a Serum-Free Microcarrier Bioreactor System", Plos One, vol. 6, No. 5, May 2011, pp. 1-9.

Lundblad, Roger L., "Approach to Assay Validation for the Development of Biopharmaceuticals", Biotechnol. Appl. Biochem., vol. 34, 2001, pp. 195-197.

Mao et al., "Comparative Analysis of the Immunogenicity and Protective Effects of Inactivated EV71 Vaccines in Mice", Plos One, vol. 7, No. 9, Sep. 2012, pp. 1-9.

McMinn, Peter C., "An Overview of the Evolution of Enterovirus 71 and its Clinical and Public Health Significance", FEMS Microbiology Reviews, vol. 26, 2002, pp. 91-107.

Meng et al., "Display of VP1 on the Surface of Baculovirus and its Immunogenicity against Heterologous Human Enterovirus 71 Strains in Mice", Plos One, vol. 6, No. 7, Jul. 2011, pp. 1-12.

Mizuta et al., "Cross-Antigenicity among EV71 Strains from Different Genogroups Isolated in Yamagata, Japan, between 1990 and 2007", Vaccine, vol. 27, 2009, pp. 3153-3158.

Morein et al., "Immunostimulating Complexes—Clinical Potential in Vaccine Development", Clinical Immunotherapeutics, vol. 3, No. 6, Jun. 1995, pp. 461-475.

Nagata et al., "Pyramidal and Extrapyramidal Involvement in Experimental Infection of Cynomolgus Monkeys with Enterovirus 71", Journal of Medical Virology, vol. 67, 2002, pp. 207-216.

Nicklas, W., "Aluminum Salts", Research in Immunology, vol. 143, No. 5, 1992, pp. 489-494.

Nilsson et al., "Inert Carriers for Immunization", Research in Immunology, vol. 143, 1992, pp. 553-557.

Nishimura et al., "Human P-Selectin Glycoprotein Ligand-1 is a Functional Receptor for Enterovirus 71", Nature Medicine, vol. 15, No. 7, Jul. 2009, pp. 794-797.

Non-Final Office Action received for U.S. Appl. No. 14/935,227, dated Mar. 23, 2017, 8 pages.

Oberste et al., "Typing of Human Enteroviruses by Partial Sequencing of VP1", Journal of Clinical Microbiology, vol. 37, No. 5, May 1999, pp. 1288-1293.

O'Hagan et al., "Recent Developments in Adjuvants for Vaccines Against Infectious Disease", Biomolecular Engineering, vol. 18, 2001, pp. 69-85.

Ong et al., "Formaldehyde-Inactivated Whole-Virus Vaccine Protects a Murine Model of Enterovirus 71 Encephalomyelitis against Disease", Journal of Virology, vol. 84, No. 1, Jan. 2010, pp. 661-665.

Ooi et al., "Clinical Features, Diagnosis, and Management of Enterovirus 71", The Lancet Neurology, vol. 9, Nov. 2010, pp. 1097-1105.

Ooi et al., "Identification and Validation of Clinical Predictors for the Risk of Neurological Involvement in Children with Hand, Foot, and Mouth Disease", BMC Infectious Diseases in Sarawak, vol. 9, No. 3, 2009, pp. 1-12.

Pallansch et al., "Enteroviruses: Polioviruses, Coxsackieviruses, Echoviruses, and Newer Enteroviruses", Fields Virology, vol. 1, Fifth Edition, 2007, pp. 839-893.

Premanand et al., "Induction of Protective Immune Responses Against EV71 in Mice by Baculovirus Encoding a Novel Expression Cassette for Capsid Protein VP1", Antiviral Research, vol. 95, 2012, pp. 311-315.

Shingler et al., "The Enterovirus 71 A-Particle Forms a Gateway to Allow Genome Release: A CryoEM Study of Picornavirus Uncoating", Plos Pathogens, vol. 9, No. 3, Mar. 2013, pp. 1-10.

Solomon et al., "Virology, Epidemiology, Pathogenesis, and Control of Enterovirus 71", The Lancet Infectious Disease, vol. 10, Nov. 2010, pp. 778-790.

Tung et al., "DNA Vaccine Constructs against Enterovirus 71 Elicit Immune Response in Mice", Genetic Vaccines and Therapy, vol. 5, No. 6, 2007, pp. 1-13.

Updates on HFMD Situation in Singapore. Hand, Foot & Mouth Disease: Updates: Singapore Ministry of Health, 2012, 3 pages.

Verdier et al., "Aluminium Assay and Evaluation of the Local Reaction at Several Time Points after Intramuscular Administration of Aluminium Containing Vaccines in the Cynomolgus Monkey", Vaccine, vol. 23, 2005, pp. 1359-1367.

Verdier, François, "Non-Clinical Vaccine Safety Assessment", Toxicology, vol. 174, 2002, pp. 37-43.

Victorio et al., "Phenotypic and Genotypic Characteristics of Novel Mouse Cell Line (NIH/3T3)-Adapted Human Enterovirus 71 Strains (EV71:TLLm and EV71:TLLmv)", Plos One, vol. 9, No. 3, Mar. 2014, pp. 1-15.

Wang et al., "A Mouse Muscle-Adapted Enterovirus 71 Strain with Increased Virulence in Mice", Microbes and Infection, vol. 13, 2011, pp. 862-870.

Wang et al., "A Mouse-Adapted Enterovirus 71 Strain Causes Neurological Disease in Mice after Oral Infection", Journal of Virology, vol. 78, No. 15, Aug. 2004, pp. 7916-7924.

Wang et al., "Clinical Spectrum of Enterovirus 71 Infection in Children in Southern Taiwan, with an Emphasis on Neurological Complications", Clinical Infectious Diseases, vol. 29, Jul. 1999, pp. 184-190.

Who, "WPRO Hand, Foot, and Mouth Disease Situation Update", Western Pacific Regional Office of the World Health Organization, May 15, 2012, pp. 1-4.

Yamayoshi et al., "Scavenger Receptor B2 is a Cellular Receptor for Enterovirus 71", Nature Medicine, vol. 15, No. 7, Jul. 2009, pp. 798-801.

Yoke-Fun et al., "Phylogenetic Evidence for Inter-Typic Recombination in the Emergence of Human Enterovirus 71 Subgenotypes", BMC Microbiology, vol. 6, No. 74, 2006, pp. 1-11.

Yoshikawa et al., "Bioactive Saponins and Glycosides. III. Horse Chestnut. (1) : The Structures, Inhibitory Effects on Ethanol Absorption, and Hypoglycemic Activity of Escins Ia, Ib, IIa, IIb, and IIIa from the Seeds of *Aesculus hippocastanum* L.", Chemical and Pharmaceutical Bulletin, vol. 44, No. 8, 1996, pp. 1454-1464.

Yu et al., "Neutralizing Antibody Provided Protection against Enterovirus Type 71 Lethal Challenge in Neonatal Mice", Journal of Biomedical Science, vol. 7, 2000, pp. 523-528.

Zhu et al., "Efficacy, Safety, and Immunology of an Inactivated Alum-Adjuvant Enterovirus 71 Vaccine in Children in China: A Multicentre, Randomised, Double-Blind, Placebo-controlled, Phase 3 Trial", Lancet, vol. 381, Jun. 8, 2013, pp. 2024-2032.

Bahnemann, Hans G., "Inactivation of Viruses in Serum with Binary Ethyleneimine", Journal of Clinical Microbiology, vol. 3, No. 2, Feb. 1976, pp. 209-210.

(56) References Cited

OTHER PUBLICATIONS

Extended European Search Report (includes Supplementary European Search Report and European Search Opinion) received for European Patent Application No. 15857562.1, dated May 30, 2018, 10 pages.
Office Action received for Malaysian Patent Application No. PI2015002711, dated May 15, 2018, 3 pages (English Translation Only).
Office Action received for Philippines Patent Application No. 1/2015/000376, dated Mar. 9, 2018, 5 pages.
Non-Final Office Action received for U.S. Appl. No. 15/796,403, dated Jun. 13, 2018, 10 pages.
Search Report and Written Opinion received for Singapore Patent Application No. 11201703711R, dated Feb. 26, 2018, 12 pages.
Office Action received for Malaysian Patent Application No. PI2015002711, dated May 15, 2019, 2 pages.
Office Action received for Philippines Patent Application No. 1/2015/000376, dated May 15, 2019, 4 pages.
Written Opinion received for Singapore Patent Application No. 10201509203P, dated Mar. 26, 2019, 6 pages.
Office Action received for European Patent Application No. 15857562.1, dated Sep. 23, 2019, 3 pages.
Office Action received for Taiwanese Patent Application No. 104136745, dated Nov. 11, 2019, English translation 2 pages.
Office Action received for Japanese Patent Application No. 2017-54336, dated Nov. 28, 2019, English translation 8 pages.
Search Report and Office Action received for Chinese Patent Application No. 201580072519.3, dated Feb. 23, 2020 and Mar. 4, 2020 with English translations, 22 pages.
Taubman et al., (1968). "Reaction of beta-propiolactone with amino acids and its specificity for methionine," Biochem J., 106(4):829-34.
Zhu et al., (2012). "Reactogenicity and Immunogenicity of an Enterovirus 71 Vaccine in Chinese Healthy Children and Infants," Pediatric Infectious Disease Journal, 31(11):1158-1165.

* cited by examiner

| | | |
|---|---|---|
| SEQ ID NO: 15 | n28297_CVA | NDPIasAVESAVHAHADTTISRVTAANTAASTHSLGTGRVPALQAAETGASSNASDENLI 60 |
| SEQ ID NO: 16 | n40428CVA6 | NDPIaNAVEGAVgtLADaTTISRVTAANTHASTHSLGTGRVPALQAAETGASSNASDENLI |
| SEQ ID NO: 17 | CVAP0 | NDPISNAHEHAVSLLADTTISRVTAANTAASSHSLGTGRVPALQAAETGASSNASDENLI |
| SEQ ID NO: 18 | CVA6 | NDPISNAHEHAVSLLADTTISRVTAANTAASSHSLGTGRVPALQAAETGASSNASDENLI |
| SEQ ID NO: 19 | CVA6_P11 | NDPISNAHEHAVStLADTTISRVTAANTAASSHSLGTGRVPALQAVETGASSNASDENLI |
| SEQ ID NO: 20 | Shizuoka_1 | NDPIaNAVESAVSALADTTIVRVTAASTAASTHSLGTGRVPALQAAETGASSNASDENLI |
| SEQ ID NO: 21 | n0854694_C | NDPITNAVESAVSALADTTISRVTAANTAMSTHSLGTGRVPALQAAETGASSNASDENLI |
| SEQ ID NO: 22 | HN421_CVA6 | NDPITNAVESAVSALADTTISRVTAANTAASTHSLGTGRVPALQAAETGASSNSSDENLI |
| SEQ ID NO: 23 | Kyoto1_CVA | NDPITNAVESAVSALADTTISRVTAANTAASTHSLGTGRVPALQAAETGASSNASDENLI |
| SEQ ID NO: 24 | Tw40910_CV | NDPITNAVESAVSALADTTISRVTAANTAASTHSLGTGRVPALQAAETGASSNASDENLI |

```
            5  10 14              33           46
```

| | | |
|---|---|---|
| SEQ ID NO: 15 | n28297_CVA 61 | ETRCVMNRNGINEASVEHFYSRAGLVGVVEVKDSGThqDGYTVWPIDVMGFVQQRRKLEL 120 |
| SEQ ID NO: 16 | n40428CVA6 | ETRCVMNRNGINEASVEHFYSRAGLVGVVEVKDSGTSqDGYTVWPIDVMGFVQQRRKLEL |
| SEQ ID NO: 17 | CVAP0 | ETRCVMNRNGVNEASVEHFYSRAGLVGVVEVKDSGTSqDGYTVWPIDVMGFVQQRRKLEL |
| SEQ ID NO: 18 | CVA6 | ETRCVMNRNGVNEASVEHFYSRAGLVGVVEVKDSGTSqDGYTVWPIDVMGFVQQRRKLEL |
| SEQ ID NO: 19 | CVA6_P11 | ETRCVMNRNGVNEASVEHFYSRAGLVGVVKVKDSGaSqDGYTVWPIDVMGFVQQRRKLEL |
| SEQ ID NO: 20 | Shizuoka_1 | ETRCVMNRNGVNEASVEHFYSRAGLVGVVEVKDSGTSLDGYTVWPIDVMGFVQQRRKLEL |
| SEQ ID NO: 21 | n0854694_C | ETRCVMNRNGVNEASVEHFYSRAGLVGVVEVKDSGTSLDGYTVWPIDVMGFVQQRRKLEL |
| SEQ ID NO: 22 | HN421_CVA6 | ETRCVMNRNGVNEASVEHFYSRAGLVGVVEVKDSGTSLDGYTVWPIDVMGFVQQRRKLEL |
| SEQ ID NO: 23 | Kyoto1_CVA | ETRCVMNRNGVNEASVEHFYSRAGLVGVVEVKDSGTSLDGYTVWPIDVMGFVQQRRKLEL |
| SEQ ID NO: 24 | Tw40910_CV | ETRCVMNRNGVNEASVEHFYSRAGLVGVVEVKDSGTSLDGYTVWPIDVMGFVQQRRKLEL |

```
                                        90   96 98
```

| | | |
|---|---|---|
| SEQ ID NO: 15 | n28297_CVA 121 | STYMRFDAEFTFVSNLNDSTTPGMLLQYMYVPPGAPKPDGRKSYQWQTATNPSIFAKLSD 180 |
| SEQ ID NO: 16 | n40428CVA6 | STYMRFDAEFTFVSNLNDSTTPGMLLQYMYVPPGAPKPDGRKSYQWQTATNPSIFAKLSD |
| SEQ ID NO: 17 | CVAP0 | STYMRFDAEFTFVSNLNDSTTPGMLLQYMYVPPGAPKPDGRKSYQWQTATNPSIFAKLSD |
| SEQ ID NO: 18 | CVA6 | STYMRFDAEFTFVSNLNDSTTPGMLLQYMYVPPGAPKPDGRKSYQWQTATNPSIFAKLSD |
| SEQ ID NO: 19 | CVA6_P11 | STYMRFDAEFTFVSNLNDSTTPGMLLQYMYVPPGAPKPDGRKSYQWQTATNPSIFAKLSD |
| SEQ ID NO: 20 | Shizuoka_1 | STYMRFDAEFTFVSNLNDSTTPGMLLQYMYVPPGAPKPDsRKSYQWQTATNPSVFAKLSD |
| SEQ ID NO: 21 | n0854694_C | STYMRFDAEFTFVSNLNDSTTPGMLLQYMYVPPGAPKPDsRKSYQWQTATNPSVFAKLSD |
| SEQ ID NO: 22 | HN421_CVA6 | STYMRFDAEFTFVSNLNDSTTPGMLLQYMYVPPGAPKPDsRKSYQWQTATNPSVFAKLSD |
| SEQ ID NO: 23 | Kyoto1_CVA | STYMRFDAEFTFVSNLNhSTTPGMLLQYMYVPPGAPKPDsRKSYQWQTATNPSVFAKLSD |
| SEQ ID NO: 24 | Tw40910_CV | STYMRFDAEFTFVSNLNDSTTPGMLLQYMYVPPGAPKPDsRKSYQWQTATNPSVFAKLSD |

| SEQ ID NO: 15 | n28297_CVA  | 181 | PPPQVyVPFMSPASAYQWFYDGYPTFGEHKQATNLQYGQCPNNMMGHFAIRTVSESTTGK | 240 |
| SEQ ID NO: 16 | n40428CVA6  |     | PPPQVSVPFMSPASAYQWFYDGYPTFGEHKQATNLQYGQCPNNMMGHFAIRTVSESTTGK |     |
| SEQ ID NO: 17 | CVAP0       |     | PPPQVSVPFMSPASAYQWFYDGYPTFGEHKQATNLQYGQCPNNMMGHFAIRTVSESTTGK |     |
| SEQ ID NO: 18 | CVA6        |     | PPPQVSVPFMSPASAYQWFYDGYPTFGEHKQATNLQYGQCPNNMMGHFAIRTVSESTTGK |     |
| SEQ ID NO: 19 | CVA6_P11    |     | PPPQVSVPFMSPASAYQWFYDGYPTFGEHKQATNLQYGQCPNNMMGHFAIRTVSESTTGK |     |
| SEQ ID NO: 20 | Shizuoka_1  |     | PPPQVSVPFMSPAHAYQWFYDGYPTFGEHKQATNLQYGQCPNNMMGHFAIRTVSESTTGK |     |
| SEQ ID NO: 21 | n0854694_C  |     | PPPQVSVPFMSPAHAYQWFYDGYPTFGEHKQATNLQYGQCPNNMMGHFAIRTVSESTTGK |     |
| SEQ ID NO: 22 | HN421_CVA6  |     | PPPQVSVPFMSPAHAYQWFYDGYPTFGEHKQATNLQYGQCPNNMMGHFAIRTVSESTTGK |     |
| SEQ ID NO: 23 | Kyoto1_CV   |     | PPPQVSVPFMSPAHAYQWFYDGYPTFGEHKQATNLQYGQCPNNMMGHFAIRTVSESTTGK |     |
| SEQ ID NO: 24 | TW40910_CV  |     | PPPQVSVPFMSPAHAYQWFYDGYPTFGEHKQATNLQYGQCPNNMMGHFAIRTVSESTTGK |     |

186 194

| SEQ ID NO: 15 | n28297_CVA  | 241 | NHHVRVYMRIKHVRAWVPRPLRSQAYMVKNYPTYnQTITNsATDRASITTT--------- | 300 |
| SEQ ID NO: 16 | n40428CVA6  |     | NHHVRVYMRIKHVRAWVPRPfRSQAYMVKNYPTVnQTITNsATDRAnITTT--------- |     |
| SEQ ID NO: 17 | CVAP0       |     | NVHVRVYMRIKHVRAWVPRPfRSQAYMVKNYPTYSQTISNTAaDRASITTTDYEGGVPAN |     |
| SEQ ID NO: 18 | CVA6        |     | NVHVRVYMRIKHVRAWVPRPfRSQAYMVKNYPTYSQTISNTAaDRASITTTDYEGGVPAN |     |
| SEQ ID NO: 19 | CVA6_P11    |     | NVHVRVYMRIKHVRAWVPRPfRSQAYMQKNYPTYSQTISNTAaDRASITTTDYEGGVPAN |     |
| SEQ ID NO: 20 | Shizuoka_1  |     | NVHVRVYMRIKHVRAWVPRPLRSQAYMVKNYPTYSQTITNTATDRASITTTDYEGGVPAN |     |
| SEQ ID NO: 21 | n0854694_C  |     | NVHVRVYMRIKHVRAWVPRPLRSQAYMVKNYPTYSQTITNTATDRASITIT--------- |     |
| SEQ ID NO: 22 | HN421_CVA6  |     | NEHVRVYMRIKHVRAWVPRPLRSQAYMVKNYPTYSQTITNTATDRASITTTDYEGGVPAN |     |
| SEQ ID NO: 23 | Kyoto1_CV   |     | NVHVRVYMRIKHVRAWVPRPLRSQAYMVKNYPTYSQTITNTATDRASITTTDYEGGVPAS |     |
| SEQ ID NO: 24 | TW40910_CV  |     | NVHVRVYMRIKHVRAWVPRPLRSQAYMVKNYPTYSQTITNTATDRASITTTDYEGGVPAN |     |

261 268 279 283

| SEQ ID NO: 15 | n28297_CVA  | 301 | -----  | 305 |
| SEQ ID NO: 16 | n40428CVA6  |     | -----  |     |
| SEQ ID NO: 17 | CVAP0       |     | PQRTf  |     |
| SEQ ID NO: 18 | CVA6        |     | PQRTf  |     |
| SEQ ID NO: 19 | CVA6_P11    |     | PQRTf  |     |
| SEQ ID NO: 20 | Shizuoka_1  |     | sQRTS  |     |
| SEQ ID NO: 21 | n0854694_C  |     | -----  |     |
| SEQ ID NO: 22 | HN421_CVA6  |     | PQRTS  |     |
| SEQ ID NO: 23 | Kyoto1_CV   |     | PQRTS  |     |
| SEQ ID NO: 24 | TW40910_CV  |     | PQRTS  |     |

CVA16 Primers

| Primers | Fragment | Size |
|---|---|---|
| 5' RACE | 1-1903 | 1903 bp |
| 3' RACE | 5668-7391 | 1724 bp |
| SeqF4-SeqR10 | 1812-5851 | 4040 bp |

Key
▭ = CVA16 Sequence
⇧ = Forward Primers, 1-12
⇩ = Reverse Primers, 1-12
⇨ = RACE Primers
| = Sequence broken into 1 kb fragments
15

FIG. 8

| | | | |
|---|---|---|---|
| SEQ ID NO: 25 | N-450B/Ind | GDSIADMIDQTVNNQVNRSLTALQVLPTAANTEASSHRLGTGVVPALQAAETGASSNASD | 60 |
| SEQ ID NO: 26 | CF361090_F | GDSIADMIDQTVNNQVNRSLTALQVmPTSANTEASSHRLGTGVVPALQAAETGASSNASD | |
| SEQ ID NO: 27 | Y-2222-05 | GDPIADMIDQTVNNQVNRSLSALQVmPTaANTEASSHRLGTGVVPALQAAETGASSNASD | |
| SEQ ID NO: 28 | CVA16/P-0 | GDPIADMIDQTVNNQVNRSLTALQVLPTAANTEASSHRLGTGVVPALQAAETGASSNASD | |
| SEQ ID NO: 29 | ESP08/5468 | GDPIADMIDQTVNNQVNRSLTALQVLPTAANTEASSHRLGTGVVPALQAAETGASSNASD | |
| SEQ ID NO: 30 | C38CMR/09 | GDSIADMIDQTVNNQVNRSLTAmQVLPTAANTEASSHRLGTGVVPALQAAETGASSNASD | |
| SEQ ID NO: 31 | Y-2286-11 | GDPIADMIDQTVNNQVNRSLTALQVLPTAANTEASSHRLGTGVVPALQAAETGASSNASD | |
| SEQ ID NO: 32 | Y-2077-09 | GDSIADMIDQTVNNQVNRSLTALQVLPTAANTEASSHRLGTGVVPALQAAETGASSNASD | |
| SEQ ID NO: 33 | Kor08 | GDPIADMIDQTVNNQVNRSLTALQVLPTAANTEASSHRLGTGVVPALQAAETGASSNASD | |
| SEQ ID NO: 34 | Y-737-98 | GDPIADMIDQTVNNQVNRSLTALQVLPTAANTEASSHRLGTGVVPALQAAETGASSNASD | |
| SEQ ID NO: 35 | TOY/419/06 | GDPIADMIDQTVNNQVNRSLTALQVLPTAANTEASSHRLGTGVVPALQAAETGASSNASD | |
| SEQ ID NO: 36 | CVA16/P-3 | GDPIADMIDQTVNNQVNRSLTALQVLPTAANTEASSHRLGTGVVPALQAAETGASSNASD | |
| SEQ ID NO: 37 | HN1726/CHN | GDPIADMIDQTVNNQVNRSLTALQVLPTAANTEASSHRLGTGVVPALQAAETGASSNASD | |
| SEQ ID NO: 38 | Y-1931-10 | GDPIADMIDQTVNNQVNRSLTALQVLPTAANTEASSHRLGTGVVPALQAAETGASSNASD | |
| SEQ ID NO: 39 | Y-721-98 | GDPIADMIDQTVNNQVNRSLTALQVLPTAANTEASSHRLGTGVVPALQAAETGASSNASD | |
| SEQ ID NO: 40 | Y-494-97 | GDPIADMIDQTVNNQVNRSLTALQVLPTAANTEASSHRLGTGVVPALQAAETGASSNASD | |
| SEQ ID NO: 41 | Y-1160-10 | GDPIADMIDQTVNNQVNRSLTALQVLPTAANTEASSHRLGTGVVPALQAAETGASSNASD | |
| SEQ ID NO: 42 | VNM/576T/0 | GDPIADMIDQTVNNQVNRSLTALQVLPTAANTEASSHRLGTGVVPALQAAETGASSNASD | |
| SEQ ID NO: 43 | FLA6916/09 | GDPIADMIDQTVSNQVNRSLTALQVLPTAANTEASSHRLGTGVVPALQAAETGASSNASD | |
| SEQ ID NO: 25 | N-450B/Ind 61 | KNLIETRCVLNHHSTQETAIGNFFSRAGLVSIITMPTTGTQNTDGYVNWDIDLMGYAQLR | 120 |
| SEQ ID NO: 26 | CF361090_F | KNLIETRCVLNHHSTQETAIGNFFSRAGLVSIITMPTTGTQNTDGYVNWDIDLMGYAQLR | |
| SEQ ID NO: 27 | Y-2222-05 | KNLIETRCVLNHHSTQETAIGNFFSRAGLVSIITMPTTGTQNTDGYVNWDIDLMGYAQLR | |
| SEQ ID NO: 28 | CVA16/P-0 | KNLIETRCVLNHHSTQETAIGNFFSRAGLVSIITMPTtdTQNTDGYVNWDIDLMGYAQLR | |
| SEQ ID NO: 29 | ESP08/5468 | KNLIETRCVLNHHSTQETAIGNFFSRAGLVSIITMPTTGTQNTDGYVNWDIDLMGYAQLR | |
| SEQ ID NO: 30 | C38CMR/09 | KNLIETRCVLNHHSTQETAIGNFFSRAGLVSIITMPTTGTQNTDGYVNWDIDLMGYAQLR | |
| SEQ ID NO: 31 | Y-2286-11 | KNLIETRCVLNHHSTQETAIGNFFSRAGLVSIITMPTTGTQNaDGYVNWDIDLMGYAQLR | |
| SEQ ID NO: 32 | Y-2077-09 | KNLIETRCVLNHHSTQETAIGNFFSRAGLVSIITMPTTGTQNTDGYVNWDIDLMGYAQLR | |
| SEQ ID NO: 33 | Kor08 | KNLIETRCVLNHHSTQETAIGNFFSRAGLVSIITMPTTGTQNTDGYVNWDIDLMGYAQLR | |
| SEQ ID NO: 34 | Y-737-98 | KNLIETRCVLNHHSTQETAIGNFFSRAGLVSIITMPTaGTQNTDGYVNWDIDLMGYAQLR | |
| SEQ ID NO: 35 | TOY/419/06 | KNLIETRCVLNHHSTQETAIGNFFSRAGLVSIITMPTaGTQNTDGYVNWDIDLMGYAQLR | |
| SEQ ID NO: 36 | CVA16/P-3 | KNLIETRCVLNHHSTQETAIGNFFSRAGLVSIITMPTTGTQNTDGYVNWDIDLMGYAQLR | |
| SEQ ID NO: 37 | HN1726/CHN | KNLIETRCVLNHHSTQETAIGNFFSRAGLVSIITMPTTGTQNTDGYVNWDIDLMGYAQLR | |
| SEQ ID NO: 38 | Y-1931-10 | KNLIETRCVLNHHSTQETAIGNFFSRAGLVSIITMPTTGTQNTDGYVNWDIDLMGYAQLR | |
| SEQ ID NO: 39 | Y-721-98 | KNLIETRCVLNHHSTQETAIGNFFSRAGLVSIITMPTTGTQNTDGYVNWDIDLMGYAQLR | |
| SEQ ID NO: 40 | Y-494-97 | KNLIETRCVLNHHSTQETAIGNFFSRAGLVSIITMPTTGTQNTDGYVNWDIDLMGYAQLR | |
| SEQ ID NO: 41 | Y-1160-10 | KNLIETRCVLNHHSTQETAIGNFFSRAGLVSIITMPTTGTQNTDGYVNWDIDLMGYAQLR | |
| SEQ ID NO: 42 | VNM/576T/0 | KNLIETRCVLNHHSTQETAIGNFFSRAGLVSIITMPTTGTQNTDGYVNWDIDLMGYAQLR | |
| SEQ ID NO: 43 | FLA6916/09 | KNLIETRCVLNHHSTQETAIGNFFSRAGLVSIITMPTTGTQNTDGYVNWDIDLMGYAQLR | |
| SEQ ID NO: 25 | N-450B/Ind 121 | RKCELFTYMRFDAEFTFVVAKPNGELVPQLLQYMYVPPGAPKPTSRDSFAWQTATNLSVF | 180 |
| SEQ ID NO: 26 | CF361090_F | RKCELFTYMRFDAEFTFVVAKPNGELVPQLLQYMYVPPGAPKPTSRDSFAWQTATNPSVF | |
| SEQ ID NO: 27 | Y-2222-05 | RKCELFTYMRFDAEFTFVVAKPNGELVPQLLQYMYVPPGAPKPTSRDSFAWQTATNPSVF | |
| SEQ ID NO: 28 | CVA16/P-0 | RKCELFTYMRFDAEFTFVVAKPNGmLVPQLLQYMYVPPGAPKPTSRDSFAWQTATNPSVF | |
| SEQ ID NO: 29 | ESP08/5468 | RKCELFTYMRFDAEFTFVVAKPNGELVPQLLQYMYVPPGAPKPTSRDSFAWQTATNPSVF | |
| SEQ ID NO: 30 | C38CMR/09 | RKCELFTYMRFDAEFTFVVAKPNGELVPQLLQYMYVPPGAPKPTSRDSFAWQTATNPSVF | |
| SEQ ID NO: 31 | Y-2286-11 | RKCELFTYMRFDAEFTFVVAKPNGELVPQLLQYMYVPPGAPKPTSRDSFAWQTATNPSVF | |
| SEQ ID NO: 32 | Y-2077-09 | RKCELFTYMRFDAEFTFVVAKPNGELVPQLLQYMYVPPGAPKPTSRDSFAWQTATNPSVF | |
| SEQ ID NO: 33 | Kor08 | RKCELFTYMRFDAEFTFVVAKPNGELVPQLLQYMYVPPGAPKPTSRDSFAWQTATNPSVF | |
| SEQ ID NO: 34 | Y-737-98 | RKCELFTYMRFDAEFTFVVAKPNGELVPQLLQYMYVPPGAPKPTSRDSFAWQTATNPSVF | |
| SEQ ID NO: 35 | TOY/419/06 | RKCELFTYMRFDAEFTFVVAKPNGELVPQLLQYMYVPPGAPKPTSRDSFAWQTATNPSVF | |
| SEQ ID NO: 36 | CVA16/P-3 | RKCELFTYMRFDAEFTFVVAKPNGELVPQLLQYMYVPPGAPKPTSRDSFAWQTATNPSVF | |
| SEQ ID NO: 37 | HN1726/CHN | RKCELFTYMRFDAEFTFVVAKPNGELVPQLLQYMYVPPGAPKPTSRDSFAWQTATNPSVF | |
| SEQ ID NO: 38 | Y-1931-10 | RKCELFTYMRFDAEFTFVVAKPNGELVPQLLQYMYVPPGAPKPTSRDSFAWQTATNPSVF | |
| SEQ ID NO: 39 | Y-721-98 | RKCELFTYMRFDAEFTFVVAKPNGELVPQLLQYMYVPPGAPKPTSRDSFAWQTATNPSVF | |
| SEQ ID NO: 40 | Y-494-97 | RKCELFTYMRFDAEFTFVVAKPNGELVPQLLQYMYVPPGAPKPTSRDSFAWQTATNPSVF | |
| SEQ ID NO: 41 | Y-1160-10 | RKCELFTYMRFDAEFTFVVAKPNGELVPQLLQYMYVPPGAPKPTSRDSFAWQTATNPSVF | |
| SEQ ID NO: 42 | VNM/576T/0 | RKCELFTYMRFDAEFTFVVAKPNGELVPQLLQYMYVPPGAPKPTSRDSFAWQTATNPSVF | |
| SEQ ID NO: 43 | FLA6916/09 | RKCELFTYMRFDAEFTFVVAKPNGELVPQLLQYMYVPPGAPKPTSRDSFAWQTATNPSVF | |

FIG. 10

| SEQ ID NO: | | | |
|---|---|---|---|
| 25 | N-450B/Ind | 181 VKMTDPPAQVSVPFMSPASAYQWFYDGYPTFGEHLQANDLDYGQCPNNMMGTFSVRTVGa | 240 |
| 26 | CF361090_F | VKMTDPPAQVSVPFMSPASAYQWFYDGYPTFGEHLQANDLDYGQCPNNMMGTFSVRTVGa | |
| 27 | Y-2222-05 | VKMTDPPAQVSVPFMSPASAYQWFYDGYPTFGEHLQANDLDYGQCPNNMMGTFSVRTVGT | |
| 28 | CVA16/P-0 | VKMTDPPAQVSVPFMSPASAYQWFYDGYPTFGEHLQANDLDYGQCPNNMMGTFSTRTVGT | |
| 29 | ESP08/5468 | VKMTDPPAQVSVPFMSPASAYQWFYDGYPTFGEHLQADLDYGQCPNNMMGTFSTRTVGT | |
| 30 | C38CMR/09 | VKMTDPPAQVSVPFMSPASAYQWFYDGYPTFGEHLQANDLDYGQCPNNMMGTFSTRTVGT | |
| 31 | Y-2286-11 | VKMTDPPAQVSVPFMSPASAYQWFYDGYPTFGEHLQANDLDYGQCPNNMMGTFSTRTVGT | |
| 32 | Y-2077-09 | VKMTDPPAQVSVPFMSPASAYQWFYDGYPTFGEHLQANDLDYGQCPNNMMGTFSTRTVGT | |
| 33 | Kor08 | VKMTDPPAQVSVPFMSPASAYQWFYDGYPTFGEHLQANDLDYGQCPNNMMGTFSTRTVGT | |
| 34 | Y-737-98 | VKMTDPPAQVSVPFMSPASAYQWFYDGYPTFGEHLQANDLDYGQCPNNMMGTFSTRTVGT | |
| 35 | TOY/419/06 | VKMTDPPAQVSVPFMSPASAYQWFYDGYPTFGEHLQANDLDYGQCPNNMMGTFSTRTVGT | |
| 36 | CVA16/P-3 | VKMTDPPAQVSVPFMSPASAYQWFYDGYPTFGEHLQANDLDYGQCPNNMMGTFSTRTVGT | |
| 37 | HN1726/CHN | VKMTDPPAQVSVPFMSPASAYQWFYDGYPTFGEHLQANDLDYGQCPNNMMGTFSTRTVGT | |
| 38 | Y-1931-10 | VKMTDPPAQVSVPFMSPASAYQWFYDGYPTFGEHLQANDLDYGQCPNNMMGTFSTRTVGT | |
| 39 | Y-721-98 | VKMTDPPAQVSVPFMSPASAYQWFYDGYPTFGEHLQANDLDYGQCPNNMMGTFSTRTVGT | |
| 40 | Y-494-97 | VKMTDPPAQVSVPFMSPASAYQWFYDGYPTFGEHLQANDLDYGQCPNNMMGTFSTRTVGT | |
| 41 | Y-1160-10 | VKMTDPPAQVSVPFMSPASAYQWFYDGYPTFGEHLQANDLDYGQCPNNMMGTFSTRTVGT | |
| 42 | VNM/576T/0 | VKMTDPPAQVSVPFMSPASAYQWFYDGYPTFGEHLQANDLDYGQCPNNMMGTFSTRTVGT | |
| 43 | FLA6916/09 | VKMTDPPAQVSVPFMSPASAYQWFYDGYPTFGEHLQANDLDYGQCPNNMMGTFSTRTVGT | |
| 25 | N-450B/Ind | 241 EKSPHSITLRVYMRIKHVRAWI--------------------------------------- | 297 |
| 26 | CF361090_F | EKSPHSITLRVYMRIKHVRAWIPRPLRNQPYLFKTNPNYKGNDIKCTSTSRDKITTL | |
| 27 | Y-2222-05 | EKSPHSITLRVYMRIKHVRAWIPRPLRNQPYLFKTNPNYKGNDIKCTSTSRDKITTL | |
| 28 | CVA16/P-0 | EKSPHSITLRVYMRIKHVRAWIPRPLRNQPYLFKTNPNYKGNDIKCTSTSRDKITTL | |
| 29 | ESP08/5468 | EKSPHSITLRVYMRIKHVRAWIPRPLRNQPYLFKTNP------------------- | |
| 30 | C38CMR/09 | EKSPHSITLRVYMRIKHVRAWIPRPLRNQPYLFKTNPNYKGND------------- | |
| 31 | Y-2286-11 | EKSPHSITLRVYMRIKHVRAWIPRPLRNQPYLFKTNPNYKGNDIKCTSTSRDKITTL | |
| 32 | Y-2077-09 | EKSPHSITLRVYMRIKHVRAWIPRPLRNQPYLFKTNPNYKGNDIKCTSTSRDKITTL | |
| 33 | Kor08 | KKSPHSITLRVYMRIKHVRAWIPRPLRNQPYLFKTNPNYKGNDIKCTSTSRDKITTL | |
| 34 | Y-737-98 | EKSPHSITLRVYMRIKHVRAWIPRPLRNQPYLFKTNPNYKGNDIKCTSTSRDKITTL | |
| 35 | TOY/419/06 | EKSPHSITLRVYMRIKHVRAWIPRPLRNQPYLFKTNPNYKGNDIKCTSTSRDKITTL | |
| 36 | CVA16/P-3 | EKSPHSITLRVYMRIKHVRAWIPRPLRNQPYLFKTNPNYKGNDIKCTSTSRDKITTL | |
| 37 | HN1726/CHN | EKSPHSITLRVYMRIKHVRAWIPRPLRNQPYLFKTNPNYKGNDIKCTSTSRDKITTL | |
| 38 | Y-1931-10 | EKSPHSITLRVYMRIKHVRAWIPRPLRNQPYLFKTNPNYKGNDIKCTSTSRDKITTL | |
| 39 | Y-721-98 | EKSPHSITLRVYMRIKHVRAWIPRPLRNQPYLFKTNPNYKGNDIKCTSTSRDKITTL | |
| 40 | Y-494-97 | EKSPHSITLRVYMRIKHVRAWIPRPLRNQPYLFKTNPNYKGNDIKCTSTSRDKITTL | |
| 41 | Y-1160-10 | EKSPHSITLRVYMRIKHVRAWIPRPLRNQPYLFKTNPNYKGNDIKCTSTSRDKITTL | |
| 42 | VNM/576T/0 | EKSPHSITLRVYMRIKHVRAWIPRPLRNQPYLFKTNPNYKGNDIKCTSTSRDKITTL | |
| 43 | FLA6916/09 | EKSPHSITLRVYMRIKHVRAWIPRPLRNQPYLFKTNPNYKGNDIKCTSTSRDKITTL | |

FIG. 10 (Cont.)

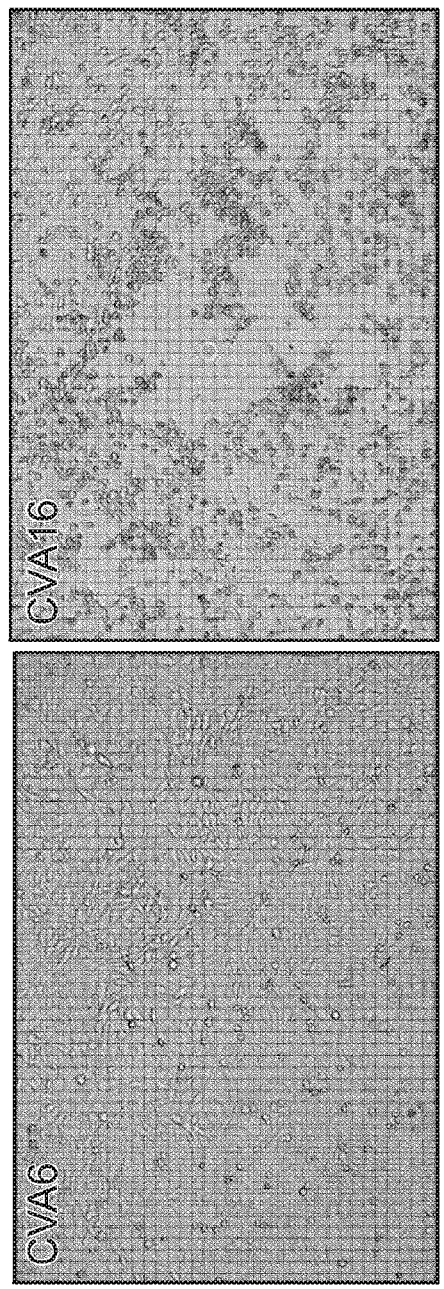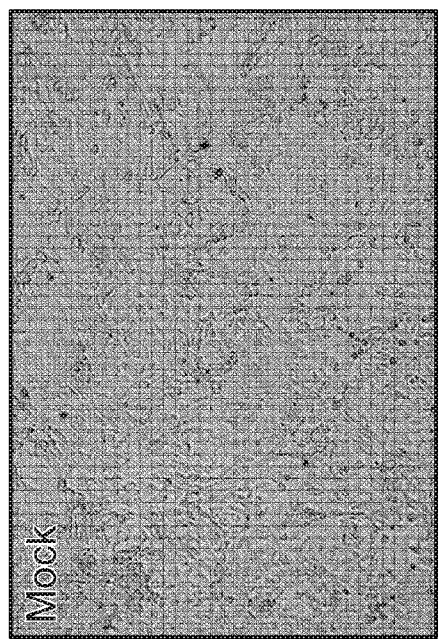
FIG. 12

| Vero | 128 | 64 | 32 | 16 | 8 | 4 | 2 | 1 | 0.5 | 0.25 | Media | Media |
|---|---|---|---|---|---|---|---|---|---|---|---|---|
| 1 | 1 | 2 | 3 | 4 | 5 | 6 | 7 | 8 | 9 | 10 | 11 | 12 |
| A | + | + | + | + | + | − | − | − | − | − | − | − |
| B | + | + | + | + | + | + | + | + | − | − | − | − |
| C | + | + | + | + | + | − | − | + | − | + | − | − |
| D | + | + | + | + | + | + | + | − | + | − | − | − |
| E | + | + | + | + | + | + | + | − | − | − | − | − |
| F | + | + | + | + | + | + | + | + | − | − | − | − |
| G | + | + | + | + | + | + | + | − | − | − | − | − |
| H | + | + | + | + | + | − | + | − | − | − | − | − |

| Vero C10 | 64 | 32 | 16 | 8 | 4 | 2 | 1 | 0.5 | 0.25 | 0.12 | 0.06 | Media |
|---|---|---|---|---|---|---|---|---|---|---|---|---|
| | 1 | 2 | 3 | 4 | 5 | 6 | 7 | 8 | 9 | 10 | 11 | 12 |
| A | - | + | + | + | + | + | + | + | - | - | - | - |
| B | + | + | + | + | + | + | + | + | + | - | - | - |
| C | + | + | + | + | + | + | + | + | + | - | - | - |
| D | - | + | + | + | + | + | + | + | - | - | - | - |
| E | + | + | + | + | + | + | + | + | + | - | - | - |
| F | + | + | + | + | + | + | + | + | + | + | - | - |
| G | + | + | + | + | + | + | + | + | + | - | - | - |
| H | + | + | + | + | + | + | - | + | - | - | - | - |

| Vero D9 | 64 | 32 | 16 | 8 | 4 | 2 | 1 | 0.5 | 0.25 | 0.12 | 0.06 | Media |
|---|---|---|---|---|---|---|---|---|---|---|---|---|
| | 1 | 2 | 3 | 4 | 5 | 6 | 7 | 8 | 9 | 10 | 11 | 12 |
| A | - | + | + | + | + | - | + | - | - | - | - | - |
| B | + | + | + | + | + | + | + | + | + | - | - | - |
| C | + | + | + | + | + | + | + | + | - | - | + | - |
| D | + | + | + | + | + | + | + | + | - | - | - | - |
| E | + | + | + | + | + | + | + | - | - | - | - | - |
| F | + | + | + | + | + | + | + | - | - | - | - | - |
| G | + | + | + | + | + | + | - | + | - | - | - | - |
| H | + | + | + | + | + | + | + | - | - | - | - | - |

| Vero F8 | 64 | 32 | 16 | 8 | 4 | 2 | 1 | 0.5 | 0.25 | 0.12 | 0.06 | Media |
|---|---|---|---|---|---|---|---|---|---|---|---|---|
| | 1 | 2 | 3 | 4 | 5 | 6 | 7 | 8 | 9 | 10 | 11 | 12 |
| A | + | + | + | + | + | - | + | - | + | - | - | - |
| B | + | + | + | + | + | - | - | - | - | - | - | - |
| C | + | + | + | + | + | + | + | - | + | - | - | - |
| D | + | + | + | + | + | + | + | - | + | - | - | - |
| E | + | + | + | + | + | + | + | - | - | - | - | - |
| F | + | + | + | + | + | - | - | + | - | + | - | - |
| G | + | + | + | + | + | - | - | + | - | - | - | - |
| H | + | + | - | + | + | - | - | + | - | - | - | - |

Calculated Titer TCID50/ml

Vero Cells — $10^4$

|   | $10^\wedge{-1}$ | $10^\wedge{-2}$ | $10^\wedge{-3}$ | $10^\wedge{-4}$ | $10^\wedge{-5}$ | $10^\wedge{-6}$ | $10^\wedge{-7}$ | $10^\wedge{-8}$ | Media | Media | Media | Media |
|---|---|---|---|---|---|---|---|---|---|---|---|---|
|   | 1 | 2 | 3 | 4 | 5 | 6 | 7 | 8 | 9 | 10 | 11 | 12 |
| A | + | + | - | - | - | - | - | - | Following 14 days of infection in Vero cells, supernatant was transferred to RD cells and CPE was recorded ||||
| B | + | + | + | - | + | - | - | - | |||||
| C | + | + | - | - | - | - | - | - | |||||
| D | + | +

```
SEQ ID NO: 36   CVA16/P-3              GDPIADMIDQTVNNQVNRSLTALQVLPTAANTEASSHRLGTGVVPALQAAETGASSNASD
SEQ ID NO: 44   CVA16/1-250-Middle     GDPIADMIDQTVNNQVNRSLTALQVLPTAANTEASSHRLGTGVVPALQAAETGASSNASD
SEQ ID NO: 28   CVA16/P-0              GDPIADMIDQTVNNQVNRSLTALQVLPTAANTEASSHRLGTGVVPALQAAETGASSNASD
                                       ************************************************************

SEQ ID NO: 36   CVA16/P-3              KNLIETRCVLNHHSTQETAIGNFFSRAGLVSIITMPTTGTQNTDGYVNWDIDLMGYAQLR
SEQ ID NO: 44   CVA16/1-250-Middle     KNLIETRCVLNHHSTQETAIGNFFSRAGLVSIITMPTTGTQNTDGYVNWDIDLMGYAQLR
SEQ ID NO: 28   CVA16/P-0              KNLIETRCVLNHHSTQETAIGNFFSRAGLVSIITMPTTDTQNTDGYVNWDIDLMGYAQLR
                                       ************************************** *********************

SEQ ID NO: 36   CVA16/P-3              RKCELFTYMRFDAEFTFVVAKPNGELVPQLLQYMYVPPGAPKPTSRDSFAWQTATNPSVF
SEQ ID NO: 44   CVA16/1-250-Middle     RKCELFTYMRFDAEFTFVVAKPNGELVPQLLQYMYVPPGAPKPTSRDSFAWQTATNPSVF
SEQ ID NO: 28   CVA16/P-0              RKCELFTYMRFDAEFTFVVAKPNGVLVPQLLQYMYVPPGAPKPTSRDSFAWQTATNPSVF
                                       ************************ ***********************************

SEQ ID NO: 36   CVA16/P-3              VKMTDPPAQVSVPFMSPASAYQWFYDGYPTFGEHLQANDLDYGQCPNNMMGTFSIRTVGT
SEQ ID NO: 44   CVA16/1-250-Middle     VKMTDPPAQVSVPFMSPASAYQWFYDGYPTFGEHLQANDLDYGQCPNNMMGTFSIRTVGT
SEQ ID NO: 28   CVA16/P-0              VKMTDPPAQVSVPFMSPASAYQWFYDGYPTFGEHLQANDLDYGQCPNNMMGTFSIRTVGT
                                       ************************************************************

SEQ ID NO: 36   CVA16/P-3              EKSPHSITLRVYMRIKHVRAWIPRPLRNQPYLFKTNPNYKGNDIKCTSTSRDKITTL
SEQ ID NO: 44   CVA16/1-250-Middle     EKSPHSITLRVYMRIKHVRAWIPRPLRNQPYLFKTNPNYKGNDIKCTSTSRDKITTL
SEQ ID NO: 28   CVA16/P-0              EKSPHSITLRVYMRIKHVRAWIPRPLRNQPYLFKTNPNYKGNDIKCTSTSRDKITTL
                                       *********************************************************
```

HAND, FOOT, AND MOUTH VACCINES AND METHODS OF MANUFACTURE AND USE THEREOF

CROSS REFERENCE TO RELATED APPLICATIONS

This application is a U.S. National Phase patent application of PCT/US2015/059587, filed Nov. 6, 2015, which claims the benefit of U.S. Provisional Patent Application No. 62/077,139, filed Nov. 7, 2014, each of which is hereby incorporated by reference in its entirety.

SUBMISSION OF SEQUENCE LISTING AS ASCII TEXT FILE

The content of the following submission on ASCII text file is incorporated herein by reference in its entirety: a computer readable form (CRF) of the Sequence Listing (file name: 606772000900SEQLIST.TXT, date recorded: May 3, 2017, size: 92 KB).

FIELD

The present disclosure relates to hand, foot, and mouth disease vaccines and immunogenic compositions having one or more antigens from at least one virus that causes hand, foot, and mouth disease in humans, and methods of manufacture, formulation, and testing, and uses thereof.

BACKGROUND

Hand, foot, and mouth disease (HFMD) is caused by several members of the human enterovirus A (HEV-A) group. It is generally a self-limiting infection affecting mostly children and is characterized by ulcers and vesicles on the hands, feet and oral cavity. However, a more severe form of disease may occur with neurological symptoms such as meningitis, encephalitis, polio-like paralysis, and brain stem encephalitis leading to pulmonary edema (Huang, C., et al., (1999) *N Engl J Med* 341: 936-942, Chang, L., et al. (1998) Lancet 352: 367-368, Ooi, M., et al. (2009) *BMC Infect Dis* 9: 3). Human enterovirus A belongs to the Picornaviridae family of non-enveloped, positive-sense RNA viruses, which also includes polioviruses and rhinoviruses. Members of the HEV-A group that can cause HFMD include Enterovirus 71 (EV71) and Coxsackieviruses, including serotypes A1, A4, A6, A10, and A16 (Pallansch and Roos, (2007) Knipe D M, Howley P M, Griffin D E, editors. Fields Virology. Philadelphia, Pa. Lippincott Williams & Wilkins. pp. 839-894; and Kobayashi M et al., *Jpn J Infect Dis* 2013; 66:260-1).

Enterovirus 71 and Coxsackieviruses contain four capsid proteins (VP1-VP4) and seven nonstructural proteins. In addition to protecting the viral RNA, the capsid proteins recognize receptors on the surface of host cells and contribute to the antigenic profile of the virus [8] (Jubelt 2014 Handbook of Clinical Neurology). Known human cell surface receptors for EV71 are the scavenger receptor B2 (SCARB2), and the P-selectin glycoprotein ligand 1 (PSGL-1) (Yamayoshi S., et al. (2009) *Nat Med* 15:798-801, Nishimura Y., et al. (2009) *Nat Med* 15: 794-797), while coxsackie A viruses bind to intracellular adhesion molecule-1 (ICAM), decay accelerating factor (DAF), Integrin $\alpha v \beta 3$, and MHC-I associated glucose regulated protein 78 (GRP78) (Bergelson, J. et al. (2013) *Adv Exp Med* 790: 24-41)).

The incidence of HFMD generally decreases with age. However, children under the age of five are particularly susceptible to the most severe form of HFMD due to CNS infection with EV71. This can result in neurological disease including aseptic meningitis, brainstem and/or cerebellar encephalitis and acute flaccid paralysis (Ooi, M., et al. (2010) *Lancet Neurol.* 9: 1097-1105, McMinn, P., et al. (2002) *FEMS Microbiol. Rev.* 26: 91-107). Some of these severe cases also result in infection in the autonomic nervous system, which can then lead to neurogenic pulmonary edema, which in turn may lead to cardiopulmonary failure. EV71 infection with CNS involvement and cardiopulmonary failure has been associated with long term neurologic sequelae, delayed neurodevelopment, and reduced cognitive functioning when compared to patients who had CNS involvement but without neurogenic pulmonary edema (Chang, L., et al., (2007) *N. Engl. J. Med.* 356:1226-1234, Ooi, M., et al. (2010) *Lancet Neurol.* 9: 1097-1105, Solomon, T., et al. (2010) *Lancet Infect. Dis.* 10: 778-790). The cause of long term neurologic sequelae is thought to be due to neuronal damage caused by direct EV71 infection of the neurons.

In Asia, HFMD epidemics occur on an annual basis, with many severe cases reported. Scattered reporting from China in 2007 showed over 80,000 cases of severe HFMD. In 2008, there were nearly 500,000 cases of severe disease reported in China. Between January and July 2009, the Chinese Ministry of Health (MOH) reported that there were over 787,000 cases of HFMD with over 10,500 severe cases, defined as CNS involvement. Recent reports from China further indicate that in 2010 there were over 1.5 million children diagnosed with HFMD.

Despite the prevalence of HFMD in China, there is currently no vaccine against HFMD available, nor is there an effective antiviral therapy for infection. Treatment of HFMD has been focused only on alleviation of symptoms. Severe oral ulcerations can create painful stomatitis, which interferes with oral intake of both food and fluids, resulting in dehydration which may require hospitalization. Meningoencephalitis and cardiopulmonary arrest requires emergent and full supportive therapy and management.

BRIEF SUMMARY

Thus, there is a need to develop vaccines and immunogenic compositions for treating and/or preventing hand, food, and mouth disease, particularly in children. In order to meet this need, the present disclosure provides vaccines and immunogenic compositions for treating and/or preventing hand, foot, and mouth disease that include antigens from at least one virus that causes hand, foot, and mouth disease in humans, such as EV71, CA6, and CA16. Advantageously, the antigens may include at least one adaptation mutation that allows for production in cultured non-human cell lines such as Vero cells. Moreover, as disclosed herein, the vaccines and immunogenic compositions of the present disclosure have been demonstrated to induce a protective immune response against viruses that cause hand, foot, and mouth disease in humans.

Accordingly, certain aspects of the present disclosure provide a hand, foot, and mouth vaccine containing one or more antigens from at least one virus that causes hand, foot and mouth disease in humans, where the one or more antigens include at least one non-human cell adaptation mutation. Accordingly, certain aspects of the present disclosure provide a hand, foot, and mouth immunogenic composition containing one or more antigens from at least one virus that causes hand, foot and mouth disease in humans, where the one or more antigens comprise at least one non-human cell adaptation mutation. Other aspects of the present disclosure provide a method for treating or preventing hand, foot, and mouth disease in a subject in need thereof, by administering to the subject a therapeutically effective amount of any of the vaccines or immunogenic compositions disclosed herein. Other aspects of the present disclosure provide a method for inducing an immune response in a subject in need thereof, by administering to the subject an immunogenic amount of any of the vaccines or immunogenic compositions disclosed herein.

Other aspects of the present disclosure provide a hand, foot, and mouth vaccine containing one or more antigens from at least one inactivated virus that causes hand, foot and mouth disease in humans, where the at least one virus is EV71, CA16, or both, and where the at least one virus was inactivated with beta-propiolactone (BPL). Other aspects of the present disclosure provide a hand, foot, and mouth immunogenic composition containing one or more antigens from at least one inactivated virus that causes hand, foot and mouth disease in humans, where the at least one virus is EV71, CA16, or both, and where the at least one virus was inactivated with beta-propiolactone (BPL). Other aspects of the present disclosure provide a method for treating or preventing hand, foot, and mouth disease in a subject in need thereof, by administering to the subject a therapeutically effective amount of any of the vaccines or immunogenic compositions disclosed herein. Other aspects of the present disclosure provide a method for inducing an immune response in a subject in need thereof, by administering to the subject an immunogenic amount of any of the vaccines or immunogenic compositions disclosed herein. Other aspects of the present disclosure provide a method for inactivating a hand, foot, and mouth virus preparation, by: (a) isolating the hand, foot, and mouth virus preparation from one or more non-human cells, where the cells are used to produce the virus preparation; (b) treating the virus preparation with an effective amount of beta-propiolactone (BPL); and (c) treating the virus preparation with an effective amount of formalin, where the step of treating with formalin occurs currently with step (b) or after step (b), and where the virus is selected from one or more of EV71, CA6, and CA16.

Other aspects of the present disclosure provide a hand, foot, and mouth vaccine containing one or more antigens from at least one inactivated virus that causes hand, foot and mouth disease in humans, where the at least one virus is CA6, CA16, or both, and where the at least one virus was inactivated with formalin. Other aspects of the present disclosure provide a hand, foot, and mouth immunogenic composition containing one or more antigens from at least one inactivated virus that causes hand, foot and mouth disease in humans, where the at least one virus is CA6, CA16, or both, and where the at least one virus was inactivated with formalin. Other aspects of the present disclosure provide a method for treating or preventing hand, foot, and mouth disease in a subject in need thereof, by administering to the subject a therapeutically effective amount of any of the vaccines or immunogenic compositions disclosed herein. Other aspects of the present disclosure provide a method for inducing an immune response in a subject in need thereof, by administering to the subject an immunogenic amount of any of the vaccines or immunogenic compositions disclosed herein. Other aspects of the present disclosure provide a method for inactivating a hand, foot, and mouth virus preparation, by: (a) isolating the hand, foot, and mouth virus preparation from one or more non-human cells, where the cells are used to produce the virus preparation; (b) treating the virus preparation with an effective amount of formalin; and (c) purifying the virus preparation from the formalin where the virus is selected from one or more of EV71, CA6, and CA16.

Other aspects of the present disclosure provide a hand, foot, and mouth vaccine containing one or more antigens from at least one virus that causes hand, foot and mouth disease in humans and an aluminum salt adjuvant, where at least 75%, at least 80%, at least 85%, at least 90%, at 95%, at least 97%, at least 99%, or 100% of the antigen is adsorbed to the aluminum salt adjuvant. Other aspects of the present disclosure provide a hand, foot, and mouth immunogenic composition containing one or more antigens from at least one virus that causes hand, foot and mouth disease in humans and an aluminum salt adjuvant, where at least 75%, at least 80%, at least 85%, at least 90%, at 95%, at least 97%, at least 99%, or 100% of the antigen is adsorbed to the aluminum salt adjuvant. Other aspects of the present disclosure provide a method for treating or preventing hand, foot, and mouth disease in a subject in need thereof, by administering to the subject a therapeutically effective amount of any of the vaccines or immunogenic compositions disclosed herein. Other aspects of the present disclosure provide a method for inducing an immune response in a subject in need thereof, by administering to the subject an immunogenic amount of any of the vaccines or immunogenic compositions disclosed herein. Other aspects of the present disclosure provide a method for preparing an adjuvanted hand, foot, and mouth vaccine, by: (a) mixing the vaccine with an aluminum salt adjuvant, where the vaccine includes one or more antigens from at least one virus that causes hand, foot and mouth disease in humans; and (b) incubating the mixture under suitable conditions for a period of time that ranges from about 16 hours to about 24 hours, where at least 75%, at least 80%, at least 85%, at least 90%, or at least 95% of the antigen is adsorbed to the aluminum salt adjuvant, and where the at least one virus that causes hand, foot and mouth disease is selected from one or more of EV71, CA6, and CA16. Other aspects of the present disclosure provide a method for preparing an adjuvanted hand, foot, and mouth immunogenic composition, by: (a) mixing the immunogenic composition with an aluminum salt adjuvant, where the immunogenic composition includes one or more antigens from at least one virus that causes hand, foot and mouth disease in humans; and (b) incubating the mixture under suitable conditions for a period of time that ranges from about 16 hours to about 24 hours, where at least 75%, at least 80%, at least 85%, at least 90%, or at least 95% of the antigen is adsorbed to the aluminum salt adjuvant, and where the at least one virus that causes hand, foot and mouth disease is selected from one or more of EV71, CA6, and CA16.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 7 shows an amino acid sequence alignment comparing the VP1 protein of several circulating CVA6 strains.

FIG. 8 shows a diagram of primers used for sequencing the full length genome of CVA16.

FIG. 10 shows an amino acid sequence alignment of the VP1 protein of circulating CVA16 strains.

FIG. 12 shows the cytopathic effects manifested by CVA6 and CVA16 in Vero cells transfected with viral RNA.

FIG. 13B shows a diagram of clones selected in the first round of limiting dilution of CVA6. FIG. 13C shows a diagram of clones selected in the second round of limiting dilution of CVA6.

FIG. 14 shows a comparison of titers of RNA-rederived CVA6 in Vero and RD cells.

FIG. 16 shows an amino acid sequence alignment of the VP1 protein between cloned CVA16 and the P-3 virus.

DETAILED DESCRIPTION

General Techniques

The techniques and procedures described or referenced herein are generally well understood and commonly employed using conventional methodology by those skilled in the art, such as, for example, the widely utilized methodologies described in Sambrook et al., *Molecular Cloning: A Laboratory Manual* 3d edition (2001) Cold Spring Harbor Laboratory Press, Cold Spring Harbor, N.Y.; *Current Protocols in Molecular Biology* (F. M. Ausubel, et al. eds., (2003)); the series *Methods in Enzymology* (Academic Press, Inc.): PCR 2: A Practical Approach (M. J. MacPherson, B. D. Hames and G. R. Taylor eds. (1995)), Harlow and Lane, eds. (1988) *Antibodies, A Laboratory Manual*, and *Animal Cell Culture* (R. I. Freshney, ed. (1987)); *Oligonucleotide Synthesis* (M. J. Gait, ed., 1984); *Methods in Molecular Biology*, Humana Press; *Cell Biology: A Laboratory Notebook* (J. E. Cellis, ed., 1998) Academic Press; *Animal Cell Culture* (R. I. Freshney), ed., 1987); *Introduction to Cell and Tissue Culture* (J. P. Mather and P. E. Roberts, 1998) Plenum Press; *Cell and Tissue Culture: Laboratory Procedures* (A. Doyle, J. B. Griffiths, and D. G. Newell, eds., 1993-8) J. Wiley and Sons; *Handbook of Experimental Immunology* (D. M. Weir and C. C. Blackwell, eds.); *Gene Transfer Vectors for Mammalian Cells* (J. M. Miller and M. P. Calos, eds., 1987); *PCR: The Polymerase Chain Reaction*, (Mullis et al., eds., 1994); *Current Protocols in Immunology* (J. E. Coligan et al., eds., 1991); *Short Protocols in Molecular Biology* (Wiley and Sons, 1999); *Immunobiology* (C. A. Janeway and P. Travers, 1997); *Antibodies* (P. Finch, 1997); *Antibodies: A Practical Approach* (D. Catty., ed., IRL Press, 1988-1989); *Monoclonal Antibodies: A Practical Approach* (P. Shepherd and C. Dean, eds., Oxford University Press, 2000); *Using Antibodies: A Laboratory Manual* (E. Harlow and D. Lane (Cold Spring Harbor Laboratory Press, 1999); *The Antibodies* (M. Zanetti and J. D. Capra, eds., Harwood Academic Publishers, 1995); and *Cancer: Principles and Practice of Oncology* (V. T. DeVita et al., eds., J.B. Lippincott Company, 1993).

Hand, Foot, and Mouth Disease Causing Viruses

Certain aspects of the present disclosure relate to at least one virus that causes hand, foot, and mouth disease that may be useful in vaccines and/or immunogenic compositions including, without limitation, purified viruses, inactivated viruses, attenuated viruses, recombinant viruses, or purified and/or recombinant viral proteins for subunit vaccines.

Figure 1:
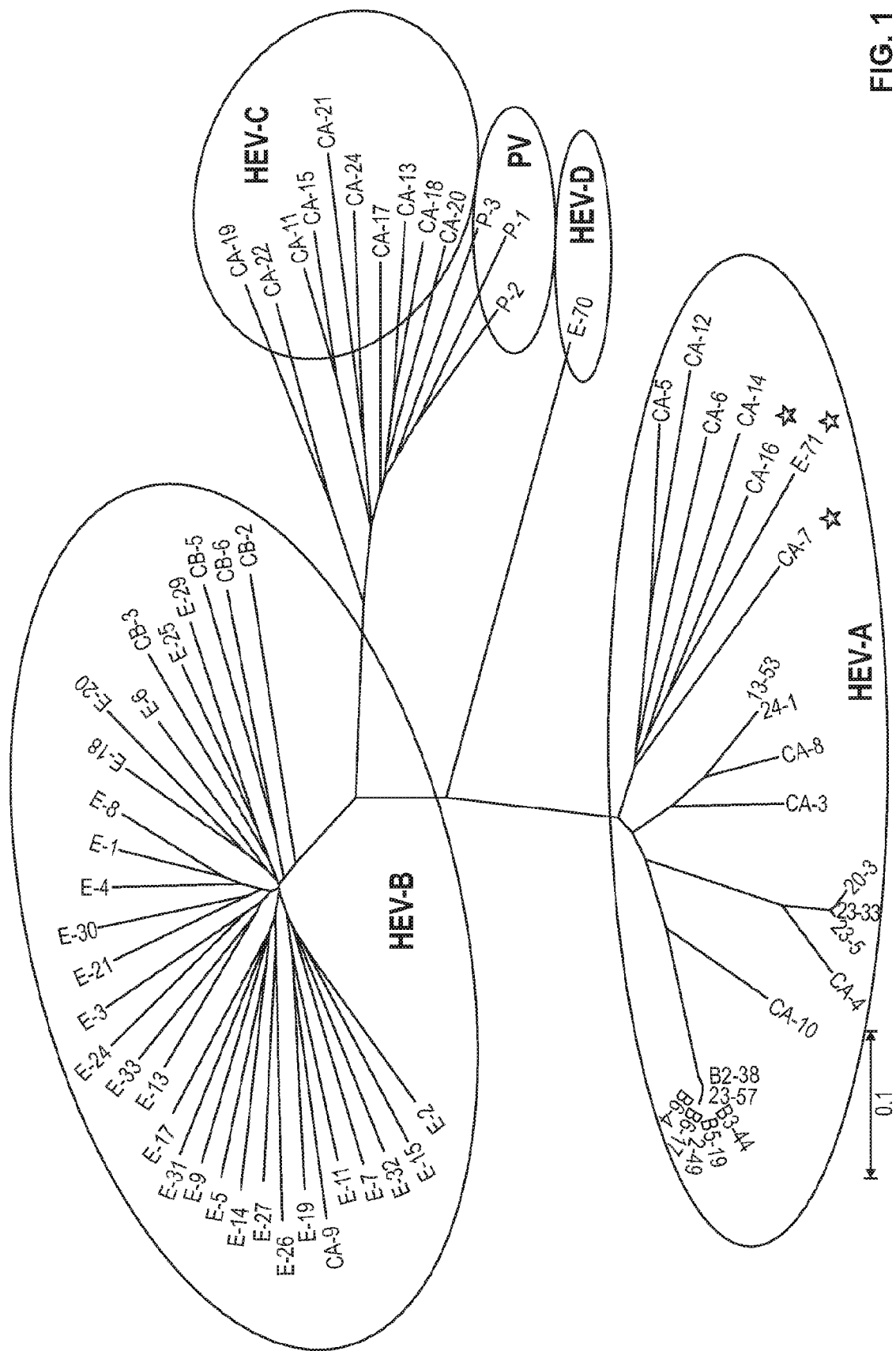
FIG. 1 shows a tree depicting the phylogenetic relationship of human enteroviruses.

Hand, foot, and mouth disease in humans (HFMD) is caused by several members of the human enterovirus A (HEV-A) group (FIG. 1). Human enterovirus A belongs to the Picornaviridae family of non-enveloped, positive-sense RNA viruses, which also includes polioviruses and rhinoviruses. Members of the HEV-A group that can cause HFMD include Enterovirus 71 (EV71) and Coxsackieviruses. Accordingly, examples of suitable viruses of the present disclosure that cause hand, foot, and mouth disease include, without limitation, Enterovirus 71 (EV71), Coxsackievirus A strains, including serotypes A1, A2, A4, A5, A6, A8, A9, A10, or A16, or Coxsackievirus B strains, including serotype B3 or B5 or any combination thereof. As used herein, the term "CA6" is used interchangeably with "CVA6" and "Coxsackievirus A6". As used herein, the term "CA16" is used interchangeably with "CVA16" and "Coxsackievirus A16". In some embodiments, the at least one virus may be one or more, two or more, or three viruses selected from EV71, CA6, and CA16. In some embodiments, the at least one virus may be EV71 and CA6. In some embodiments, the at least one virus may be EV71 and CA16. In some embodiments, the at least one virus may be CA6 and CA16. In some embodiments, the at least one virus may be EV71.

Accordingly, in some embodiments, viruses of the present disclosure that cause hand, foot, and mouth disease may be used in any of the vaccines and/or immunogenic compositions disclosed herein. For example, viruses of the present disclosure that cause hand, foot, and mouth disease may be used to provide one or more antigens useful for treating or preventing hand, foot, and mouth disease in a subject in need thereof and/or inducing an immune response, such as a protective immune response, against hand, foot, and mouth disease in a subject in need thereof.

Viral Antigens

Other aspects of the present disclosure relate to one or more antigens from at least one virus that causes hand, foot and mouth disease that may be useful in vaccines and/or immunogenic compositions including, without limitation, purified viruses, inactivated viruses, attenuated viruses, recombinant viruses, or purified and/or recombinant viral proteins for subunit vaccines.

Antigens of the present disclosure may be any substance capable of eliciting an immune response. Examples of suitable antigens include, but are not limited to, whole virus, attenuated virus, inactivated virus, proteins, polypeptides (including active proteins and individual polypeptide epitopes within proteins), glycopolypeptides, lipopolypeptides, peptides, polysaccharides, polysaccharide conjugates, peptide and non-peptide mimics of polysaccharides and other molecules, small molecules, lipids, glycolipids, and carbohydrates.

In some embodiments, antigens of the present disclosure may be from any virus known to cause HFMD, including, without limitation, Enterovirus 71(EV71), Coxsackievirus A strains, including serotypes A1, A2, A4, A5, A6, A8, A9, A10, or A16, or Coxsackievirus B strains, including serotype B3 or B5, or any combination thereof. In some embodiments, antigens of the present disclosure may be one or more, two or more, three or more, four or more, five or more, six or more, seven or more, eight or more, nine or more, or ten or more antigens selected from EV71, CA6, and CA16. In some embodiments, antigens of the present disclosure may be from EV71 and CA6. In some embodiments, antigens of the present disclosure may be from EV71 and CA16. In some embodiments, antigens of the present disclosure may be from CA6 and CA16. In some embodiments, antigens of the present disclosure may be from EV71. In some embodiments, antigens of the present disclosure may be from CA6. In some embodiments, antigens of the present disclosure may be from CA16.

Antigens of the present disclosure may include at least one non-human cell adaptation mutation. Adaptation mutations may be generated by adapting a virus to growth in a particular cell line. For example, a cell may be transfected with a virus and passaged such that the virus replicates and its nucleic acid mutates. Nucleic acid mutations may be point mutations, insertion mutations, or deletion mutations. Nucleic acid mutations may lead to amino acid changes within viral proteins that facilitate growth of the virus in a non-human cell. Adaptation mutations may facilitate phenotypic changes in the virus, including altered plaque size, growth kinetics, temperature sensitivity, drug resistance, virulence, and virus yield in cell culture. These adaptive mutations may be useful in vaccine manufacture by increasing the speed and yield of virus cultured in a cell line. In addition, adaptive mutations may enhance immunogenicity of viral antigens by altering the structure of immunogenic epitopes.

Accordingly, in certain embodiments, antigens of the present disclosure from at least one virus that causes hand, foot and mouth disease include at least one non-human cell adaptation mutation. In certain embodiments, the adaptation mutations are mutations of a viral antigen to a non-human cell. In some embodiments, the non-human cell may be a mammalian cell. Examples of non-human mammalian cells include, without limitation, VERO cells (from monkey kidneys), MDBK cells, MDCK cells, ATCC CCL34 MDCK (NBL2) cells, MDCK 33016 (deposit number DSM ACC 2219 as described in WO97/37001) cells, BHK21-F cells, HKCC cells, or Chinese hamster ovary cells (CHO cells). In some embodiments, the non-human cell may be a monkey cell. In some embodiments, the monkey cell is from a Vero cell line. Examples of suitable Vero cell lines include, without limitation, WHO Vero 10-87, ATCC CCL-81, Vero 76 (ATCC Accession No. CRL-1587), or Vero C1008 (ATCC Accession No. CRL-1586).

Figure 2:
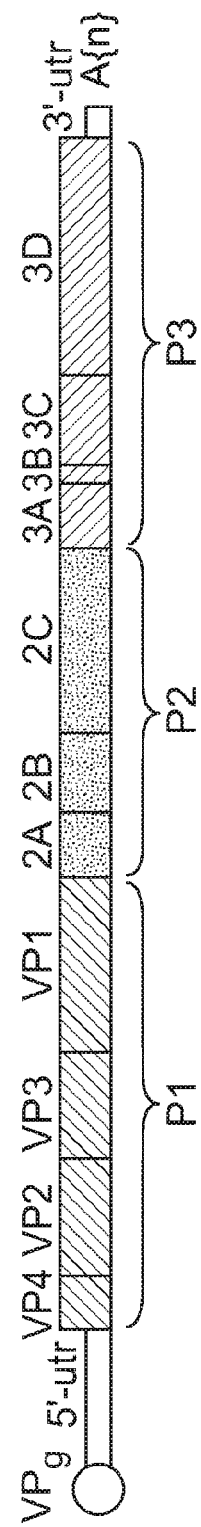
FIG. 2 shows the genetic structure of an exemplary EV71 strain.

EV71, CA6, and CA16 possess linear, positive sense, single-stranded RNA genomes (FIG. 2). Each of these viral genomes encodes both structural and nonstructural polypeptides. Structural polypeptides encoded by each of these viruses include, without limitation, VP1, VP2, VP3, and VP4, which together may compose the viral capsid. Non-structural polypeptides encoded by each of these viruses include, without limitation, 2A, 2B, 2C, 3A, 3B, 3C, and 3D, which are involved in, for example, virus replication and virulence.

Accordingly, in certain embodiments, antigens of the present disclosure may contain at least one, at least two, at least three, at least four, at least five, at least six, at least seven, at least eight, at least nine, at least 10, at least 11, at least 12, at least 13, at least 14, at least 15, at least 16, at least 17, at least 18, at least 19, at least 20, or more non-human cell adaptation mutations within one or more, two or more, three or more, four or more, five or more, six or more, seven or more, eight or more, nine or more, or ten or more viral antigens, including, without limitation, VP1, VP2, VP3, 2A, 2B, 2C, 3A, 3B, 3C, and 3D. In some embodiments, antigens of the present disclosure include whole, inactivated virus that may contain at least one, at least two, at least three, at least four, at least five, at least six, at least seven, at least eight, at least nine, at least 10, or more non-human cell adaptation mutations within the 5' or 3' untranslated region (UTR) of the virus.

In some embodiments, the at least one non-human cell adaptation mutation is within the VP1 polypeptide of EV71. The amino acid sequence of the VP1 polypeptide from an exemplary EV71 strain is set forth as:

```
                                        (SEQ ID NO: 1)
GDRVADVIESSIGDSVSRALTQALPAPTGQNTQVSSHRLDTGEVPALQAA

EIGASSNTSDESMIETRCVLNSHSTAETTLDSFFSRAGLVGEIDLPLEGT

TNPNGYANWDIDITGYAQMRRKVELFTYMRFDAEFTFVACTPTGEVVPQL

LQYMFVPPGAPKPESRESLAWQTATNPSVFVKLTDPPAQVSVPFMSPASA

YQWFYDGYPTFGEHKQEKDLEYGACPNNMMGTFSVRTVGSSKSKYPLVVR

IYMRMKHVRAWIPRPMRNQNYLFKANPNYAGNSIKPTGTSRNAITTL.
```

In some embodiments, the at least one non-human cell adaptation mutation occurs at one or more amino acid positions within the VP1 polypeptide of EV71. In some embodiments, the mutation may occur at one or more, two or more, three or more, or four amino acid positions selected from 7, 14, 145, and 282 of SEQ ID NO: 1, or at positions corresponding to positions 7, 14, 145, or 282 of SEQ ID NO: 1 when the VP1 polypeptide of EV71 is aligned to SEQ ID NO: 1 using a pairwise alignment algorithm. In some embodiments, the mutation occurs at position 7 of SEQ ID NO: 1 or at a position corresponding to position 7 of SEQ ID NO: 1 when aligned to SEQ ID NO: 1 using a pairwise alignment algorithm. In some embodiments, the mutation occurs at position 7 of SEQ ID NO: 1, or at two or more, three or more, or all four of positions 7, 14, 145, or 282 of SEQ ID NO: 1, or at position corresponding to position 7, 14, 145, or 282 of SEQ ID NO: 1 when the VP1 polypeptide of EV71 is aligned to SEQ ID NO: 1 using a pairwise alignment algorithm. In some embodiments, the mutation at position 7 is a valine to methionine substitution. In some embodiments, the mutation at position 14 is an aspartic acid to asparagine substitution. In some embodiments, the mutation at position 145 is a glutamic acid to glutamine substitution. In some embodiments, the mutation at position 282 is an asparagine to aspartic acid substitution.

In some embodiments, the at least one non-human cell adaptation mutation is within the VP1 polypeptide of CA6. The amino acid sequence of the VP1 polypeptide from an exemplary CA6 strain is set forth as:

(SEQ ID NO: 2)
NDPISNAIENAVSTLADTTISRVTAANTAASSHSLGTGRVPALQAAETGA

SSNASDENLIETRCVMNRNGVNEASVEHFYSRAGLVGVVEVKDSGTSQDG

YTVWPIDVMGFVQQRRKLELSTYMRFDAEFTFVSNLNDSTTPGMLLQYMY

VPPGAPKPDGRKSYQWQTATNPSIFAKLSDPPPQVSVPFMSPASAYQWFY

DGYPTFGEHKQATNLQYGQCPNNMMGHFAIRTVSESTTGKNVHVRVYMRI

KHVRAWVPRPFRSQAYMVKNYPTYSQTISNTAADRASITTTDYEGGVPAN

PQRTF.

In some embodiments, the at least one non-human cell adaptation mutation occurs at one or more amino acid positions within the VP1 polypeptide of CA6. In some embodiments, the mutation may occur at one or more, two or more, three or more, or four amino acid positions selected from 46, 90, 96, and 268 of SEQ ID NO: 2, or at positions corresponding to positions 46, 90, 96, and 268 of SEQ ID NO: 2 when the VP1 polypeptide of CA6 is aligned to SEQ ID NO: 2 using a pairwise alignment algorithm. In some embodiments, the mutation occurs at one or more, two or more, three or more, or all four of positions 46, 90, 96, and 268 of SEQ ID NO: 2, or at position corresponding to position 46, 90, 96, and 268 of SEQ ID NO: 2 when the VP1 polypeptide of CA6 is aligned to SEQ ID NO: 2 using a pairwise alignment algorithm. In some embodiments, the mutation at position 46 is an alanine to valine substitution. In some embodiments, the mutation at position 90 is a glutamic acid to lysine substitution. In some embodiments, the mutation at position 96 is a threonine to alanine substitution. In some embodiments, the mutation at position 268 is a valine to isoleucine substitution.

In some embodiments, the at least one non-human cell adaptation mutation is within the VP2 polypeptide of CA6. The amino acid sequence of the VP2 polypeptide from an exemplary CA6 strain is set forth as:

(SEQ ID NO: 3)
SPSVEACGYSDRVAQLTVGNSTITTQEAANIVLSYGEWPGYCPSTDATAV

DKPTRPDVSVNRFYTLSTKSWKTESTGWYWKFPDVLNDTGVFGQNAQFHY

LYRSGFCMHVQCNASKFHQGALLVVVIPEFVVAASSPAMKPNGQGLYPDF

AHTNPGKEGQVFRDPYVLDAGIPLSQALVFPHQWINLRTNNCATIIMPYV

NALPFDSALNHSNFGLAVIPISPLKYCNGATTEVPITLTIAPLNSEFSGL

RQAIKQ.

In some embodiments, the mutation may occur at amino acid position 144 of SEQ ID NO: 3, or at a position corresponding to position 144 of SEQ ID NO: 3 when the VP2 polypeptide of CA6 is aligned to SEQ ID NO: 3 using a pairwise alignment algorithm. In some embodiments, the mutation at position 144 is a glutamine to lysine substitution.

In some embodiments, the at least one non-human cell adaptation mutation is within the VP3 polypeptide of CA6. The amino acid sequence of the VP3 polypeptide from an exemplary CA6 strain is set forth as:

(SEQ ID NO: 4)
GLPTELKPGTNQFLTTDDGTSPPILPGFEPTPLIHIPGEFTSLLDLCRIE

TILEVNNTTGTTGVNRLLIPVRAQNNVDQLCASFQVDPGRNGPWQSTMVG

QICRYYTQWSGSLKVTFMFTGSFMATGKMLIAYTPPGSAQPTTREAAMLG

THIVWDFGLQSSVTLVIPWISNTHFRAVKTGGVYDYYATGIVTIWYQTNF

VVPPDTPSEANIIALGAAQENFTLKLCKDTDEIRQTAEYQ.

In some embodiments, the at least one non-human cell adaptation mutation occurs at one or more amino acid positions within the VP3 polypeptide of CA6. In some embodiments, the mutation may occur at amino acid position 102 of SEQ ID NO: 4, or at a position corresponding to position 102 of SEQ ID NO: 4 when the VP3 polypeptide of CA6 is aligned to SEQ ID NO: 4 using a pairwise alignment algorithm. In some embodiments, the mutation at position 102 is an isoleucine to valine substitution.

In some embodiments, the at least one non-human cell adaptation mutation is within the 5' UTR of CA6. The nucleic acid sequence of the 5' UTR from an exemplary CA6 strain is set forth as:

(SEQ ID NO: 8)
TTAAAACAGCTAGTGGGTTGCACCCACTCACAGGGCCCACTGGGCGCTAG

CACACTGATTTCCCGGAATCCTTGTGCGCCTGTTTTATATCCCCTCCCCC

ATGCGCAACTTAGAAGCAATCTACACCTTCGATCAATAGCAGGCGTGGCG

CGCCAGCCATGTCTAGATCAAGCACTTCTGTTTCCCCGGACTGAGTATCA

ATAAACTGCTCACGCGGTTGAAGGAGAAAATGTTCGTTACCCGGCTAACT

ACTTCGAGAAACCTAGTAGCACCATGAAAATTGCAGAGCGTTtCGcTCAG

CGcTtCCCCcGCGtAGATCAGGCTGATGAGTCACTGCATTCCTCACGGGC

GACCGTGGCAGTGGCTGCGTTGGCGGCCTGCCCATGGGGTAACCCATGGG

ACGCTCTAATATGGACATGGTGTGAAGAGTCTATTGAGCTAGTTAGTAGT

CCTCCGGCCCCTGAATGCGGCTAATCCTAACTGCGGAGCACATACCCCCA

AACCAGGGGGCGGTGTGTCGTAACGGGCAACTCTGCAGCGGAACCGACTA

CTTTGGGTGTCCGTGTTTCCTTTTATTCTTATATTGGCTGCTTATGGTGA

CAATTGAAAGATTGTTACCATATAGCTATTGGATTGGCCATCCGGTGAAT

AACAGAGCCTTGATATACCTTTTTGTAGGGTTTATACCACTTACTCTTCG

CGTTGTTGAGACTCTAAAGTACATTCTAATCTTGAACACTAGAAA.

In some embodiments, the at least one non-human cell adaptation mutation occurs at one or more nucleic acid positions within the 5' UTR of CA6. In some embodiments, the mutation may occur at one or more, two or more, three or more, four or more, five or more, six or more, seven or more, eight or more, or nine nucleic acid positions selected from 1, 13, 14, 15, 16, 21, 23, 34, and 40 of SEQ ID NO: 8, or at positions corresponding to positions 1, 13, 14, 15, 16, 21, 23, 34, and 40 of SEQ ID NO: 8 when the 5' UTR of CA6 is aligned to SEQ ID NO: 8 using a pairwise alignment algorithm. In some embodiments, the mutation occurs at one or more, two or more, three or more, four or more, five or more, six or more, seven or more, eight or more, or all nine of positions 1, 13, 14, 15, 16, 21, 23, 34, and 40 of SEQ ID NO: 8, or at position corresponding to position 1, 13, 14, 15, 16, 21, 23, 34, and 40 of SEQ ID NO: 8 when the 5' UTR of CA6 is aligned to SEQ ID NO: 8 using a pairwise alignment algorithm. In some embodiments, the mutation at position 1 is a thymine to guanine substitution. In some embodiments, the mutation at position 13 is a guanine to adenine substitution. In some embodiments, the mutation at position 14 is a thymine to guanine substitution. In some embodiments, the mutation at position 15 is a guanine to cytosine substitution. In some embodiments, the mutation at position 16 is a guanine to adenine substitution. In some embodiments, the mutation at position 21 is a cytosine to thymine substitution. In some embodiments, the mutation at position 23 is a cytosine to thymine substitution. In some embodiments, the mutation at position 34 is a guanine to thymine substitution. In some embodiments, the mutation at position 40 is a cytosine to guanine substitution.

In some embodiments, the at least one non-human cell adaptation mutation is within the 2A polypeptide of CA16. The amino acid sequence of the 2A polypeptide from an exemplary CA16 strain is set forth as:

(SEQ ID NO: 5)
GKFGQQSGAIYVGNYRVVNRHLATHNDWANLVWEDSSRDLLVSSTTAQGC

DTIARCDCQTGIYYCSSKRKHYPVSFTKPSLIFVEASEYYPARYQSHLML

AVGHSEPGDCGGILRCQHGVVGIVSTGGNGLVGFADVRDLLWLDEEAMEQ.

In some embodiments, the at least one non-human cell adaptation mutation occurs at one or more amino acid positions within the 2A polypeptide of CA16. In some embodiments, the mutation may occur at amino acid position 2 of SEQ ID NO: 5, or at a position corresponding to position 2 of SEQ ID NO: 5 when the 2A polypeptide of CA16 is aligned to SEQ ID NO: 5 using a pairwise alignment algorithm. In some embodiments, the mutation at position 2 is a lysine to glutamic acid substitution.

In some embodiments, the at least one non-human cell adaptation mutation is within the VP2 polypeptide of CA16. The amino acid sequence of the VP2 polypeptide from an exemplary CA16 strain is set forth as:

(SEQ ID NO: 6)
SPSAEACGYSDRVAQLTIGNSTITTQEAANIVIAYGEWPEYCPDTDATAV

DKPTRPDVSVNRFFTLDTKSWAKDSKGWYWKFPDVLTEVGVFGQNAQFHY

LYRSGFCVHVQCNASKFHQGALLVAVLPEYVLGTIAGGTGNENSHPPYAT

TQPGQVGAVLMHPYVLDAGIPLSQLTVCPHQWINLRTNNCATIIVPYMNT

VPFDSALNHCNFGLLVIPVVPLDFNAGATSEIPITVTIAPMCAEFAGLRQ

AVKQ.

In some embodiments, the at least one non-human cell adaptation mutation occurs at one or more amino acid positions within the VP2 polypeptide of CA16. In some embodiments, the mutation may occur at amino acid position 161 of SEQ ID NO: 6, or at a position corresponding to position 161 of SEQ ID NO: 6 when the VP2 polypeptide of CA16 is aligned to SEQ ID NO: 6 using a pairwise alignment algorithm. In some embodiments, the mutation at position 161 is a methionine to threonine substitution.

In some embodiments, the at least one non-human cell adaptation mutation is within the VP1 polypeptide of CA16. The amino acid sequence of the VP1 polypeptide from an exemplary CA16 strain is set forth as:

(SEQ ID NO: 7)
GDPIADMIDQTVNNQVNRSLTALQVLPTAANTEASSHRLGTGVVPALQAA

ETGASSNASDKNLIETRCVLNHHSTQETAIGNFFSRAGLVSIITMPTTDT

QNTDGYVNWDIDLMGYAQLRRKCELFTYMRFDAEFTFVVAKPNGVLVPQL

LQYMYVPPGAPKPTSRDSFAWQTATNPSVFVKMTDPPAQVSVPFMSPASA

YQWFYDGYPTFGEHLQANDLDYGQCPNNMMGTFSIRTVGTEKSPHSITLR

VYMRIKHVRAWIPRPLRNQPYLFKTNPNYKGNDIKCTSTSRDKITTL.

In some embodiments, the at least one non-human cell adaptation mutation occurs at one or more amino acid positions within the VP1 polypeptide of CA16. In some embodiments, the mutation may occur at one or more, or two amino acid positions selected from 99 and 145 of SEQ ID NO: 7, or at a position corresponding to position 99 or 145 of SEQ ID NO: 7 when the VP1 polypeptide of CA16 is aligned to SEQ ID NO: 7 using a pairwise alignment algorithm. In some embodiments, the mutation at position 99 is an aspartic acid to glycine substitution. In some embodiments, the mutation at position 145 is a valine to glutamic acid substitution.

In some embodiments, the at least one non-human cell adaptation mutation is within the 5' UTR of CA16. The nucleic acid sequence of the 5' UTR from an exemplary CA16 strain is set forth as:

(SEQ ID NO: 9)
AGCCTGTGGGTTGTTCCCACCCACAGGGCCCAGTGGGCGCTAGCACACTG

ATTCTGCGGGATCTTTGTGCGCCTGTTTTATAACCCCTTCCCTAAGCAGC

AACTTAGAAGTTTCACACAATCACGACCAGTAGTGGGCGTGGCGCGCCAG

TCACGTCTTGGTCAAGCACTTCTGTTCCCCCGGACTGAGTATCAATAGAC

TGCTCACGCGGTTGAAGGAGAAAACGTTCGTTATCCGGCTAACTACTTCG

AGAAACCTAGtAGCACCGTGAAAGTTGCGGAGtGTttCGCTCAGCACTTC

CCCCGTGTAGATCAGGTCGATGAGTCACTGTAAACCCCACGGGCGACCGT

GACAGTGGCTGCGTTGGCGGCCTGCCCATGGGGTAACCCATGGGACGCTC

TAATACAGACATGGTGTGAAGAGTCTATTGAGCTAGTTAGTAGTCCTCCG

GCCCCTGAATGCGGCTAATCCTAACTGCGGAGCACGCACCCTCAACCCAG

GGGGCGGCGTGTCGTAATGGGTAACTCTGCAGCGGAACCGACTACTTTGG

GTGTCCGTGTTTCCTTTTATTCCTTATTGGCTGCTTATGGTGACAATTGA

AAAGTTGTTACCATATAGCTATTGGATTGGCCATCCGGTGTCTAACAGAG

CTATTGTTTACCTATTTATTGGATACGTCCCTCTTAATCTCAAGGCCATT

CAAACTCTTGATTATATATTGCTCCTTAACTGTAAGAAA.

In some embodiments, the at least one non-human cell adaptation mutation occurs at one or more nucleic acid positions within the 5' UTR of CA16. In some embodiments, the mutation may occur at one or more or two nucleic acid positions selected from 6 and 33 of SEQ ID NO: 9, or at positions corresponding to positions 6 or 33 of SEQ ID NO: 9 when the 5' UTR of CA16 is aligned to SEQ ID NO: 9 using a pairwise alignment algorithm. In some embodiments, the mutation occurs at both of positions 6 and 33 of SEQ ID NO: 9, or at positions corresponding to positions 6 and 33 of SEQ ID NO: 9 when the 5' UTR of CA16 is aligned to SEQ ID NO: 9 using a pairwise alignment algorithm. In some embodiments, the mutation at position 6 is a guanine to adenine substitution. In some embodiments, the mutation at position 33 is a guanine to cytosine substitution.

In the above embodiments of the present disclosure, an exemplary pairwise alignment algorithm is the Needleman-Wunsch global alignment algorithm, using default parameters (e.g. with Gap opening penalty=10.0, and with Gap extension penalty=0.5, using the EBLOSUM62 scoring matrix). This algorithm is conveniently implemented in the needle tool in the EMBOSS package.

In some embodiments, antigens of the present disclosure from at least one virus that causes hand, foot and mouth disease may be used in any of the vaccines and immunogenic compositions of the present disclosure. For example, the antigens of the present disclosure may be useful for treating or preventing hand, foot, and mouth disease in a subject in need thereof and/or inducing an immune response, such as a protective immune response, against hand, foot, and mouth disease in a subject in need thereof.

Production of Vaccines and Immunogenic Compositions

Other aspects of the present disclosure relate to hand, foot, and mouth vaccines and immunogenic compositions containing one or more antigens of the present disclosure from at least one virus that causes hand, foot and mouth disease. Such vaccines and immunogenic compositions may be useful, for example, for treating or preventing hand, foot, and mouth disease in a subject in need thereof and/or inducing an immune response, such as a protective immune response, against hand, foot, and mouth disease in a subject in need thereof. Vaccines and/or immunogenic compositions of the present disclosure may include, without limitation, purified viruses, inactivated viruses, attenuated viruses, recombinant viruses, purified and/or recombinant viral proteins for subunit vaccines. Vaccines and/or immunogenic compositions of the present disclosure may further include a purified antigen vaccine or immunogenic composition, a subunit vaccine or immunogenic composition, an inactivated whole virus vaccine or immunogenic composition, or an attenuated virus vaccine or immunogenic composition.

Production of vaccines and/or immunogenic compositions of the present disclosure includes growth of at least one virus that causes hand, foot, and mouth disease, with antigens being prepared from the grown virus. Growth in cell culture is a method for preparing vaccines and/or immunogenic compositions of the present disclosure. Cells for viral growth may be cultured in suspension or in adherent conditions.

Cell lines suitable for growth of the at least one virus of the present disclosure are preferably of mammalian origin, and include but are not limited to: VERO cells (from monkey kidneys), horse, cow (e.g. MDBK cells), sheep, dog (e.g. MDCK cells from dog kidneys, ATCC CCL34 MDCK (NBL2) or MDCK 33016, deposit number DSM ACC 2219 as described in WO97/37001), cat, and rodent (e.g. hamster cells such as BHK21-F, HKCC cells, or Chinese hamster ovary cells (CHO cells)), and may be obtained from a wide variety of developmental stages, including for example, adult, neonatal, fetal, and embryo. In certain embodiments, the cells are immortalized (e.g. PERC.6 cells, as described in WO01/38362 and WO02/40665, and as deposited under ECACC deposit number 96022940). In preferred embodiments, mammalian cells are utilized, and may be selected from and/or derived from one or more of the following non-limiting cell types: fibroblast cells (e.g. dermal, lung), endothelial cells (e.g. aortic, coronary, pulmonary, vascular, dermal microvascular, umbilical), hepatocytes, keratinocytes, immune cells (e.g. T cell, B cell, macrophage, NK, dendritic), mammary cells (e.g. epithelial), smooth muscle cells (e.g. vascular, aortic, coronary, arterial, uterine, bronchial, cervical, retinal pericytes), melanocytes, neural cells (e.g. astrocytes), prostate cells (e.g. epithelial, smooth muscle), renal cells (e.g. epithelial, mesangial, proximal tubule), skeletal cells (e.g. chondrocyte, osteoclast, osteoblast), muscle cells (e.g. myoblast, skeletal, smooth, bronchial), liver cells, retinoblasts, and stromal cells. WO97/37000 and WO97/37001 describe production of animal cells and cell lines that capable of growth in suspension and in serum free media and are useful in the production and replication of viruses.

Culture conditions for the above cell types are known and described in a variety of publications, or alternatively culture medium, supplements, and conditions may be purchased commercially, such as for example, as described in the catalog and additional literature of Cambrex Bioproducts (East Rutherford, N.J.).

In certain embodiments, the cells used in the methods described herein are cultured in serum free and/or protein free media. A medium is referred to as a serum-free medium in the context of the present disclosure in which there are no additives from serum of human or animal origin. Protein-free is understood to mean cultures in which multiplication of the cells occurs with exclusion of proteins, growth factors, other protein additives and non-serum proteins, but can optionally include proteins such as trypsin or other proteases that may be necessary for viral growth. The cells growing in such cultures naturally contain proteins themselves.

Known serum-free media include Iscove's medium, Ultra-CHO medium (BioWhittaker) or EX-CELL (JRH Bioscience). Ordinary serum-containing media include Eagle's Basal Medium (BME) or Minimum Essential Medium (MEM) (Eagle, Science, 130, 432 (1959)) or Dulbecco's Modified Eagle Medium (DMEM or EDM), which are ordinarily used with up to 10% fetal calf serum or similar additives. Optionally, Minimum Essential Medium (MEM) (Eagle, Science, 130, 432 (1959)) or Dulbecco's Modified Eagle Medium (DMEM or EDM) may be used without any serum containing supplement. Protein-free media like PF-CHO (JHR Bioscience), chemically-defined media like ProCHO 4CDM (BioWhittaker) or SMIF 7 (Gibco/BRL Life Technologies) and mitogenic peptides like Primactone, Pepticase or HyPep™ (all from Quest International) or lactalbumin hydrolyzate (Gibco and other manufacturers) are also adequately known in the prior art. The media additives based on plant hydrolyzates have the special advantage that contamination with viruses, mycoplasma or unknown infectious agents can be ruled out.

Cell culture conditions (temperature, cell density, pH value, etc.) are variable over a very wide range owing to the suitability of the cell line employed according to the present disclosure and can be adapted to the requirements of particular viral strains.

The method for propagating virus in cultured cells generally includes the steps of inoculating the cultured cells with the strain to be cultured, cultivating the infected cells for a desired time period for virus propagation, such as for example as determined by virus titer or antigen expression (e.g. between 24 and 168 hours after inoculation) and collecting the propagated virus. The cultured cells are inoculated with a virus (measured by PFU or TCID50) to cell ratio of 1:500 to 1:1, preferably 1:100 to 1:5, more preferably 1:50 to 1:10. The virus is added to a suspension of the cells or is applied to a monolayer of the cells, and the virus is absorbed on the cells for at least 60 minutes but usually less than 300 minutes, preferably between 90 and 240 minutes at 25° C. to 40° C., preferably 28° C. to 37° C. The infected cell culture (e.g. monolayers) may be removed either by freeze-thawing or by enzymatic action to increase the viral content of the harvested culture supernatants. The harvested fluids are then either inactivated or stored frozen. Cultured cells may be infected at a multiplicity of infection ("m.o.i.") of about 0.0001 to 10, preferably 0.002 to 5, more preferably to 0.001 to 2. Still more preferably, the cells are infected at an m.o.i of about 0.01. Infected cells may be harvested from 30 to 60 hours post infection, or 4 to 10 days post infection. In certain embodiments, the cells are harvested 34 to 48 hours post infection. In certain preferred embodiments, the cells are harvested 4 to 7 hours post infection. More preferably, the cells are harvested 4 to 5 days post infection. In some embodiments, proteases (e.g., trypsin) may be added during cell culture to allow viral release, and the proteases may be added at any suitable stage during the culture. Alternatively, in certain embodiments, the supernatant of infected cell cultures may be harvested and the virus may isolated or otherwise purified from the supernatant.

The viral inoculum and the viral culture are preferably free from (i.e. will have been tested for and given a negative result for contamination by) herpes simplex virus, respiratory syncytial virus, parainfluenza virus 3, SARS coronavirus, adenovirus, rhinovirus, reoviruses, polyomaviruses, bimaviruses, circoviruses, and/or parvoviruses [WO2006/027698].

Where virus has been grown on a cell line then it is standard practice to minimize the amount of residual cell line DNA in the final vaccine, in order to minimize any oncogenic activity of the DNA. Contaminating DNA can be removed during vaccine preparation using standard purification procedures e.g. chromatography, etc. Removal of residual host cell DNA can be enhanced by nuclease treatment e.g. by using a DNase. A convenient method for reducing host cell DNA contamination is disclosed in references [Lundblad (2001) Biotechnology and Applied Biochemistry 34:195-197, *Guidance for Industry: Bioanalytical Method Validation*. U.S. Department of Health and Human Services Food and Drug Administration Center for Drug Evaluation and Research (CDER) Center for Veterinary Medicine (CVM). May 2001.] involving a two-step treatment, first using a DNase (e.g. Benzonase), which may be used during viral growth, and then a cationic detergent (e.g. CTAB), which may be used during virion disruption. Removal by β-propiolactone treatment can also be used.

Production of Antigens

Antigens of the present disclosure for use in vaccines and/or immunogenic compositions including, without limitation, purified viruses, inactivated viruses, attenuated viruses, recombinant viruses, or purified and/or recombinant viral proteins for subunit vaccines to treat or prevent hand, foot, and mouth disease and/or induce an immune response, such as a protective immune response, against hand, foot, and mouth disease, may be produced and/or purified or otherwise isolated by any suitable method known in the art. Antigens of the present disclosure may include, without limitation, whole virus, attenuated virus, inactivated virus, proteins, polypeptides (including active proteins and individual polypeptide epitopes within proteins), glycopolypeptides, lipopolypeptides, peptides, polysaccharides, polysaccharide conjugates, peptide and non-peptide mimics of polysaccharides and other molecules, small molecules, lipids, glycolipids, and carbohydrates produced, derived, purified, and/or otherwise isolated from at least one virus that causes hand, foot, and mouth disease. For example, suitable antigens may include, without limitation, structural polypeptides such as VP1, VP2, VP3, and VP4, and non-structural polypeptides, such as 2A, 2B, 2C, 3A, 3B, 3C, and 3D from viruses such as EV71, CA6, and CA16.

Antigen of the present disclosure may be synthesized chemically or enzymatically, produced recombinantly, isolated from a natural source, or a combination of the foregoing. In certain embodiments, antigens of the present disclosure are produced, purified, isolated, and/or derived from at least one virus of the present disclosure that causes hand, foot, and mouth disease, such as EV71, CA6, and CA16. Antigens of the present disclosure may be purified, partially purified, or a crude extract. In some embodiments, antigens of the present disclosure are viruses, such as inactivated viruses, produced as described in the above section entitled "Production of Vaccines and Immunogenic Compositions."

In certain embodiments, one or more antigens of the present disclosure may be produced by culturing a non-human cell. Cell lines suitable for production of the one or more antigens of the present disclosure are preferably of mammalian origin, and include but are not limited to: VERO cells (from monkey kidneys), horse, cow (e.g. MDBK cells), sheep, dog (e.g. MDCK cells from dog kidneys, ATCC CCL34 MDCK (NBL2) or MDCK 33016, deposit number DSM ACC 2219 as described in WO97/37001), cat, and rodent (e.g. hamster cells such as BHK21-F, HKCC cells, or Chinese hamster ovary cells (CHO cells)), and may be obtained from a wide variety of developmental stages, including for example, adult, neonatal, fetal, and embryo. In certain embodiments, the cells are immortalized (e.g. PERC.6 cells, as described in WO01/38362 and WO02/40665, and as deposited under ECACC deposit number 96022940). In preferred embodiments, mammalian cells are utilized, and may be selected from and/or derived from one or more of the following non-limiting cell types: fibroblast cells (e.g. dermal, lung), endothelial cells (e.g. aortic, coronary, pulmonary, vascular, dermal microvascular, umbilical), hepatocytes, keratinocytes, immune cells (e.g. T cell, B cell, macrophage, NK, dendritic), mammary cells (e.g. epithelial), smooth muscle cells (e.g. vascular, aortic, coronary, arterial, uterine, bronchial, cervical, retinal pericytes), melanocytes, neural cells (e.g. astrocytes), prostate cells (e.g. epithelial, smooth muscle), renal cells (e.g. epithelial, mesangial, proximal tubule), skeletal cells (e.g. chondrocyte, osteoclast, osteoblast), muscle cells (e.g. myoblast, skeletal, smooth, bronchial), liver cells, retinoblasts, and stromal cells. WO97/37000 and WO97/37001 describe production of animal cells and cell lines that capable of growth in suspension and in serum free media and are useful in the production of viral antigens. In certain embodiments, the non-human cell is cultured in serum-free media.

Polypeptide antigens may be isolated from natural sources using standard methods of protein purification known in the art, including, but not limited to, liquid chromatography (e.g., high performance liquid chromatography, fast protein liquid chromatography, etc.), size exclusion chromatography, gel electrophoresis (including one-dimensional gel electrophoresis, two-dimensional gel electrophoresis), affinity chromatography, or other purification technique. In many embodiments, the antigen is a purified antigen, e.g., from about 50% to about 75% pure, from about 75% to about 85% pure, from about 85% to about 90% pure, from about 90% to about 95% pure, from about 95% to about 98% pure, from about 98% to about 99% pure, or greater than 99% pure.

One may employ solid phase peptide synthesis techniques, where such techniques are known to those of skill in the art. See Jones, The Chemical Synthesis of Peptides (Clarendon Press, Oxford) (1994). Generally, in such methods a peptide is produced through the sequential additional of activated monomeric units to a solid phase bound growing peptide chain.

Well-established recombinant DNA techniques can be employed for production of polypeptides, where, e.g., an expression construct comprising a nucleotide sequence encoding a polypeptide is introduced into an appropriate host cell (e.g., a eukaryotic host cell grown as a unicellular entity in in vitro cell culture, e.g., a yeast cell, an insect cell, a mammalian cell, etc.) or a prokaryotic cell (e.g., grown in in vitro cell culture), generating a genetically modified host cell; under appropriate culture conditions, the protein is produced by the genetically modified host cell.

Besides killed and attenuated virus immunogenic compositions, one can use a subunit immunogenic composition or other type of immunogenic composition which presents to the animal the antigenic components of hand, foot, and mouth disease virus. The antigenic component may be a protein, glycoprotein, lipid-conjugated protein or glycoprotein, a modified lipid moiety, or other viral component which, when injected into a human, stimulates an immune response in the human such that the human develops protective immunity against hand, foot, and mouth disease. For a subunit immunogenic composition, the virus can be cultured on mammalian cells, as described above. The cell culture can be homogenized and an immunogenic composition can be isolated by passage of the cell culture homogenate over the appropriate column or through the appropriate pore size filter or via centrifugation of the cell culture homogenate.

If the antigenic component is a protein, then one can isolate the nucleic acid which encodes that protein and generate an immunogenic composition that contains that isolated nucleic acid. The nucleic acid encoding the antigenic component can be placed on a plasmid downstream of a signal sequence of a eukaryotic promoter. That plasmid can contain one or more selectable markers and be transfected into an attenuated prokaryotic organism, such as *Salmonella* spp., *Shigella* spp., or other suitable bacteria. The bacteria can then be administered to the human so that the human can generate a protective immune response to the antigenic component. Alternatively, the nucleic acid encoding the antigenic component can be placed downstream of a prokaryotic promoter, have one or more selectable markers, and be transfected into an attenuated prokaryotic organism such as *Salmonella* spp., *Shigella* spp., or other suitable bacteria. The bacteria can then be administered to the eukaryotic subject for which immune response to the antigen of interest is desired. See, for example, U.S. Pat. No. 6,500,419 to Hone, et al.

For a subunit immunogenic composition, the nucleic acid encoding a proteinaceous antigenic component of a hand, foot, and mouth disease virus can be cloned into a plasmid such as those described in International Patent Application Publication Number WO 00/32047 (Galen) and International Patent Application Publication Number WO 02/083890 (Galen). Then the plasmid can be transfected into bacteria and the bacteria can produce the desired antigenic protein. One can isolate and purify the desired antigenic protein by a variety of methods described in both patent applications.

Virus Inactivation

Certain aspects of the present disclosure relate to hand, foot, and mouth vaccines and immunogenic compositions containing one or more antigens from at least one virus that causes hand, foot and mouth disease. Vaccines and/or immunogenic compositions of the present disclosure may include a purified virus, a whole virus, a recombinant virus, a live attenuated whole virus or, preferably, an inactivated whole virus, or subunits, polypeptides, and/or antigens from an inactivated virus. As such, certain embodiments of the present disclosure relate to hand, foot, and mouth vaccines and/or immunogenic compositions containing one or more antigens from at least one inactivated virus that causes hand, foot and mouth disease. Methods of inactivating or killing viruses to destroy their ability to infect mammalian cells are known in the art. Such methods include both chemical and physical means. Suitable means for inactivating a virus include, without limitation, treatment with an effective amount of one or more agents selected from detergents, formalin (also referred to herein as "formaldehyde"), beta-propiolactone (BPL), binary ethylamine (BEI), acetyl ethyleneimine, heat, electromagnetic radiation, x-ray radiation, gamma radiation, ultraviolet radiation (UV radiation), UV-A radiation, UV-B radiation, UV-C radiation, methylene blue, psoralen, carboxyfullerene (C60) and any combination of any thereof.

In certain embodiments of the present disclosure the at least one virus is chemically inactivated. Agents for chemical inactivation and methods of chemical inactivation are well-known in the art and described herein. In some embodiments, the at least one virus is chemically inactivated with one or more of BPL, formalin, or BEI. In certain embodiments where the at least one virus is chemically inactivated with BPL, the virus may contain one or more modifications. In some embodiments, the one or more modifications may include a modified nucleic acid. In some embodiments, the modified nucleic acid is an alkylated nucleic acid. In other embodiments, the one or more modifications may include a modified polypeptide. In some embodiments, the modified polypeptide contains a modified amino acid residue including one or more of a modified cysteine, methionine, histidine, aspartic acid, glutamic acid, tyrosine, lysine, serine, and threonine. In certain embodiments where the at least one virus is chemically inactivated with formalin, the virus may contain one or more modifications. In some embodiments, the one or more modifications may include a modified polypeptide. In some embodiments, the one or more modifications may include a cross-linked polypeptide. In some embodiments where the at least one virus is chemically inactivated with formalin, the vaccine or immunogenic composition further includes formalin. In certain embodiments where the at least one virus is chemically inactivated with BEI, the virus may contain one or more modifications. In some embodiments, the one or more modifications may include a modified nucleic acid. In some embodiments, the modified nucleic acid is an alkylated nucleic acid.

In some embodiments where the at least one virus is chemically inactivated with BEI or BPL, any residual unreacted BEI or BPL may be neutralized (i.e., hydrolyzed) with sodium thiosulfate. Generally, sodium thiosulfate is added in excess. In some embodiments, sodium thiosulfate may be added at a concentration that ranges from about 25 mM to about 100 mM, from, about 25 mM to about 75 mM, or from about 25 mM to about 50 mM. In certain embodiments, sodium thiosulfate may be added at a concentration of about 25 mM, about 26 mM, about 27 mM, about 28 mM, about 29 mM, about 30 mM, about 31 mM, about 32 mM, about 33 mM, about 34 mM, about 35 mM, about 36 mM, about 37 mM, about 38 mM, about 39 mM, or about 40 mM at a ratio of 1 part concentrated sodium thiosulfate to 20 parts of BEI. In some embodiments, the solutions may be mixed using a mixer, such as an in-line static mixer, and subsequently filtered (e.g., clarified). Generally, the pumping of the two solutions through the mixer results in complete mixing and neutralization of BEI by the sodium thiosulfate.

Certain embodiments of the present disclosure relate to a method for inactivating a hand, foot, and mouth virus preparation. In some embodiments, the method involves (a) isolating the hand, foot, and mouth virus preparation from one or more non-human cells that are used to produce the virus preparation and (b) treating the virus preparation with an effective amount of BEI. In certain embodiments, treating with an effective amount of BEI includes, without limitation, treating with BEI in an amount that ranges from about 0.25% v/v to about 3.0% v/v. In certain embodiments, the isolated and treated virus is selected from one or more of EV71, CA6, and CA16. In certain embodiments of the method, the virus preparation is treated with BEI at a temperature that ranges from about 25° C. to about 42° C. In certain embodiments of the method, the virus preparation is treated with BEI for a period of time that ranges from about 1 hour to about 10 hours. In certain embodiments, the method further involves inactivating (i.e., hydrolyzing) unreacted BEI with an effective amount of sodium thiosulfate. In some embodiments, the effective amount of sodium thiosulfate ranges from about 25 mM to about 100 mM, from, about 25 mM to about 75 mM, or from about 25 mM to about 50 mM.

In some embodiments, the method involves (a) isolating the hand, foot, and mouth virus preparation from one or more non-human cells that are used to produce the virus preparation; (b) treating the virus preparation with an effective amount of beta-propiolactone (BPL); and, optionally, (c) treating the virus preparation with an effective amount of formalin concurrently with or after step (b). Alternatively, in some embodiments, the method involves (a) isolating the hand, foot, and mouth virus preparation from one or more non-human cells that are used to produce the virus preparation; (b) treating the virus preparation with an effective amount of beta-propiolactone (BPL) for a first period of time; and (c) treating the virus preparation with an effective amount of BPL for a second period of time to completely inactivate the virus preparation. In some embodiments the first and/or second period of time ranges from about 12 hours to about 36 hours. In certain embodiments the first and/or second period of time is about 24 hours. In certain embodiments, treating with an effective amount of BPL includes, without limitation, treating with BPL in an amount that ranges from about 0.05% v/v to about 3.0% v/v, from 0.1% v/v to about 2% v/v, or about 0.1% v/v to about 1% v/v. In certain embodiments, treating with an effective amount of BPL includes, without limitation, treating with 0.05% v/v, 0.06% v/v, 0.07% v/v, 0.08% v/v, 0.09% v/v, 0.1% v/v, 0.2% v/v, 0.3% v/v, 0.4% v/v, 0.5% v/v, 0.6% v/v, 0.7% v/v, 0.8% v/v, 0.9% v/v, or 1% v/v BPL. In certain embodiments, the isolated and treated virus is selected from one or more of EV71, CA6, and CA16. In certain embodiments of the method, the virus preparation is treated with BEI at a temperature that ranges from about 2° C. to about 8° C. In certain embodiments, the method involves heating the virus preparation at a temperature of 37° C. for a period of time sufficient to hydrolyze the BPL. In certain embodiments, the period of time ranges from about 1 hour to about 6 hours. Alternatively, in some embodiments, the method further involves inactivating (i.e., hydrolyzing) unreacted BPL with an effective amount of sodium thiosulfate. In some embodiments, the effective amount of sodium thiosulfate ranges from about 25 mM to about 100 mM, from, about 25 mM to about 75 mM, or from about 25 mM to about 50 mM.

In some embodiments, the method involves (a) isolating the hand, foot, and mouth virus preparation from one or more non-human cells that are used to produce the virus preparation; (b) treating the virus preparation with an effective amount of formalin; and (c) purifying the virus preparation from the formalin. In certain embodiments, treating with an effective amount of formalin includes, without limitation, treating with formalin in an amount that ranges from about 0.05% v/v to about 3.0% v/v, from 0.1% v/v to about 2% v/v, or about 0.1% v/v to about 1% v/v. In certain embodiments, the isolated and formalin treated virus is selected from one or more of EV71, CA6, and CA16. In certain embodiments, the virus preparation is purified to a high degree from the formalin in an amount that is about 70%, about 75%, about 80%, about 85%, 0%, a 90%, about 95%, about 96%, about 97%, about 98%, about 99%, or more.

The vaccines and/or immunogenic compositions of the present disclosure containing one or more antigens from at least one inactivated virus that causes hand, foot and mouth disease, may be useful for treating or preventing hand, foot, and mouth disease in a subject in need thereof and/or inducing an immune response, such as a protective immune response, against hand, foot, and mouth disease in a subject in need thereof.

Formulations of Vaccines and/or Immunogenic Compositions

Further aspects of the present disclosure relate to formulations of vaccines and/or immunogenic compositions of the present disclosure containing one or more antigens from at least one virus that causes hand, foot and mouth disease. Such vaccines and/or immunogenic compositions of the present disclosure containing one or more antigens from at least one virus that causes hand, foot and mouth disease, may be useful for treating or preventing hand, foot, and mouth disease in a subject in need thereof and/or inducing an immune response, such as a protective immune response, against hand, foot, and mouth disease in a subject in need thereof.

Typically, vaccines and/or immunogenic compositions of the present disclosure are prepared as injectables either as liquid solutions or suspensions; solid forms suitable for solution in, or suspension in, liquid prior to injection may also be prepared. Such preparations may also be emulsified or produced as a dry powder. The active immunogenic ingredient is often mixed with excipients which are pharmaceutically acceptable and compatible with the active ingredient. Suitable excipients are, for example, water, saline, dextrose, sucrose, glycerol, ethanol, or the like, and combinations thereof. In addition, if desired, the vaccine or immunogenic composition may contain auxiliary substances such as wetting or emulsifying agents, pH buffering agents, or adjuvants which enhance the effectiveness of the vaccine or immunogenic composition.

Vaccines or immunogenic compositions may be conventionally administered parenterally, by injection, for example, either subcutaneously, transcutaneously, intradermally, subdermally or intramuscularly. Additional formulations which are suitable for other modes of administration include suppositories and, in some cases, oral, peroral, intranasal, buccal, sublingual, intraperitoneal, intravaginal, anal and intracranial formulations. For suppositories, traditional binders and carriers may include, for example, polyalkalene glycols or triglycerides; such suppositories may be formed from mixtures containing the active ingredient in the range of 0.5% to 10%, or even 1-2%. In certain embodiments, a low melting wax, such as a mixture of fatty acid glycerides or cocoa butter is first melted and the hand, foot, and mouth disease vaccine or immunogenic composition antigens described herein are dispersed homogeneously, for example, by stirring. The molten homogeneous mixture is then poured into conveniently sized molds, allowed to cool, and to solidify.

Formulations suitable for intranasal delivery include liquids (e.g., aqueous solution for administration as an aerosol or nasal drops) and dry powders (e.g. for rapid deposition within the nasal passage). Formulations include such normally employed excipients as, for example, pharmaceutical grades of mannitol, lactose, sucrose, trehalose, xylitol, and chitosan. Mucosadhesive agents such as chitosan can be used in either liquid or powder formulations to delay mucociliary clearance of intranasally-administered formulations. Sugars such as mannitol and sucrose can be used as stability agents in liquid formulations and as stability, bulking, or powder flow and size agents in dry powder formulations. In addition, adjuvants such as monophosphoryl lipid A (MLA), or derivatives thereof, or CpG oligonucleotides can be used in both liquid and dry powder formulations as an immunostimulatory adjuvant.

Formulations suitable for oral delivery include liquids, solids, semi-solids, gels, tablets, capsules, lozenges, and the like. Formulations suitable for oral delivery include tablets, lozenges, capsules, gels, liquids, food products, beverages, nutraceuticals, and the like. Formulations include such normally employed excipients as, for example, pharmaceutical grades of mannitol, lactose, starch, magnesium stearate, sodium saccharine, cellulose, magnesium carbonate, and the like. Other hand, foot, and mouth disease vaccine and immunogenic compositions may take the form of solutions, suspensions, pills, sustained release formulations or powders and contain 10-95% of active ingredient, or 25-70%. For oral formulations, cholera toxin is an interesting formulation partner (and also a possible conjugation partner).

The hand, foot, and mouth disease vaccines and/or immunogenic compositions when formulated for vaginal administration may be in the form of pessaries, tampons, creams, gels, pastes, foams or sprays. Any of the foregoing formulations may contain agents in addition to hand, foot, and mouth disease vaccine and immunogenic composition antigens, such as carriers, known in the art to be appropriate.

In some embodiments, the hand, foot, and mouth disease vaccines and/or immunogenic compositions of the present disclosure may be formulated for systemic or localized delivery. Such formulations are well known in the art. Parenteral vehicles include sodium chloride solution, Ringer's dextrose, dextrose and sodium chloride, lactated Ringer's or fixed oils. Intravenous vehicles include fluid and nutrient replenishers, electrolyte replenishers (such as those based on Ringer's dextrose), and the like. Systemic and localized routes of administration include, e.g., intradermal, topical application, intravenous, intramuscular, etc.

The vaccines and/or immunogenic compositions of the present disclosure may be administered in a manner compatible with the dosage formulation, and in such amount as will be therapeutically effective and immunogenic. The quantity to be administered depends on the subject to be treated, including, e.g., the capacity of the individual's immune system to mount an immune response, and the degree of protection desired. Suitable dosage ranges are of the order of several hundred micrograms active ingredient per vaccination with an exemplary range from about 0.1 μg to 10 μg (even though higher amounts in the 1-10 mg range are contemplated), such as in the range from about 0.1 μg to 5 μg, or even in the range from 0.6 μg to 3 μg or in the range from about 1 μg to 3 μg, or even in the range of 0.1 μg to 1 μg. In certain embodiments, the dosage can be about 0.1 μg, about 0.2 μg, about 0.3 μg, about 0.4 μg, about 0.5 μg, about 0.6 μg, about 0.7 μg, about 0.8 μg, about 0.9 μg, about 1 μg, about 1.1 μg, about 1.2 μg, about 1.3 μg, about 1.4 μg, about 1.5 μg, about 1.6 μg, about 1.7 μg, about 1.8 μg, about 1.9 μg, about 2 μg, about 2.1 μg, about 2.2 μg, about 2.3 μg, about 2.4 μg, about 2.5 μg, about 2.6 μg, about 2.7 μg, about 2.8 μg, about 2.9 μg, or about 3 μg per dose. In certain embodiments, vaccines and/or immunogenic compositions of the present disclosure may be administered in an amount of 1 μg per dose. In vaccines and/or immunogenic compositions of the present disclosure that are multivalent, for example divalent or trivalent vaccines and/or immunogenic compositions comprising antigens from two or more of EV71, CA6, and CA16, the dosage of each component is administered at an equivalent dosage ratio (i.e., 1:1 for divalent and 1:1:1 for trivalent vaccines and/or immunogenic compositions).

Suitable regimens for initial administration and booster shots are also variable but are typified by an initial administration followed by subsequent inoculations or other administrations.

The manner of application may be varied widely. Any of the conventional methods for administration of a vaccine or immunogenic composition are applicable. These include oral application on a solid physiologically acceptable base or in a physiologically acceptable dispersion, parenterally, by injection or the like. The dosage of the vaccine or immunogenic composition will depend on the route of administration and will vary according to the age of the person to be vaccinated and the formulation of the antigen. The vaccine or immunogenic composition can have a unit dosage volume of more than 0.5 mL, of 0.5 mL or of less than 0.5 mL, as described herein. For instance, it can be administered at a volume of 0.25 mL.

Delivery agents that improve mucoadhesion can also be used to improve delivery and immunogenicity especially for intranasal, oral or lung based delivery formulations. One such compound, chitosan, the N-deacetylated form of chitin, is used in many pharmaceutical formulations. It is an attractive mucoadhesive agent for intranasal vaccine delivery due to its ability to delay mucociliary clearance and allow more time for mucosal antigen uptake and processing. In addition, it can transiently open tight junctions which may enhance transepithelial transport of antigen to the NALT. In a recent human trial, a trivalent inactivated influenza vaccine administered intranasally with chitosan but without any additional adjuvant yielded seroconversion and HI titers that were only marginally lower than those obtained following intramuscular inoculation.

Chitosan can also be formulated with adjuvants that function well intranasally such as the genetically detoxified *E. coli* heat-labile enterotoxin mutant LTK63. This adds an immunostimulatory effect on top of the delivery and adhesion benefits imparted by chitosan resulting in enhanced mucosal and systemic responses.

Finally, it should be noted that chitosan formulations can also be prepared in a dry powder format that has been shown to improve vaccine stability and result in a further delay in mucociliary clearance over liquid formulations. This was seen in a recent human clinical trial involving an intranasal dry powder diphtheria toxoid vaccine formulated with chitosan in which the intranasal route was as effective as the traditional intramuscular route with the added benefit of secretory IgA responses. The vaccine was also very well tolerated. Intranasal dry powdered vaccines for anthrax containing chitosan and MLA, or derivatives thereof, induce stronger responses in rabbits than intramuscular inoculation and are also protective against aerosol spore challenge.

Intranasal vaccines represent an exemplary formulation as they can affect the upper and lower respiratory tracts in contrast to parenterally administered vaccines which are better at affecting the lower respiratory tract. This can be beneficial for inducing tolerance to allergen-based vaccines and inducing immunity for pathogen-based vaccines.

In addition to providing protection in both the upper and lower respiratory tracts, intranasal vaccines avoid the complications of needle inoculations and provide a means of inducing both mucosal and systemic humoral and cellular responses via interaction of particulate and/or soluble antigens with nasopharyngeal-associated lymphoid tissues (NALT).

Vaccines and/or immunogenic compositions of the present disclosure are pharmaceutically acceptable. They may include components in addition to the antigen and adjuvant e.g. they will typically include one or more pharmaceutical carrier(s) and/or excipient(s). A thorough discussion of such components is available in Gennaro (2000) Remington: The Science and Practice of Pharmacy. 20th edition, ISBN: 0683306472.

To control tonicity, it is preferred to include a physiological salt, such as a sodium salt. Sodium chloride (NaCl) is preferred, which may be present at between 1 and 20 mg/ml. Other salts that may be present include potassium chloride, potassium dihydrogen phosphate, disodium phosphate dehydrate, magnesium chloride, calcium chloride, etc.

Vaccines and/or immunogenic compositions of the present disclosure may include one or more buffers. Typical buffers include: a phosphate buffer; a Tris buffer; a borate buffer; a succinate buffer; a histidine buffer (particularly with an aluminum hydroxide adjuvant); or a citrate buffer. Buffers will typically be included in the 5-20 mM range.

The pH of a vaccine or immunogenic composition will generally be between 5.0 and 8.1, and more typically between 6.0 and 8.0 e.g. 6.5 and 7.5, or between 7.0 and 7.8. A manufacturing process of the present disclosure may therefore include a step of adjusting the pH of the bulk vaccine prior to packaging.

The vaccine or immunogenic composition is preferably sterile. It is preferably non pyrogenic e.g. containing <1 EU (endotoxin unit, a standard measure) per dose, and preferably <0.1 EU per dose. It is preferably gluten free.

In certain embodiments, the vaccines and/or immunogenic compositions of the present disclosure may include a detergent in an effective concentration. In some embodiments, an effective amount of detergent may include without limitation, about 0.00005% v/v to about 5% v/v or about 0.0001% v/v to about 1% v/v. In certain embodiments, an effective amount of detergent is about 0.001% v/v, about 0.002% v/v, about 0.003% v/v, about 0.004% v/v, about 0.005% v/v, about 0.006% v/v, about 0.007% v/v, about 0.008% v/v, about 0.009% v/v, or about 0.01% v/v. Without wishing to be bound by theory, detergents help maintain the vaccines and/or immunogenic compositions of the present disclosure in solution and helps to prevent the vaccines and/or immunogenic compositions from aggregating.

Suitable detergents include, for example, polyoxyethylene sorbitan ester surfactant (known as 'Tweens'), octoxynol (such as octoxynol-9 (Triton×100) or t octylphenoxypolyethoxyethanol), cetyl trimethyl ammonium bromide ('CTAB'), and sodium deoxycholate, particularly for a split or surface antigen vaccine. The detergent may be present only at trace amounts. Other residual components in trace amounts could be antibiotics (e.g. neomycin, kanamycin, polymyxin B). In some embodiments, the detergent contains polysorbate. In some embodiments, the effective concentration of detergent includes ranges from about 0.00005% v/v to about 5% v/v.

The vaccines and/or immunogenic compositions are preferably stored at between 2° C. and 8° C. They should not be frozen. They should ideally be kept out of direct light. The antigen and emulsion will typically be in admixture, although they may initially be presented in the form of a kit of separate components for extemporaneous admixing. Vaccines and/or immunogenic compositions will generally be in aqueous form when administered to a subject.

Adjuvants

Other aspects of the present disclosure relate to hand, foot, and mouth vaccines and/or immunogenic compositions containing one or more antigens from at least one virus that causes hand, foot and mouth disease in combination with one or more adjuvants. Such adjuvanted vaccines and/or immunogenic compositions of the present disclosure may be useful for treating or preventing hand, foot, and mouth disease in a subject in need thereof and/or inducing an immune response, such as a protective immune response, against hand, foot, and mouth disease in a subject in need thereof.

Various methods of achieving an adjuvant effect for vaccines are known and may be used in conjunction with the hand, foot, and mouth vaccines and/or immunogenic compositions disclosed herein. General principles and methods are detailed in "The Theory and Practical Application of Adjuvants", 1995, Duncan E. S. Stewart-Tull (ed.), John Wiley & Sons Ltd, ISBN 0-471-95170-6, and also in "Vaccines: New Generation Immunological Adjuvants", 1995, Gregoriadis G et al. (eds.), Plenum Press, New York, ISBN 0-306-45283-9.

In some embodiments, a hand, foot, and mouth vaccine or immunogenic composition includes the antigens and an adjuvant. Antigens may be in a mixture with at least one adjuvant, at a weight-based ratio of from about 10:1 to about $10^{10}$:1 antigen:adjuvant, e.g., from about 10:1 to about 100:1, from about 100:1 to about $10^3$:1, from about $10^3$:1 to about $10^4$:1, from about $10^4$:1 to about $10^5$:1, from about $10^5$:1 to about $10^6$:1, from about $10^6$:1 to about $10^7$:1, from about $10^7$:1 to about $10^8$:1, from about $10^8$:1 to about $10^9$:1, or from about $10^9$:1 to about $10^{10}$:1 antigen:adjuvant. One of skill in the art can readily determine the appropriate ratio through information regarding the adjuvant and routine experimentation to determine optimal ratios.

Exemplary adjuvants may include, but are not limited to, aluminum salts, toll-like receptor (TLR) agonists, monophosphoryl lipid A (MLA), MLA derivatives, synthetic lipid A, lipid A mimetics or analogs, cytokines, saponins, muramyl dipeptide (MDP) derivatives, CpG oligos, lipopolysaccharide (LPS) of gram-negative bacteria, polyphosphazenes, emulsions, virosomes, cochleates, poly(lactide-co-glycolides) (PLG) microparticles, poloxamer particles, microparticles, liposomes, Complete Freund's Adjuvant (CFA), and Incomplete Freund's Adjuvant (IFA). In some embodiments, the adjuvant is MLA or derivatives thereof.

In some embodiments, the adjuvant is an aluminum salt. In some embodiments, the adjuvant includes at least one of alum, aluminum phosphate, aluminum hydroxide, potassium aluminum sulfate, and Alhydrogel 85. In some embodiments, aluminum salt adjuvants of the present disclosure have been found to increase adsorption of the antigens of the HFMD vaccines and/or immunogenic compositions of the present disclosure. Accordingly, in some embodiments, at least 75%, at least 80%, at least 85%, at least 90%, at least 91%, at least 92%, at least 93%, at least 94%, at least 95%, at least 96%, at least 97%, at least 98%, at least 99%, or 100% of the antigen is adsorbed to the aluminum salt adjuvant.

Certain embodiments of the present disclosure include a method for preparing an adjuvanted hand, foot, and mouth vaccine or immunogenic composition, which involves (a) mixing the vaccine or immunogenic composition with an aluminum salt adjuvant, with the vaccine or immunogenic composition including one or more antigens from at least one virus that causes hand, foot, and mouth disease and (b) incubating the mixture under suitable conditions for a period of time that ranges from about 16 hours to about 24 hours, with at least 75%, at least 80%, at least 85%, at least 90%, at least 91%, at least 92%, at least 93%, at least 94%, at least 95%, at least 96%, at least 97%, at least 98%, at least 99%, or 100% of the antigen adsorbed to the aluminum salt adjuvant. In certain embodiments of the method, the at least one virus that causes hand, foot, and mouth disease is selected from one or more of EV71, CA6, and CA16. In some embodiments of the method, the mixture is incubated at a temperature that ranges from about 2° C. to about 8° C. In some embodiments of the method, the mixture is incubated under constant mixing using any suitable mixer known in the art. In some embodiments of the method, the mixture is incubated at pH that ranges in value from about 6.5 to about 8, from about 6.8 to about 7 8, from about 6.9 to about 7.6, or from about 7 to about 7.5. In certain preferred embodiments, the mixture is incubated at a neutral pH. In some embodiments of the method, the aluminum salt adjuvant is selected from alum, aluminum phosphate, aluminum hydroxide, potassium aluminum sulfate, and Alhydrogel 85.

Monophosphoryl Lipid A (MLA), a non-toxic derivative of lipid A from *Salmonella*, is a potent TLR-4 agonist that has been developed as a vaccine adjuvant (Evans et al. 2003). In pre-clinical murine studies intranasal MLA has been shown to enhance secretory, as well as systemic, humoral responses (Baldridge et al. 2000; Yang et al. 2002). It has also been proven to be safe and effective as a vaccine adjuvant in clinical studies of greater than 120,000 patients (Baldrick et al., 2002; 2004). MLA stimulates the induction of innate immunity through the TLR-4 receptor and is thus capable of eliciting nonspecific immune responses against a wide range of infectious pathogens, including both gram negative and gram positive bacteria, viruses, and parasites (Baldrick et al. 2004; Persing et al. 2002). Inclusion of MLA in intranasal formulations should provide rapid induction of innate responses, eliciting nonspecific immune responses from viral challenge while enhancing the specific responses generated by the antigenic components of the vaccine.

Accordingly, in one embodiment, the present disclosure provides a composition comprising monophosphoryl lipid A (MLA), 3 De-O-acylated monophosphoryl lipid A (3D-MLA), or a derivative thereof as an enhancer of adaptive and innate immunity. Chemically 3D-MLA is a mixture of 3 De-O-acylated monophosphoryl lipid A with 4, 5 or 6 acylated chains. A preferred form of 3 De-O-acylated monophosphoryl lipid A is disclosed in European Patent 0 689 454 B1 (SmithKline Beecham Biologicals SA). In another embodiment, the present disclosure provides a composition comprising synthetic lipid A, lipid A mimetics or analogs, such as BioMira's PET Lipid A, or synthetic derivatives designed to function like TLR-4 agonists.

Additional exemplary adjuvants include, without limitation, polypeptide adjuvants that may be readily added to the antigens described herein by co-expression with the polypeptide components or fusion with the polypeptide components to produce chimeric polypeptides. Bacterial flagellin, the major protein constituent of flagella, is an adjuvant which has received increasing attention as an adjuvant protein because of its recognition by the innate immune system by the toll-like receptor TLR5 (65). Flagellin signaling through TLR5 has effects on both innate and adaptive immune functions by inducing DC maturation and migration as well as activation of macrophages, neutrophils, and intestinal epithelial cells resulting in production of proinflammatory mediators (66-72).

TLR5 recognizes a conserved structure within flagellin monomers that is unique to this protein and is required for flagellar function, precluding its mutation in response to immunological pressure (73). The receptor is sensitive to a 100 fM concentration but does not recognize intact filaments. Flagellar disassembly into monomers is required for binding and stimulation.

As an adjuvant, flagellin has potent activity for induction of protective responses for heterologous antigens administered either parenterally or intranasally and adjuvant effects for DNA vaccines have also been reported. A Th2 bias is observed when flagellin is employed which would be appropriate for a respiratory virus such as influenza but no evidence for IgE induction in mice or monkeys has been observed. In addition, no local or systemic inflammatory responses have been reported following intranasal or systemic administration in monkeys. The Th2 character of responses elicited following use of flagellin is somewhat surprising since flagellin signals through TLR5 in a MyD88-dependent manner and all other MyD88-dependent signals through TLRs have been shown to result in a Th1 bias. Importantly, pre-existing antibodies to flagellin have no appreciable effect on adjuvant efficacy making it attractive as a multi-use adjuvant.

A common theme in many recent intranasal vaccine trials is the use of adjuvants and/or delivery systems to improve vaccine efficacy. In one such study an influenza H3 vaccine containing a genetically detoxified *E. coli* heat-labile enterotoxin adjuvant (LT R192G) resulted in heterosubtypic protection against H5 challenge but only following intranasal delivery. Protection was based on the induction of cross neutralizing antibodies and demonstrated important implications for the intranasal route in development of new vaccines.

Cytokines, colony-stimulating factors (e.g., GM-CSF, CSF, and the like); tumor necrosis factor; interleukin-2, -7, -12, interferons and other like growth factors, may also be used as adjuvants as they may be readily included in the hand, foot, and mouth vaccines or immunogenic compositions by admixing or fusion with the polypeptide component.

In some embodiments, the hand, foot, and mouth vaccine and immunogenic compositions disclosed herein may include other adjuvants that act through a Toll-like receptor such as a nucleic acid TLR9 ligand comprising a 5'-TCG-3' sequence; an imidazoquinoline TLR7 ligand; a substituted guanine TLR7/8 ligand; other TLR7 ligands such as Loxoribine, 7-deazadeoxyguanosine, 7-thia-8-oxodeoxyguanosine, Imiquimod (R-837), and Resiquimod (R-848).

Certain adjuvants facilitate uptake of the vaccine molecules by APCs, such as dendritic cells, and activate these. Non-limiting examples are selected from the group consisting of an immune targeting adjuvant; an immune modulating adjuvant such as a toxin, a cytokine, and a mycobacterial derivative; an oil formulation; a polymer; a micelle forming adjuvant; a saponin; an immunostimulating complex matrix (ISCOM matrix); a particle; DDA; aluminum adjuvants; DNA adjuvants; MLA; and an encapsulating adjuvant.

Additional examples of adjuvants include agents such as aluminum salts such as hydroxide or phosphate (alum), commonly used as 0.05 to 0.1 percent solution in buffered saline (see, e.g., Nicklas (1992) Res. Immunol. 143:489-493), admixture with synthetic polymers of sugars (e.g. Carbopol®) used as 0.25 percent solution, aggregation of the protein in the vaccine by heat treatment with temperatures ranging between 70° to 101° C. for 30 second to 2 minute periods respectively and also aggregation by means of cross-linking agents are possible. Aggregation by reactivation with pepsin treated antibodies (Fab fragments) to albumin, mixture with bacterial cells such as C. parvum or endotoxins or lipopolysaccharide components of gram-negative bacteria, emulsion in physiologically acceptable oil vehicles such as mannide mono-oleate (Aracel A) or emulsion with 20 percent solution of a perfluorocarbon (Fluosol-DA) used as a block substitute may also be employed. Admixture with oils such as squalene and IFA may also be used.

DDA (dimethyldioctadecylammonium bromide) is an interesting candidate for an adjuvant, but also Freund's complete and incomplete adjuvants as well as quillaja saponins such as QuilA and QS21 are interesting. Further possibilities include poly[di(earboxylatophenoxy)phosphazene (PCPP) derivatives of lipopolysaccharides such as monophosphoryl lipid A (MLA), muramyl dipeptide (MDP) and threonyl muramyl dipeptide (tMDP). The lipopolysaccharide based adjuvants may also be used for producing a predominantly Th1-type response including, for example, a combination of monophosphoryl lipid A, such as 3-de-O-acylated monophosphoryl lipid A, together with an aluminum salt.

Liposome formulations are also known to confer adjuvant effects, and therefore liposome adjuvants may be used in conjunction with the hand, foot, and mouth disease vaccines and/or immunogenic compositions.

Immunostimulating complex matrix type (ISCOM® matrix) adjuvants may also be used with the hand, foot, and mouth disease vaccine antigens and immunogenic compositions, especially since it has been shown that this type of adjuvants are capable of up-regulating MHC Class II expression by APCs. An ISCOM matrix consists of (optionally fractionated) saponins (triterpenoids) from *Quillaja saponaria*, cholesterol, and phospholipid. When admixed with the immunogenic protein such as the hand, foot, and mouth disease vaccine or immunogenic composition antigens, the resulting particulate formulation is what is known as an ISCOM particle where the saponin may constitute 60-70% w/w, the cholesterol and phospholipid 10-15% w/w, and the protein 10-15% w/w. Details relating to composition and use of immunostimulating complexes can for example be found in the above-mentioned text-books dealing with adjuvants, but also Morein B et al., 1995, Clin. Immunother. 3: 461-475 as well as Barr I G and Mitchell G F, 1996, Immunol. and Cell Biol. 74: 8-25 provide useful instructions for the preparation of complete immunostimulating complexes.

The saponins, whether or not in the form of iscoms, that may be used in the adjuvant combinations with the hand, foot, and mouth disease vaccine antigens and immunogenic compositions disclosed herein include those derived from the bark of Quillaja *Saponaria* Molina, termed Quil A, and fractions thereof, described in U.S. Pat. No. 5,057,540 and "Saponins as vaccine adjuvants", Kensil, C. R., Crit Rev Ther Drug Carrier Syst, 1996, 12 (1-2):1-55; and EP 0 362 279 B1. Exemplary fractions of Quil A are QS21, QS7, and QS17.

β-Escin is another hemolytic saponins for use in the adjuvant compositions of the hand, foot, and mouth disease vaccines and/or immunogenic compositions. Escin is described in the Merck index (12th ed: entry 3737) as a mixture of saponins occurring in the seed of the horse chestnut tree, Lat: *Aesculus hippocastanum*. Its isolation is described by chromatography and purification (Fiedler, Arzneimittel-Forsch. 4, 213 (1953)), and by ion-exchange resins (Erbring et al., U.S. Pat. No. 3,238,190). Fractions of escin have been purified and shown to be biologically active (Yoshikawa M, et al. (*Chem Pharm Bull* (Tokyo) 1996 August; 44(8):1454-1464)). β-escin is also known as aescin.

Another hemolytic saponin for use in the hand, foot, and mouth disease vaccines and/or immunogenic compositions is Digitonin. Digitonin is described in the Merck index (12$^{th}$ Edition, entry 3204) as a saponin, being derived from the seeds of Digitalis purpurea and purified according to the procedure described Gisvold et al., J. Am. Pharm. Assoc., 1934, 23, 664; and Ruhenstroth-Bauer, Physiol. Chem., 1955, 301, 621. Its use is described as being a clinical reagent for cholesterol determination.

Another interesting possibility of achieving adjuvant effect is to employ the technique described in Gosselin et al., 1992. In brief, the presentation of a relevant antigen such as an antigen in a hand, foot, and mouth disease vaccines and/or immunogenic compositions of the present disclosure can be enhanced by conjugating the antigen to antibodies (or antigen binding antibody fragments) against the Fc receptors on monocytes/macrophages. Especially conjugates between antigen and anti-FcRI have been demonstrated to enhance immunogenicity for the purposes of vaccination. The antibody may be conjugated to the hand, foot, and mouth disease vaccine or immunogenic composition antigens after generation or as a part of the generation including by expressing as a fusion to any one of the polypeptide components of the hand, foot, and mouth disease vaccine and immunogenic composition antigens. Other possibilities involve the use of the targeting and immune modulating substances (i.e. cytokines). In addition, synthetic inducers of cytokines such as poly I:C may also be used.

Suitable mycobacterial derivatives may be selected from the group consisting of muramyl dipeptide, complete Freund's adjuvant, RIBI, (Ribi ImmunoChem Research Inc., Hamilton, Mont.) and a diester of trehalose such as TDM and TDE.

Examples of suitable immune targeting adjuvants include CD40 ligand and CD40 antibodies or specifically binding fragments thereof (cf. the discussion above), mannose, a Fab fragment, and CTLA-4.

Examples of suitable polymer adjuvants include a carbohydrate such as dextran, PEG, starch, mannan, and mannose; a plastic polymer; and latex such as latex beads.

Yet another interesting way of modulating an immune response is to include the immunogen (optionally together with adjuvants and pharmaceutically acceptable carriers and vehicles) in a "virtual lymph node" (VLN) (a proprietary medical device developed by ImmunoTherapy, Inc., 360 Lexington Avenue, New York, N.Y. 10017-6501). The VLN (a thin tubular device) mimics the structure and function of a lymph node. Insertion of a VLN under the skin creates a site of sterile inflammation with an upsurge of cytokines and chemokines. T- and B-cells as well as APCs rapidly respond to the danger signals, home to the inflamed site and accumulate inside the porous matrix of the VLN. It has been shown that the necessary antigen dose required to mount an immune response to an antigen is reduced when using the VLN and that immune protection conferred by vaccination using a VLN surpassed conventional immunization using Ribi as an adjuvant. The technology is described briefly in Gelber C et al., 1998, "Elicitation of Robust Cellular and Humoral Immune Responses to Small Amounts of Immunogens Using a Novel Medical Device Designated the Virtual Lymph Node", in: "From the Laboratory to the Clinic, Book of Abstracts, Oct. 12-15, 1998, Seascape Resort, Aptos, Calif."

Oligonucleotides may be used as adjuvants in conjunction with the hand, foot, and mouth disease vaccine and immunogenic composition antigens and may contain two or more dinucleotide CpG motifs separated by at least three or more or even at least six or more nucleotides. CpG-containing oligonucleotides (in which the CpG dinucleotide is unmethylated) induce a predominantly Th1 response. Such oligonucleotides are well known and are described, for example, in WO 96/02555, WO 99/33488 and U.S. Pat. Nos. 6,008,200 and 5,856,462.

Such oligonucleotide adjuvants may be deoxynucleotides. In certain embodiments, the nucleotide backbone in the oligonucleotide is phosphorodithioate, or a phosphorothioate bond, although phosphodiester and other nucleotide backbones such as PNA including oligonucleotides with mixed backbone linkages may also be used. Methods for producing phosphorothioate oligonucleotides or phosphorodithioate are described in U.S. Pat. Nos. 5,666,153, 5,278,302 and WO95/26204.

Exemplary oligonucleotides have the following sequences. The sequences may contain phosphorothioate modified nucleotide backbones:

```
                                        (SEQ ID NO: 10)
OLIGO 1: TCC ATG ACG TTC CTG ACG TT (CpG 1826);

(SEQ ID NO: 11)
OLIGO 2: TCT CCC AGC GTG CGC CAT (CpG 1758);

(SEQ ID NO: 12)
OLIGO 3: ACC GAT GAC GTC GCC GGT GAC GGC ACC ACG;

(SEQ ID NO: 13)
OLIGO 4: TCG TCG TTT TGT CGT TTT GTC GTT (CpG

2006);
and (SEQ ID NO: 14)
OLIGO 5: TCC ATG ACG TTC CTG ATG CT (CpG 1668)
```

Alternative CpG oligonucleotides include the above sequences with inconsequential deletions or additions thereto. The CpG oligonucleotides as adjuvants may be synthesized by any method known in the art (e.g., EP 468520). For example, such oligonucleotides may be synthesized utilizing an automated synthesizer. Such oligonucleotide adjuvants may be between 10-50 bases in length.

Another adjuvant system involves the combination of a CpG-containing oligonucleotide and a saponin derivative particularly the combination of CpG and QS21 is disclosed in WO 00/09159.

Many single or multiphase emulsion systems have been described. One of skill in the art may readily adapt such emulsion systems for use with hand, foot, and mouth disease vaccine and immunogenic composition antigens so that the emulsion does not disrupt the antigen's structure. Oil in water emulsion adjuvants per se have been suggested to be useful as adjuvant compositions (EPO 399 843B), also combinations of oil in water emulsions and other active agents have been described as adjuvants for vaccines (WO 95/17210; WO 98/56414; WO 99/12565; WO 99/11241). Other oil emulsion adjuvants have been described, such as water in oil emulsions (U.S. Pat. No. 5,422,109; EP 0 480 982 B2) and water in oil in water emulsions (U.S. Pat. No. 5,424,067; EP 0 480 981 B).

The oil emulsion adjuvants for use with the hand, foot, and mouth disease vaccines and/or immunogenic compositions described herein may be natural or synthetic, and may be mineral or organic. Examples of mineral and organic oils will be readily apparent to one skilled in the art.

In order for any oil in water composition to be suitable for human administration, the oil phase of the emulsion system may include a metabolizable oil. The meaning of the term metabolizable oil is well known in the art. Metabolizable can be defined as "being capable of being transformed by metabolism" (Dorland's Illustrated Medical Dictionary, W.B. Sanders Company, 25th edition (1974)). The oil may be any vegetable oil, fish oil, animal oil or synthetic oil, which is not toxic to the recipient and is capable of being transformed by metabolism. Nuts (such as peanut oil), seeds, and grains are common sources of vegetable oils. Synthetic oils may also be used and can include commercially available oils such as NEOBEE® and others. Squalene (2,6,10,15,19,23-Hexamethyl-2,6,10,14,18,22-tetracosahexaene) is an unsaturated oil which is found in large quantities in shark-liver oil, and in lower quantities in olive oil, wheat germ oil, rice bran oil, and yeast, and may be used with the hand, foot, and mouth disease vaccine and immunogenic composition antigens. Squalene is a metabolizable oil virtue of the fact that it is an intermediate in the biosynthesis of cholesterol (Merck index, 10th Edition, entry no. 8619).

Exemplary oil emulsions are oil in water emulsions, and in particular squalene in water emulsions.

In addition, the oil emulsion adjuvants for use with the hand, foot, and mouth disease vaccine and immunogenic composition antigens may include an antioxidant, such as the oil α-tocopherol (vitamin E, EP 0 382 271 B1).

WO 95/17210 and WO 99/11241 disclose emulsion adjuvants based on squalene, α-tocopherol, and TWEEN 80™, optionally formulated with the immunostimulants QS21 and/or 3D-MLA. WO 99/12565 discloses an improvement to these squalene emulsions with the addition of a sterol into the oil phase. Additionally, a triglyceride, such as tricaprylin ($C_{27}H_{50}O_6$), may be added to the oil phase in order to stabilize the emulsion (WO 98/56414).

The size of the oil droplets found within the stable oil in water emulsion may be less than 1 micron, may be in the range of substantially 30-600 nm, substantially around 30-500 nm in diameter, or substantially 150-500 nm in diameter, and in particular about 150 nm in diameter as measured by photon correlation spectroscopy. In this regard, 80% of the oil droplets by number may be within these ranges, more than 90% or more than 95% of the oil droplets by number are within the defined size ranges. The amounts of the components present in oil emulsions are conventionally in the range of from 2 to 10% oil, such as squalene; and when present, from 2 to 10% alpha tocopherol; and from 0.3 to 3% surfactant, such as polyoxyethylene sorbitan monooleate. The ratio of oil:alpha tocopherol may be equal or less than 1 as this provides a more stable emulsion. SPAN 85™ may also be present at a level of about 1%. In some cases it may be advantageous that the hand, foot, and mouth disease vaccines and/or immunogenic compositions disclosed herein will further contain a stabilizer.

The method of producing oil in water emulsions is well known to one skilled in the art. Commonly, the method includes the step of mixing the oil phase with a surfactant such as a PBS/TWEEN80® solution, followed by homogenization using a homogenizer, it would be clear to one skilled in the art that a method comprising passing the mixture twice through a syringe needle would be suitable for homogenizing small volumes of liquid. Equally, the emulsification process in microfluidizer (M110S microfluidics machine, maximum of 50 passes, for a period of 2 minutes at maximum pressure input of 6 bar (output pressure of about 850 bar)) could be adapted by one skilled in the art to produce smaller or larger volumes of emulsion. This adaptation could be achieved by routine experimentation comprising the measurement of the resultant emulsion until a preparation was achieved with oil droplets of the required diameter.

Alternatively the hand, foot, and mouth disease vaccines and/or immunogenic compositions may be combined with vaccine vehicles composed of chitosan (as described above) or other polycationic polymers, polylactide and polylactide-coglycolide particles, poly-N-acetyl glucosamine-based polymer matrix, particles composed of polysaccharides or chemically modified polysaccharides, liposomes and lipid-based particles, particles composed of glycerol monoesters, etc. The saponins may also be formulated in the presence of cholesterol to form particulate structures such as liposomes or ISCOMs. Furthermore, the saponins may be formulated together with a polyoxyethylene ether or ester, in either a non-particulate solution or suspension, or in a particulate structure such as a paucilamelar liposome or ISCOM.

Additional illustrative adjuvants for use in the hand, foot, and mouth disease vaccines and/or immunogenic compositions as described herein include SAF (Chiron, Calif., United States), MF-59 (Chiron, see, e.g., Granoff et al. (1997) Infect Immun. 65 (5):1710-1715), the SBAS series of adjuvants (e.g., SB-AS2 (an oil-in-water emulsion containing MLA and QS21); SBAS-4 (adjuvant system containing alum and MLA), available from SmithKline Beecham, Rixensart, Belgium), Detox (Enhanzyn®) (GlaxoSmithKline), RC-512, RC-522, RC-527, RC-529, RC-544, and RC-560 (GlaxoSmithKline) and other aminoalkyl glucosaminide 4-phosphates (AGPs), such as those described in pending U.S. patent application Ser. Nos. 08/853,826 and 09/074,720.

Other examples of adjuvants include, but are not limited to, Hunter's TiterMax® adjuvants (CytRx Corp., Norcross, Ga.); Gerbu adjuvants (Gerbu Biotechnik GmbH, Gaiberg, Germany); nitrocellulose (Nilsson and Larsson (1992) Res. Immunol. 143:553-557); alum (e.g., aluminum hydroxide, aluminum phosphate) emulsion based formulations including mineral oil, non-mineral oil, water-in-oil or oil-in-water emulsions, such as the Seppic ISA series of Montamide adjuvants (e.g., ISA-51, ISA-57, ISA-720, ISA-151, etc.; Seppic, Paris, France); and PROVAX® (IDEC Pharmaceuticals); OM-174 (a glucosamine disaccharide related to lipid A); *Leishmania* elongation factor; non-ionic block copolymers that form micelles such as CRL 1005; and Syntex Adjuvant Formulation. See, e.g., O'Hagan et al. (2001) Biomol Eng. 18(3):69-85; and "Vaccine Adjuvants: Preparation Methods and Research Protocols" D. O'Hagan, ed. (2000) Humana Press.

Other exemplary adjuvants include adjuvant molecules of the general formula:

$$HO(CH_2CH_2O)_n\text{-A-R,} \qquad (I)$$

where, n is 1-50, A is a bond or —C(O)—, R is $C_{1-50}$ alkyl or Phenyl $C_{1-50}$ alkyl.

One embodiment consists of a vaccine formulation comprising a polyoxyethylene ether of general formula (I), where n is between 1 and 50, 4-24, or 9; the R component is $C_{1-50}$, $C_4$-$C_{20}$ alkyl, or $C_{12}$ alkyl, and A is a bond. The concentration of the polyoxyethylene ethers should be in the range 0.1-20%, from 0.1-10%, or in the range 0.1-1%. Exemplary polyoxyethylene ethers are selected from the following group: polyoxyethylene-9-lauryl ether, polyoxyethylene-9-steoryl ether, polyoxyethylene-8-steoryl ether, polyoxyethylene-4-lauryl ether, polyoxyethylene-35-lauryl ether, and polyoxyethylene-23-lauryl ether. Polyoxyethylene ethers such as polyoxyethylene lauryl ether are described in the Merck index ($12^{th}$ edition: entry 7717). These adjuvant molecules are described in WO 99/52549.

The polyoxyethylene ether according to the general formula (I) above may, if desired, be combined with another adjuvant. For example, an adjuvant combination may include the CpG as described above.

Further examples of suitable pharmaceutically acceptable excipients for use with the hand, foot, and mouth disease vaccines and/or immunogenic compositions disclosed herein include water, phosphate buffered saline, isotonic buffer solutions.

Methods of the Present Disclosure

Further aspects of the present disclosure relate to methods for using vaccines and/or or immunogenic compositions of the present disclosure containing one or more antigens from at least one virus that causes hand, foot and mouth disease to treat or prevent hand, foot, and mouth disease in a subject in need thereof and/or to induce an immune response to hand, foot, and mouth disease in a subject in need thereof. In some embodiments, the present disclosure relates to methods for treating or preventing hand, foot, and mouth disease in a subject in need thereof by administering to the subject a therapeutically effective amount of a vaccine and/or or immunogenic composition of the present disclosure containing one or more antigens from at least one virus that causes hand, foot, and mouth disease. In some embodiments, the present disclosure relates to methods for inducing an immune response to hand, foot, and mouth disease in a subject in need thereof by administering to the subject a therapeutically effective amount of a vaccine and/or or immunogenic composition of the present disclosure containing one or more antigens from at least one virus that causes hand, foot and mouth disease.

In some embodiments, the administering step induces a protective immune response in the subject. In some embodiments, the protective immune response includes an immune response against one or more of EV71, CA6, and CA16. In some embodiments, the protective immune response includes an immune response against one or more EV7 viral genotypes such as B4, C2, C4, and C5.

The hand, foot, and mouth disease vaccines and/or immunogenic compositions disclosed herein may be used to protect or treat a mammal or bird susceptible to, or suffering from a viral infection, by means of administering the vaccine by intranasal, peroral, oral, buccal, sublingual, intramuscular, intraperitoneal, intradermal, transdermal, subdermal, intravaginal, anal, intracranial, intravenous, transcutaneous, or subcutaneous administration. Methods of systemic administration of the vaccines and/or immunogenic compositions of the present disclosure may include conventional syringes and needles, or devices designed for ballistic delivery of solid vaccines (WO 99/27961), or needleless pressure liquid jet device (U.S. Pat. Nos. 4,596,556; 5,993,412), or transdermal patches (WO 97/48440; WO 98/28037). The hand, foot, and mouth disease vaccines and/or immunogenic compositions of the present disclosure may also be applied to the skin (transdermal or transcutaneous delivery WO 98/20734; WO 98/28037). The hand, foot, and mouth disease vaccines and/or immunogenic compositions of the present disclosure therefore may include a delivery device for systemic administration, pre-filled with the hand, foot, and mouth disease vaccine or immunogenic compositions. Accordingly there is provided methods for treating or preventing hand, foot, and mouth disease and for inducing an immune response in a subject such as a mammal or bird, including the step of administering a vaccine or immunogenic composition of the present disclosure and optionally including an adjuvant and/or a carrier, to the subject, where the vaccine or immunogenic composition is administered via the parenteral or systemic route.

The vaccines and/or immunogenic compositions of the present disclosure may be used to protect or treat a mammal or bird susceptible to, or suffering from a viral infection, by means of administering the vaccine or immunogenic composition via a mucosal route, such as the oral/alimentary or nasal route. Alternative mucosal routes are intravaginal and intra-rectal. The mucosal route of administration may be via the nasal route, termed intranasal vaccination. Methods of intranasal vaccination are well known in the art, including the administration of a droplet, spray, or dry powdered form of the vaccine into the nasopharynx of the individual to be immunized. Nebulized or aerosolized vaccine formulations are potential forms of the hand, foot, and mouth disease vaccines and/or immunogenic compositions disclosed herein. Enteric formulations such as gastro resistant capsules and granules for oral administration, suppositories for rectal or vaginal administration are also formulations of the vaccines and/or immunogenic compositions of the present disclosure.

The hand, foot, and mouth disease vaccines and/or immunogenic compositions of the present disclosure may also be administered via the oral route. In such cases the pharmaceutically acceptable excipient may also include alkaline buffers, or enteric capsules or microgranules. The hand, foot, and mouth disease vaccines and/or immunogenic compositions of the present disclosure may also be administered by the vaginal route. In such cases, the pharmaceutically acceptable excipients may also include emulsifiers, polymers such as CARBOPOL®, and other known stabilizers of vaginal creams and suppositories. The hand, foot, and mouth disease vaccines and/or immunogenic compositions may also be administered by the rectal route. In such cases the excipients may also include waxes and polymers known in the art for forming rectal suppositories.

In some embodiments, the administering step includes one or more administrations. Administration can be by a single dose schedule or a multiple dose (prime-boost) schedule. In a multiple dose schedule the various doses may be given by the same or different routes e.g. a parenteral prime and mucosal boost, a mucosal prime and parenteral boost, etc. Typically they will be given by the same route. Multiple doses will typically be administered at least 1 week apart (e.g. about 2 weeks, about 3 weeks, about 4 weeks, about 6 weeks, about 8 weeks, about 12 weeks, about 16 weeks, etc.). Giving two doses separated by from 25-30 days (e.g. 28 days) is particularly useful.

The methods of the present disclosure include administration of a therapeutically effective amount or an immunogenic amount of the vaccines and/or immunogenic compositions of the present disclosure. A therapeutically effective amount or an immunogenic amount may be an amount of the vaccines and/or immunogenic compositions of the present disclosure that will induce a protective immunological response in the uninfected, infected or unexposed subject to which it is administered. Such a response will generally result in the development in the subject of a secretory, cellular and/or antibody-mediated immune response to the vaccine. Usually, such a response includes but is not limited to one or more of the following effects; the production of antibodies from any of the immunological classes, such as immunoglobulins A, D, E, G or M; the proliferation of B and T lymphocytes; the provision of activation, growth and differentiation signals to immunological cells; expansion of helper T cell, suppressor T cell, and/or cytotoxic T cell.

Preferably, the therapeutically effective amount or immunogenic amount is sufficient to bring about treatment or prevention of disease symptoms. The exact amount necessary will vary depending on the subject being treated; the age and general condition of the subject to be treated; the capacity of the subject's immune system to synthesize antibodies; the degree of protection desired; the severity of the condition being treated; the particular hand, foot, and mouth disease antigen polypeptide selected and its mode of administration, among other factors. An appropriate therapeutically effective amount or immunogenic amount can be readily determined by one of skill in the art. A therapeutically effective amount or immunogenic amount will fall in a relatively broad range that can be determined through routine trials.

ENUMERATED EMBODIMENTS

The following enumerated embodiments are representative of some aspects of the invention.
1. A hand, foot, and mouth vaccine comprising one or more antigens from at least one virus that causes hand, foot and mouth disease in humans, wherein the one or more antigens comprise at least one non-human cell adaptation mutation.
2. A hand, foot, and mouth immunogenic composition comprising one or more antigens from at least one virus that causes hand, foot and mouth disease in humans, wherein the one or more antigens comprise at least one non-human cell adaptation mutation.
3. The vaccine or immunogenic composition of embodiment 1 or embodiment 2, wherein the at least one virus is selected from one or more of EV71, CA6, and CA16.
4. The vaccine or immunogenic composition of embodiment 1 or embodiment 2, wherein the at least one virus comprises EV71, CA6, and CA16.
5. The vaccine or immunogenic composition of embodiment 1 or embodiment 2, wherein the at least one virus comprises EV71 and CA6.
6. The vaccine or immunogenic composition of embodiment 1 or embodiment 2, wherein the at least one virus comprises EV71 and CA16.

7. The vaccine or immunogenic composition of embodiment 1 or embodiment 2, wherein the at least one virus comprises CA6 and CA16.
8. The vaccine or immunogenic composition of embodiment 1 or embodiment 2, wherein the at least one virus is EV71.
9. The vaccine or immunogenic composition of embodiment 1 or embodiment 2, wherein the one or more antigens are selected from EV71, CA6, CA16, and any combination thereof.
10. The vaccine or immunogenic composition of embodiment 9, wherein the one or more antigens are from EV71.
11. The vaccine or immunogenic composition of any one of embodiments 1-10, wherein the one or more antigens comprise the VP1 polypeptide of EV71, and wherein the VP1 polypeptide comprises the at least one non-human cell adaptation mutation.
12. The vaccine or immunogenic composition of embodiment 11, wherein the at least one non-human cell adaptation mutation occurs at position 7 of SEQ ID NO: 1, or at a position corresponding to position 7 of SEQ ID NO: 1 when aligned to SEQ ID NO: 1 using a pairwise alignment algorithm; or at two or more, three or more, or all four of positions 7, 14, 145, or 282 of SEQ ID NO: 1, or of positions corresponding to positions 7, 14, 145, or 282 of SEQ ID NO: 1 when aligned to SEQ ID NO: 1 using a pairwise alignment algorithm.
13. The vaccine or immunogenic composition of embodiment 12, wherein the mutation at position 7 of SEQ ID NO: 1, or at a position corresponding to position 7 of SEQ ID NO: 1 when aligned to SEQ ID NO: 1 using a pairwise alignment algorithm, is a valine to methionine substitution.
14. The vaccine or immunogenic composition of embodiment 12, wherein the mutation at position 14 of SEQ ID NO: 1, or at a position corresponding to position 14 of SEQ ID NO: 1 when aligned to SEQ ID NO: 1 using a pairwise alignment algorithm, is an aspartic acid to asparagine substitution.
15. There vaccine or immunogenic composition of embodiment 12, wherein the mutation at position 145 of SEQ ID NO: 1, or at a position corresponding to position 145 of SEQ ID NO: 1 when aligned to SEQ ID NO: 1 using a pairwise alignment algorithm, is a glutamic acid to glutamine substitution.
16. The vaccine or immunogenic composition of embodiment 12, wherein the mutation at position 282 of SEQ ID NO: 1, or at a position corresponding to position 282 of SEQ ID NO: 1 when aligned to SEQ ID NO: 1 using a pairwise alignment algorithm, is an asparagine to aspartic acid substitution.
17. The vaccine or immunogenic composition of any one of embodiments 1-16, wherein the one or more antigens comprise the VP1 polypeptide of CA6 and wherein the VP1 polypeptide comprises the at least one non-human cell adaptation mutation.
18. The vaccine or immunogenic composition of embodiment 17, wherein the at least one non-human cell adaptation mutation occurs at one or more, two or more, three or more, or all four of positions 46, 90, 96, or 268 of SEQ ID NO: 2, or of positions corresponding to positions 46, 90, 96, or 268 of SEQ ID NO: 2 when aligned to SEQ ID NO: 2 using a pairwise alignment algorithm.
19. The vaccine or immunogenic composition of embodiment 18, wherein the mutation at position 46 of SEQ ID NO: 2, or at a position corresponding to position 46 of SEQ ID NO: 2 when aligned to SEQ ID NO: 2 using a pairwise alignment algorithm, is an alanine to valine substitution.
20. The vaccine or immunogenic composition of embodiment 18, wherein the mutation at position 90 of SEQ ID NO: 2, or at a position corresponding to position 90 of SEQ ID NO: 2 when aligned to SEQ ID NO: 2 using a pairwise alignment algorithm, is a glutamic acid to lysine substitution.
21. There vaccine or immunogenic composition of embodiment 18, wherein the mutation at position 96 of SEQ ID NO: 2, or at a position corresponding to position 96 of SEQ ID NO: 2 when aligned to SEQ ID NO: 2 using a pairwise alignment algorithm, is a threonine to alanine substitution.
22. The vaccine or immunogenic composition of embodiment 18, wherein the mutation at position 268 of SEQ ID NO: 2, or at a position corresponding to position 268 of SEQ ID NO: 2 when aligned to SEQ ID NO: 2 using a pairwise alignment algorithm, is a valine to isoleucine substitution.
23. The vaccine or immunogenic composition of any one of embodiments 1-22, wherein the one or more antigens comprise the VP2 polypeptide of CA6, and where in the VP2 polypeptide comprises the at least one non-human cell adaptation mutation.
24. The vaccine or immunogenic composition of embodiment 23, wherein the at least one non-human cell adaptation mutation occurs at position 144 of SEQ ID NO: 3, or at a position corresponding to position 144 of SEQ ID NO: 3 when aligned to SEQ ID NO: 3 using a pairwise alignment algorithm.
25. The vaccine or immunogenic composition of embodiment 24, wherein the mutation at position 144 of SEQ ID NO: 3, or at a position corresponding to position 144 of SEQ ID NO: 3 when aligned to SEQ ID NO: 3 using a pairwise alignment algorithm, is a glutamine to lysine substitution.
26. The vaccine or immunogenic composition of any one of embodiments 1-25, wherein the one or more antigens comprise the VP3 polypeptide of CA6, and wherein the VP3 polypeptide comprises the at least one non-human cell adaptation mutation.
27. The vaccine or immunogenic composition of embodiment 26, wherein the at least one non-human cell adaptation mutation occurs at position 102 of SEQ ID NO: 4, or at a position corresponding to position 102 of SEQ ID NO: 4 when aligned to SEQ ID NO: 4 using a pairwise alignment algorithm.
28. The vaccine or immunogenic composition of embodiment 27, wherein the mutation at position 102 of SEQ ID NO: 4, or at a position corresponding to position 102 of SEQ ID NO: 4 when aligned to SEQ ID NO: 4 using a pairwise alignment algorithm, is an isoleucine to valine substitution.
29. The vaccine or immunogenic composition of any one of embodiments 1-28, wherein the one or more antigens comprise the 5' untranslated region (UTR) of CA6, and wherein the 5' UTR of CA6 comprises the at least one non-human cell adaptation mutation.
30. The vaccine or immunogenic composition of embodiment 29, wherein the at least one non-human cell adaptation mutation occurs at one or more, two or more, three or more, four or more, five or more, six or more, seven or more, eight or more, or all nine of positions 1, 13, 14, 15, 16, 21, 23, 34, or 40 of SEQ ID NO: 8, or at position corresponding to position 1, 13, 14, 15, 16, 21, 23, 34, or 40 of SEQ ID NO: 8 when the 5' UTR of CA6 is aligned to SEQ ID NO: 8 using a pairwise alignment algorithm.

31. The vaccine or immunogenic composition of embodiment 30, wherein the mutation at position 1 of SEQ ID NO: 8, or at a position corresponding to position 1 of SEQ ID NO: 8 when aligned to SEQ ID NO: 8 using a pairwise alignment algorithm, is a thymine to guanine substitution; the mutation at position 13 of SEQ ID NO: 8, or at a position corresponding to position 13 of SEQ ID NO: 8 when aligned to SEQ ID NO: 8 using a pairwise alignment algorithm, is a guanine to adenine substitution; the mutation at position 14 of SEQ ID NO: 8, or at a position corresponding to position 14 of SEQ ID NO: 8 when aligned to SEQ ID NO: 8 using a pairwise alignment algorithm, is a thymine to guanine substitution; the mutation at position 15 of SEQ ID NO: 8, or at a position corresponding to position 15 of SEQ ID NO: 8 when aligned to SEQ ID NO: 8 using a pairwise alignment algorithm, is a guanine to cytosine substitution; the mutation at position 16 of SEQ ID NO: 8, or at a position corresponding to position 16 of SEQ ID NO: 8 when aligned to SEQ ID NO: 8 using a pairwise alignment algorithm, is a guanine to adenine substitution; the mutation at position 21 of SEQ ID NO: 8, or at a position corresponding to position 21 of SEQ ID NO: 8 when aligned to SEQ ID NO: 8 using a pairwise alignment algorithm, is a cytosine to thymine substitution; the mutation at position 23 of SEQ ID NO: 8, or at a position corresponding to position 23 of SEQ ID NO: 8 when aligned to SEQ ID NO: 8 using a pairwise alignment algorithm, is a cytosine to thymine substitution; the mutation at position 34 of SEQ ID NO: 8, or at a position corresponding to position 34 of SEQ ID NO: 8 when aligned to SEQ ID NO: 8 using a pairwise alignment algorithm, is a guanine to thymine substitution; or the mutation at position 40 of SEQ ID NO: 8, or at a position corresponding to position 40 of SEQ ID NO: 8 when aligned to SEQ ID NO: 8 using a pairwise alignment algorithm, is a cytosine to guanine substitution.

32. The vaccine or immunogenic composition of any one of embodiments 1-31, wherein the one or more antigens comprise the 2A polypeptide of CA16, and wherein the 2A polypeptide comprises the at least one non-human cell adaptation mutation.

33. The vaccine or immunogenic composition of embodiment 32, wherein the at least one non-human cell adaptation mutation occurs at position 2 of SEQ ID NO: 5, or at a position corresponding to position 2 of SEQ ID NO: 5 when aligned to SEQ ID NO: 5 using a pairwise alignment algorithm.

34. The vaccine or immunogenic composition of embodiment 33, wherein the mutation at position 2 of SEQ ID NO: 5, or at a position corresponding to position 2 of SEQ ID NO: 5 when aligned to SEQ ID NO: 5 using a pairwise alignment algorithm, is a lysine to glutamic acid substitution.

35. The vaccine or immunogenic composition of any one of embodiments 1-34, wherein the one or more antigens comprise the VP2 polypeptide of CA16, and wherein the VP2 polypeptide comprises the at least one non-human cell adaptation mutation.

36. The vaccine or immunogenic composition of embodiment 35, wherein the at least one non-human cell adaptation mutation occurs at position 161 of SEQ ID NO: 6, or at a position corresponding to position 161 of SEQ ID NO: 6 when aligned to SEQ ID NO: 6 using a pairwise alignment algorithm.

37. The vaccine or immunogenic composition of embodiment 36, wherein the mutation at position 161 of SEQ ID NO: 6, or at a position corresponding to position 161 of SEQ ID NO: 6 when aligned to SEQ ID NO: 6 using a pairwise alignment algorithm, is a methionine to threonine substitution.

38. The vaccine or immunogenic composition of any one of embodiments 32-37, further comprising at least one additional non-human cell adaptation mutation in the VP1 polypeptide of CA16.

39. The vaccine or immunogenic composition of embodiment 38, wherein the at least one additional non-human cell adaptation mutation occurs at one or more or both of position 99 or 145 of SEQ ID NO: 7, or at a position corresponding to position 99 or 145 of SEQ ID NO: 7 when aligned to SEQ ID NO: 7 using a pairwise alignment algorithm.

40. The vaccine or immunogenic composition of embodiment 39, wherein the mutation at position 99 of SEQ ID NO: 7, or at a position corresponding to position 99 of SEQ ID NO: 7 when aligned to SEQ ID NO: 7 using a pairwise alignment algorithm, is an aspartic acid to glycine substitution.

41. The vaccine or immunogenic composition of embodiment 39, wherein the mutation at position 145 of SEQ ID NO: 7, or at a position corresponding to position 145 of SEQ ID NO: 7 when aligned to SEQ ID NO: 7 using a pairwise alignment algorithm, is a valine to glutamic acid substitution.

42. The vaccine or immunogenic composition of any one of embodiments 1-41, wherein the one or more antigens comprise the 5' untranslated region (UTR) of CA16, and wherein the 5' UTR of CA16 comprises the at least one non-human cell adaptation mutation.

43. The vaccine or immunogenic composition of embodiment 42, wherein the at least one non-human cell adaptation mutation occurs at one or two of positions 6 or 33 of SEQ ID NO: 9, or at position corresponding to position 6 or 33 of SEQ ID NO: 9 when the 5' UTR of CA6 is aligned to SEQ ID NO: 8 using a pairwise alignment algorithm.

44. The vaccine or immunogenic composition of embodiment 43, wherein the mutation at position 6 of SEQ ID NO: 9, or at a position corresponding to position 6 of SEQ ID NO: 9 when aligned to SEQ ID NO: 8 using a pairwise alignment algorithm is a guanine to adenine substitution; or the mutation at position 33 of SEQ ID NO: 9, or at a position corresponding to position 33 of SEQ ID NO: 9 when aligned to SEQ ID NO: 8 using a pairwise alignment algorithm is a guanine to cytosine substitution.

45. The vaccine or immunogenic composition of any one of embodiments 1-44, wherein the non-human cell is a mammalian cell.

46. The vaccine or immunogenic composition of any one of embodiments 1-44, wherein the non-human cell is a monkey cell.

47. The vaccine or immunogenic composition of embodiment 46, wherein the monkey cell is a from a Vero cell line.

48. The vaccine or immunogenic composition of embodiment 47, wherein the Vero cell line is selected from WHO Vero 10-87, ATCC CCL-81, Vero 76 (ATCC Accession No. CRL-1587), and Vero C1008 (ATCC Accession No. CRL-1586).

49. The vaccine or immunogenic composition of any one of embodiments 1-48, wherein the one or more antigens were produced by culturing the non-human cell.

50. The vaccine or immunogenic composition of embodiment 49, wherein the cell was cultured in serum-free media.
51. The vaccine or immunogenic composition of any one of embodiments 1-50, wherein the vaccine or immunogenic composition is a purified antigen vaccine or immunogenic composition, a subunit vaccine or immunogenic composition, an inactivated whole virus vaccine or immunogenic composition, or an attenuated virus vaccine or immunogenic composition.
52. The vaccine or immunogenic composition of any one of embodiments 1-51, wherein the at least one virus was chemically inactivated.
53. The vaccine or immunogenic composition of embodiment 52, wherein the at least one virus was chemically inactivated with one or more of beta-propiolactone (BPL), formalin, or binary ethylenimine (BEI).
54. The vaccine or immunogenic composition of embodiment 52, wherein the at least one virus was chemically inactivated with BPL.
55. The vaccine or immunogenic composition of embodiment 52, wherein the at least one virus was chemically inactivated with formalin.
56. The vaccine or immunogenic composition of embodiment 52, wherein the at least one virus was chemically inactivated with a combination of BPL and formalin.
57. The vaccine or immunogenic composition of any one of embodiments 53, 54, or 56, wherein the at least one virus inactivated by BPL comprises one or more modifications.
58. The vaccine or immunogenic composition of embodiment 57, wherein the one or more modifications comprise a modified nucleic acid.
59. The vaccine or immunogenic composition of embodiment 58, wherein the modified nucleic acid is an alkylated nucleic acid.
60. The vaccine or immunogenic composition of embodiment 57, wherein the one or more modifications comprise a modified polypeptide.
61. The vaccine or immunogenic composition of embodiment 60, wherein the modified polypeptide comprises a modified amino acid residue are selected from one or more of cysteine, methionine, histidine, aspartic acid, glutamic acid, tyrosine, lysine, serine, and threonine.
62. The vaccine or immunogenic composition of any one of embodiments 53, 55, or 56, wherein the at least one virus inactivated by formalin comprises one or more modifications.
63. The vaccine or immunogenic composition of embodiment 62, wherein the one or more modifications comprise a modified polypeptide.
64. The vaccine or immunogenic composition of embodiment 62, wherein the one or more modifications comprise a cross-linked polypeptide.
65. The vaccine or immunogenic composition of any one of embodiments 62-64, wherein the vaccine or immunogenic composition further comprises formalin.
66. The vaccine or immunogenic composition of embodiment 52, wherein the at least one virus was chemically inactivated with BEI.
67. The vaccine or immunogenic composition of embodiment 53 or embodiment 66, wherein the at least one virus inactivated by BEI comprises one or more modifications.
68. The vaccine or immunogenic composition of embodiment 67, wherein the one or more modifications comprise a modified nucleic acid.
69. The vaccine or immunogenic composition of embodiment 68, wherein the modified nucleic acid is an alkylated nucleic acid.
70. The vaccine or immunogenic composition of anyone of embodiments 66-69, wherein unreacted BEI was hydrolyzed with sodium thiosulfate.
71. The vaccine or immunogenic composition of any one of embodiments 1-70, further comprising a detergent in an effective concentration.
72. The vaccine or immunogenic composition of embodiment 71, wherein the detergent comprises polysorbate [80]. 73. The vaccine or immunogenic composition of embodiment 72, wherein the effective concentration ranges from about 0.001% to about 0.01%.
74. The vaccine or immunogenic composition of any one of embodiments 1-73, further comprising an adjuvant.
75. The vaccine or immunogenic composition of embodiment 74, wherein the adjuvant is selected from the group consisting of aluminum salts, toll-like receptor (TLR) agonists, monophosphoryl lipid A (MLA), synthetic lipid A, lipid A mimetics or analogs, MLA derivatives, cytokines, saponins, muramyl dipeptide (MDP) derivatives, CpG oligos, lipopolysaccharide (LPS) of gram-negative bacteria, polyphosphazenes, emulsions, virosomes, cochleates, poly(lactide-co-glycolides) (PLG) microparticles, poloxamer particles, microparticles, liposomes, Complete Freund's Adjuvant (CFA), and Incomplete Freund's Adjuvant (IFA).
76. The vaccine or immunogenic composition of embodiment 75, wherein the adjuvant is an aluminum salt.
77. The vaccine or immunogenic composition of embodiment 75, wherein the adjuvant is selected from alum, aluminum phosphate, aluminum hydroxide, potassium aluminum sulfate, and Alhydrogel 85.
78. The vaccine or immunogenic composition of embodiment 76 or embodiment 77, wherein at least 75%, at least 80%, at least 85%, at least 90%, at 95%, at least 97%, at least 99%, or 100% of the antigen is adsorbed to the adjuvant.
79. The vaccine or immunogenic composition of embodiment 75, wherein the adjuvant is monophoshporyl lipid A (MLA) and derivatives thereof.
80. A method for treating or preventing hand, foot, and mouth disease in a subject in need thereof, comprising administering to the subject a therapeutically effective amount of the vaccine or immunogenic composition of any one of embodiments 1-79.
81. A method for inducing an immune response in a subject in need thereof, comprising administering to the subject an immunogenic amount of the vaccine or immunogenic composition of any one of embodiments 1-79.
82. The method of embodiment 80 or embodiment 81, wherein the administering induces a protective immune response in the subject.
83. The method of embodiment 82, wherein the immune response comprises an immune response against one or more of EV71, CA6, and CA16.
84. The method of embodiment 82, wherein the immune response comprises an immune response against one or more EV71 viral genotypes selected from B4, C2, C4, and C5.
85. The method of any one of embodiments 80-84, wherein the administering is selected from the group consisting of subcutaneous delivery, transcutaneous delivery, intradermal delivery, subdermal delivery, intramuscular delivery, peroral delivery, oral delivery, intranasal delivery, buccal delivery, sublingual delivery, intraperitoneal delivery, intravaginal delivery, anal delivery and intracranial delivery.

86. The method of any one of embodiments 80-85, wherein the administering comprises one or more administrations.

87. A hand, foot, and mouth vaccine comprising one or more antigens from at least one inactivated virus that causes hand, foot and mouth disease in humans, wherein the at least one virus is EV71, CA16, or both, and wherein the at least one virus was inactivated with beta-propiolactone (BPL).

88. A hand, foot, and mouth immunogenic composition comprising one or more antigens from at least one inactivated virus that causes hand, foot and mouth disease in humans, wherein the at least one virus is EV71, CA16, or both, and wherein the at least one virus was inactivated with beta-propiolactone (BPL).

89. The vaccine or immunogenic composition of embodiment 87 or embodiment 88, wherein the at least one inactivated virus comprises one or more modifications.

90. The vaccine or immunogenic composition of embodiment 89, wherein the one or more modifications comprise a modified nucleic acid.

91. The vaccine or immunogenic composition of embodiment 90, wherein the modified nucleic acid is an alkylated nucleic acid.

92. The vaccine or immunogenic composition of embodiment 89, wherein the one or more modifications comprise a modified polypeptide.

93. The vaccine or immunogenic composition of embodiment 92, wherein the modified polypeptide comprises a modified amino acid residue are selected from one or more of cysteine, methionine, histidine, aspartic acid, glutamic acid, tyrosine, lysine, serine, and threonine.

94. The vaccine or immunogenic composition of any one of embodiments 87-93, further comprising one or more antigens from CA6.

95. The vaccine or immunogenic composition of embodiment 94, wherein the one or more antigens comprise at least one non-human cell adaptation mutation.

96. The vaccine or immunogenic composition of embodiment 95, wherein the one or more antigens comprise the VP1 polypeptide of EV71, and wherein the VP1 polypeptide comprises the at least one non-human cell adaptation mutation.

97. The vaccine or immunogenic composition of embodiment 96, wherein the at least one non-human cell adaptation mutation occurs at position 7 of SEQ ID NO: 1, or at a position corresponding to position 7 of SEQ ID NO: 1 when aligned to SEQ ID NO: 1 using a pairwise alignment algorithm; or at two or more, three or more, or all four of positions 7, 14, 145, or 282 of SEQ ID NO: 1, or of positions corresponding to positions 7, 14, 145, or 282 of SEQ ID NO: 1 when aligned to SEQ ID NO: 1 using a pairwise alignment algorithm.

98. The vaccine or immunogenic composition of embodiment 97, wherein the mutation at position 7 of SEQ ID NO: 1, or at a position corresponding to position 7 of SEQ ID NO: 1 when aligned to SEQ ID NO: 1 using a pairwise alignment algorithm, is a valine to methionine substitution.

99. The vaccine or immunogenic composition of embodiment 97, wherein the mutation at position 14 of SEQ ID NO: 1, or at a position corresponding to position 14 of SEQ ID NO: 1 when aligned to SEQ ID NO: 1 using a pairwise alignment algorithm, is an aspartic acid to asparagine substitution.

100. There vaccine or immunogenic composition of embodiment 97, wherein the mutation at position 145 of SEQ ID NO: 1, or at a position corresponding to position 145 of SEQ ID NO: 1 when aligned to SEQ ID NO: 1 using a pairwise alignment algorithm, is a glutamic acid to glutamine substitution.

101. The vaccine or immunogenic composition of embodiment 97, wherein the mutation at position 282 of SEQ ID NO: 1, or at a position corresponding to position 282 of SEQ ID NO: 1 when aligned to SEQ ID NO: 1 using a pairwise alignment algorithm, is an asparagine to aspartic acid substitution.

102. The vaccine or immunogenic composition of embodiment 95-101, wherein the one or more antigens comprise the VP1 polypeptide of CA6 and wherein the VP1 polypeptide comprises the at least one non-human cell adaptation mutation.

103. The vaccine or immunogenic composition of embodiment 102, wherein the at least one non-human cell adaptation mutation occurs at one or more, two or more, three or more, or all four of positions 46, 90, 96, or 268 of SEQ ID NO: 2, or of positions corresponding to positions 46, 90, 96, or 268 of SEQ ID NO: 2 when aligned to SEQ ID NO: 2 using a pairwise alignment algorithm.

104. The vaccine or immunogenic composition of embodiment 103, wherein the mutation at position 46 of SEQ ID NO: 2, or at a position corresponding to position 46 of SEQ ID NO: 2 when aligned to SEQ ID NO: 2 using a pairwise alignment algorithm, is an alanine to valine substitution.

105. The vaccine or immunogenic composition of embodiment 103, wherein the mutation at position 90 of SEQ ID NO: 2, or at a position corresponding to position 90 of SEQ ID NO: 2 when aligned to SEQ ID NO: 2 using a pairwise alignment algorithm, is a glutamic acid to lysine substitution.

106. There vaccine or immunogenic composition of embodiment 103, wherein the mutation at position 96 of SEQ ID NO: 2, or at a position corresponding to position 96 of SEQ ID NO: 2 when aligned to SEQ ID NO: 2 using a pairwise alignment algorithm, is a threonine to alanine substitution.

107. The vaccine or immunogenic composition of embodiment 103, wherein the mutation at position 268 of SEQ ID NO: 2, or at a position corresponding to position 268 of SEQ ID NO: 2 when aligned to SEQ ID NO: 2 using a pairwise alignment algorithm, is a valine to isoleucine substitution.

108. T The vaccine or immunogenic composition of embodiment 95-107, wherein the one or more antigens comprise the VP2 polypeptide of CA6, and where in the VP2 polypeptide comprises the at least one non-human cell adaptation mutation.

109. The vaccine or immunogenic composition of embodiment 108, wherein the at least one non-human cell adaptation mutation occurs at position 144 of SEQ ID NO: 3, or at a position corresponding to position 144 of SEQ ID NO: 3 when aligned to SEQ ID NO: 3 using a pairwise alignment algorithm.

110. The vaccine or immunogenic composition of embodiment 109, wherein the mutation at position 144 of SEQ ID NO: 3, or at a position corresponding to position 144 of SEQ ID NO: 3 when aligned to SEQ ID NO: 3 using a pairwise alignment algorithm, is a glutamine to lysine substitution.

111. The vaccine or immunogenic composition of embodiment 95-110, wherein the one or more antigens comprise the VP3 polypeptide of CA6, and wherein the VP3 polypeptide comprises the at least one non-human cell adaptation mutation.

112. The vaccine or immunogenic composition of embodiment 111, wherein the at least one non-human cell adaptation mutation occurs at position 102 of SEQ ID NO: 4, or at a position corresponding to position 102 of SEQ ID NO: 4 when aligned to SEQ ID NO: 4 using a pairwise alignment algorithm.

113. The vaccine or immunogenic composition of embodiment 112, wherein the mutation at position 102 of SEQ ID NO: 4, or at a position corresponding to position 102 of SEQ ID NO: 4 when aligned to SEQ ID NO: 4 using a pairwise alignment algorithm, is an isoleucine to valine substitution.

114. The vaccine or immunogenic composition of embodiment 95-113, wherein the one or more antigens comprise the 5' untranslated region (UTR) of CA6, and wherein the 5' UTR of CA6 comprises the at least one non-human cell adaptation mutation.

115. The vaccine or immunogenic composition of embodiment 114, wherein the at least one non-human cell adaptation mutation occurs at one or more, two or more, three or more, four or more, five or more, six or more, seven or more, eight or more, or all nine nucleic acid positions 1, 13, 14, 15, 16, 21, 23, 34, or 40 of SEQ ID NO: 8, or at position corresponding to position 1, 13, 14, 15, 16, 21, 23, 34, or 40 of SEQ ID NO: 8 when the 5' UTR of CA6 is aligned to SEQ ID NO: 8 using a pairwise alignment algorithm.

116. The vaccine or immunogenic composition of embodiment 115, wherein the mutation at position 1 of SEQ ID NO: 8, or at a position corresponding to position 1 of SEQ ID NO: 8 when aligned to SEQ ID NO: 8 using a pairwise alignment algorithm, is a thymine to guanine substitution; the mutation at position 13 of SEQ ID NO: 8, or at a position corresponding to position 13 of SEQ ID NO: 8 when aligned to SEQ ID NO: 8 using a pairwise alignment algorithm, is a guanine to adenine substitution; the mutation at position 14 of SEQ ID NO: 8, or at a position corresponding to position 14 of SEQ ID NO: 8 when aligned to SEQ ID NO: 8 using a pairwise alignment algorithm, is a thymine to guanine substitution; the mutation at position 15 of SEQ ID NO: 8, or at a position corresponding to position 15 of SEQ ID NO: 8 when aligned to SEQ ID NO: 8 using a pairwise alignment algorithm, is a guanine to cytosine substitution; the mutation at position 16 of SEQ ID NO: 8, or at a position corresponding to position 16 of SEQ ID NO: 8 when aligned to SEQ ID NO: 8 using a pairwise alignment algorithm, is a guanine to adenine substitution; the mutation at position 21 of SEQ ID NO: 8, or at a position corresponding to position 21 of SEQ ID NO: 8 when aligned to SEQ ID NO: 8 using a pairwise alignment algorithm, is a cytosine to thymine substitution; the mutation at position 23 of SEQ ID NO: 8, or at a position corresponding to position 23 of SEQ ID NO: 8 when aligned to SEQ ID NO: 8 using a pairwise alignment algorithm, is a cytosine to thymine substitution; the mutation at position 34 of SEQ ID NO: 8, or at a position corresponding to position 34 of SEQ ID NO: 8 when aligned to SEQ ID NO: 8 using a pairwise alignment algorithm, is a guanine to thymine substitution; or the mutation at position 40 of SEQ ID NO: 8, or at a position corresponding to position 40 of SEQ ID NO: 8 when aligned to SEQ ID NO: 8 using a pairwise alignment algorithm, is a cytosine to guanine substitution.

117. The vaccine or immunogenic composition of embodiment 95-116, wherein the one or more antigens comprise the 2A polypeptide of CA16, and wherein the 2A polypeptide comprises the at least one non-human cell adaptation mutation.

118. The vaccine or immunogenic composition of embodiment 117, wherein the at least one non-human cell adaptation mutation occurs at position 2 of SEQ ID NO: 5, or at a position corresponding to position 2 of SEQ ID NO: 5 when aligned to SEQ ID NO: 5 using a pairwise alignment algorithm.

119. The vaccine or immunogenic composition of embodiment 118, herein the mutation at position 2 of SEQ ID NO: 5, or at a position corresponding to position 2 of SEQ ID NO: 5 when aligned to SEQ ID NO: 5 using a pairwise alignment algorithm, is a lysine to glutamic acid substitution.

120. The vaccine or immunogenic composition of embodiment 95-119, wherein the one or more antigens comprise the VP2 polypeptide of CA16, and wherein the VP2 polypeptide comprises the at least one non-human cell adaptation mutation.

121. The vaccine or immunogenic composition of embodiment 120, wherein the at least one non-human cell adaptation mutation occurs at position 161 of SEQ ID NO: 6, or at a position corresponding to position 161 of SEQ ID NO: 6 when aligned to SEQ ID NO: 6 using a pairwise alignment algorithm.

122. The vaccine or immunogenic composition of embodiment 121, wherein the mutation at position 161 of SEQ ID NO: 6, or at a position corresponding to position 161 of SEQ ID NO: 6 when aligned to SEQ ID NO: 6 using a pairwise alignment algorithm, is a methionine to threonine substitution.

123. The vaccine or immunogenic composition of any one of embodiments 117-122, further comprising at least one additional non-human cell adaptation mutation in the VP1 polypeptide of CA16.

124. The vaccine or immunogenic composition of embodiment 123, wherein the at least one additional non-human cell adaptation mutation occurs at one or more or both of position 99 or 145 of SEQ ID NO: 7, or at a position corresponding to position 99 or 145 of SEQ ID NO: 7 when aligned to SEQ ID NO: 7 using a pairwise alignment algorithm.

125. The vaccine or immunogenic composition of embodiment 124, wherein the mutation at position 99 of SEQ ID NO: 7, or at a position corresponding to position 99 of SEQ ID NO: 7 when aligned to SEQ ID NO: 7 using a pairwise alignment algorithm, is an aspartic acid to glycine substitution.

126. The vaccine or immunogenic composition of embodiment 124, wherein the mutation at position 145 of SEQ ID NO: 7, or at a position corresponding to position 145 of SEQ ID NO: 7 when aligned to SEQ ID NO: 7 using a pairwise alignment algorithm, is a valine to glutamic acid substitution.

127. The vaccine or immunogenic composition of embodiment 95-126, wherein the one or more antigens comprise the 5' untranslated region (UTR) of CA16, and wherein the 5' UTR of CA16 comprises the at least one non-human cell adaptation mutation.

128. The vaccine or immunogenic composition of 127, wherein the at least one non-human cell adaptation mutation occurs at one or two of positions 6 or 33 of SEQ ID NO: 9, or at position corresponding to position 6 or 33 of SEQ ID NO: 9 when the 5' UTR of CA6 is aligned to SEQ ID NO: 8 using a pairwise alignment algorithm.
129. The vaccine or immunogenic composition of 128, wherein the mutation at position 6 of SEQ ID NO: 9, or at a position corresponding to position 6 of SEQ ID NO: 9 when aligned to SEQ ID NO: 8 using a pairwise alignment algorithm is a guanine to adenine substitution; or the mutation at position 33 of SEQ ID NO: 9, or at a position corresponding to position 33 of SEQ ID NO: 9 when aligned to SEQ ID NO: 8 using a pairwise alignment algorithm is a guanine to cytosine substitution.
130. The vaccine or immunogenic composition of any one of embodiments 87-129, wherein the non-human cell is a mammalian cell.
131. The vaccine or immunogenic composition of any one of embodiments 87-129, wherein the non-human cell is a monkey cell.
132. The vaccine or immunogenic composition of embodiment 131, wherein the monkey cell is a from a Vero cell line.
133. The vaccine or immunogenic composition of embodiment 132, wherein the Vero cell line is selected from WHO Vero 10-87, ATCC CCL-81, Vero 76 (ATCC Accession No. CRL-1587), and Vero C1008 (ATCC Accession No. CRL-1586).
134. The vaccine or immunogenic composition of any one of embodiments 87-133, wherein the one or more antigens were produced by culturing the non-human cell.
135. The vaccine or immunogenic composition of embodiment 134, wherein the cell was cultured in serum-free media.
136. The vaccine or immunogenic composition of any one of embodiments 87-135, wherein the vaccine or immunogenic composition is a purified antigen vaccine or immunogenic composition, a subunit vaccine or immunogenic composition, an inactivated whole virus vaccine or immunogenic composition, or an attenuated virus vaccine or immunogenic composition.
137. The vaccine or immunogenic composition of any one of embodiments 87-136, wherein the at least one virus was inactivated with BPL in combination with formalin.
138. The vaccine or immunogenic composition of embodiment 137, wherein the at least one virus inactivated by formalin comprises one or more modifications.
139. The vaccine or immunogenic composition of embodiment 138, wherein the one or more modifications comprise a modified polypeptide.
140. The vaccine or immunogenic composition of embodiment 138, wherein the one or more modifications comprise a cross-linked polypeptide.
141. The vaccine or immunogenic composition of any one of embodiments 137-140, wherein the vaccine or immunogenic composition further comprises formalin.
142. The vaccine or immunogenic composition of any one of embodiments 87-141, further comprising a detergent in an effective concentration.
143. The vaccine or immunogenic composition of embodiment 142, wherein the detergent comprises polysorbate [80]. 144. The vaccine or immunogenic composition of embodiment 143, wherein the effective concentration ranges from about 0.001% to about 0.01%.
145. The vaccine or immunogenic composition of any one of embodiments 87-144, further comprising an adjuvant.
146. The vaccine or immunogenic composition of embodiment 145, wherein the adjuvant is selected from the group consisting of aluminum salts, toll-like receptor (TLR) agonists, monophosphoryl lipid A (MLA), synthetic lipid A, lipid A mimetics or analogs, MLA derivatives, cytokines, saponins, muramyl dipeptide (MDP) derivatives, CpG oligos, lipopolysaccharide (LPS) of gram-negative bacteria, polyphosphazenes, emulsions, virosomes, cochleates, poly(lactide-co-glycolides) (PLG) microparticles, poloxamer particles, microparticles, liposomes, Complete Freund's Adjuvant (CFA), and Incomplete Freund's Adjuvant (IFA).
147. The vaccine or immunogenic composition of embodiment 146, wherein the adjuvant is an aluminum salt.
148. The vaccine or immunogenic composition of embodiment 146, wherein the adjuvant is selected from alum, aluminum phosphate, aluminum hydroxide, potassium aluminum sulfate, and Alhydrogel 85.
149. The vaccine or immunogenic composition of embodiment 147 or embodiment 148, wherein at least 75%, at least 80%, at least 85%, at least 90%, at 95%, at least 97%, at least 99%, or 100% of the antigen is adsorbed to the adjuvant.
150. The vaccine or immunogenic composition of embodiment 146, wherein the adjuvant is monophoshporyl lipid A (MLA) and derivatives thereof.
151. A method for treating or preventing hand, foot, and mouth disease in a subject in need thereof, comprising administering to the subject a therapeutically effective amount of the vaccine or immunogenic composition of any one of embodiments 87-150.
152. A method for inducing an immune response in a subject in need thereof, comprising administering to the subject an immunogenic amount of the vaccine or immunogenic composition of any one of embodiments 87-150.
153. The method of embodiment 151 or embodiment 152, wherein the administering induces a protective immune response in the subject.
154. The method of embodiment 153, wherein the immune response comprises an immune response against one or more of EV71, CA6, and CA16.
155. The method of embodiment 153, wherein the immune response comprises an immune response against one or more EV71 viral genotypes selected from B4, C2, C4, and C5.
156. The method of any one of embodiments 151-155, wherein the administering is selected from the group consisting of subcutaneous delivery, transcutaneous delivery, intradermal delivery, subdermal delivery, intramuscular delivery, peroral delivery, oral delivery, intranasal delivery, buccal delivery, sublingual delivery, intraperitoneal delivery, intravaginal delivery, anal delivery and intracranial delivery.
157. The method of any one of embodiments 151-156, wherein the administering comprises one or more administrations.
158. A method for inactivating a hand, foot, and mouth virus preparation, comprising:
   (a) isolating the hand, foot, and mouth virus preparation from one or more non-human cells, wherein the cells are used to produce the virus preparation;
   (b) treating the virus preparation with an effective amount of beta-propiolactone (BPL); and
   (c) treating the virus preparation with an effective amount of formalin, wherein the step of treating with formalin occurs currently with step (b) or after step (b), and wherein the virus is selected from one or more of EV71, CA6, and CA16.

159. The method of embodiment 158, wherein the method further comprises heating the virus preparation at a temperature of 37° C. for a period of time sufficient to hydrolyze the BPL.

160. The method of embodiment 159, wherein the period of time ranges from about 1 hour to about 6 hours.

161. The method of any one of embodiments 158-160, wherein the inactivated virus preparation comprises one or more modifications.

162. The method of embodiment 161, wherein the one or more modifications comprise a modified nucleic acid.

163. The method of embodiment 162, wherein the modified nucleic acid is an alkylated nucleic acid.

164. The method of embodiment 161, wherein the one or more modifications comprise a modified polypeptide.

165. The method of embodiment 164, wherein the modified polypeptide comprises a modified amino acid residue are selected from one or more of cysteine, methionine, histidine, aspartic acid, glutamic acid, tyrosine, lysine, serine, and threonine.

166. A hand, foot, and mouth vaccine comprising one or more antigens from at least one inactivated virus that causes hand, foot and mouth disease in humans, wherein the at least one virus is CA6, CA16, or both, and wherein the at least one virus was inactivated with formalin.

167. A hand, foot, and mouth immunogenic composition comprising one or more antigens from at least one inactivated virus that causes hand, foot and mouth disease in humans, wherein the at least one virus is CA6, CA16, or both, and wherein the at least one virus was inactivated with formalin.

168. The vaccine or immunogenic composition of embodiment 166 or embodiment 167, wherein the at least one virus inactivated by formalin comprises one or more modifications.

169. The vaccine or immunogenic composition of embodiment 168, wherein the one or more modifications comprise a modified polypeptide.

170. The vaccine or immunogenic composition of embodiment 168, wherein the one or more modifications comprise a cross-linked polypeptide.

171. The vaccine or immunogenic composition of any one of embodiments 166-170, wherein the vaccine or immunogenic composition further comprises formalin.

172. The vaccine or immunogenic composition of any one of embodiments 166-171, further comprising one or more antigens from EV71.

173. The vaccine or immunogenic composition of embodiment 172, wherein the one or more antigens comprise at least one non-human cell adaptation mutation.

174. The vaccine or immunogenic composition of embodiment 173, wherein the one or more antigens comprise the VP1 polypeptide of EV71, and wherein the VP1 polypeptide comprises the at least one non-human cell adaptation mutation.

175. The vaccine or immunogenic composition of embodiment 174, wherein the at least one non-human cell adaptation mutation occurs at position 7 of SEQ ID NO: 1, or at a position corresponding to position 7 of SEQ ID NO: 1 when aligned to SEQ ID NO: 1 using a pairwise alignment algorithm; or at two or more, three or more, or all four of positions 7, 14, 145, or 282 of SEQ ID NO: 1, or of positions corresponding to positions 7, 14, 145, or 282 of SEQ ID NO: 1 when aligned to SEQ ID NO: 1 using a pairwise alignment algorithm.

176. The vaccine or immunogenic composition of embodiment 175, wherein the mutation at position 7 of SEQ ID NO: 1, or at a position corresponding to position 7 of SEQ ID NO: 1 when aligned to SEQ ID NO: 1 using a pairwise alignment algorithm, is a valine to methionine substitution.

177. The vaccine or immunogenic composition of embodiment 175, wherein the mutation at position 14 of SEQ ID NO: 1, or at a position corresponding to position 14 of SEQ ID NO: 1 when aligned to SEQ ID NO: 1 using a pairwise alignment algorithm, is an aspartic acid to asparagine substitution.

178. There vaccine or immunogenic composition of embodiment 175, wherein the mutation at position 145 of SEQ ID NO: 1, or at a position corresponding to position 145 of SEQ ID NO: 1 when aligned to SEQ ID NO: 1 using a pairwise alignment algorithm, is a glutamic acid to glutamine substitution.

179. The vaccine or immunogenic composition of embodiment 175, wherein the mutation at position 282 of SEQ ID NO: 1, or at a position corresponding to position 282 of SEQ ID NO: 1 when aligned to SEQ ID NO: 1 using a pairwise alignment algorithm, is an asparagine to aspartic acid substitution.

180. The vaccine or immunogenic composition of embodiment 173-179, wherein the one or more antigens comprise the VP1 polypeptide of CA6 and wherein the VP1 polypeptide comprises the at least one non-human cell adaptation mutation.

181. The vaccine or immunogenic composition of embodiment 180, wherein the at least one non-human cell adaptation mutation occurs at one or more, two or more, three or more, or all four of positions 46, 90, 96, or 268 of SEQ ID NO: 2, or of positions corresponding to positions 46, 90, 96, or 268 of SEQ ID NO: 2 when aligned to SEQ ID NO: 2 using a pairwise alignment algorithm.

182. The vaccine or immunogenic composition of embodiment 181, wherein the mutation at position 46 of SEQ ID NO: 2, or at a position corresponding to position 46 of SEQ ID NO: 2 when aligned to SEQ ID NO: 2 using a pairwise alignment algorithm, is an alanine to valine substitution.

183. The vaccine or immunogenic composition of embodiment 181, wherein the mutation at position 90 of SEQ ID NO: 2, or at a position corresponding to position 90 of SEQ ID NO: 2 when aligned to SEQ ID NO: 2 using a pairwise alignment algorithm, is a glutamic acid to lysine substitution.

184. There vaccine or immunogenic composition of embodiment 181, wherein the mutation at position 96 of SEQ ID NO: 2, or at a position corresponding to position 96 of SEQ ID NO: 2 when aligned to SEQ ID NO: 2 using a pairwise alignment algorithm, is a threonine to alanine substitution.

185. The vaccine or immunogenic composition of embodiment 181, wherein the mutation at position 268 of SEQ ID NO: 2, or at a position corresponding to position 268 of SEQ ID NO: 2 when aligned to SEQ ID NO: 2 using a pairwise alignment algorithm, is a valine to isoleucine substitution.

186. The vaccine or immunogenic composition of embodiment 173-185, wherein the one or more antigens comprise the VP2 polypeptide of CA6, and where in the VP2 polypeptide comprises the at least one non-human cell adaptation mutation.

187. The vaccine or immunogenic composition of embodiment 186, wherein the at least one non-human cell adaptation mutation occurs at position 144 of SEQ ID NO: 3, or at a position corresponding to position 144 of SEQ ID NO: 3 when aligned to SEQ ID NO: 3 using a pairwise alignment algorithm.
188. The vaccine or immunogenic composition of embodiment 187, wherein the mutation at position 144 of SEQ ID NO: 3, or at a position corresponding to position 144 of SEQ ID NO: 3 when aligned to SEQ ID NO: 3 using a pairwise alignment algorithm, is a glutamine to lysine substitution.
189. The vaccine or immunogenic composition of embodiment 173-188, wherein the one or more antigens comprise the VP3 polypeptide of CA6, and wherein the VP3 polypeptide comprises the at least one non-human cell adaptation mutation.
190. The vaccine or immunogenic composition of embodiment 189, wherein the at least one non-human cell adaptation mutation occurs at position 102 of SEQ ID NO: 4, or at a position corresponding to position 102 of SEQ ID NO: 4 when aligned to SEQ ID NO: 4 using a pairwise alignment algorithm.
191. The vaccine or immunogenic composition of embodiment 190, wherein the mutation at position 102 of SEQ ID NO: 4, or at a position corresponding to position 102 of SEQ ID NO: 4 when aligned to SEQ ID NO: 4 using a pairwise alignment algorithm, is an isoleucine to valine substitution.
192. The vaccine or immunogenic composition of embodiment 173-191, wherein the one or more antigens comprise the 5' untranslated region (UTR) of CA6, and wherein the 5' UTR of CA6 comprises the at least one non-human cell adaptation mutation.
193. The vaccine or immunogenic composition of embodiment 192, wherein the at least one non-human cell adaptation mutation occurs at one or more, two or more, three or more, four or more, five or more, six or more, seven or more, eight or more, or all nine nucleic acid positions 1, 13, 14, 15, 16, 21, 23, 34, or 40 of SEQ ID NO: 8, or at position corresponding to position 1, 13, 14, 15, 16, 21, 23, 34, or 40 of SEQ ID NO: 8 when the 5' UTR of CA6 is aligned to SEQ ID NO: 8 using a pairwise alignment algorithm.

194. The vaccine or immunogenic composition of embodiment 193, wherein the mutation at position 1 of SEQ ID NO: 8, or at a position corresponding to position 1 of SEQ ID NO: 8 when aligned to SEQ ID NO: 8 using a pairwise alignment algorithm, is a thymine to guanine substitution; the mutation at position 13 of SEQ ID NO: 8, or at a position corresponding to position 13 of SEQ ID NO: 8 when aligned to SEQ ID NO: 8 using a pairwise alignment algorithm, is a guanine to adenine substitution; the mutation at position 14 of SEQ ID NO: 8, or at a position corresponding to position 14 of SEQ ID NO: 8 when aligned to SEQ ID NO: 8 using a pairwise alignment algorithm, is a thymine to guanine substitution; the mutation at position 15 of SEQ ID NO: 8, or at a position corresponding to position 15 of SEQ ID NO: 8 when aligned to SEQ ID NO: 8 using a pairwise alignment algorithm, is a guanine to cytosine substitution; the mutation at position 16 of SEQ ID NO: 8, or at a position corresponding to position 16 of SEQ ID NO: 8 when aligned to SEQ ID NO: 8 using a pairwise alignment algorithm, is a guanine to adenine substitution; the mutation at position 21 of SEQ ID NO: 8, or at a position corresponding to position 21 of SEQ ID NO: 8 when aligned to SEQ ID NO: 8 using a pairwise alignment algorithm, is a cytosine to thymine substitution; the mutation at position 23 of SEQ ID NO: 8, or at a position corresponding to position 23 of SEQ ID NO: 8 when aligned to SEQ ID NO: 8 using a pairwise alignment algorithm, is a cytosine to thymine substitution; the mutation at position 34 of SEQ ID NO: 8, or at a position corresponding to position 34 of SEQ ID NO: 8 when aligned to SEQ ID NO: 8 using a pairwise alignment algorithm, is a guanine to thymine substitution; or the mutation at position 40 of SEQ ID NO: 8, or at a position corresponding to position 40 of SEQ ID NO: 8 when aligned to SEQ ID NO: 8 using a pairwise alignment algorithm, is a cytosine to guanine substitution.

195. The vaccine or immunogenic composition of embodiment 173-194, wherein the one or more antigens comprise the 2A polypeptide of CA16, and wherein the 2A polypeptide comprises the at least one non-human cell adaptation mutation.

196. The vaccine or immunogenic composition of embodiment 195, wherein the at least one non-human cell adaptation mutation occurs at position 2 of SEQ ID NO: 5, or at a position corresponding to position 2 of SEQ ID NO: 5 when aligned to SEQ ID NO: 5 using a pairwise alignment algorithm 197. The vaccine or immunogenic composition of embodiment 196, wherein the mutation at position 2 of SEQ ID NO: 5, or at a position corresponding to position 2 of SEQ ID NO: 5 when aligned to SEQ ID NO: 5 using a pairwise alignment algorithm, is a lysine to glutamic acid substitution.

198. The vaccine or immunogenic composition of embodiment 173-197, wherein the one or more antigens comprise the VP2 polypeptide of CA16, and wherein the VP2 polypeptide comprises the at least one non-human cell adaptation mutation.

199. The vaccine or immunogenic composition of embodiment 198, wherein the at least one non-human cell adaptation mutation occurs at position 161 of SEQ ID NO: 6, or at a position corresponding to position 161 of SEQ ID NO: 6 when aligned to SEQ ID NO: 6 using a pairwise alignment algorithm.

200. The vaccine or immunogenic composition of embodiment 199, wherein the mutation at position 161 of SEQ ID NO: 6, or at a position corresponding to position 161 of SEQ ID NO: 6 when aligned to SEQ ID NO: 6 using a pairwise alignment algorithm, is a methionine to threonine substitution.

201. The vaccine or immunogenic composition of any one of embodiments 195-200, further comprising at least one additional non-human cell adaptation mutation in the VP1 polypeptide of CA16.

202. The vaccine or immunogenic composition of embodiment 201, wherein the at least one additional non-human cell adaptation mutation occurs at one or more or both of position 99 or 145 of SEQ ID NO: 7, or at a position corresponding to position 99 or 145 of SEQ ID NO: 7 when aligned to SEQ ID NO: 7 using a pairwise alignment algorithm.

203. The vaccine or immunogenic composition of embodiment 202, wherein the mutation at position 99 of SEQ ID NO: 7, or at a position corresponding to position 99 of SEQ ID NO: 7 when aligned to SEQ ID NO: 7 using a pairwise alignment algorithm, is an aspartic acid to glycine substitution.

204. The vaccine or immunogenic composition of embodiment 202, wherein the mutation at position 145 of SEQ ID NO: 7, or at a position corresponding to position 145 of SEQ ID NO: 7 when aligned to SEQ ID NO: 7 using a pairwise alignment algorithm, is a valine to glutamic acid substitution.
205. The vaccine or immunogenic composition of embodiment 173-204, wherein the one or more antigens comprise the 5' untranslated region (UTR) of CA16, and wherein the 5' UTR of CA16 comprises the at least one non-human cell adaptation mutation.
206. The vaccine or immunogenic composition of embodiment 205, wherein the at least one non-human cell adaptation mutation occurs at one or two of positions 6 or 33 of SEQ ID NO: 9, or at position corresponding to position 6 or 33 of SEQ ID NO: 9 when the 5' UTR of CA6 is aligned to SEQ ID NO: 8 using a pairwise alignment algorithm.
207. The vaccine or immunogenic composition of embodiment 206, wherein the mutation at position 6 of SEQ ID NO: 9, or at a position corresponding to position 6 of SEQ ID NO: 9 when aligned to SEQ ID NO: 8 using a pairwise alignment algorithm is a guanine to adenine substitution; or the mutation at position 33 of SEQ ID NO: 9, or at a position corresponding to position 33 of SEQ ID NO: 9 when aligned to SEQ ID NO: 8 using a pairwise alignment algorithm is a guanine to cytosine substitution.
208. The vaccine or immunogenic composition of any one of embodiments 166-207, wherein the non-human cell is a mammalian cell.
209. The vaccine or immunogenic composition of any one of embodiments 166-207, wherein the non-human cell is a monkey cell.
210. The vaccine or immunogenic composition of embodiment 209, wherein the monkey cell is a from a Vero cell line.
211. The vaccine or immunogenic composition of embodiment 210, wherein the Vero cell line is selected from WHO Vero 10-87, ATCC CCL-81, Vero 76 (ATCC Accession No. CRL-1587), and Vero C1008 (ATCC Accession No. CRL-1586).
212. The vaccine or immunogenic composition of any one of embodiments 166-211 wherein the one or more antigens were produced by culturing the non-human cell.
213. The vaccine or immunogenic composition of embodiment 212, wherein the cell was cultured in serum-free media.
214. The vaccine or immunogenic composition of any one of embodiments 166-213, wherein the vaccine or immunogenic composition is a purified antigen vaccine or immunogenic composition, a subunit vaccine or immunogenic composition, an inactivated whole virus vaccine or immunogenic composition, or an attenuated virus vaccine or immunogenic composition.
215. The vaccine or immunogenic composition of any one of embodiments 166-214, wherein the at least one virus was inactivated with formalin in combination with BPL.
216. The vaccine or immunogenic composition of embodiment 215, wherein the at least one virus inactivated by BPL comprises one or more modifications.
217. The vaccine or immunogenic composition of embodiment 216, wherein the one or more modifications comprise a modified nucleic acid.
218. The vaccine or immunogenic composition of embodiment 217, wherein the modified nucleic acid is an alkylated nucleic acid.
219. The vaccine or immunogenic composition of embodiment 216, wherein the one or more modifications comprise a modified polypeptide.
220. The vaccine or immunogenic composition of embodiment 219, wherein the modified polypeptide comprises a modified amino acid residue are selected from one or more of cysteine, methionine, histidine, aspartic acid, glutamic acid, tyrosine, lysine, serine, and threonine.
221. The vaccine or immunogenic composition of any one of embodiments 166-215, further comprising a detergent in an effective concentration.
222. The vaccine or immunogenic composition of embodiment 221, wherein the detergent comprises polysorbate [80].
223. The vaccine or immunogenic composition of embodiment 222, wherein the effective concentration ranges from about 0.001% to about 0.01%.
224. The vaccine or immunogenic composition of any one of embodiments 166-223, further comprising an adjuvant.
225. The vaccine or immunogenic composition of embodiment 224, wherein the adjuvant is selected from the group consisting of aluminum salts, toll-like receptor (TLR) agonists, monophosphoryl lipid A (MLA), synthetic lipid A, lipid A mimetics or analogs, MLA derivatives, cytokines, saponins, muramyl dipeptide (MDP) derivatives, CpG oligos, lipopolysaccharide (LPS) of gram-negative bacteria, polyphosphazenes, emulsions, virosomes, cochleates, poly(lactide-co-glycolides) (PLG) microparticles, poloxamer particles, microparticles, liposomes, Complete Freund's Adjuvant (CFA), and Incomplete Freund's Adjuvant (IFA).
226. The vaccine or immunogenic composition of embodiment 225, wherein the adjuvant is an aluminum salt.
227. The vaccine or immunogenic composition of embodiment 225, wherein the adjuvant is selected from alum, aluminum phosphate, aluminum hydroxide, potassium aluminum sulfate, and Alhydrogel 85.
228. The vaccine or immunogenic composition of embodiment 226 or embodiment 227, wherein at least 75%, at least 80%, at least 85%, at least 90%, at 95%, at least 97%, at least 99%, or 100% of the antigen is adsorbed to the adjuvant.
229. The vaccine or immunogenic composition of embodiment 225, wherein the adjuvant is monophoshporyl lipid A (MLA) and derivatives thereof.
230. A method for treating or preventing hand, foot, and mouth disease in a subject in need thereof, comprising administering to the subject a therapeutically effective amount of the vaccine or immunogenic composition of any one of embodiments 166-229.
231. A method for inducing an immune response in a subject in need thereof, comprising administering to the subject an immunogenic amount of the vaccine or immunogenic composition of any one of embodiments 166-229.
232. The method of embodiment 230 or embodiment 231, wherein the administering induces a protective immune response in the subject.
233. The method of embodiment 232, wherein the immune response comprises an immune response against one or more of EV71, CA6, and CA16.
234. The method of embodiment 232, wherein the immune response comprises an immune response against one or more EV71 viral genotypes selected from B4, C2, C4, and C5.
235. The method of any one of embodiments 230-234, wherein the administering is selected from the group consisting of subcutaneous delivery, transcutaneous delivery, intradermal delivery, subdermal delivery, intramuscular delivery, peroral delivery, oral delivery, intranasal delivery, buccal delivery, sublingual delivery, intraperitoneal delivery, intravaginal delivery, anal delivery and intracranial delivery.

236. The method of any one of embodiments 230-235, wherein the administering comprises one or more administrations.

237. A method for inactivating a hand, foot, and mouth virus preparation, comprising:
(a) isolating the hand, foot, and mouth virus preparation from one or more non-human cells, wherein the cells are used to produce the virus preparation;
(b) treating the virus preparation with an effective amount of formalin; and
(c) purifying the virus preparation from the formalin wherein the virus is selected from one or more of EV71, CA6, and CA16.

238. The method of embodiment 237, wherein the inactivated virus preparation comprises one or more modifications.

239. The method of embodiment 238, wherein the one or more modifications comprise a modified polypeptide.

240. The method of embodiment 238, wherein the one or more modifications comprise a cross-linked polypeptide.

241. The method of any one of embodiments 237-240, wherein the vaccine or immunogenic composition further comprises formalin.

242. A hand, foot, and mouth vaccine comprising one or more antigens from at least one virus that causes hand, foot and mouth disease in humans and an aluminum salt adjuvant, wherein at least 75%, at least 80%, at least 85%, at least 90%, at 95%, at least 97%, at least 99%, or 100% of the antigen is adsorbed to the aluminum salt adjuvant.

243. A hand, foot, and mouth immunogenic composition comprising one or more antigens from at least one virus that causes hand, foot and mouth disease in humans and an aluminum salt adjuvant, wherein at least 75%, at least 80%, at least 85%, at least 90%, at 95%, at least 97%, at least 99%, or 100% of the antigen is adsorbed to the aluminum salt adjuvant.

244. The vaccine or immunogenic composition of embodiment 242 or embodiment 243, wherein the adjuvant is selected from alum, aluminum phosphate, aluminum hydroxide, potassium aluminum sulfate, and Alhydrogel 85.

245. The vaccine or immunogenic composition of any one of embodiments 242-244, wherein the at least one virus is selected from one or more of EV71, CA6, and CA16.

246. The vaccine or immunogenic composition of any one of embodiments 242-244, wherein the at least one virus comprises EV71, CA6, and CA16.

247. The vaccine or immunogenic composition of any one of embodiments 242-244, wherein the at least one virus comprises EV71 and CA6.

248. The vaccine or immunogenic composition of any one of embodiments 242-244, wherein the at least one virus comprises EV71 and CA16.

249. The vaccine or immunogenic composition of any one of embodiments 242-244, wherein the at least one virus comprises CA6 and CA16.

250. The vaccine or immunogenic composition of any one of embodiments 242-244, wherein the at least one virus is EV71.

251. The vaccine or immunogenic composition of any one of embodiments 242-244, wherein the one or more antigens are selected from EV71, CA6, CA16, and any combination thereof.

252. The vaccine or immunogenic composition of embodiment 251, wherein the one or more antigens are from EV71.

253. The vaccine or immunogenic composition of any one of embodiments 242-252, wherein the one or more antigens comprise at least one non-human cell adaptation mutation.

254. The vaccine or immunogenic composition of embodiment 253, wherein the one or more antigens comprise the VP1 polypeptide of EV71, and wherein the VP1 polypeptide comprises the at least one non-human cell adaptation mutation.

255. The vaccine or immunogenic composition of embodiment 254, wherein the at least one non-human cell adaptation mutation occurs at position 7 of SEQ ID NO: 1, or at a position corresponding to position 7 of SEQ ID NO: 1 when aligned to SEQ ID NO: 1 using a pairwise alignment algorithm; or at two or more, three or more, or all four of positions 7, 14, 145, or 282 of SEQ ID NO: 1, or of positions corresponding to positions 7, 14, 145, or 282 of SEQ ID NO: 1 when aligned to SEQ ID NO: 1 using a pairwise alignment algorithm.

256. The vaccine or immunogenic composition of embodiment 255, wherein the mutation at position 7 of SEQ ID NO: 1, or at a position corresponding to position 7 of SEQ ID NO: 1 when aligned to SEQ ID NO: 1 using a pairwise alignment algorithm, is a valine to methionine substitution.

257. The vaccine or immunogenic composition of embodiment 255, wherein the mutation at position 14 of SEQ ID NO: 1, or at a position corresponding to position 14 of SEQ ID NO: 1 when aligned to SEQ ID NO: 1 using a pairwise alignment algorithm, is an aspartic acid to asparagine substitution.

258. There vaccine or immunogenic composition of embodiment 255, wherein the mutation at position 145 of SEQ ID NO: 1, or at a position corresponding to position 145 of SEQ ID NO: 1 when aligned to SEQ ID NO: 1 using a pairwise alignment algorithm, is a glutamic acid to glutamine substitution.

259. The vaccine or immunogenic composition of embodiment 255, wherein the mutation at position 282 of SEQ ID NO: 1, or at a position corresponding to position 282 of SEQ ID NO: 1 when aligned to SEQ ID NO: 1 using a pairwise alignment algorithm, is an asparagine to aspartic acid substitution.

260. The vaccine or immunogenic composition of embodiment 253-259, wherein the one or more antigens comprise the VP1 polypeptide of CA6 and wherein the VP1 polypeptide comprises the at least one non-human cell adaptation mutation.

261. The vaccine or immunogenic composition of embodiment 260, wherein the at least one non-human cell adaptation mutation occurs at one or more, two or more, three or more, or all four of positions 46, 90, 96, or 268 of SEQ ID NO: 2, or of positions corresponding to positions 46, 90, 96, or 268 of SEQ ID NO: 2 when aligned to SEQ ID NO: 2 using a pairwise alignment algorithm.

262. The vaccine or immunogenic composition of embodiment 261, wherein the mutation at position 46 of SEQ ID NO: 2, or at a position corresponding to position 46 of SEQ ID NO: 2 when aligned to SEQ ID NO: 2 using a pairwise alignment algorithm, is an alanine to valine substitution.

263. The vaccine or immunogenic composition of embodiment 261, wherein the mutation at position 90 of SEQ ID NO: 2, or at a position corresponding to position 90 of SEQ ID NO: 2 when aligned to SEQ ID NO: 2 using a pairwise alignment algorithm, is a glutamic acid to lysine substitution.

264. There vaccine or immunogenic composition of embodiment 261, wherein the mutation at position 96 of SEQ ID NO: 2, or at a position corresponding to position 96 of SEQ ID NO: 2 when aligned to SEQ ID NO: 2 using a pairwise alignment algorithm, is a threonine to alanine substitution.

265. The vaccine or immunogenic composition of embodiment 261, wherein the mutation at position 268 of SEQ ID NO: 2, or at a position corresponding to position 268 of SEQ ID NO: 2 when aligned to SEQ ID NO: 2 using a pairwise alignment algorithm, is a valine to isoleucine substitution.

266. The vaccine or immunogenic composition of embodiment 253-265, wherein the one or more antigens comprise the VP2 polypeptide of CA6, and where in the VP2 polypeptide comprises the at least one non-human cell adaptation mutation.

267. The vaccine or immunogenic composition of embodiment 266, wherein the at least one non-human cell adaptation mutation occurs at position 144 of SEQ ID NO: 3, or at a position corresponding to position 144 of SEQ ID NO: 3 when aligned to SEQ ID NO: 3 using a pairwise alignment algorithm.

268. The vaccine or immunogenic composition of embodiment 267, wherein the mutation at position 144 of SEQ ID NO: 3, or at a position corresponding to position 144 of SEQ ID NO: 3 when aligned to SEQ ID NO: 3 using a pairwise alignment algorithm, is a glutamine to lysine substitution.

269. The vaccine or immunogenic composition of embodiment 253-268, wherein the one or more antigens comprise the VP3 polypeptide of CA6, and wherein the VP3 polypeptide comprises the at least one non-human cell adaptation mutation.

270. The vaccine or immunogenic composition of embodiment 269, wherein the at least one non-human cell adaptation mutation occurs at position 102 of SEQ ID NO: 4, or at a position corresponding to position 102 of SEQ ID NO: 4 when aligned to SEQ ID NO: 4 using a pairwise alignment algorithm.

271. The vaccine or immunogenic composition of embodiment 270, wherein the mutation at position 102 of SEQ ID NO: 4, or at a position corresponding to position 102 of SEQ ID NO: 4 when aligned to SEQ ID NO: 4 using a pairwise alignment algorithm, is an isoleucine to valine substitution.

272. The vaccine or immunogenic composition of embodiment 253-271, wherein the one or more antigens comprise the 5' untranslated region (UTR) of CA6, and wherein the 5' UTR of CA6 comprises the at least one non-human cell adaptation mutation.

273. The vaccine or immunogenic composition of embodiment 272, wherein the at least one non-human cell adaptation mutation occurs at one or more, two or more, three or more, four or more, five or more, six or more, seven or more, eight or more, or all nine nucleic acid positions 1, 13, 14, 15, 16, 21, 23, 34, or 40 of SEQ ID NO: 8, or at position corresponding to position 1, 13, 14, 15, 16, 21, 23, 34, or 40 of SEQ ID NO: 8 when the 5' UTR of CA6 is aligned to SEQ ID NO: 8 using a pairwise alignment algorithm.

274. The vaccine or immunogenic composition of embodiment 273, wherein the mutation at position 1 of SEQ ID NO: 8, or at a position corresponding to position 1 of SEQ ID NO: 8 when aligned to SEQ ID NO: 8 using a pairwise alignment algorithm, is a thymine to guanine substitution; the mutation at position 13 of SEQ ID NO: 8, or at a position corresponding to position 13 of SEQ ID NO: 8 when aligned to SEQ ID NO: 8 using a pairwise alignment algorithm, is a guanine to adenine substitution; the mutation at position 14 of SEQ ID NO: 8, or at a position corresponding to position 14 of SEQ ID NO: 8 when aligned to SEQ ID NO: 8 using a pairwise alignment algorithm, is a thymine to guanine substitution; the mutation at position 15 of SEQ ID NO: 8, or at a position corresponding to position 15 of SEQ ID NO: 8 when aligned to SEQ ID NO: 8 using a pairwise alignment algorithm, is a guanine to cytosine substitution; the mutation at position 16 of SEQ ID NO: 8, or at a position corresponding to position 16 of SEQ ID NO: 8 when aligned to SEQ ID NO: 8 using a pairwise alignment algorithm, is a guanine to adenine substitution; the mutation at position 21 of SEQ ID NO: 8, or at a position corresponding to position 21 of SEQ ID NO: 8 when aligned to SEQ ID NO: 8 using a pairwise alignment algorithm, is a cytosine to thymine substitution; the mutation at position 23 of SEQ ID NO: 8, or at a position corresponding to position 23 of SEQ ID NO: 8 when aligned to SEQ ID NO: 8 using a pairwise alignment algorithm, is a cytosine to thymine substitution; the mutation at position 34 of SEQ ID NO: 8, or at a position corresponding to position 34 of SEQ ID NO: 8 when aligned to SEQ ID NO: 8 using a pairwise alignment algorithm, is a guanine to thymine substitution; or the mutation at position 40 of SEQ ID NO: 8, or at a position corresponding to position 40 of SEQ ID NO: 8 when aligned to SEQ ID NO: 8 using a pairwise alignment algorithm, is a cytosine to guanine substitution.

275. The vaccine or immunogenic composition of embodiment 253-274, wherein the one or more antigens comprise the 2A polypeptide of CA16, and wherein the 2A polypeptide comprises the at least one non-human cell adaptation mutation.

276. The vaccine or immunogenic composition of embodiment 275, wherein the at least one non-human cell adaptation mutation occurs at position 2 of SEQ ID NO: 5, or at a position corresponding to position 2 of SEQ ID NO: 5 when aligned to SEQ ID NO: 5 using a pairwise alignment algorithm.

277. The vaccine or immunogenic composition of embodiment 276, wherein the mutation at position 2 of SEQ ID NO: 5, or at a position corresponding to position 2 of SEQ ID NO: 5 when aligned to SEQ ID NO: 5 using a pairwise alignment algorithm, is a lysine to glutamic acid substitution.

278. The vaccine or immunogenic composition of embodiment 253-277, wherein the one or more antigens comprise the VP2 polypeptide of CA16, and wherein the VP2 polypeptide comprises the at least one non-human cell adaptation mutation.

279. The vaccine or immunogenic composition of embodiment 278, wherein the at least one non-human cell adaptation mutation occurs at position 161 of SEQ ID NO: 6, or at a position corresponding to position 161 of SEQ ID NO: 6 when aligned to SEQ ID NO: 6 using a pairwise alignment algorithm.

280. The vaccine or immunogenic composition of embodiment 279, wherein the mutation at position 161 of SEQ ID NO: 6, or at a position corresponding to position 161 of SEQ ID NO: 6 when aligned to SEQ ID NO: 6 using a pairwise alignment algorithm, is a methionine to threonine substitution.

281. The vaccine or immunogenic composition of any one of embodiments 275-280, further comprising at least one additional non-human cell adaptation mutation in the VP1 polypeptide of CA16.
282. The vaccine or immunogenic composition of embodiment 281, wherein the at least one additional non-human cell adaptation mutation occurs at one or more or both of position 99 or 145 of SEQ ID NO: 7, or at a position corresponding to position 99 or 145 of SEQ ID NO: 7 when aligned to SEQ ID NO: 7 using a pairwise alignment algorithm.
283. The vaccine or immunogenic composition of embodiment 282, wherein the mutation at position 99 of SEQ ID NO: 7, or at a position corresponding to position 99 of SEQ ID NO: 7 when aligned to SEQ ID NO: 7 using a pairwise alignment algorithm, is an aspartic acid to glycine substitution.
284. The vaccine or immunogenic composition of embodiment 282, wherein the mutation at position 145 of SEQ ID NO: 7, or at a position corresponding to position 145 of SEQ ID NO: 7 when aligned to SEQ ID NO: 7 using a pairwise alignment algorithm, is a valine to glutamic acid substitution.
285. The vaccine or immunogenic composition of embodiment 253-284, wherein the one or more antigens comprise the 5' untranslated region (UTR) of CA16, and wherein the 5' UTR of CA16 comprises the at least one non-human cell adaptation mutation.
286. The vaccine or immunogenic composition of embodiment 285, wherein the at least one non-human cell adaptation mutation occurs at one or two of positions 6 or 33 of SEQ ID NO: 9, or at position corresponding to position 6 or 33 of SEQ ID NO: 9 when the 5' UTR of CA6 is aligned to SEQ ID NO: 8 using a pairwise alignment algorithm.
287. The vaccine or immunogenic composition of embodiment 286, wherein the mutation at position 6 of SEQ ID NO: 9, or at a position corresponding to position 6 of SEQ ID NO: 9 when aligned to SEQ ID NO: 8 using a pairwise alignment algorithm is a guanine to adenine substitution; or the mutation at position 33 of SEQ ID NO: 9, or at a position corresponding to position 33 of SEQ ID NO: 9 when aligned to SEQ ID NO: 8 using a pairwise alignment algorithm is a guanine to cytosine substitution.
288. The vaccine or immunogenic composition of any one of embodiments 242-287, wherein the non-human cell is a mammalian cell.
289. The vaccine or immunogenic composition of any one of embodiments 242-287, wherein the non-human cell is a monkey cell.
290. The vaccine or immunogenic composition of embodiment 289, wherein the monkey cell is a from a Vero cell line.
291. The vaccine or immunogenic composition of embodiment 290, wherein the Vero cell line is selected from WHO Vero 10-87, ATCC CCL-81, Vero 76 (ATCC Accession No. CRL-1587), and Vero C1008 (ATCC Accession No. CRL-1586).
292. The vaccine or immunogenic composition of any one of embodiments 242-291, wherein the one or more antigens were produced by culturing the non-human cell.
293. The vaccine or immunogenic composition of embodiment 292, wherein the cell was cultured in serum-free media.
294. The vaccine or immunogenic composition of any one of embodiments 242-293, wherein the vaccine or immunogenic composition is a purified antigen vaccine or immunogenic composition, a subunit vaccine or immunogenic composition, or an attenuated virus vaccine or immunogenic composition.
295. The vaccine or immunogenic composition of any one of embodiments 242-294, wherein the at least one virus was chemically inactivated.
296. The vaccine or immunogenic composition of embodiment 295, wherein the at least one virus was chemically inactivated with one or more of beta-propiolactone (BPL), formalin, or binary ethylenimine (BEI).
297. The vaccine or immunogenic composition of embodiment 295, wherein the at least one virus was chemically inactivated with BPL.
298. The vaccine or immunogenic composition of embodiment 295, wherein the at least one virus was chemically inactivated with formalin.
299. The vaccine or immunogenic composition of embodiment 295, wherein the at least one virus was chemically inactivated with a combination of BPL and formalin.
300. The vaccine or immunogenic composition of any one of embodiments 296, 297, or 299, wherein the at least one virus inactivated by BPL comprises one or more modifications.
301. The vaccine or immunogenic composition of embodiment 300, wherein the one or more modifications comprise a modified nucleic acid.
302. The vaccine or immunogenic composition of embodiment 301, wherein the modified nucleic acid is an alkylated nucleic acid.
303. The vaccine or immunogenic composition of embodiment 300, wherein the one or more modifications comprise a modified polypeptide.
304. The vaccine or immunogenic composition of embodiment 303, wherein the modified polypeptide comprises a modified amino acid residue are selected from one or more of cysteine, methionine, histidine, aspartic acid, glutamic acid, tyrosine, lysine, serine, and threonine.
305. The vaccine or immunogenic composition of any one of embodiments 296, 298, or 299, wherein the at least one virus inactivated by formalin comprises one or more modifications.
306. The vaccine or immunogenic composition of embodiment 305, wherein the one or more modifications comprise a modified polypeptide.
307. The vaccine or immunogenic composition of embodiment 305, wherein the one or more modifications comprise a cross-linked polypeptide.
308. The vaccine or immunogenic composition of any one of embodiments 305-307, wherein the vaccine or immunogenic composition further comprises formalin.
309. The vaccine or immunogenic composition of embodiment 295, wherein the at least one virus was chemically inactivated with BEI.
310. The vaccine or immunogenic composition of embodiment 296 or embodiment 309, wherein the at least one virus inactivated by BEI comprises one or more modifications.
311. The vaccine or immunogenic composition of embodiment 310, wherein the one or more modifications comprise a modified nucleic acid.
312. The vaccine or immunogenic composition of embodiment 311, wherein the modified nucleic acid is an alkylated nucleic acid.

313. The vaccine or immunogenic composition of any one of embodiments 309-312, wherein unreacted BEI was hydrolyzed with sodium thiosulfate.

314. The vaccine or immunogenic composition of any one of embodiments 242-313, further comprising a detergent in an effective concentration.

315. The vaccine or immunogenic composition of embodiment 314, wherein the detergent comprises polysorbate [80].

316. The vaccine or immunogenic composition of embodiment 315, wherein the effective concentration is from about 0.001% to about 0.01%.

317. The vaccine or immunogenic composition of any one of embodiments 242-316, further comprising at least one additional adjuvant.

318. The vaccine or immunogenic composition of embodiment 317, wherein the at least one additional adjuvant is selected from the group consisting of toll-like receptor (TLR) agonists, monophosphoryl lipid A (MLA), synthetic lipid A, lipid A mimetics or analogs, MLA derivatives, cytokines, saponins, muramyl dipeptide (MDP) derivatives, CpG oligos, lipopolysaccharide (LPS) of gram-negative bacteria, polyphosphazenes, emulsions, virosomes, cochleates, poly(lactide-co-glycolides) (PLG) microparticles, poloxamer particles, microparticles, liposomes, Complete Freund's Adjuvant (CFA), and Incomplete Freund's Adjuvant (IFA).

319. A method for treating or preventing hand, foot, and mouth disease in a subject in need thereof, comprising administering to the subject a therapeutically effective amount of the vaccine or immunogenic composition of any one of embodiments 242-318.

320. A method for inducing an immune response in a subject in need thereof, comprising administering to the subject an immunogenic amount of the vaccine or immunogenic composition of any one of embodiments 242-318.

321. The method of embodiment 319 or embodiment 320, wherein the administering induces a protective immune response in the subject.

322. The method of embodiment 321, wherein the immune response comprises an immune response against one or more of EV71, CA6, and CA16.

323. The method of embodiment 321, wherein the immune response comprises an immune response against one or more EV71 viral genotypes selected from B4, C2, C4, and C5.

324. The method of any one of embodiments 319-323, wherein the administering is selected from the group consisting of subcutaneous delivery, transcutaneous delivery, intradermal delivery, subdermal delivery, intramuscular delivery, peroral delivery, oral delivery, intranasal delivery, buccal delivery, sublingual delivery, intraperitoneal delivery, intravaginal delivery, anal delivery and intracranial delivery.

325. The method of any one of embodiments 319-324, wherein the administering comprises one or more administrations.

326. A method for preparing an adjuvanted hand, foot, and mouth vaccine, comprising:
(a) mixing the vaccine with an aluminum salt adjuvant, wherein the vaccine comprises one or more antigens from at least one virus that causes hand, foot and mouth disease in humans; and
(b) incubating the mixture under suitable conditions for a period of time that ranges from about 16 hours to about 24 hours,
wherein at least 75%, at least 80%, at least 85%, at least 90%, at 95%, at least 97%, at least 99%, or 100% of the antigen is adsorbed to the aluminum salt adjuvant, and wherein the at least one virus that causes hand, foot and mouth disease is selected from one or more of EV71, CA6, and CA16.

327. A method for preparing an adjuvanted hand, foot, and mouth immunogenic composition, comprising:
(a) mixing the immunogenic composition with an aluminum salt adjuvant, wherein the immunogenic composition comprises one or more antigens from at least one virus that causes hand, foot and mouth disease in humans; and
(b) incubating the mixture under suitable conditions for a period of time that ranges from about 16 hours to about 24 hours,
wherein at least 75%, at least 80%, at least 85%, at least 90%, at 95%, at least 97%, at least 99%, or 100% of the antigen is adsorbed to the aluminum salt adjuvant, and wherein the at least one virus that causes hand, foot and mouth disease is selected from one or more of EV71, CA6, and CA16.

328. The method of embodiment 326 or embodiment 327, wherein the mixture is incubated at a temperature that ranges from about 2° C. to about 8° C.

329. The method of any one of embodiments 326-328, wherein the adjuvant is selected from alum, aluminum phosphate, aluminum hydroxide, potassium aluminum sulfate, and Alhydrogel 85.

The present disclosure will be more fully understood by reference to the following Examples. They should not, however, be construed as limiting any aspect or scope of the present disclosure in any way.

EXAMPLES

Example 1: Adaptation of EV71 in Vero Cells

Enterovirus 71 (EV71) was subjected to two rounds of whole virus genome RNA extraction and transfection in Vero cells, followed by two rounds of plaque purification, yielding a novel, adapted strain of sub-genogroup B2 EV71 as described below. Sequencing of the viral genome identified four adaptive mutations in the VP1 polypeptide. The adapted virus was used to generate a pre-Master Virus Seed (pre-MVS) for subsequent use in manufacture of an EV71 vaccine.

Source Viral Strain

The EV71/7423/MS/87 strain viral seed used to prepare the adapted virus was obtained from the John Hopkins's Institute, Singapore. [GenBank Accession No. U22522].

Vero Cell Line

The Vero cell line used for EV71/7423/MS/87 strain adaptation and viral production was derived from Vero cell line WHO Vero 10-87, which is derived from the ATCC CCL-81 Vero cell line.

Transfection and Plaque Purification

The EV71 virus seed obtained from the John Hopkins's Institute, Singapore was used to infect 80% confluent monolayers of Vero cells in T25 flasks grown in Eagle's minimal essential media (MEM) plus 10% Fetal Bovine Serum (FBS). The FBS used in all procedures involving EV71 propagation was obtained from an Australian source to minimize the risk of raw material derived transmissible spongiform encephalopathies. After adsorption of 1.5h, the virus supernatant was aspirated and MEM plus 2% FBS media was added. On days 3 and 6 after infection, when cytopathic effect (CPE) was observed, the virus supernatant was harvested. The virus harvest on Day 6 was further amplified in Vero cells (four additional passages) using a similar procedure.

Viral RNA was extracted using the Roche High Pure Viral RNA kit for recovery of EV71 virus and RNA transfection. Vero cells from SVCR0059 were grown in MEM containing 10% FBS, seeded onto 6-well plates at 5×105 cells/well, and incubated at 36±1° C. for one day. Following this incubation, the cells in each well had grown to >90% confluency. EV71 whole genome RNA was transfected into the Vero cells using the Qiagen TransMessenger™ Transfection Reagent. Cells were washed with PBS after approximately 3 hrs and 2.5 mL of MEM (serum free) was added to each well. At day 4 post transfection, CPE was observed and the cells and virus supernatant were harvested, frozen at ≤−60° C. for 1 hr, and then thawed. The sample was centrifuged and the passage 1 (PN 1) virus supernatant stock was aliquoted and stored at ≤−60° C. until further use. The RNA extraction and transfection procedures were repeated using the PN 1 stock to generate the PN 2 virus stock.

Plaque purification was performed in 6-well plates with a Neutral Red stained Sea plaque agarose overlay on a Vero cell monolayer. The PN 2 virus stock was used to generate 4 well isolated plaques (PN 3) which were individually amplified in Vero cells. The amplified individual harvests containing cells and virus were each subjected to freeze thaw treatment and benzonase treatment, before centrifugation to separate the virus containing supernatant (at PN 4) for storage at ≤−60° C. The 50% tissue culture infectious dose (TCID50) titers of the PN 4 virus stocks were determined on Vero cells.

The two virus stocks with the highest titers were again plaque purified using the same procedures and stored as PN 6 virus stocks. After this second round of plaque purification, the clonal population of virus yielding the highest TCID50 titer was selected for further amplification in Vero cells at a multiplicity of infection (MOI) of 0.1. On day 4 post-infection, cells showed 90% CPE, and were harvested and subjected to one freeze thaw cycle. After centrifugation the supernatant containing virus stock (PN 7) was collected and stored at ≤−60° C. The PN 7 virus stock was used to infect Vero cells in a two-tier cell factory (1,264 cm2 surface area) at an MOI of 0.1 for the production of the pre-MVS. On day 3 post infection, CPE was observed in the culture. The infected culture was subjected to the same freeze-thaw cycle and centrifugation as describe above, after which the virus supernatant was distributed into 40×5 mL and 126×1.5 mL aliquots and stored at ≤−60° C. This PN 8 virus stock was designated as the adapted EV71, and subsequently used as the pre-MVS.

Sequencing of Adapted EV71

Viral RNA was isolated from the adapted EV71 (PN8) using a QIAmp Viral RNA minikit (Qiagen catalog number 52904) according to the manufacturer's instruction. Two reverse transcription reactions and a control reaction lacking reverse transcriptase were performed using the RNA random primers. The resulting cDNA products were then used as a template in PCR amplifications using primer pairs designed based on the reference sequence the EV71/7423/MS/87 strain [GenBank Accession No. U22522]. The amplification products were visualized by agarose gel electrophoresis and purified using the ExoSAP-IT PCR product clean-up kit (GE Healthcare catalog number US78200) according to the manufacturer's instructions. The PCR amplicons were then sequenced using the BigDye Terminator v1.1 Cycle Sequencing Kit (Applied Biosystems catalog number 4337451) and the sequences detected using an Applied Biosystems 3730xl DNA Analyzer. The sequence data generated were assembled into contiguous sequences using Sequencher Software version 4.9. A minimum of four-fold coverage was obtained with two-fold covering each DNA strand for the viral sequence with the exceptions of four-fold coverage in a single direction in a few short interior stretches and at the 5' and 3' ends of the sequence. The complete nucleotide sequence of the adapted EV71 was determined by Beckman Coulter Genomics, as a sub-contractor to BioOutsource. The consensus nucleotide sequence for the EV71 MVS, as determined by Beckman Coulter Genomics, is provided in Genogrouping based on sequence analysis of the VP1 gene revealed that the adapted EV71 strain was classified as a B2 subgenogroup. Comparison of the VP1 gene sequence to that of strain MS/7423/87 revealed 12 nucleotide differences. Of these, 8 differences were silent and 4 alterations resulted in four amino acid differences in the VP1. The four amino acid substitutions and their respective positions within SEQ ID NO: 1 are shown in Table 1 below. PGPubs, CRC per instructions from the PTO.

TABLE 1

Sequencing of full length genome of EV71: P-0 vs P-8

| | Amino Acid Sequence | |
|---|---|---|
| | EV71 P0 | EV71 P8-Adapted strain |
| VP1 | 7-V | 7-M |
| | 14-D | 14-N |
| | 145-E | 145-Q |
| | 282-N | 282-D |

Example 2: Vaccine Manufacture and Formulation

The adapted EV71 virus produced in Example 1 was used in the manufacture of an inactivated Hand, Foot, and Mouth disease vaccine. To manufacture the vaccine, the virus was grown in Vero cells, harvested, and inactivated with binaryethylenimine (BEI). The non-infectious inactivated virus particles was then purified and formulated with aluminum hydroxide.

Preparation of Master Cell Bank and Master Virus Seed
Preparation of a Vero Master Cell Bank (MCB)

One vial of the Vero (WHO) 10-87 cell seed stock from ATCC was rapidly thawed at 37±1° C., centrifuged and resuspended in Dulbecco's Modified Eagle Medium (DMEM) plus 10% FBS plus L-glutamine (DGEM) before seeding in a T150 flask (designated PN 135). The flask was incubated at 36±1° C. in a 5±0.5% CO2 atmosphere incubator. On day 4, when the cells reached confluency, the Vero cells were dislodged from the flask using TrypLE Select® solution and split into five T225 flasks (PN 136). After the formation of a confluent monolayers, the flasks were removed from the incubator, the cells dislodged with TrypLE Select® solution and split into one 10-tier cell factory (CF10) with a surface area of 6,320 cm2 (PN 137). Another passage was performed in a similar fashion with the cells seeded into four CF10s (PN 138).

The Vero cells from four CF10s were dislodged and harvested using TrypLE Select® solution. A cell count was performed and freezing media (DMEM+20% FBS+20% DMSO) was added to adjust the cell concentration to 1.0×10⁷ cells/ml. The cells were aliquoted into 224 vials at a volume of 1 mL per vial and designated as the MCB.

Preparation of Adapted EV71 Master Virus Seed.

Vero cells from one vial of the MCB at PN 138 were thawed, centrifuged and used to seed 2 T25 flasks containing DGEM (PN 139). Following 5 days of incubation at 37±1° C. in a 5±1% CO2 atmosphere, the cell monolayers were passaged into 1 T225 flask (PN 140). For this and all subsequent cell passages, the cell monolayers were washed with Dulbecco's phosphate buffered saline (DPBS) without Ca and Mg, treated with TrypLE Select® solution followed by the addition of fresh DGEM and incubated at 37±1° C. in a 5±1% CO2 atmosphere. Following 3 days incubation the cells were passaged a second time (PN 141) into 1 T150 and 8 T225 flasks. Following 3 days incubation the cells were passaged a third time (PN 142) into 1 2-tier cell factory (CF2; 1,264 cm2 surface area). After 4 days incubation the cells were passaged a fourth time (PN 143) into 1 T225 and 2 10-tier cell factories (CF10; 6,320 cm2 surface area).

The T225 flask and 2 CF10s were incubated for 3 days when the monolayers were approximately 90 to 100% confluent. The cells from the 1 T225 flask were dislodged by treatment with TrypLE Select® solution and counted to determine the approximate cell density per cm2 of surface area in the CF10s. The monolayers in each cell factory were washed with DPBS without Ca and Mg to remove any residual growth medium. Two bottles of infection media, each containing 1 L of fresh serum-free DMEM plus L-glutamine, were prepared for infection of the CF10s. Two vials of the adapted EV71 pre-MVS from Example 1 were thawed and 0.95 mL was added to each of the two bottles of infection media to achieve an MOI of approximately 0.05. The infection media was added to the 2 CF10s according to the manufacturer's instructions. The infected CF10s were incubated at 37±1° C. in a 5±1% CO2 atmosphere. Following 3 days of incubation, the CF10s were removed from the incubator and the infected culture supernatants were harvested, pooled and distributed amongst 4 centrifuge bottles. The crude harvest material was centrifuged at 1,424×g for 10 minutes and the supernatants collected and temporarily stored at 5±3° C. Each of the cell pellets was resuspended in 100 mL of DMEM and subjected to 3 freeze-thaw cycles, followed by centrifugation at 1,424×g for 10 minutes. These supernatants were collected and pooled together with the supernatants from the first centrifugation step. The solution was then filtered through a millipak 100 filter assembly with a nominal 0.22 m pore size and the filtrate collected. This bulk MVS solution was aliquoted into 506 cryovials (5 mL) at a volume of 4 mL per vial. All vials were transferred to controlled storage at ≤−60° C. at SAFC in Carlsbad Calif., USA.

Vaccine Manufacture

Step 1: Vero Cell Initiation

One vial of VERO MCB (LN 173-09001) at PN 138 was rapidly thawed at 37±3° C. with constant swirling until a small amount of ice remains. The vial was then removed from the water bath, allowed to stand until completely thawed and the contents added directly to a sterile disposable 15 mL centrifuge tube containing 9 mL of DGEM. The cells were centrifuged at 200×g for 5 minutes at 18±3° C. The supernatant was removed and the cell pellet was resuspended in 2.0 mL of DGEM. The entire contents of the resuspended cells were added to a T75 flask containing 15 mL of DGEM and the flask was incubated at 37±2° C. in a 5±2% CO2 incubator.

Step 2: Media Change

After 3-4 days incubation, a media change was performed. The cell culture medium was removed by aspiration and 15 mL of fresh DGEM was added to the T75 flask.

Step 3: First Cell Passage

The T75 flask was observed for monolayer formation. Once the monolayer was approximately 80-100% confluent (typically day 6), the spent media was aspirated and the cells were washed once with 10 mL of DPBS without Ca and Mg to remove cell debris. After removal of the DPBS, the cells were dislodged by adding 3 mL of TrypLE Select® solution, rocking the flask to and fro to disperse the solution. The flask was incubated at 37±1° C. for 4±2 minutes after which the flask was gently tapped to suspend the cells. Nine mL of fresh DGEM was added to the flask and the cells were triturated to break up any cell clumps. The entire volume (approximately 12 mL) was added to a conical 15 mL centrifuge tube and centrifuged at 200×g for 5 minutes at 16±2° C. The supernatant was aspirated and the cell pellet was carefully resuspended in 2 mL of DGEM. A sample of the cell suspension was removed for cell count and viability determination. Based on the cell count, a maximum amount of the cell suspension was used to seed an appropriate number of T75, T175 and T225 flasks containing 15, 35 or 45 mL DGEM each respectively, at a seeding density of approximately 1×104 cells/cm2. The flasks were incubated at 37±2° C. in a 5±2% CO2 incubator until confluent (typically 3 days).

Step 4: Second Cell Passage

The tissue culture flasks from step 3 were observed for monolayer formation. Once the monolayer was approximately 80-100% confluent (typically day 9), the spent media was aspirated and the cells were washed with an appropriate amount of DPBS (10 mL each for T75 flasks and 20 mL each for T175 and T225 flasks). After removal of the DPBS, the cells were dislodged by adding an appropriate amount of TrypLE Select® solution (5 mL each for T75 flasks and 7 mL each for T175 and T225 flasks), rocking the flasks to and fro to disperse the solution. The flasks were incubated at 37±1° C. for 4±2 minutes after which the flasks were gently tapped to suspend the cells. Twelve mL of DGEM was added to each flask, regardless of size, and the cells were triturated to break up any cell clumps. The cell suspensions were pooled in a sterile disposable 50 mL centrifuge tube and centrifuged at 200×g for 5 minutes at 16±2° C. The supernatant was removed and the cell pellet was resuspended in 3.0 mL of DGEM. A sample of the cell suspension was removed for cell count and viability determination. Based on the cell count, an appropriate amount of the cell suspension was used to seed 8-10×T225 flasks, each containing 45 mL of fresh DGEM, at a density of approximately 1×104 cells/cm2. The flasks were incubated at 37±2° C. in a 5±2% CO2 incubator until confluent (typically 3 days).

Step 5: Third Cell Passage

The 8-10×T225 flasks were observed for monolayer formation. Once the monolayer was approximately 80-100% confluent (typically day 12), the spent media was aspirated and the cells in each flask were washed with 20 mL of DPBS. After removal of the DPBS, the cells were dislodged by adding 7.0 mL of TrypLE Select® solution to each flask and incubated at 37±2° C. for 4±2 minutes after which the flasks were gently tapped to suspend the cells. Twenty eight mL of DGEM was added to each flask and the cells were triturated to break up any cell clumps. The cell suspensions were pooled in a sterile 500 mL centrifuge bottle and centrifuged at 200×g for 5 minutes at 16±2° C. The supernatant was aspirated and the cell pellet was resuspended in 10 mL of DGEM and the suspension was transferred to a sterile disposable 50 mL tube. The 500 mL centrifuge bottle was rinsed with 20 mL of DGEM and the rinse was added to the above 50 mL tube. The cell suspension was gently mixed and a sample was removed for cell count and viability determination. Based on the cell count, an appropriate amount of the cell suspension was used to seed 2×10-tier cell factories (CF10, 6,320 cm2 surface area) at a density of approximately 1×104 cells/cm2. For each CF10, the appropriate amount of cell suspension was aseptically added through the injection port of a 5 L Stedim bag containing 2,000 mL of fresh DGEM. The bag was gently mixed and the contents were aseptically transferred to the CF10 according to the manufacturer's instructions. The CF10s were incubated at 37±2° C. in a 5±1% CO2 incubator until confluent (typically 4 days).

Step 6: Fourth Cell Passage

The 2×CF10s were observed for monolayer formation. Once the monolayer was approximately 80-100% confluent (typically day 16), the cells from each CF10 were sequentially removed as follows: The spent media was removed from the first CF10 and the cells were washed with 400 mL of DPBS according to the manufacturer's instructions. After removal of the DPBS, the cells were dislodged by adding 150 mL of TrypLE Select® solution to the first CF10. The TrypLE Select® solution was allowed to spread evenly across the surface of each tray and after 0.5-1 min excess solution was removed. The CF10 was incubated at 37±2° C. for 4±1 minutes to facilitate detachment of the cells. After this incubation period, the cells were observed under phase contrast microscopy to monitor cell detachment. Three hundred mL of DGEM was added to the first CF10 according to the manufacturer's instructions and allowed to spread evenly across the surface of each tray. At this point the first CF10 was set aside while the second CF10 was processed in the same manner. The cell suspensions from both CF10s were pooled into a sterile, disposable 2 L Erlenmeyer flask and gently mixed. The pooled cell suspension was aseptically transferred to 2×500 mL centrifuge bottles and centrifuged at 200×g for 5 minutes at 16±2° C. The supernatants were aspirated and each cell pellet was resuspended in 40.0 mL of DGEM and pooled. The pooled cell suspension was gently mixed and a sample was removed for cell count and viability determination. Based on the cell count, an appropriate amount of the cell suspension was used to seed 10×CF10s at a density of approximately 1×104 cells/cm2. For each CF10, the appropriate amount of cell suspension was aseptically added through the injection port of a 5 L Stedim bag containing 2,000 mL of fresh DGEM. The bag was gently mixed and the contents were aseptically transferred to the CF10 according to the manufacturer's instructions. The CF10s were incubated at 37±2° C. in a 5±1% CO2 incubator until confluent (typically 4 days).

Step 7: Infection of Cells

On the day before the planned infection (typically day 19), 10×5 L Stedim bags, each containing 2,000 mL of serum free DMEM, were incubated at 37±2° C. to pre-warm the medium for infection. On the day of infection when the monolayers were approximately 90 to 100% confluent (typically day 20), 2 vials of EV71 MVS (LN 173-10001) were rapidly thawed in a 37±2° C. water bath and 0.6 mL of MVS was added through the injection port of each Stedim bag to result in a MOI of approximately 0.03. This MOI was calculated based on the assumption that there was an average cell density of 2×105 cells/cm2 and that the EV71 MVS virus titer was 3.4×107 TCID50/mL. For each CF10, the spent media was removed and the cells washed with 400 mL of DPBS as described in step 6 above. Each CF10 was infected by the addition of one of the virus-containing 2,000 mL serum free DMEM preparations described above, according to the CF10 manufacturer's instructions. The infected CF10s were incubated at 37±2° C. in a 5±1% CO2 incubator until 100% CPE was observed (typically 4 days).

Step 8: Virus Harvest

At the end of the virus infection period (typically day 24), each cell factory was observed under phase contrast microscopy to ensure 100% CPE. The supernatants from the 10×CF10s were aseptically collected and pooled into a Stedim 20 L Flexboy bag according to the CF10 manufacturer's instructions. This represented the crude virus harvest.

Step 9: Benzonase Treatment

The appropriate amounts of a 250,000 U/mL benzonase solution and a 1M MgCl2 solution were aseptically added through the injection port of the 20 L Stedim bag containing the crude virus harvest to achieve a final concentration of 20 U/ml and 2 mM respectively. The contents of the bag were mixed, followed by incubation at 37±1° C. for 18-24 h.

Step 10: Virus Inactivation

The BEI inactivation solution was prepared immediately prior to use by the addition of 6.2 g of 2-bromoethylamine hydrobromide (BEA) to 300 mL of 175 mM NaOH and incubation at 37±1° C. in a water bath. Once the BEA was dissolved, the pH value of the BEI solution was routinely checked until the pH fell within the range of pH 8-9. The BEI solution was used for inactivation within 60 minutes of the pH value falling in this range by pumping the solution through a 0.2m filter capsule directly into the 20 L bag containing the benzonase treated crude virus harvest using a peristaltic pump. The BEI-crude virus harvest was mixed by hand for at least 5 min and then to facilitate further mixing, the BEI crude harvest solution was pumped into a new 20 L Stedim Flexboy bag. The BEI-crude virus harvest was again mixed by hand for at least 5 min, and then incubated at 37±1° C. for 6-7 h.

Step 11: BEI Neutralization

Residual BEI was hydrolyzed with the addition of 1 L of 32 mM Na-thiosulfate. The Flexboy bag containing BEI treated crude harvest was connected in parallel with a bag containing the 1 L of 32 mm Na-thiosulfate using a Y connector. An in-line static mixer was included in the tubing downstream of the Y connector. The BEI treated crude harvest and the 32 mM Na-thiosulfate solutions were simultaneously pumped, at 1 L/min and 50 mL/min respectively, into the Y connector, through the static mixer and collected into a new Flexboy bag. The inactivated and neutralized crude harvest was then immediately clarified as described below.

Step 12: Clarification

The benzonase treated, inactivated, neutralized virus pool was clarified using a 4-stage filtration assembly. The assembly consists of a Sartorius Sartoclean GF filter capsule upstream and in series with a Sartorious Sartopore 2 filter capsule. The first two filtration stages were housed in the Sartoclean GF capsule with nominal 3.0 μm and 0.8 μm cellulose acetate filters. The third and fourth stages were housed in the Sartopore 2 filter capsule with nominal 0.45 μm and 0.2 μm polyethersulfone membrane filter. The virus pool was pumped through the filtration assembly and collected in 5×5 L Flexboy bags (approximately 4 L each). A final 5 L Flexboy bag was connected to the outlet of the filtration assembly and 3 L of PBST was pumped through the assembly to wash the filters and collect any residual inactivated virus.

Step 13: Concentration and Diafiltration

Three Sartorius Slice disposable crossflow filtration cassettes, each with a 0.1m2, 100-kDa molecular weight cutoff Sartorius Hydrosart membrane, were connected in parallel to concentrate the clarified inactivated virus pool 10-fold in volume via tangential flow filtration (TFF). TFF was followed by constant volume diafiltration with 10 volumes of PBS-Tween 80 (10 mM Na—PO4, 150 mM NaCl, 0.002% Tween 80), pH 7.5. A constant flux of 300 L/m2/hour (LMH) and transmembrane pressure (TMP) of 0.40 to 0.45 bar was maintained throughout the run. An equal volume of buffer was used to wash the TFF cassette assembly in order to improve virus recovery. The final retentate concentration was approximately 5-fold prior to filtration through sterile 0.45 μm and 0.2 μm filters. The filtered retentate was stored at 5±3° C. for not more than 7 days or ≤−60° C. up to 4 weeks prior to chromatographic purification.

Step 14: Anion Exchange Chromatography

The first purification step was performed using anion exchange chromatography with Fractogel® EMD TMAE (Merck) media to capture the EV71, which partially removes contaminating host cell proteins and any residual host nucleic acids. At this stage of product development, the anion exchange chromatography (AEX) medium was considered single-use and a product-dedicated column was re-packed for each production run. A GE Healthcare 70×500 mm (ID×height) INdEX column was packed with approximately 390 mL of Fractogel® EMD TMAE chromatography medium to yield a bed height of approximately 100 mm. Once packed, the column was loaded with 4 mL of AEX testing solution (20 mM Na-phosphate buffer, 2 mM MgCl2, 1 M NaCl, pH 7.5) to measure the height equivalent to a theoretical plate (HETP) and asymmetry (As). A column was accepted for use if the HETP and As were >3,000 plates/m and 0.8-1.8 respectively. The column was operated at room temperature with a linear flow rate of 150 cm/h (approximately 96 mL/min) and the absorbance of the column eluate was monitored using a GE Healthcare UVis 920 detector at 215 nm set at 2,000 mAU range. The column was sanitized with 2 column volumes (CV) of 0.5 M NaOH and equilibrated with 3-5 CV of binding buffer (20 mM Na-phosphate buffer, 2 mM MgCl2, 100 mM NaCl, pH 7.5) prior to loading of the filtered retentate from step 13. Binding capacity of this column was approximately 1.96 mg protein/mL of resin and the sample was loaded at 40-80% of column breakthrough. The filtered retentate from step 13 was loaded onto the AEX column with the flow rate being reduced (if necessary) to avoid the introduction of air. Once the filtered retentate was loaded, the column was washed with binding buffer until a baseline absorbance was obtained (approximately 2-5 CV). The EV71 antigen containing material was eluted in a step gradient fashion with elution buffer (20 mM Na-phosphate buffer, 2 mM MgCl2, 250 mM NaCl, pH 7.5). Fraction collection was initiated when the detector indicated 100 mAU and continued until the absorbance fell below 100 mAU (approximately 2-4 CV). The volume size and protein concentration of the filtered retentate from step 13, taken together with the AEX column dimensions and binding capacity, typically necessitated 2 cycles of AEX chromatography to complete the processing of all material. At the end of the first run, the AEX column was stripped with 5 CV of regeneration buffer (20 mM Na-phosphate buffer, 2 mM MgCl2, 2M NaCl, pH 7.5), followed by equilibration with 3-5 CV of binding buffer (until baseline absorbance was obtained) prior to loading the remainder of the filtered retentate. Once all AEX runs were complete, the EV71 containing eluant fractions were pooled and the column was stripped with 5 CV of regeneration buffer and sanitized with 2 CV of 0.5m NaOH and 5 CV of 0.01 M NaOH prior to storage. The pooled AEX eluate fractions were stored at 5±3° C. for not more than 3 days prior to cation exchange chromatography as described below.

Step 15: Cation Exchange Chromatography

The second purification step was performed using cation exchange chromatography with Fractogel® EMD SO3 (Merck) media to further remove impurities, which was in the flow-through fraction(s). At this stage of product development, the cation exchange chromatography (CEX) medium was considered single-use and a product-dedicated column was re-packed for each production run. An Omnifit 35×250 mm (ID×height) BenchMark column was packed with approximately 100 mL of Fractogel® EMD SO3 chromatography medium to yield a bed height of approximately 100 mm. The binding buffer, elution buffer, regeneration buffer, linear flow rate (150 cm/h, approximately 24 mL/min) and monitoring conditions were the same as those used in anion exchange purification step 14 above. Once packed, the column was loaded with 0.5 mL of regeneration buffer to measure the HETP and As. A column was accepted for use if the HETP and As were >4,000 plates/m and 0.8-1.8 respectively. The column was sanitized with 2 column volumes (CV) of 0.5 M NaOH and equilibrated with 3-5 column volumes (CV) of binding buffer prior to sample loading. The EV71-containing eluate fraction (250 mM NaCl) from the anion exchange step above was diluted (approximately 3×) with 20 mM Na-phosphate buffer, 2 mM MgCl2, pH 7.5 prior to loading to reduce the salt concentration. Binding capacity of this column was 2.7 mg protein/mL of resin and the diluted EV71 eluate was loaded at 40-80% of column breakthrough onto the CEX column with the flow rate being reduced (if necessary) to avoid the introduction of air. Once the diluted AEX sample was loaded, the column was washed with binding buffer until a baseline absorbance was obtained (approximately 2-5 CV). The EV71 antigen containing material was eluted from the cation exchange column with elution buffer. Fraction collection was initiated when the detector indicated 50 mAU and continued until the absorbance fell below 50 mAU (approximately 3-5 CV). The volume size and protein concentration of the pooled AEX eluate fractions from step 14, taken together with the CEX column dimensions and binding capacity, typically necessitated 2 cycles of CEX chromatography to complete the processing of all material. At the end of the first run, the CEX column was stripped with 5 CV of regeneration buffer, followed by equilibration with 3-5 CV of binding buffer (until baseline absorbance was obtained) prior to loading the remainder of the pooled AEX eluate fraction. Once all CEX runs were complete, the EV71 containing eluant fractions were pooled and the column was stripped with 5 CV of regeneration buffer and sanitized with 2 CV of 0.5m NaOH and 5 CV of 0.01 M NaOH prior to storage. The pooled CEX eluate fractions were stored at 5±3° C. for no longer than 3 days prior to size exclusion chromatography as described below.

Step 16: Size Exclusion Chromatography

Size exclusion chromatography with Sephacryl S-400 HR (GE healthcare) media was used as a final polishing step in the EV71 antigen purification process. At this stage of product development, the size exclusion chromatography (SEC) medium was considered single-use and product-dedicated columns were re-packed for each production run. Two GE Healthcare 100×500 mm (ID×height) BPG columns were packed with approximately 2.35 L each of Sephacryl S-400 HR chromatography medium to yield a bed height of 250-300 mm per column. Once packed, the columns were individually loaded with 25 mL each of SEC testing solution (10 mM Na—PO4, 2 M NaCl, 0.002% Tween 80, pH 7.5) to measure the HETP and As. A column was accepted for use if the HETP and As were >4,000 plates/m and 0.8-1.8 respectively. The two columns were individually sanitized with 1 CV of 0.5 M NaOH, equilibrated with 3-5 CV of running buffer (PBST: 10 mM Na—PO4, 150 mM NaCl, 0.002% Tween 80, pH 7.5) and then assembled in series for use. The pooled CEX eluate fractions from step 16 above were loaded onto the SEC column assembly at 2.5-5.0% of the total column volume and the column was operated isocratically at room temperature with linear flow rate of 24 cm/h (31.4 mL/min). The absorbance of the column eluate was monitored using a GE Healthcare UV is 920 detector at 215 nm set at 100 mAU range. Fractions of 50-100 mL each were collected from the observed elution peaks. Fraction sizes were adjusted based on the appearance of the chromatogram. From previous experience, the ≥90% purity EV71 fractions were eluted at approximately 0.45 0.60 CV. The volume size of the pooled CEX eluate fractions and the column dimensions typically necessitated 4 cycles of SEC chromatography to complete the processing of all material. At the end of each cycle the column was re-equilibrated with 3-5 CV of running buffer until baseline absorbance was obtained. Once all SEC runs were complete, the column was sanitized with 1 CV of 0.5m NaOH followed by 2 CV of 0.01 M NaOH prior to storage. Individual fractions were analyzed by SDS PAGE and Western blot to permit selection and pooling of those fractions which contain ≥90% purity of the EV71 antigen. The selected ≥90% purity adapted EV71 vaccine eluate fractions were pooled and stored at 5±3° C. for not more than 3 days prior to concentration.

Step 17: Concentration

Concentration was performed using TFF with a 2×30 kDa molecular weight cut off Sartorius Hydrosart membrane cassettes assembled in a Sartorius Sartocon® Slice 200 holder. A constant flux of 300 LMH was maintained throughout the process and the TMP fluctuated between 0.40-0.45 bar. The concentration fold was in the range of 10-40×, depending on the total protein concentration in the selected pooled SEC fractions from step 16 and the formulation requirements. The concentrated solution was filtered through a 0.2 m filter, and stored at ≤−60° C. for up to 6 months or at 5±2° C. for up to 2 weeks.

Vaccine Formulation

Step 1: Adsorption to Aluminum Hydroxide

An appropriate amount of the adapted EV71 vaccine product was removed from storage and mixed with PBST (PBS+0.002% Tween 80) to yield the dose-level specific dilute vaccine product for formulation with aluminum hydroxide. Tween 80 was added to decrease vaccine aggregation. The dilute vaccine product was filtered through a 0.2 m pore size filter (Pall Acropak) directly into a mixing vessel. One tenth of a volume of sterile aluminum hydroxide suspension (Alhydrogel 85) was added to the mixing vessel and the contents were mixed on a stir plate for 16-24 h at 5±3° C. The aluminum hydroxide adjuvant used in the preparation of the adapted EV71 vaccine was manufactured by Brenntag Biosector of Frederiksund Denmark and sold a 2% (w/v) solution under the trade name of Alhydrogel 85. Adsorption onto the Alhydrogel 85 was approximately 100%.

Step 2: Fill

The adapted EV71 vaccine was aseptically filled into sterile 3 mL glass (USP Type I) vials (Schott) using a validated hand-fill operation. The filling operation was carried out in a Class 100 (ISO 5) biosafety cabinet located within a Class 10,000 (ISO 7) room. The filled vials were stoppered with sterile chlorobutyl rubber stoppers (West Pharma) and sealed with sterile flip-off aluminum seals (West Pharma) using a semi-automatic vial crimping station (Kebby Pro-Seal). Once sealed, the vials were hand labeled with 1.50"×0.75" opaque, white, laser printed cryo-tag labels (Diversified Biotech, LCRY-1200).

Step 3: Visual Inspection and Storage

All vials were visually inspected and were rejected if they were under-filled, have loose caps, loose glass pieces, or other particles. After visual inspection, the vaccine Product was stored at 5±3° C.

Mass Spectrometry of the Adapted Vaccine

Mass spectrometry (MS) analysis was performed by M-Scan (United Kingdom) on the adapted vaccine drug substance. Samples were reduced in dithiothreitol, carboxymethylated with iodoacetic acid, concentrated in ammonium bicarbonate buffer with a spin column (3 kDa cut off membrane), digested with trypsin on the membrane, and the resulting peptides eluted and analyzed by LC-ES-MS/MS (high pressure liquid chromatography electrospray quadrapole time of flight mass spectrometry). Peptide sequences were generated from spectra obtained with high energy MS, and the resulting sequences used to interrogate the NCBI database using MASCOT software. In concordance with the above, the MS analysis demonstrated that the capsid proteins VP1, VP2, VP3 and VP4 were the major components in the test samples.

Example 3: Immunopotency Studies

Immunopotency testing was used to demonstrate the potency of the adapted EV71 vaccine. The assay was designed to report the effectiveness and stability of the adapted EV71 vaccine by assessing the specific EV71-immune response of adapted EV71 vaccine-inoculated mice regularly over time. As such, it also incorporated a TCID50 viral neutralization method within the assay.

Briefly, mice (six per group) were each inoculated with low dose or high dose adapted EV71 vaccine on Day 0 and Day 14 via 2×50 µL IM injections on the same limb to target the same lymph nodes. Because of the injection volume limitations in mice (total of 100 µL), animals received ⅕ of the formulated vaccine dose, with the low dose immunized mice receiving 0.12 µg protein and 0.1 mg of alhydrogel per dose and the high dose immunized animals receiving 0.6 µg protein and 0.1 mg of alhydrogel per dose. A control group of six animals receive an alhydrogel only formulation containing 0.1 mg of alhydrogel per dose. To assess immunopotency, serum was collected from each animal on three occasions as pre-immunization bleeds on Day 0 and Day 14 and as a final bleed on Day 28. Serum samples from each group were heat inactivated and pooled. The pooled serum from each group was serially diluted in Vero cell assay medium (MEM containing 2% FBS) and a known amount of live adapted EV71 virus (100 TCID50 per 50 µL) was added to these samples and the mixtures incubated for 1.5 hours.

These samples and control samples (EV71 100 TCID50 per 50 μl as positive control; assay medium as negative control) were then added to Vero cells in 96-well plates as described for TCID50. CPE was observed on Days 3-5 and the results expressed as the serum neutralization titer that was defined as the maximum serum dilution in which at least two of the three replicates were negative for CPE. The results of these experiments are provided in Tables 2-4 below.

TABLE 2

Serum neutralization titer from control group

| | Individual Animal | | | | | |
|---|---|---|---|---|---|---|
| Day | 1 | 2 | 3 | 4 | 5 | 6 |
| 0 | NR | NR | NR | NR | NR | NR |
| 14 | NT | NT | NT | NT | NT | NT |
| 28 | NR | NR | NR | NR | NR | NR |

Day 5 results for Alum only control group;
NT = Not Tested,
NR = Antibody response <1 in 128.

As shown in Table 2, the negative control provided a negative response in each of the six individual animals at both Day 0 and Day 28, demonstrating that Alum alone does not cause an increase in anti-EV71 antibodies.

TABLE 3

Serum neutralization titer from low dose group

| | Individual Animal | | | | | |
|---|---|---|---|---|---|---|
| Day | 1 | 2 | 3 | 4 | 5 | 6 |
| 0 | NR | NR | NR | NR | NR | NR |
| 14 | NR | NR | NR | NR | NA | NR |
| 28 | NR | 128 | 128 | 1024 | 512 | 128 |

Day 5 results for low dose group;
NA = Insufficient Sample Volume for analysis,
NR = Antibody response <1 in 128.

As shown in Table 3, no neutralizing antibody response was detected from the low dose group in the pre-bleeds harvested at Day 0, indicating that the animals had not previously been exposed to an EV-71-like virus. Negative results were also obtained at Day 14, demonstrating that a single dose after a 14 day interval was not sufficient to produce a detectable immune response. However, by Day 28, 5 out of 6 animals provided a measurable antiserum neutralizing titer. When a pool was prepared from each of the 6 animals in the low dose group, a measurable neutralizing antiserum response was detected.

TABLE 4

Serum neutralization titer from high dose group

| | Individual Animal | | | | | |
|---|---|---|---|---|---|---|
| Day | 1 | 2 | 3 | 4 | 5 | 6 |
| 0 | NR | NR | NR | NR | NR | NR |
| 14 | NR | NR | NR | NR | NR | NR |
| 28 | 2048 | 2048 | 2048 | 1024 | 4096 | 2048 |

Day 5 results for high dose group;
NR = Antibody response <1 in 128.

As shown in Table 4, no neutralizing antibody response was detected from the high dose group in the pre-bleeds harvested at Day 0, indicating that the animals had not previously been exposed to an EV-71-like virus. Negative results were also obtained at Day 14, demonstrating that a single dose after a 14 day interval was not sufficient to produce a detectable immune response. However, by Day 28, all animals provided a measurable antiserum neutralizing titer. When a pool was prepared from each of the 6 animals in the high dose group, a neutralizing antibody titer of 1 in 512 was produced. When a pool was prepared from each of the 4 animals that received the high dose on Day 14, a neutralizing antibody titer of 1 in 1,024 was produced.

These results demonstrate the immunopotency of the adapted EV71 vaccine. Both low and high dose treatments induced a measurable neutralizing antibody response.

Example 4: EV71 Antigen Formulated with and without Alum Adjuvant at 3 Dose Levels This Example evaluated the immune response of the adapted EV71 vaccine antigen at various dose levels formulated with or without alum adjuvant in male Balb/c mice. Three dose levels (0.12, 0.6 and 3 μg EV71 antigen/dose) were evaluated in animals; each group of animals consisted of 8 mice per group. The negative controls for formulations without alum (Group 1) and with alum (Group 5) were PBST (phosphate buffered saline+0.002% v/v Tween 80) and aluminum hydroxide, respectively. The amount of alum (Alhydrogel 85) was constant at 0.5 mg/dose in all formulations containing this adjuvant. Mice were immunized on Day 0 and Day 28 by IM injection. Serum was collected on Day 0 (preimmunization), Day 28 (pre-boost immunization) and Day 56 (terminal bleed) to assess the neutralizing antibody titers and seroconversion rate at each dose level for each treatment group. Serum neutralizing antibody titers were determined using a TCID50-based neutralization assay. The immune response, in terms of neutralizing antibody titers, was compared to control, which was EV71 antigen formulated without adjuvant. Geometric mean titers (GMT) were calculated for each group from the individual reciprocal neutralization titers. The seroconversion rate was defined as the percentage of animals in a given group with a reciprocal neutralizing titer ≥128.

The results of this study are presented in Table 5 below.

TABLE 5

| Immunogenicity of EV71 Antigen With and Without Alum Adjuvant | | | | | | | |
|---|---|---|---|---|---|---|---|
| | | Day 28 | | Day 42 | | Day 56 | |
| Group | Treatment | GMT | % SCR (N)[b] | GMT | % SCR (N) | GMT | % SCR (N) |
| 1 | PBST[a] control | 1 | 0 | 1 | 0 | 1 | 0 |
| 2 | 0.12 μg EV71 | 3 | 12.5 (1/8) | 256 | 100 (8/8) | 304 | 100 (8/8) |
| 3 | 0.6 μg EV71 | 8 | 12.5 (1/8) | 395 | 87.5 (7/8) | 724 | 100 (8/8) |

TABLE 5-continued Immunogenicity of EV71 Antigen With and Without Alum Adjuvant

| | | Day 28 | | Day 42 | | Day 56 | |
|---|---|---|---|---|---|---|---|
| Group | Treatment | GMT | % SCR (N)[b] | GMT | % SCR (N) | GMT | % SCR (N) |
| 4 | 3 μg EV71 | 45 | 37.5 (3/8) | 395 | 100 (8/8) | 362 | 100 (8/8) |
| 5 | Alum control | 1 | 0 | 1 | 0 | 1 | 0 |
| 6 | 0.12 μg EV71 + Alum | 41 | 37.5 (3/8) | 1328 | 100 (8/8) | 1448 | 100 (8/8) |
| 7 | 0.6 μg EV71 + Alum | 181 | 100 (8/8) | 1579 | 100 (8/8) | 1722 | 100 (8/8) |
| 8 | 3 μg EV71 + Alum | 512 | 100 (8/8) | 2435 | 100 (8/8) | 3158 | 100 (8/8) |

[a]PBST = Phosphate Buffered Saline + 0.002% (v/v) Tween 80, buffer base for purified, inactivated EV71
[b]Seroconversion rate (SCR) is defined as the percentage of animals with a reciprocal neutralizing titer ≥128

All animals had no measurable neutralizing antibody titer at Day 0 prior to immunization. EV71 antigen formulated with aluminum hydroxide generated higher neutralizing antibody titers in mice at all dose levels as compared to mice that received the same dose of EV71 antigen without adjuvant. The addition of alum adjuvant also had an effect on the seroconversion rates, as noted after a single dose administration (Day 28 samples) of the 0.6 and 3 μg dose levels.

The results indicate that the inclusion of alum adjuvant in the formulation of the EV71 antigen improved the overall immunogenicity of the adapted EV71 vaccine. This was demonstrated by the higher GMT neutralizing titers in the groups with alum adjuvant, ranging from 11- to 23-fold higher GMTs at Day 28 (after 1 dose), 4- to 6-fold higher GMTs at Day 42 (after 2 doses) and 2.4- to 9-fold higher GMTs at Day 56 (after 2 doses). This was important, particularly with regards to the longevity of the immune response and the ability of the vaccine to provide protection against heterologous circulating EV71 sub-genogroups.

Example 5: Dose Ranging Study in Mice

This Example demonstrates the ability of different doses of adapted EV71 vaccine, formulated with alum adjuvant, to induce neutralizing antibodies in mice. Male Balb/c mice were immunized twice (Day 0 and Day 28) with adapted EV71 vaccine at 0.12, 0.6, 3, 9 and 15 μg per dose via IM injection. The amount of alum was constant at 0.5 mg/dose in all formulations. Reciprocal neutralizing antibody titers were determined on Days 0, 28 and 56 using the TCID50 EV71 virus neutralization assay. The data generated from this study were used to determine the dose levels to be used in human trials. All animals had no measurable neutralizing antibodies at Day 0 prior to immunization (Table 6).

TABLE 6

Dose Ranging Study of the INV21 Vaccine in Mice

| | | Day 28 | | Day 56 | |
|---|---|---|---|---|---|
| Group | Dose | GMT | % SCR (N)[a] | GMT | % SCR (N) |
| 1 | Alum control | 1 | 0 (0/10) | 1 | 0 (0/10) |
| 2 | 0.12 μg EV71 + Alum | 2 | 10 (1/10) | 64 | 50 (5/10) |
| 3 | 0.6 μg EV71 + Alum | 18 | 20 (2/10) | 1261 | 90 (9/10) |
| 4 | 3 μg EV71 + Alum | 128 | 70 (7/10) | 2048 | 100 (10/10) |
| 5 | 9 μg EV71 + Alum | 56 | 40 (4/10) | 1448 | 100 (10/10) |
| 6 | 15 μg EV71 + Alum | 239 | 80 (8/10) | 2702 | 100 (10/10) |

[a]Seroconversion rate (SCR) is defined as the percentage of animals with a reciprocal neutralizing titer ≥128

The control alum only group (0 μg dose of adapted EV71 vaccine antigen) did not generate any neutralizing antibodies at any time points analyzed. Following one dose of the adapted EV71 vaccine, only the 3 μg and the 15 μg dose levels resulted in high levels of neutralizing antibodies, as indicated by GMT ≥128 on Day 28. Following two doses of the vaccine, high levels of neutralizing antibodies (GMT ≥128 on Day 56) were observed in animals receiving doses of 0.6 μg or higher. The highest GMT (2702) was seen in the group of animals receiving the highest dose of 15 μg. The boosting effect of the second vaccine administration was evident at Day 56 in all dose groups.

Figure 3:
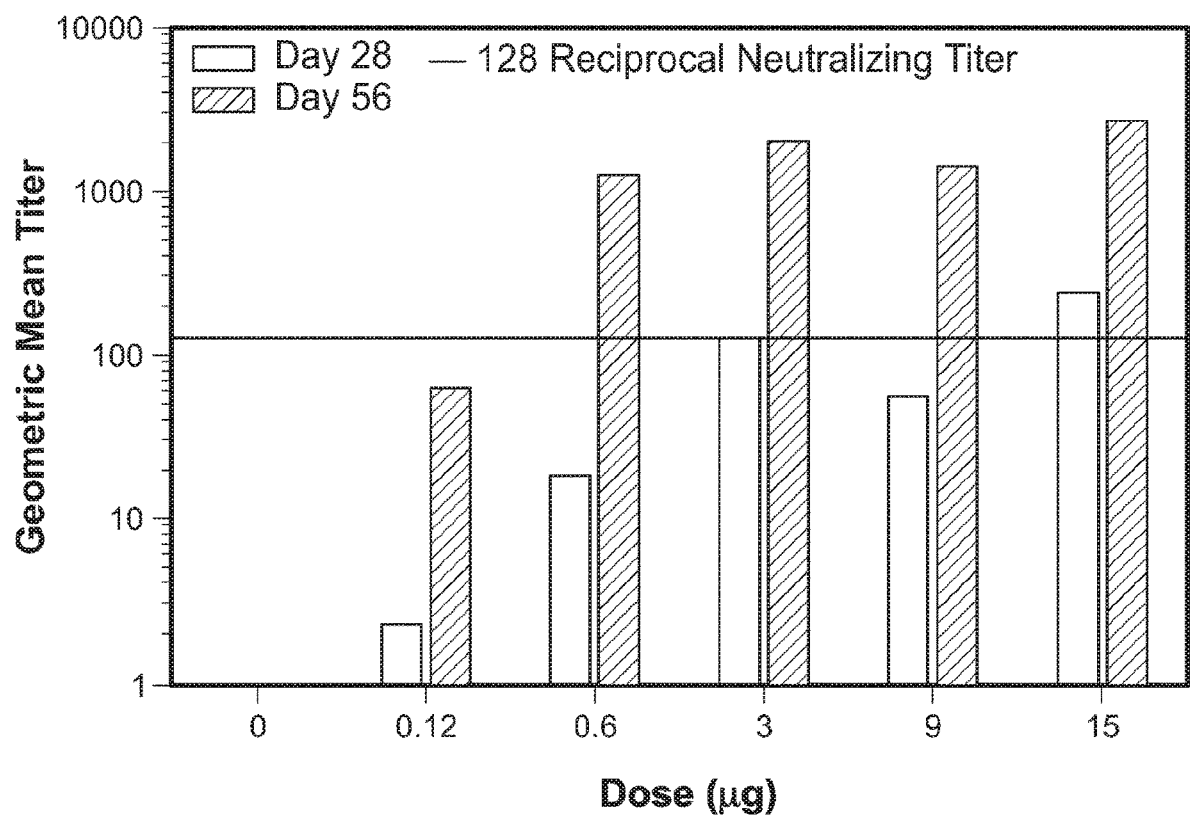
FIG. 3 shows immunogenicity of adapted enterovirus 71 vaccine at different dose levels in mice, with geometric mean tiers values from a TCID50 neutralization assay displayed in graphical form across longitudinal time points.

For the purposes of calculating seroconversion rates, a reciprocal neutralizing titer ≥128 was used to classify an individual animal as having seroconverted. Incomplete seroconversion was seen at all dose levels following one dose of the vaccine (at Day 28), ranging from 10% (0.12 μg dose level) to 80% (15 μg dose level). Following two doses of adapted EV71 vaccine, higher SCRs (at Day 56) were achieved at each dose level compared to Day 28, with 50% of animals seroconverting in the 0.12 μg dose, 90% in the 0.6 μg dose and 100% in the 3, 9 and 15 μg dose levels. The GMTs for all dose groups compared to the 128 reciprocal neutralizing titer (dashed line) are shown in FIG. 3.

The results are comparable to the results from Example 4 above demonstrating that two doses of adapted EV71 vaccine are optimal for the generation of high levels of neutralizing antibody titers. No protective titer in man has been established for neutralizing antibody levels against EV71; however a reciprocal neutralizing titer ≥128 was described by Yu et. al. (2000) as being the minimum protective titer in a mouse challenge model of EV71 infection. Similar protective titers were described by Wu et. al. (2002) in a related mouse model of EV71 passive vaccination and challenge. This titer level is represented as a horizontal dashed line in FIG. 3. The results of this study show that adapted EV71 vaccine doses of 0.6 μg and above were able to generate GMTs in excess of this threshold after two immunizations. Taken together, the data from this study along with the data from Example 4 enabled the conclusion that a low and high dose formulation of adapted EV71 vaccine, at 0.6 μg and 3.0 μg per dose respectively, are suitable for human testing.

Example 6: Cross-Neutralization of Adapted EV71 Vaccine Immune Response Against Selected EV71Sub-Genogroups Low titer rat and high titer rabbit sera from animals immunized with adapted EV71 vaccine were assayed for the ability to neutralize three strains of EV71 from other sub-genogroups (B4, B5 and C4) in vitro. The B2 sub-genogroup, which is the same as the vaccine strain, was included as a positive control. The assay used in this experiment was a TCID50 neutralization assay modified to permit longer observation time post-infection (up to 10 days instead of 5 days) due to the longer time required by the B4, B5 and C4 strain isolates to cause cytopathic effect in Vero cells. The neutralizing titer of the test sample was defined as the highest dilution that inhibits infection of Vero cells in ≥50% of replicates.

Figure 4:
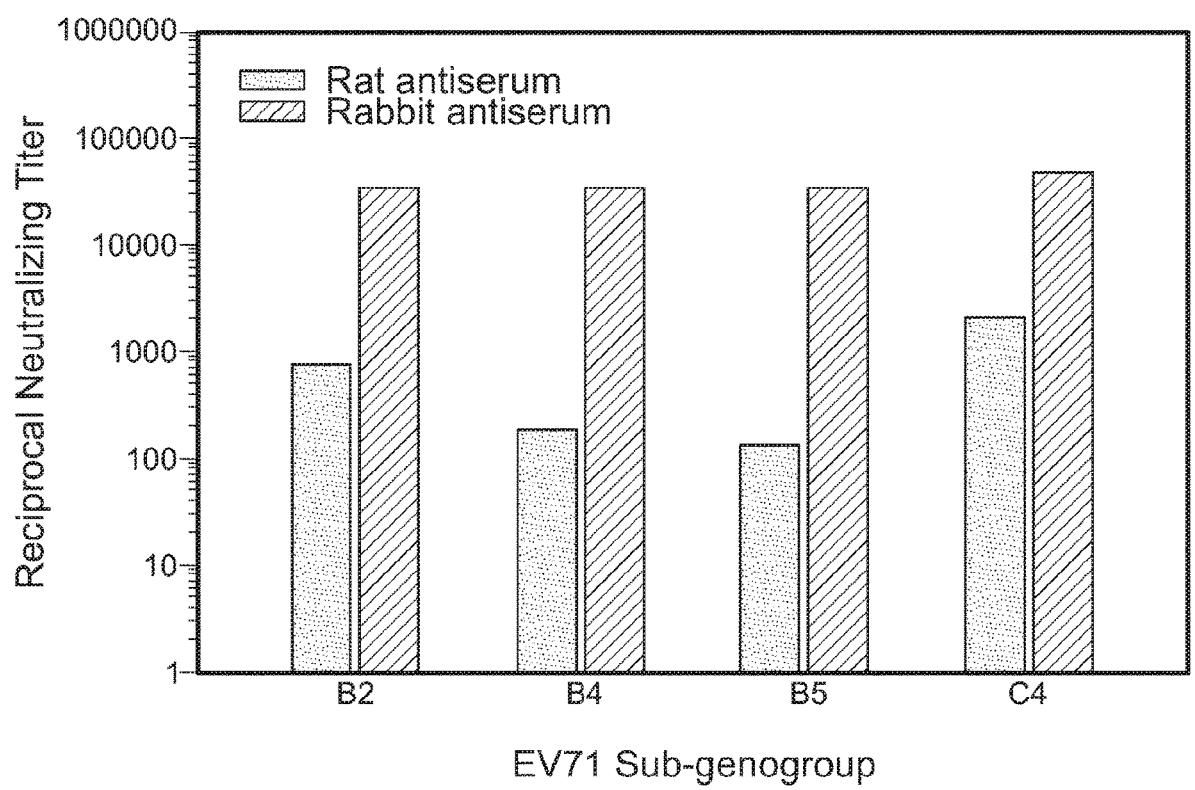
FIG. 4 shows cross-neutralization of EV71 antiserum against selected EV71 sub-genogroups.
Figure 5:
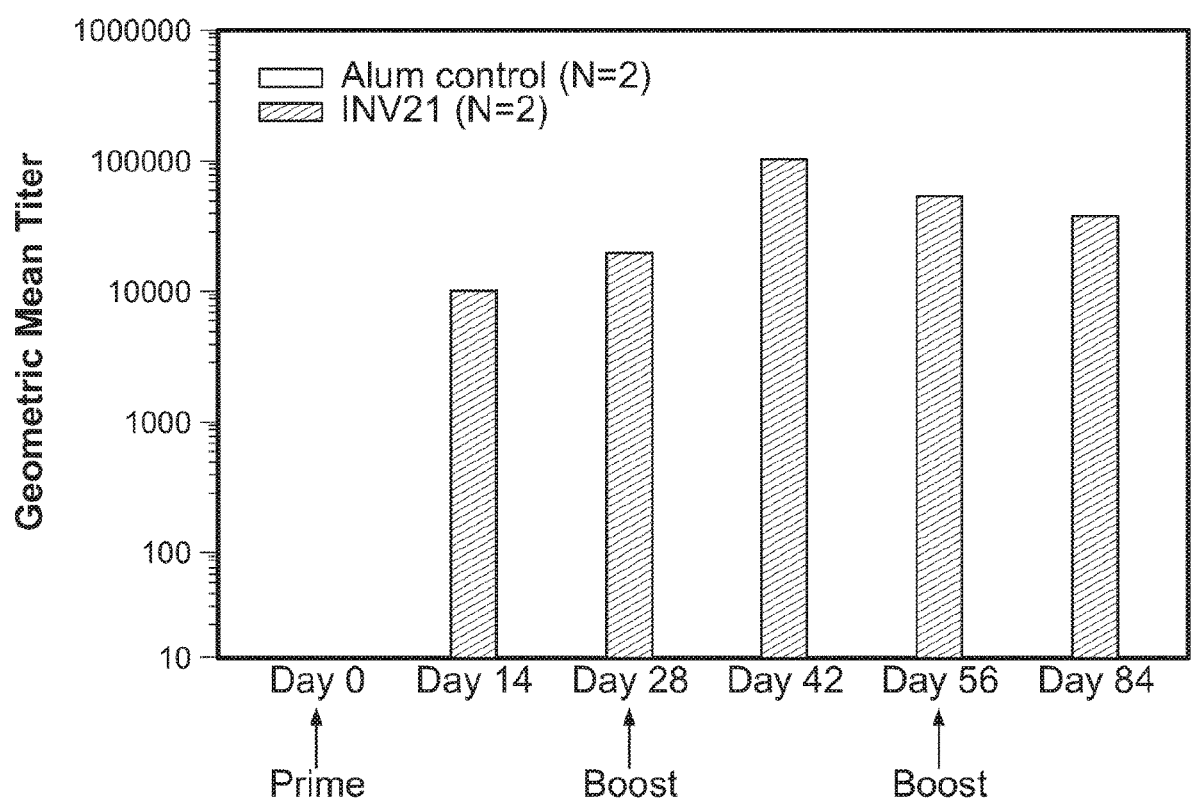
FIG. 5 shows immunogenicity of adapted enterovirus 71 vaccine in NZW rabbits, with geometric mean titer values from a TCID50 neutralization assay displayed in graphical form across longitudinal time points.

Rabbit anti-EV71 serum had the same reciprocal neutralizing titer against B4 and B5 sub-genogroups as compared to the titer obtained against the homologous B2 subgenogroup (FIG. 4). The reciprocal neutralizing titer of the rabbit serum against the C4 sub-genogroup was approximately 1.4-fold higher than the B2 titer. The reciprocal neutralizing titers of rat antiserum against the B4, B5, and C4 viruses were approximately 0.25-, 0.18-, and 2.8-fold as compared to the titer obtained against the homologous B2 subgenogroup, respectively (Table 7).

TABLE 7

Reciprocal Neutralizing Titers of INV21 against Homologous and Heterologous EV71 Sub-Genogroups

| Antiserum | Sub-genogroup | | | |
|---|---|---|---|---|
| | B2 | B4 | B5 | C4 |
| Rat | 724 | 181 | 128 | 2048 |
| Rabbit | 32768 | 32768 | 32768 | 46341 |

In conclusion, the results demonstrate that serum raised against the adapted EV71 vaccine can induce cross-neutralizing antibodies against heterologous strains of EV71 in at least two animal species.

Example 7: Toxicology Studies

Toxicology Study in Rabbits

A toxicology study was conducted as an initial evaluation of the use of NZW rabbits as an appropriate species in which to conduct the toxicity assessments to support dosing in humans. In this study, the immune response following three doses of adapted EV71 vaccine was evaluated in NZW rabbits. Two groups of animals (2 male rabbits per group) were immunized with either 15 μg adapted EV71 vaccine formulated with alum at 0.5 mg/dose or with an alum-only control formulation (0.5 mg/dose in PBS) by IM injection. Animals were immunized on Days 0, 28 and 56, and the levels of neutralizing antibodies were determined at various time points throughout the study up to Day 84. The third immunization was included to generate sera with high antibody titers for use as an assay development reagent and reference standard. Neutralizing antibody titers were measured using a TCID50 neutralization assay.

All animals that received the adapted EV71 vaccine elicited good immune responses, as indicated by the high reciprocal neutralizing antibody titers starting at Day 14 (after one immunization) and up to Day 84 at terminal bleed (after three immunizations) (Table 8).

TABLE 8

Immunogenicity of INV21 in NZW Rabbits

| | GMT | | | | | |
|---|---|---|---|---|---|---|
| Group | Day 0 | Day 14 | Day 28 | Day 42 | Day 56 | Day 84 |
| 1. Alum control | 1 | 1 | 1 | 1 | 1 | 1 |
| 2. INV21 | 1 | 8192 | 16384 | 92682 | 46341 | 32768 |

Reciprocal neutralizing antibody titers were highest at Day 42, 14 days after administering the second dose of adapted EV71 vaccine. The third dose of adapted EV71 did not result in an increase in the reciprocal neutralizing titers measured at Day 84 (FIG. 5). No neutralizing antibodies were detected in animals in the alum control group at all-time points assayed.

The results demonstrate the appropriateness of the NZW rabbits as a species in which to conduct the GLP toxicology study, as demonstrated by the high levels of neutralizing antibodies following immunization with the adapted EV71 vaccine.

GLP Toxicology Study and Local Tolerance

The toxicity of the adapted EV71 vaccine was further evaluated in NZW rabbits. In addition, local tolerance of the vaccine was evaluated. The objectives of this study were to assess the toxicity and local tolerance of the adapted EV71 vaccine following repeated IM immunizations and to assess the reversibility of any effects over a two to four week treatment free period. The test articles used in this study were the low dose and high dose adapted EV71 vaccine formulations, consisting of 0.6 μg EV71/dose and 3.0 μg EV71/dose respectively, formulated with alum adjuvant at 0.5 mg/dose (Table 9).

TABLE 9

Treatment Groups in Repeat Dose and Local Tolerance Study of INV21 (NC-NSP-007)

| Group | Treatment | EV71 (μg) | Alum (mg) | Dose Volume (mL) | Immunization Days | Days of Sacrifice[a] | No. of Aninials M | F | Total |
|---|---|---|---|---|---|---|---|---|---|
| G1 | Normal Saline Placebo | 0 | 0 | 0.5 | 0, 28 | 30, 56 | 6 | 6 | 12 |
| G2 | Vaccine Placebo[b] | 0 | 0.5 | 0.5 | 0, 28 | 30, 56 | 8 | 8 | 16 |
| G3 | Vaccine Low Dose | 0.6 | 0.5 | 0.5 | 0, 28 | 30, 56 | 10 | 10 | 20 |

TABLE 9-continued Treatment Groups in Repeat Dose and Local Tolerance Study of INV21 (NC-NSP-007)

| Group | Treatment | EV71 (µg) | Alum (mg) | Dose Volume (mL) | Immunization Days | Days of Sacrifice[a] | No. of Animals | | |
|---|---|---|---|---|---|---|---|---|---|
| | | | | | | | M | F | Total |
| G4 | Vaccine High Dose | 3.0 | 0.5 | 0.5 | 0, 28, 42 | 44, 56 | 10 | 10 | 20 |

M—male;
F—female
[a] Half the number of animals in each group were sacrificed 2 days after the last immunization, either on Day 30 or Day 44 (G4) and the remainder of the groups were sacrificed on Day 56 (terminal sacrifice).
[b] The Vaccine Placebo group received an alum-only adjuvant formulation.

The controls included were normal saline placebo (PBS) and an alum-only adjuvant formulation (0.5 mg/dose), the latter referred to as the Vaccine Placebo in this study. The test articles and controls were given as IM injections on Day 0 and Day 28 for animals in all Groups. Animals in Group 4 (Vaccine High Dose) received an additional immunization on Day 42, which exceeds by one dose the intended two dose regimen in the Phase 1 study. All animals were observed for any gross clinical changes, local reactions at the site of injection, mortality and morbidity, clinical pathology, hematology, clinical chemistry, gross pathology and histopathology.

In relation to overall adapted EV71 vaccine toxicity, both the low dose (0.6 µg/dose) and the high dose (3.0 µg/dose) formulations given by IM injections to NZW rabbits on two and three occasions, respectively, did not result in mortality or morbidity and there were no treatment related significant alterations in hematology or clinical chemistry. In addition, there were no treatment related changes in mean body weight, food consumption, respiratory rate or rectal temperature as well as gross pathological examination, absolute and relative organ weights. Furthermore, there was no treatment related neurotoxicity, renal or hematological adverse effects observed in the study. With regards to local tolerance, no erythema or edema was observed in any animals. Microscopically, some muscular lesions at the site of injection were observed, however these effects were reversible in the 14 or 28 day treatment free period following the last immunization. Muscular degeneration, with or without mononuclear cell (MNC)/eosinophil infiltration, was observed in a sub-population of animals in all groups receiving formulations containing alum adjuvant. Muscular degeneration with or without MNC/eosinophil infiltration was not observed in group G1, which received the normal saline placebo (PBS). The number of animals in which muscular degeneration was observed is shown in Table 10.

TABLE 10

Number of Rabbits with Muscular Degeneration at the Site of Injection

| Group | Treatment | Dose of EV71 (µg) | Muscle Degeneration (No./Group)[a] | | |
|---|---|---|---|---|---|
| | | | Without Infiltration | With Infiltration | Total[b] |
| G1 | Normal Saline Placebo | 0 | 0/12 | 0/12 | 0/12 |
| G2 | Vaccine Placebo[c] | 0 | 4/16 | 2/16 | 6/16 |
| G3 | Vaccine Low Dose | 0.6 | 4/20 | 6/20 | 10/20 |

TABLE 10-continued

Number of Rabbits with Muscular Degeneration at the Site of Injection

| Group | Treatment | Dose of EV71 (µg) | Muscle Degeneration (No./Group)[a] | | |
|---|---|---|---|---|---|
| | | | Without Infiltration | With Infiltration | Total[b] |
| G4 | Vaccine High Dose | 3.0 | 0/20 | 8/20 | 8/20 |

[a] Values are presented as the number of animals with at least one observation/total number of animals per treatment group
[b] Values shown under total are the total number of observations of muscle degeneration with and without MNC/eosinophil infiltration.
[c] The Vaccine Placebo group received an alum-only adjuvant formulation.

Muscular lesions at the site of injection comprised a varying degree of degeneration with or without MNC/eosinophil infiltration in all groups except G1 (normal saline PBS control). These lesions were consistent with known changes associated with aluminum salt adjuvants in vaccine preparations (Gherardi 1998; Gherardi 2001; Verdier 2005). Furthermore, regression of lesions was noted in all animals sacrificed on Day 56. It is therefore concluded that the muscular lesions at the site of injection are considered to be the effects of alum adjuvant used to formulate the adapted EV71 vaccine and not as a result of the presence of the EV71 antigen and that the effects were reversible.

Different histopathological changes were observed in visceral organs of animals in the Vaccine Low Dose and Vaccine High Dose groups, which were comparable with the Vaccine Placebo and Normal Saline groups. Furthermore, the lesions were considered nonspecific, not significant and did not follow any pattern and as such, these changes were considered as spontaneous or incidental in nature.

The results indicate that local reactions, typical of alum formulated vaccine preparations, were observed at the site of injection, with the low and the high dose adapted EV71 vaccine formulations as well as with the alum-only control formulation and were found to be reversible. In addition, both the low and high dose adapted EV71 vaccine formulations did not induce any treatment related physiological or pathological changes. Overall, the results of this study demonstrate that the adapted EV71 vaccine was safe and well tolerated.

Example 8: Adapted EV71 Vaccine is Safe, Immunogenic, and Induces Cross-Neutralizing Antibody Responses in Adult Volunteers The adapted EV71 vaccine described in Examples 1-7 was evaluated in a Phase I clinical trial in healthy adults. Thirty-six healthy males and females aged 21 to 45 years were enrolled into a randomized, double-blind, placebo-controlled study at the Investigational Medicine Unit, National University Hospital, Singapore. This study was a First in Human study for the adapted EV71 vaccine. Data from animal studies has demonstrated that the adapted EV71 vaccine elicits high levels of virus neutralizing antibodies in multiple animal species and is the basis for the selection of the immunogenicity endpoints.

Subjects

After signing informed consent, subjects were screened for eligibility in the study, as described below. At the screening visit, procedures included a physical examination, vital signs, ECG and laboratory tests. Screening could occur up to 42 days prior to vaccination.

In order to be eligible for the study, subjects had to meet the following criteria: male or female aged 21 to 45 years, inclusive, at the time of screening; in good health as determined by medical history and physical examination; normal clinical safety laboratory examinations [Na, K, Cl, Glucose, BUN, creatinine, phosphate, calcium, protein, albumin, alanine transaminase (ALT), aspartate transaminase (AST), bilirubin, white blood cell (WBC), hemoglobin, platelets and urinalysis. Normal ranges for safety laboratory tests were according to those used in the laboratory performing the safety laboratory tests. If any of these laboratory results were out of the normal range, the test was to be repeated. If the repeated results were out of the normal range, the subject could be enrolled, but only upon the approval of both the Investigator and the Medical Monitor]; have a body mass index (BMI) in the range of 19-28 kg/m$^2$; documented negative serology for Human Immunodeficiency Virus (HIV), Hepatitis C antibody, and Hepatitis B surface antigen; females of child bearing potential must have a negative urine pregnancy test result during screening and a negative urine pregnancy test immediately prior to vaccination and be willing to use oral, implantable, transdermal or injectable contraceptives or another reliable means of contraception approved by the Investigator (intrauterine device, female condom, diaphragm with spermicidal, cervical cap, use of condom by the sexual partner or a sterile sexual partner, or abstinence) from screening until after the last blood sample (at Day 196); willing and able to give written informed consent to participate; willing and able to communicate with the Investigator and understand the requirements of the study; and show low levels of EV71 neutralizing antibody, as described below.

Ideally only EV71 naive subjects were recruited for this study in order to obtain early indication of immunogenicity. Although some subjects had pre-immunity to EV71, only those with a reciprocal neutralizing titer of <8 or the lowest reciprocal neutralizing titers, whichever came first from the population of healthy volunteers screened at the site, were included in the study to enable some assessment of immunogenicity in the absence of pre-existing immunity.

Subjects who met any of the following criteria were not eligible for participation in the study: any medical, psychiatric, social condition, occupational reason or other responsibility that, in the judgment of the investigator, was a contraindication to protocol participation or impair a volunteer's ability to give informed consent; clinically significant hematological (including bleeding disorders), renal, hepatic, pulmonary (including asthma), central nervous system (including epilepsy, seizures, convulsions, or chronic migraines), cardiovascular, or gastrointestinal disorders, according to Investigator's judgment; ongoing rash or other dermatologic disease; abnormal ECG as assessed by the Investigator; febrile illness (temperature ≥38° C.) or moderate or severe acute illness or infection within three days prior to vaccination; history of diabetes mellitus; hypersensitivity to any vaccine; history of severe HFMD with CNS involvement; receipt of any vaccine in the 4 weeks preceding the first trial vaccination; planned receipt of any vaccine in the 4 weeks following each of the vaccinations in this study; known or suspected congenital or acquired immunodeficiency, immunosuppressive or cytotoxic therapy such as anti-cancer chemotherapy or radiation therapy within the preceding 6 months prior to the first vaccination, or long-term (at least 2 weeks within the previous 3 months) systemic corticosteroids therapy (at a dose of at least 0.5 mg/kg/day) prior to the first vaccination; history of thymic pathology, thymectomy, myasthenia or any immunodeficiency; history of recurring migraines or on prescription medication for treatment of recurring headaches or migraines; use of any non-steroidal anti-inflammatory drugs (NSAIDs), acetaminophen or antihistamines for the 3 days immediately prior to each vaccination; use of prescription or over the counter medications 7 days before the first vaccination (Day 0), excluding contraceptives; positive urine test for cocaine, amphetamines, opiates, or cannabinoids; participation or planned participation in any clinical trial, including receipt of another investigational product, from one month prior to the first vaccination through to one month following the last vaccination; receipt of blood products or immunoglobulins 8 weeks before the first vaccination (Day 0) or planned use during the study period; donation of blood 6 weeks before the first vaccination (Day 0) or at any time during the study; or females who were pregnant or lactating.

The trial protocol was approved by an independent ethics committee. The study was conducted in full conformance with the principles of the 'Declaration of Helsinki' (1964) including subsequent revisions or with the local laws and regulations. This study was to fully adhere to the principles outlined in the 'Guideline for Good Clinical Practice' International conference on Harmonization (ICH) Tripartite (1996) or with local laws and regulations. All prospective subjects were provided with a copy of the approved version of the Information Sheet and Consent Form to read. The study investigators were responsible for ensuring that all participants entered into the trial understood what they were undertaking and had read the information sheet. Subjects were advised that they were free to refuse to participate in, or to withdraw from the study at any time, and that the medical care they received would not be affected by their agreement or refusal to participate in the study.

Product Administration

Once enrolled, subjects were allocated to either Group 1 (low dose) or Group 2 (high dose) and randomized to receive adapted EV71 vaccine or placebo, with the exception of the sentinel subject who received the vaccination adapted EV71 vaccine first before the remaining subjects in each cohort on two occasions (Day 0 and Day 28). Low Dose included 12 subjects on adapted EV71 vaccine (0.6 µg EV71/dose) and 6 on placebo; High Dose included 12 subjects on adapted EV71 vaccine (3 µg EV71/dose) and 6 on placebo. Placebo treatment was phosphate buffered saline (PBS), administered as per the test product. Subjects were enrolled into two cohorts of 18 subjects at each dose level (low or high). In each cohort, one sentinel subject received the prime dose before the rest of the cohort. As such, the randomization schedule determined the treatment for the remaining subjects within each cohort (N=17). Subjects were randomized to receive vaccine or placebo. A Randomization Statistician not involved in the analysis of the study prepared the randomization list to randomly assign subject numbers to group and treatment. An appropriate blocking scheme was used to ensure that the balance between treatment assignments was maintained. The composition and dose volumes of all treatments are provided in Table 11 below.

TABLE 11

| Dose Level | EV71 Antigen | Aluminum hydroxide | Dose Volume |
| --- | --- | --- | --- |
| Low | 0.6 µg | 0.5 mg/dose | 0.5 mL |
| High | 3.0 µg | 0.5 mg/dose | 0.5 mL |
| Placebo | Phosphate Buffered Saline | | 0.5 mL |

The dose of the adapted EV71 vaccine was based on the EV71 antigen amount in the formulation. This study evaluated the safety and immunogenicity of two dose levels of adapted EV71 vaccine, a low dose formulation and a higher dose formulation, in which the absolute EV71 protein amount differed 5-fold between dose levels. The amount of alum adjuvant was constant for both dose levels (0.5 mg/dose).

The composition of the low dose formulation was intended to provide an initial assessment of the safety of the adapted EV71 vaccine in human volunteers. Both the low dose and high dose formulations were tested in a pivotal safety study conducted in rabbits. Furthermore, three doses were administered in the rabbit study, which exceeded by one dose the intended two dose regimen which was used in this study.

The proposed dose levels to be tested in this study were based on a dose ranging study in mice, whereby the lowest dose to elicit adequate neutralizing titers based on the reported protective titer of 1:128 in the literature after two doses of the adapted EV71 vaccine was 0.6 µg/dose. With the exception of the 9 µg/dose level where the reciprocal neutralizing titers and Seroconversion Rate (SCR) were lower than those of the 3 µg/dose, 3 and 15 µg/dose levels did not result in marked differences in neutralizing titers and SCR. Therefore 3 µg was selected as the high dose level to be evaluated in this study.

Subjects received two injections (prime dose on day 0; booster dose on day 28) intramuscularly in the deltoid region. Blood samples were taken at regular intervals for assessments of safety (hematology, serum chemistry) and immunogenicity (neutralizing antibodies against EV71). Subjects were given diaries, which were to be completed for 14 days after each vaccination to record oral temperature and any symptoms (local and systemic) experienced after vaccination. Any adverse event occurring during the study was recorded.

The following medications were not permitted in the study: NSAIDs, acetaminophen or antihistamines for the 3 days prior to each vaccination. The following medications and treatment were permitted in this study: NSAIDs, acetaminophen or antihistamines could be used during the first 7 days after each vaccination if the subject had a fever ≥37.8° C. or if the subject had significant arm pain, myalgia, or headache. NSAIDs or acetaminophen were only to be taken after documentation of symptom or fever on the subject diary and were not to be taken prophylactically; low-dose aspirin, not exceeding 100 mg once per day; and low dose narcotics such as Percocet, which contains oxycodon and acetaminophen, were only to be taken after documentation of symptoms in the subject diary and should not be taken prophylactically.

Subjects and the Investigator were blinded to treatment (vaccine or placebo) by employing an Unblinded Study Coordinator or designee to prepare the investigational product, including the masking of syringes, and labeling the syringes with the unique syringe number and subject identification. The syringe containing the product was masked with a label to prevent the color of the contents from being visible. The laboratories performing hematology, serum chemistry, urinalysis, and neutralizing antibody assays were blinded to treatment as the samples were only labeled with the subject's unique identification number, date and protocol number. The person administering the investigational product (Investigator or a qualified designee) and personnel involved in safety assessments remained blinded throughout the study.

The randomization schedule was not available to the Investigator, the blinded monitors or to the study team during the study. Unblinding was only to occur if specifically requested by the Investigator in the case of a serious adverse event or a medical emergency. In the event the treatment code was to be broken, it was broken ONLY for the subject(s) in question and upon the written request of the Investigator or Sub-Investigator to the Unblinded Study Coordinator or Randomization Statistician in order to enable decision making regarding continuation of the study.

Subjects were required to return to the site for a follow-up safety and immunogenicity assessments at 2 months (Day 84) and 6 months (Day 196) after the last dose. In total, each subject's participation was approximately 8.5 months including 42 days for screening and 6 months follow-up after the last dose (Day 196 visit).

The study schedule of events, including all safety and efficacy measurements, is summarized in Tables 12 and 13 below.

TABLE 12

Schedule of Events for Study Days −42 to −14 (Prime Dose)

| Study Month | Screening | | | 1 | | | | |
|---|---|---|---|---|---|---|---|---|
| Study Day | −42 to −1 | Re-screen[1] | 0 | 1 | 2 | 3 | 7 | 14 |
| Visit Number | 1 | | 2 | Sentinel[2] | 3 | | 4 | 5 |
| Informed consent | X | | | | | | | |
| Review I/E criteria | X | X | X[3] | | | | | |
| Medical history | X | X | | | | | | |
| Demographics | X | | | | | | | |
| Physical examination [10] | X | X | X[3] | | | | | |
| Concomitant medications | X | X | X | X | X | X | X | X |
| Urine pregnancy test (♀) | X | X | X[4] | | | | | |
| Urine drugs of abuse test | X | X | X[3] | | | | | |
| 12-lead ECG | X | X | | | | | | |
| Serology (EV71, HIV, Hep B/C) | X | X | | | | | | |
| Vaccine administration[10] | | | X[5] | | | | | |
| Vital signs | X | X | X[6] | X | X | X | X | X |
| Injection site evaluation[10] | | | X[7] | X | X | X | X | X |
| Serum chemistry | X | X | X[3] | | | | X | X |
| Hematology | X | X | X[3] | | | | X | X |
| Urinalysis[8] | X | X | X[3] | | | | X | X |
| Serum neutralizing antibodies | | | X[3] | | | | | X |
| Subject diary distribution | | | X | | | | | |
| Subject diary review | | | | X | X | X | X | X[9] |
| Document adverse events | | | | X | X | X | X | X |

[1]Eligible subjects who were not randomized in the low dose cohort could be randomized into the high dose cohort provided they were within the 42 day screening period. If they were outside the 42 day screening period, they were to be re-screened whereby all tests and procedures were repeated except for informed consent process and collection of demographic data.
[2]A sentinel subject in each cohort was dosed first before the rest of the cohort. Sentinel subjects were observed for 2 days and were required to return to the Unit on Day 1 and Day 2 for safety assessments.
[3]Inclusion/Exclusion (I/E) criteria and physical examination were reviewed or performed prior to vaccination. Samples for drugs of abuse test, serum chemistry, hematology, urinalysis and serum neutralizing antibodies were collected prior to vaccine administration.
[4]Urine pregnancy test results were obtained prior to vaccine administration and were negative for the subject to continue in the study.
5Record of the arm in which the vaccine was administered.
[6]Prior to and at 5, 30 and 60 min after vaccine administration.
[7]At 5, 30 and 60 min after vaccine administration.
[8]For urinalysis, record if female subjects were menstruating at time of sample collection.
[9]Subject diaries were collected from the subject at the Day 14 visit.
[10]The physical examination, vaccination and injection site evaluations were to be performed by the Investigator or his designee.

TABLE 13

Schedule of Events for Study Days 28 to 196 (Booster Dose)

| Study Month | 2 | | | | 3 | 4 | 8 | N/A |
|---|---|---|---|---|---|---|---|---|
| Study Day | 28[1] | 31 | 35 | 42 | 56[2] | 84[3] | 196[4] | N/A |
| Visit Number | 6 | 7[5] | 8[6] | 9[7] | 10 | 11 | 12 | Follow-up[8] |
| Physical examination[20] | X[9] | | | | X | | | X |
| Concomitant medications | X | X | X | X | X | X | X | X |
| Urine pregnancy test (♀) | X[10] | | | | X | | | |
| Urine drugs of abuse test | X[9] | | | | | | | |
| Vaccine administration[20] | X[11] | | | | | | | |
| Vital signs | X[12] | X | X | X | X | X | X | X |
| Injection site evaluation[20] | X[13] | X | X | X | | | | X[14] |
| Serum chemistry | X[9] | | X | X | X | | | X |
| Hematology | X[9] | | X | X | X | | | X |
| Urinalysis[15] | X[9] | | X | X | X | | | X |
| Serum neutralizing antibodies | X[9] | | | X | X | X | X | X[16] |
| Subject diary distribution | X | | | | | | | |
| Subject diary review | | X | X | X[17] | | | | |
| Document adverse events[1] | X | X | X | X | X | | | |
| Follow-up for SAEs[19] | | | | | | X | X | |

[1]Day 28 visit for the booster dose may occur on Day 28 ± 3 days
[2]Day 56 visit may occur on Day 56 ± 3 days
[3]Day 84 visit may occur on Day 84 ± 5 days
[4]Day 196 visit may occur on Day 196 ± 7 days
[5]Visit 7 will always occur 3 days after the boost (ie. on Day 31 if the boost was administered on Day 28; on Day 33 if the boost was administered on Day 30; on Day 29 if the boost was administered on Day 26)
[6]Visit 8 will always occur 7 days after the boost (ie. on Day 35 if the boost was administered on Day 28; on Day 37 if the boost was administered on Day 30; on Day 33 if the boost was administered on Day 26)
[7]Visit 9 will always occur 14 days after the boost (ie. on Day 42 if the boost was administered on Day 28; on Day 44 if the boost was administered on Day 30; on Day 40 if the boost was administered on Day 26)
[8]Follow-up visit is only applicable if a subject does not complete the study up to Day 196 or who is discontinued from the study early (early termination)
[9]Physical examination must be performed prior to vaccination. Samples for drugs of abuse test, serum chemistry, hematology, urinalysis and serum neutralizing antibodies must be collected prior to vaccine administration
[10]Urine pregnancy test result must be obtained prior to vaccine administration and must be negative for the subject to continue in the study
[11]Record the arm in which the vaccine was administered
[12]Prior to and at 5, 30 and 60 min after vaccine administration
[13]At 5, 30 and 60 min after vaccine administration
[14]Injection site will be evaluated if early termination occurs within 14 days of either the first or second vaccination
[15]For urinalysis, record if female subjects are menstruating at time of sample collection
[16]Blood will be collected for serum neutralizing antibodies if early termination occurs within 14 days of either the first or second dose of the vaccine
[17]Subject diaries will be collected from the subject at the Day 42 visit
[18]All adverse events will be recorded from the first vaccination (Day 0) to 28 days post last dose (Day 56)
[19]Subjects will be questioned regarding any SAEs that they may have experienced within 6 months after the last dose at Day 84 and Day 196 visits
[20]The physical examination, vaccination and injection site evaluations are to be performed by the Investigator or his designee.

Safety Measurements Assessed

A complete medical history was assessed, including a review of all major body systems. Significant past and present medical history was obtained by interview during the screening visit. Details of prescription and over-the-counter medications (including vitamins and supplements) that were currently used or used in the previous three (3) months prior to screening were recorded during the screening visit. Concomitant medications records were reviewed at each visit and any new medications were documented.

Demographics included the age, height, weight, BMI and race as described by the subject. Subjects had weight and height measured while wearing light street clothing and with shoes off. BMI was calculated in metric units using the following formula: BMI=weight (kg)/height (m)$^2$. Demographics were obtained during screening.

A complete physical examination was done by the Investigator or his designee for each subject at screening, prior to vaccine administration on Days 0 and 28, and on Day 56. The examination consisted of assessment of the following organs/systems: Head; Eyes; Ears, nose, throat; Neck; Cardiovascular; Chest; Respiratory; Abdomen; Genitourinary; Extremities; Musculoskeletal; Nervous system; Dermatological; and Other conditions of note. Any changes noted during the physical examination from the previous examination were recorded.

Vital signs included oral temperature, blood pressure, pulse rate and respiratory rate. Vital signs were obtained at screening, on Day 0 (prior to and at 5, 30 and 60 minutes after vaccine administration), on Day 1 (sentinels only), Day 2 (sentinels only), Days 3, 7, 14, on Day 28 (prior to and at 5, 30 and 60 minutes after vaccine administration), and on Days 31, 35, 42, 56, 84 and 196. Blood pressure was measured from the subject's arm while the subject was seated and after a 5 minute rest, with the arm supported at the level of the heart. Blood pressure was recorded to the nearest mmHg. When vital signs were scheduled at the same time as blood collection, vital signs were obtained first, except on Day 0 and Day 28 when vital signs were obtained pre- and post-vaccination.

All subjects were required to have a normal ECG prior to enrolment into the study. A standard 12-lead ECG was performed at screening. Each ECG interpretation was reviewed and confirmed by the Investigator. A machine interpretation was acceptable as long as it was confirmed by the Investigator.

Prior to injection, the study staff responsible for administering the investigational product drew a circle (~1" in diameter) using an indelible marker around the actual injection site. The procedures were detailed in the study manual of procedures. The arm in which the injection was administered was recorded.

The injection site was evaluated for local reactogenicity using the assessment scales on Day 0 (at 5, 30 and 60 minutes post vaccination), Day 1 (sentinels only), Day 2 (sentinels only), Days 3, 7, 14, Day 28 (at 5, 30 and 60 minutes post vaccination), Days 31, 35 and 42. In the event injection site reactions are observed, the Investigator provided appropriate care. Injection site reactions were photographed with a ruler clearly visible in the photograph. Photographs were identified only by subject identification code, visit number and date to ensure protection of the identity of the subject.

Subjects were asked to complete a diary ("Diary of Symptoms") beginning on the day of each vaccination and for 14 days thereafter (Days 0 to 14 and Days 28 to 42). During this time, subjects were required to take their oral temperature (at the same time each day) and record it in the diary. In addition, they were asked to record any symptoms they were experiencing during this time period, including: Injection site reactions such as Pain, Redness (erythema), Swelling (edema/induration), and Itching (pruritis); General body symptoms such as Headache, Muscle pain (myalgia), Tiredness (fatigue), Body rash, Nausea, and Vomiting (number of times); and Other symptoms. Subjects were required to bring their diary to each visit, which was reviewed by the Investigator or his designee during the visit.

Clinical Laboratory Evaluations

Clinical laboratory evaluations consisted of hematology, serum chemistry, and urinalysis. Hematology, serum chemistry, and urinalysis was done at screening and on Days 0 (pre-dose), 7, 14, 28 (pre-dose), 35, 42 and 56. The parameters tested are listed in Table 14.

TABLE 14

List of Clinical Laboratory, Urinalysis and Other Tests

| Hematology | Serum Chemistry | Urinalysis* | Others |
|---|---|---|---|
| Hemoglobin | Sodium | Glucose | Urine pregnancy test |
| Platelets | Potassium | Protein | Serology (EV71, HIV-1 |
| WBC (white | Chloride | Blood | and-2 antibodies, |
| blood cell) | Glucose | | hepatitis B surface |
| | Blood Urea | Microscopic: | antigen, and hepatitis C |
| | Nitrogen | Rbc/hpf (red | antibody) |
| | Creatinine | blood cells per | |
| | Phosphate | high powered | |
| | Calcium | field) | |
| | Total Protein | | |

TABLE 14-continued

List of Clinical Laboratory, Urinalysis and Other Tests

| Hematology | Serum Chemistry | Urinalysis* | Others |
|---|---|---|---|
| | Albumin | | |
| | ALT (alanine transaminase) | | |
| | AST (aspartate transaminase) | | |
| | Total Bilirubin | | |

*A clean-catch urinalysis obtained from a female contaminated by squamous epithelial cells could be repeated to obtain a clean specimen without squamous epithelial cells. For females, a record of if the subject was menstruating at the time of the sample collection was captured.

All female subjects were required to have a negative urine pregnancy test result at screening and prior to administration of investigational product on Days 0 and 28. Urine pregnancy test was repeated on Day 56. Any positive test result was followed-up accordingly.

All subjects were required to have a negative test result for drugs of abuse (cocaine, opiates, cannabinoids and amphetamines) at screening to participate in the study. In addition, this test was done prior to dosing on Day 0 and Day 28. Any positive test result was reported to the proper authorities.

Blood samples were obtained on Days 0 (pre-dose), 14, 28 (pre-dose), 42 and 56 for measurement of neutralizing antibody levels against EV71. Longer term immunogenicity was assessed by measuring the levels of neutralizing antibodies in samples obtained on Day 84 and Day 196. Efficacy endpoints included: geometric mean neutralizing antibody titers (GMTs) based on neutralizing antibody titers at 14, 28, 42, and 56 days after the prime vaccination; Measurement of fold-increase over baseline of neutralizing titers against EV71; and Durability of immune response as assessed by neutralizing antibodies to EV71 and GMTs at 2 months (Day 84) and 6 months (Day 196) after the boost vaccination.

Data Quality and Assurance

Accurate and reliable data collection was assured by verification and cross-check of the Case Report Forms (CRFs) against source documents (source data verification). The data collected were entered into an electronic database and subjected to quality assurance checks prior to database lock.

Monitoring visits to the study site were made periodically during the study to ensure that all aspects of the protocol were followed. Sponsor personnel or their designee (Study Monitor) contacted and visited the Investigator and were allowed, on request, to inspect various study related records and source documents provided that subjects' confidentiality was maintained in accordance with local requirements. Source documents were defined as original documents, data and records including, but not limited to, the Investigator's File, study medication, subject records, informed consent documentation as well as review of CRFs and associated documents.

It was the monitor's responsibility to inspect the CRFs at regular intervals throughout the study to verify the adherence to the protocol and the completeness, consistency and accuracy of the data being entered into them. The monitor had access to the laboratory test reports and other records needed to verify the entries on the CRF. It was important that the Investigator and other study personnel were available during the monitoring visits and that sufficient time was devoted to the process to ensure that any issues detected in the course of these monitoring visits were resolved.

The study site could also have been subject to quality assurance audits by the Sponsor or by independent auditors to verify that the study had been conducted according to the protocol, GCP, ICH requirements and the applicable regulations. In such circumstances, the Sponsor-designated auditor contacted the site in advance to arrange an auditing visit. The auditor could request to visit the facilities where laboratory samples were collected, where the medication was stored and prepared, and any other facility used during the study. In addition, there was the possibility that this study could have been audited by national or international regulatory authorities. If the study site was contacted for an inspection by any regulatory agency, the Sponsor was to be notified immediately. The Investigator was to allow direct access to study documents during inspections and audits.

The study statistical analysis plan (SAP) was prepared by Copper Rock Research, Inc. prior to database lock. It included the following specifications.

The safety population consisted of all randomized subjects who received at least one dose of study vaccine and for whom post-dosing safety data had been obtained. Subjects were analyzed according to the treatment actually received.

The full analysis set consisted of all randomized subjects who received at least one dose of study vaccine and for whom valid pre and post dosing blood samples for immunogenicity had been received. Subjects were analyzed according to the treatment assigned at randomization regardless of the treatment they actually received.

The Per-Protocol Population consisted of all randomized subjects who completed the study without any major protocol violations as defined prior to database lock. Subjects were analyzed according to the treatment they actually received. Summaries of enrolment, disposition and important protocol deviations were presented for all randomized subjects. Summaries of demographics, baseline characteristics and safety data were based on the safety population. Summaries of immunogenicity data was based on the full analysis set as well as the per-protocol population. Data listings displayed all available data for all randomized subjects.

The summary of subject disposition displayed the number of subjects who were randomized, received study vaccine, completed the study, or discontinued. Also included in this summary were subject discontinuations showing the number of subjects who did not complete the study according to the reason for study termination/discontinuation. A summary of the number and percentage of subjects included in each analysis set was summarized by treatment group for all randomized subjects. A listing of subjects and reasons for exclusion from any analysis set were also provided. Subject disposition, exclusion from randomization with reason, assignment to the treatment arms, inclusion in the analysis sets with reasons of exclusion, and study completion with reasons of early termination were presented in data listings.

Important protocol deviations reported during the study were recorded. Important protocol deviations (IPDs) were defined as deviations that could potentially affect the conclusions of the study. Prior to study database lock, protocol deviations were reviewed and IPDs were identified. These IPDs were summarized in a data listing. Medical history was presented in a data listing.

Demographic data (age, gender, and race) and baseline characteristics (height, weight, body mass index [BMI]) were summarized using descriptive statistics and frequency tables.

The neutralizing antibodies against EV71 were summarized by calculating the GMTs at each study day using a log-transformation, and were exponentiated back to original units for reporting purposes. Descriptive statistics included the number of subjects (n), geometric mean, and 95% confidence interval for the geometric mean.

The fold increase over baseline of neutralizing antibody titers against EV71 was calculated at each study day, using untransformed titer values, by dividing the titer value at each post-baseline study day by the baseline value. The fold increase over baseline was summarized using descriptive statistics by study day and treatment group. Additionally, the number and percent of subjects achieving seroconversion, defined as a four-fold increase over baseline, at each study day was summarized. An overall summary of the number and percent of subjects achieving seroconversion at any time after the first vaccination was provided. The durability of immune response was assessed by repeating the above analyses for geometric mean neutralizing antibody titers (GMT), fold increase over baseline, and percent seroconversion at 2 months (Study Day 84) and 6 months (Study Day 196) after the boost vaccination.

Unsolicited treatment-emergent adverse events, categorized by MedDRA (Version 12.0) system organ class (SOC) and preferred term, were listed and summarized in frequency tables. The frequency tables included the number of events, the number of unique subjects experiencing each event one or more times, and the percentage of subjects experiencing each event one or more times for treatment group. A frequency table of adverse events (AEs) which are related to study drug was also provided.

Adverse events were also tabulated in terms of the number and percentage of subjects experiencing events by maximum severity. In the tabulation by maximum severity, a subject with more than one event coded to the same preferred term was classified according to the most severe event. The duration of each adverse event was calculated as the AE stop date−AE start date+1. The duration was summarized by SOC, preferred term, and treatment using descriptive statistics. Serious AEs, deaths, and AEs leading to premature discontinuation from the study were presented in data listings.

Solicited adverse events were summarized by vaccination dose (first or second) and treatment group. These frequency tables included the number of events, the number of unique subjects experiencing each event one or more times, and the percentage of subjects experiencing each event one or more times for each vaccination dose and treatment group. The denominator for percentages is the number of subjects who received the vaccination dose for the relevant summary table. Solicited AEs were also be summarized by highest intensity. In this tabulation, a subject who experienced an AE multiple times was classified according to the most intense AE.

The cumulative number of days each symptom was reported on the diary during each 14 day follow-up period was summarized by symptom, treatment group, and vaccination dose using descriptive statistics. Any symptoms reported on Day 14 of each follow-up period were presented in a separate data listing. Additional items from the subject diary, including oral temperature, size of redness and swelling, number of times of vomiting, and the overall assessment of vaccine tolerability were summarized by vaccination dose, and treatment group. Subject Diary of Symptoms including solicited AEs and any additional symptoms and comments reported by the subject, were displayed in a data listing.

Injection site reactions of pain, tenderness, erythema/redness, induration/swelling, and pruritis/itching were summarized using frequency tables showing the number and percent of subjects experiencing each reaction by severity grade at each study day and time point. The injection site reactions recorded on Study Days 1 and 2 for the two sentinel subjects were not summarized, but were displayed in the data listing. The injection site reactions recorded for all other study days for the two sentinel subjects were included in the summary tables, which were summarized by vaccination dose and treatment group.

Physical examination results (normal, abnormal) were summarized in a frequency table by body system and study day.

Two summary tables of descriptive statistics (e.g., N, mean, SD, min, median, max) were presented for the observed vital signs data. The first table included a summary of observed values of descriptive statistics for each study day to Day 196 for oral temperature (° C.), pulse rate (beats per minute), respiration rate (breaths per minute), and blood pressure (systolic and diastolic in mmHg).

The second summary table included a summary of descriptive statistics for change from observed baseline values to each post-dose time point on each dosing day for the vital signs parameters referenced above until Day 196. Vital signs recorded on Study Days 1 and 2 for the two sentinel subjects were not summarized as described above, but were displayed in the data listing. Data from the sentinel subjects for all other study days were included in the summary tables. Results of the 12-lead ECG results performed at screening were presented in a data listing only.

The hematology and clinical chemistry observed data was summarized with descriptive statistics (mean, SD, median, minimum and maximum) by study day and treatment group for observed values and changes from baseline. The hematology, clinical chemistry and urinalysis data was also summarized in shift tables that compared toxicity grade shifts from baseline.

All other clinical laboratory data was presented only in data listings. In all listings of laboratory data, if a normal range was available for a given parameter, it was included in the listing. Additionally, out-of-range values were flagged with a "L" or "H" (less than lower limit of normal or greater than upper limit of normal, respectively). The listings also provide the toxicity grades, maximum grade shift from baseline and result changes from baseline. If a hematology or clinical chemistry test was repeated, the value from the initial scheduled collection was used in statistical summaries. All values were included in data listings.

Medications stopped before the first dose of study vaccine were considered prior medications. Medications started prior to the first dose of study vaccine and continued into the study, or medications started on or after the first dose of study vaccine were reported as concomitant medications. Prior and concomitant medications were presented by subject in a separate data listing.

The following additional data was presented by subject as data listings only: Inclusion and Exclusion Criteria, Randomization and Informed Consent, Study Drug Administration, Comments Log, and Log Completion Verification.

This study was an exploratory trial to assess the short-term safety and tolerability and immunogenicity of vaccination with two dose levels of an inactivated EV71 vaccine in healthy adults. Therefore, this study was not powered to detect any differences in potential safety and immunogenicity data between the treatment groups. The sample size of 36 was chosen to provide data from a minimal number of subjects to provide early data on safety and tolerability.

A total of 36 subjects were enrolled in the study. Thirty five of the 36 subjects completed the study as planned (ie. completed the study through to Day 56) and received both doses of investigational product as planned. One subject in the high dose group withdrew consent due to administrative reasons after the first dose.

Protocol deviation listings were obtained from observations made by the study monitor at the site and from review of the study database. Protocol deviations were reported for 28 of the 36 subjects. The majority of protocol deviations were associated with eligibility deviations and late subject visits.

Efficacy Evaluation

All subjects were included in the Safety Population, Full Analysis Set and Per-Protocol Population, and thus all subjects were used for all data sets that were analyzed. No formal statistical analysis was performed on efficacy data obtained in this study. For any subjects withdrawn from the study early, all immunogenicity and safety data collected at the early termination visit were excluded from summary tables but were presented in data listings.

A summary of the mean demographics for gender, age, height, weight and BMI across the dose groups are presented in Table 15.

TABLE 15

Summary of Mean (SD) Demographics

| | Low Dose | | High Dose | |
|---|---|---|---|---|
| | Adapted EV71 vaccine (N = 12) | Placebo (N = 6) | Adapted EV71 vaccine (N = 12) | Placebo (N = 6) |
| Gender N (%) | Male, 5 (42%) Female, 7 (58%) | Male, 5 (83%) Female, 1 (17%) | Male, 7 (58%) Female, 5 (42%) | Male, 6 (100%) Female, 0 |
| Age (years) Mean (SD) Median | 33.7 (7.9) 32 | 31.2 (5.5) 32.5 | 30.9 (5.8) 30.5 | 30.2 (7.2) 29.5 |
| Height (m) Mean (SD) Median | 1.633 (0.106) 1.61 | 1.697 (0.082) 1.72 | 1.660 (0.086) 1.685 | 1.710 (0.055) 1.71 |
| Weight (kg) Mean (SD) Median | 61.13 (13.55) 54.4 | 68.27 (10.86) 69.1 | 62.08 (9.17) 61.1 | 69.95 (10.13) 66.05 |
| BMI (kg/m$^2$) Mean (SD) Median | 22.62 (2.52) 22.2 | 23.62 (2.21) 23.7 | 22.53 (2.83) 21.5 | 23.83 (2.10) 23.15 |

All subjects enrolled in the study were Asian. Subjects were well matched across the treatment groups with regards to age, height, weight and BMI. The mean age was 31-34 years for the adapted EV71 vaccine groups and 30-31 years for the placebo groups. The BMI range was 22.5-23.8 across all treatment groups. With regards to gender, subjects were relatively well matched in the adapted EV71 vaccine dose groups. There was a higher proportion of male subjects in the placebo groups. Medical history was recorded at screening. The target population for this study was healthy adults. No subjects enrolled in the study had any clinically significant ongoing medical history at screening. A standard 12-lead ECG was performed at screening. All subjects had a normal ECG prior to enrolment into the study. Levels of EV71 reciprocal neutralizing antibody titer were measured at screening and presented in Table 16.

Serum was prepared from blood samples obtained on Days 0 (pre-dose), 14, 28 (pre-dose), 42 56, 84 and 196 for analysis of EV71 neutralizing antibody levels. Immunogenicity data are presented as GMT and fold-increase in GMT and seroconversion in Table 17 below.

TABLE 17

Summary of Geometric Means of EV71 Neutralizing Antibody Titers

| | Low Dose | | | | High Dose | | | |
|---|---|---|---|---|---|---|---|---|
| | Vaccine | | Placebo | | Vaccine | | Placebo | |
| Visit | N | GMT (95% CI)$^a$ | N | GMT (95% CI) | N | GMT (95% CI) | N | GMT (95% CI) |
| Screening | 12 | 20.2 (11.7-34.7) | 6 | 25.4 (6.6-98.4) | 12 | 28.5 (12.1-67.2) | 6 | 25.4 (7.7-83.3) |
| Day 0 | 12 | 20.2 (11.7-34.7) | 6 | 32.0 (7.5-137.1) | 12 | 28.5 (11.9-68.6) | 6 | 22.6 (6.3-81.4) |
| Day 14 | 12 | 128.0 (32.2-508.8) | 6 | 20.2 (4.2-97.0) | 12 | 143.7 (29.9-690.1) | 5 | 36.8 (8.9-151.2) |
| Day 28 | 12 | 80.6 (22.5-289.5) | 6 | 28.5 (5.0-163.5) | 11 | 99.5 (20.6-481.1) | 6 | 22.6 (6.3-81.4) |
| Day 42 | 12 | 322.5 (144.3-720.7) | 6 | 32.0 (6.1-168.1) | 11 | 451.4 (163.4-1247) | 6 | 32.0 (7.0-147.2) |
| Day 56 | 12 | 203.2 (76.1-542.4) | 5 | 24.3 (3.3-175.9) | 11 | 350.8 (122.9-1001) | 6 | 25.4 (6.1-106.2) |
| Day 84 | 12 | 143.7 (53.3-386.9) | 6 | 28.5 (6.5-125.8) | 11 | 290.4 (94.9-888.2) | 6 | 28.5 (5.0-163.5) |
| Day 196 | 12 | 80.6 (31.9-203.6) | 6 | 25.4 (6.6-98.4) | 11 | 145.2 (53.7-392.6) | 6 | 22.6 (6.3-81.4) |

$^a$GMT (95% CI) = Geometric Mean Titer (95% Confidence Interval)

TABLE 16

EV71 Reciprocal Neutralizing Antibody Titer at Screening

| EV71 Reciprocal Neutralizing Antibody Titer | Low Dose (vaccine and placebo combined) N = 18 N (% Total) | High Dose (vaccine and placebo combined) N = 18 N (% Total) |
|---|---|---|
| <8 | 0 (0%) | 2 (11.1%) |
| 8 | 6 (33.3%) | 5 (27.8%) |
| 16 | 5 (27.8%) | 2 (11.1%) |
| 32 | 2 (11.1%) | 3 (16.7%) |
| 64 | 3 (16.7%) | 1 (5.6%) |
| 128 | 2 (11.1%) | 4 (22.2%) |
| 256 | 0 (0%) | 1 (5.6%) |

As shown in Table 16, in the low dose group, the majority of subjects (72.2%) had low levels of EV71 neutralizing antibodies at screening with 6 (33.3%) subjects having a reciprocal EV71 titer of 8, 5 (27.8%) subjects of 16 and 2 (11.1%) subjects of 32. Similarly, in the high dose group, the majority of subjects had low levels of EV71 neutralizing antibodies at screening with 2 (11.1%) subjects having a reciprocal EV71 titer of <8, 5 (27.8%) subjects of 8, 2 (11.1%) subjects of 16 and 3 (16.7%) subjects of 32.

The level of EV71 neutralizing antibodies, presented as GMT, was highest at Day 42 (14 days after the second dose) in both the low dose and high dose groups. In the low dose group, following one dose of adapted EV71 vaccine, the GMT increased from 20.2 to 128.0 at 14 days after dosing. Following the second dose, the GMT increased from 80.6 (Day 28; pre-dose) to 322.5 at 14 days post vaccination (Day 42). Although the GMT decreased slightly at Day 56 through Day 196 (203.2 and 80.6, respectively), they remained high and around four times above baseline values up to 6 months after the second dose. The GMTs in the placebo group were similar to the baseline values at all time points analyzed during the study.

Similarly, in the high dose group, following one dose of adapted EV71 vaccine, GMT increased from 28.5 at Day 0 (pre-dose) to 143.7 at 14 days post vaccination. Following the second dose, the GMT increased from 99.5 (Day 28; pre-dose) to 451.4 at 14 days post vaccination (Day 42). Although the GMT decreased slightly at Day 56 through Day 196 (203.2 and 145.2, respectively), they remained high and at least five times above the baseline values up to 6 months after the second dose. The GMTs in the placebo group were similar to the baseline values at all time points analyzed during the study.

The magnitude of increase in GMTs over time, represented as the fold increase over baseline (Day 0) of neutralizing antibody titers against EV71, was calculated at each study day and summarized using descriptive statistics. Table 18 provides a summary of the fold-increase in GMT over time and between treatment groups.

TABLE 18

Summary of Mean (SD) Neutralizing Antibody Titers: Fold Increase over Baseline

| | Low Dose | | | | High Dose | | | |
|---|---|---|---|---|---|---|---|---|
| | Vaccine | | Placebo | | Vaccine | | Placebo | |
| Visit | N | Mean (SD) | N | Mean (SD) | N | Mean (SD) | N | Mean (SD) |
| Day 14 | 12 | 19.6667 (35.9351) | 6 | 0.7708 (0.3743) | 12 | 11.7500 (18.7040) | 5 | 1.4000 (0.5477) |
| Day 28 | 12 | 10.1250 (17.8149) | 6 | 1.0000 (0.5477) | 11 | 11.2727 (19.6168) | 6 | 1.0000 (0.0000) |
| Day 42 | 12 | 23.0000 (21.1746) | 6 | 1.0833 (0.4916) | 11 | 31.6364 (36.4178) | 6 | 1.5000 (0.5477) |
| Day 56 | 12 | 15.5000 (17.3126) | 5 | 0.9000 (0.2236) | 11 | 29.4545 (37.2676) | 6 | 1.1667 (0.4082) |
| Day 84 | 12 | 10.8333 (10.9365) | 6 | 1.0000 (0.5477) | 11 | 20.0000 (18.6548) | 6 | 1.5000 (1.2247) |
| Day 196 | 12 | 5.7500 (5.2936) | 6 | 0.8333 (0.2582) | 11 | 7.6364 (4.8015) | 6 | 1.0000 (0.0000) |

As shown in Table 18, higher increases in GMTs, expressed as fold increase over baseline, were observed in the high dose group compared to the low dose group at Day 28 to Day 196. The greatest increases in GMTs were observed at Day 42 in both the low and high dose groups with a 23-fold and 32-fold increase in titers, respectively, compared to Day 0. The high antibody levels at Day 42 could be explained by the booster dose of adapted EV71 vaccine given at Day 28. In the placebo groups the increases in GMTs were minimal.

Seroconversion was defined as a post-baseline antibody titer increase of at least 4-fold. A summary of Seroconversion Rates (SCR) is presented in Table 19. Overall study SCR was defined as the percentage of subjects who achieve seroconversion at any time point in the study.

TABLE 19

Summary of Seroconversion Rates

| | Low Dose | | | | High Dose | | | |
|---|---|---|---|---|---|---|---|---|
| | Vaccine | | Placebo | | Vaccine | | Placebo | |
| Visit | N | SCR (%) | N | SCR (%) | N | SCR (%) | N | SCR (%) |
| Day 14 | 12 | 58.3 | 6 | 0.0 | 12 | 58.3 | 5 | 0.0 |
| Day 28 | 12 | 50.0 | 6 | 0.0 | 11 | 54.5 | 6 | 0.0 |
| Day 42 | 12 | 100 | 6 | 0.0 | 11 | 100 | 6 | 0.0 |
| Day 56 | 12 | 91.7 | 5 | 0.0 | 11 | 81.8 | 6 | 0.0 |
| Day 84 | 12 | 91.7 | 6 | 0.0 | 11 | 81.8 | 6 | 16.7 |
| Day 196 | 12 | 58.3 | 6 | 0.0 | 11 | 81.8 | 6 | 0.0 |
| Overall Study | 12 | 100 | 6 | 0.0 | 12 | 100 | | 16.7 |

These results demonstrated that the percentage of subjects achieving seroconversion was similar between the low and high adapted EV71 vaccine dose groups at Days 14, 28, 42, 56 and 84. At Day 196 a higher percentage of subjects in the high dose group compared to the low dose group (81.8% versus 58.3% respectively) achieved seroconversion. No subject in the low dose placebo group seroconverted at any time during the study. One subject in the high dose placebo group seroconverted at Day 84, however the GMTs for the placebo groups remained low throughout the study up to Day 196.

For the subject who withdrew early from the study early, all immunogenicity and safety data was collected at the early termination visit was excluded from summary tables but was presented in data listings. A missing value was defined as one which was blank, unknown, not done or not applicable on the CRF. Missing baseline assessments were not imputed unless there was a screening measure for the same assessment and the screening visit was performed within 42 days prior to date of first dose of study vaccine. Immunogenicity endpoints that were missing at a scheduled visit were not imputed. The neutralizing antibody titers against EV71 that were below the limit of detection were reported as <8. These titers were set equal to 8 for analysis purposes. Data listings displayed the data as "<8" where applicable. Missing dates for unsolicited AEs and concomitant medications were imputed for the purpose of establishing the time of event in relation to study treatment. All data listings displayed the imputed dates rather than the data as reported on the CRF. Three unblinded interim analyses of immunogenicity data were conducted.

Immunogenicity Conclusions

An additional objective of this study was to assess the immunogenicity of the adapted EV71 vaccine by measuring the levels of EV71 neutralizing antibodies in the serum collected at various time points throughout the study.

Higher GMTs were observed in the high dose group compared to the low dose group. The immune response observed in terms of neutralizing titers followed a similar pattern in both the low dose and high dose groups, whereby an increase in GMT was observed at 14 days post first dose (at Day 14) and post second dose (at Day 42). Highest GMTs were observed at Day 42 in both dose groups. The GMTs declined slightly over time from Day 56 to Day 196 in both dose groups; however, they remained well above baseline values during this time. The GMTs for both the placebo groups (low dose and high dose) remained at baseline levels throughout the duration of the study.

Seroconversion (defined as a ≥4-fold increase in the level of EV71 neutralizing antibodies from baseline) was similar between the high and low dose groups at Days 14, 28, 42, 56 and 84. At Day 196 a higher percentage of subjects in the high dose group compared to the low dose group (81.8% versus 58.3% respectively) achieved seroconversion. All subjects in the low dose and high dose groups seroconverted at Day 42 (14 days after the second dose). One subject in the placebo group seroconverted at Day 84; however the GMTs for the placebo groups remained low throughout the study up to Day 196.

In summary, higher GMTs were observed in the high dose group compared to the low dose group. The immune response observed in terms of neutralizing titers followed a similar pattern in both the low dose and high dose groups. Highest GMTs were observed at Day 42 in both dose groups. All subjects in the Low Dose and High Dose groups seroconverted at Day 42 (14 days after the second dose) and seroconversion rates were similar between the high and low dose groups. The GMTs declined slightly over time from Day 56 to Day 196 in both dose groups; however, they remained well above baseline values during this time.

Safety Evaluation

A total of 36 subjects were included in the safety analysis. Thirty five of the 36 subjects received both doses (Day 0 and Day 28) of adapted EV71 vaccine. Subject 147 in the high dose group, assigned to adapted EV71 vaccine, did not receive the second dose due to withdrawal of consent.

A total of 42 AEs were reported by 22 of the 36 subjects across the two dose groups up to Day 56. In the low dose group, 11 of the 18 subjects reported a total of 22 AEs. In the high dose group, 11 of the 18 subjects reported a total of 20 AEs.

All AEs were considered to be mild in severity with the exception of one event that was of moderate severity (hemorrhoids). Only two events were deemed to be associated with investigational product. Both of the events occurred in the low dose group in subjects randomized to placebo. One of these subjects experienced musculoskeletal stiffness, and the other experienced headache.

The most frequently reported adverse events were of the system organ class of 'respiratory, thoracic and mediastinal disorders' and included cough, rhinorrhea and oropharyngeal pain. There were no significant adverse events (SAEs) reported in this study. No subjects were withdrawn from the study due to AEs. The most frequently reported AEs occurring across all treatment groups are presented in Table 20.

TABLE 20

Summary of Adverse Events

| System Organ Class*/ Preferred Term** | Low Dose | | High Dose | |
|---|---|---|---|---|
| | Vaccine (N = 12) Frequency; N (%) of Subjects | Placebo (N = 6) Frequency; N (%) of Subjects | Vaccine (N = 12) Frequency; N (%) of Subjects | Placebo (N = 6) Frequency; N (%) of Subjects |
| Respiratory, thoracic and mediastinal disorders | 4 (33%) | 1 (17%) | 3 (25%) | 2 (33%) |
| Cough | 3 (25%) | 1 (17%) | 1 (8%) | — |
| Rhinorrhea | 1 (8%) | — | 2 (17%) | 2 (33%) |
| Oropharyngeal pain | 3 (25%) | — | — | — |
| Sneezing | 1 (8%) | — | — | — |
| Throat irritation | 1 (8%) | — | — | — |
| Gastrointestinal disorders | 1 (8%) | — | 4 (33%) | — |
| Abdominal distension | — | — | 1 (8%) | — |
| Abdominal pain upper | 1 (8%) | — | — | — |
| Diarrhoea | 1 (8%) | — | — | — |
| Gastrooesophageal reflux disease | — | — | 1 (8%) | — |
| Haemorrhoids | — | — | 1 (8%) | — |
| Mouth ulceration | — | — | 1 (8%) | — |
| Vomiting | — | — | 1 (8%) | — |
| General disorders and administration site conditions | 1 (8%) | — | 3 (25%) | — |
| Pyrexia | 1 (8%) | 1 (17%) | 2 (17%) | — |
| Vessel puncture site haematoma | — | — | 1 (8%) | — |
| Infections and infestations | 2 (17%) | 1 (17%) | 1 (8%) | 1 (17%) |
| Influenza | — | 1 (17%) | 1 (8%) | 1 (17%) |
| Nasopharyngitis | 1 (8%) | — | — | — |
| Tonsillitis | 1 (8%) | — | — | — |
| Urinary tract infection | 1 (8%) | — | — | — |
| Musculoskeletal and connective tissue disorders | 1 (8%) | 1 (17%) | — | — |
| Back pain | 1 (8%) | — | — | — |
| Musculoskeletal stiffness | — | 1 (17%) | — | — |
| Nervous system disorders | — | 1 (17%) | 1 (8%) | — |
| Headache | — | 1 (17%) | 1 (8%) | — |
| Skin and subcutaneous tissue disorders | 1 (8%) | — | 1 (8%) | — |

TABLE 20-continued

Summary of Adverse Events

| | Low Dose | | High Dose | |
|---|---|---|---|---|
| System Organ Class*/ Preferred Term** | Vaccine (N = 12) Frequency; N (%) of Subjects | Placebo (N = 6) Frequency; N (%) of Subjects | Vaccine (N = 12) Frequency; N (%) of Subjects | Placebo (N = 6) Frequency; N (%) of Subjects |
| Rash | — | — | 1 (8%) | — |
| Rash maculo-papular | 1 (8%) | — | — | — |
| Injury, poisoning and procedural complications | — | — | 1 (8%) | — |
| Hand fracture | — | — | 1 (8%) | — |
| Limb injury | — | — | 1 (8%) | — |

Adverse events from the system organ class of 'respiratory, thoracic and mediastinal disorders' were the most frequently reported events across both the high and low dose groups. The most frequently reported AEs in this system organ class were cough and oropharyngeal pain with the greatest incidence in the low dose group, both events observed in 3 (25%) subjects. One subject (17%) in the low dose placebo group also reported cough. In the high dose group no subjects reported oropharyngeal pain and only 1 (8%) subject reported cough. Rhinorrhea was only observed in the high dose group. This event was experienced by 2 (17%) subjects in the adapted EV71 vaccine group and 2 (33%) subjects in the placebo group.

Other frequently reported AEs were classified within the system organ class of 'gastrointestinal disorders'. These were most frequently reported in the high dose group, 4 (33%) subjects compared to 1 (8%) subject in the low dose group and none in the placebo group. Gastrointestinal disorders in the high dose group included abdominal distension, gastroesophageal reflux disease, hemorrhoids, mouth ulceration and vomiting. In the low dose group one subject experienced upper abdominal pain and diarrhea.

General disorders and administration site conditions were reported more frequently in the high dose group; 3 (25%) subjects compared to 1 (8%) subjects in the low dose group. In the low dose group, pyrexia was experienced by 1 (8%) subject in the adapted EV71 vaccine group and 1 (17%) subject in placebo group. In the high dose group, pyrexia was reported in 2 (17%) subjects.

All of the AEs were mild in severity with the exception of one event experienced which was moderate in severity. The event was hemorrhoids, which occurred 8 days after the first vaccination and lasted for 2 days.

Adverse events were considered related if they were deemed to be definitely or possibly related to the administration of the investigational product. There were only 2 adverse events that were deemed to be related with the investigational product administration, both subjects were in the low dose group and assigned to placebo. The events were stiff neck and headache. Both events were mild in severity.

The injection site was evaluated for pain, tenderness, erythema, induration and pruritis on Day 0 (at 5, 30 and 60 minutes post vaccination), Days 3, 7, 14, Day 28 (at 5, 30 and 60 minutes post vaccination), Days 31, 35 and 42.

Tables 21 and 22 provide a summary of the number of subjects that had injection site reactions. The assessment was performed by the Investigator and the following grades were used for each symptom: Grade 1 (mild), Grade 2 (moderate), Grade 3 (severe) or Grade 4 (life threatening). Pain, tenderness and pruritis were graded according to the severity of the symptom, whilst erythema and induration were graded according to the size of the affected area (Grade 1=2.5-5 cm; Grade 2=5.1-10 cm; Grade 3=>10 cm; Grade 4=necrosis).

TABLE 21

Injection Site Reactions after the First Dose

| | | Low Dose | | | | High Dose (N = 12) | | | |
|---|---|---|---|---|---|---|---|---|---|
| | | Vaccine (N = 12) | | Placebo (N = 6) | | Vaccine (N = 12) | | Placebo (N = 6) | |
| Visit | Symptom | None | Grade 1 | None | Grade 1 | None | Grade 1 | None | Grade 1 |
| Day 0[a] | Erythema | 12 (100%) | 0 (0%) | 5 (83%) | 1 (17%) | 11 (92%) | 1 (8%) | 6 (100%) | 0 (0%) |
| Day 3 | Pain | 12 (100%) | 0 (0%) | 6 (100%) | 0 (0%) | 11 (92%) | 1 (8%) | 6 (100%) | 0 (0%) |
| Day 7 | Any | 12 (100%) | 0 (0%) | 6 (100%) | 0 (0%) | 12 (100%) | 0 (0%) | 6 (100%) | 0 (0%) |
| Day 14 | Any | 12 (100%) | 0 (0%) | 6 (100%) | 0 (0%) | 12 (100%) | 0 (0%) | 5 (83%)[b] | 0 (0%) |

[a]Injection site was assessed at 5, 30 and 60 minutes post-dose on Day 0;

[b]One subject did not complete assessments on Day 14.

TABLE 22

Injection Site Reactions after the Second Dose

| | | Low Dose | | | | High Dose (N = 12) | | | |
|---|---|---|---|---|---|---|---|---|---|
| | | Vaccine (N = 12) | | Placebo (N = 6) | | Vaccine (N = 12)[b] | | Placebo (N = 6) | |
| Visit | Symptom | None | Grade 1 | None | Grade 1 | None | Grade 1 | None | Grade 1 |
| Day 28[a] | Pain | 11 (92%) | 1 (8%) | 5 (83%) | 1 (17%) | 10 (83%) | 1 (8%) | 6 (100%) | 0 (0%) |
| Day 31 | Pain | 10 (83%)[c] | 1 (8%) | 5 (83%)[c] | 0 (0%) | 11 (92%) | 1 (8%) | 6 (100%) | 0 (0%) |
| | Induration | 11 (92%)[c] | 0 (0%) | 5 (83%)[c] | 0 (0%) | 9 (75%) | 1 (8%) | 6 (100%) | 0 (0%) |
| Day 35 | Any | 12 (100%) | 0 (0%) | 5 (83%)[d] | 0 (0%) | 11 (92%) | 0 (0%) | 6 (100%) | 0 (0%) |
| Day 42 | Any | 12 (100%) | 0 (0%) | 6 (100%) | 0 (0%) | 11 (92%) | 0 (0%) | 6 (100%) | 0 (0%) |

[a]Injection site was assessed at 5, 30 and 60 minutes post-dose on Day 0;
[b]One subject withdrew prior to Day 28;

Overall, there were few injection site reactions reported. At most, only one subject in any treatment group (adapted EV71 vaccine or placebo) reported any symptom at a given assessment time point. There was no difference in the frequency of reactions between the adapted EV71 vaccine group and placebo group or between low dose and high dose groups or between first and second dose.

c One subject did not complete Day 31 assessments; d One subject did not complete Day 35 assessments Solicited adverse events were collected using the subject diaries. Subjects were asked to complete a diary beginning on the day of each vaccination and for 14 days thereafter (Days 0 to 14 and Days 28 to 42). It should be noted that these events were in addition to the unsolicited events. Table 23 provides a summary of the recorded symptoms that were captured in the subject diaries.

adapted EV71 vaccine treatment groups. Headache was reported in 4 (33%) subjects in the high dose adapted EV71 vaccine group compared to 1 (8%) subject in the low dose adapted EV71 vaccine group. One subject in each of the placebo groups 1 (17%) experienced headaches. Edema at the injection site was reported by subjects in the high dose adapted EV71 vaccine group only (4 [33%] subjects). Similarly, nausea was reported by subjects in the high dose adapted EV71 vaccine group only (2 [17%] subjects).

The incidence of pruritis and erythema at the injection sites was the same between the low and high dose groups, reported in 1 [8%] subjects in each group, but not reported by subjects in the placebo groups. In summary the number of recorded diary symptoms was greater in the high and low dose treatment groups compared to placebo.

TABLE 23

Summary of Diary Symptoms

| | Low Dose | | High Dose | |
|---|---|---|---|---|
| System Organ Class*/ Preferred Term** | Vaccine (N = 12) Frequency; N (%) of Subjects | Placebo (N = 6) Frequency; N (%) of Subjects | Vaccine (N = 12) Frequency; N (%) of Subjects | Placebo (N = 6) Frequency; N (%) of Subjects |
| Pain at Injection Site | 10 (83%) | 2 (33%) | 9 (75%) | 1 (17%) |
| Muscle Pain | 6 (50%) | 2 (33%) | 5 (42%) | 0 |
| Tiredness | 5 (42%) | 2 (33%) | 5 (42%) | 1 (17%) |
| Headache | 1 (8%) | 1 (17%) | 4 (33%) | 1 (17%) |
| Edema at Injection Site | 0 | 0 | 4 (33%) | 0 |
| Rash on Body | 3 (25%) | 0 | 1 (8%) | 0 |
| Pruritis at Injection Site | 1 (8%) | 0 | 1 (8%) | 0 |
| Erythema at Injection Site | 1 (8%) | 0 | 1 (8%) | 0 |
| Nausea | 0 | 0 | 2 (17%) | 0 |

The most frequently captured event in the subject diary was pain at the injection site. The incidence was similar between treatment groups, and was reported in 10 (83%) subjects in the low dose adapted EV71 vaccine group and in 9 (75%) subjects in the high dose adapted EV71 vaccine group. Fewer subjects in both the low and high dose placebo group experienced pain at the injection site, 2 (33%) subjects in the low dose placebo group and 1 (17%) subject in the high dose placebo group.

The incidence of muscle pain and tiredness was also similar between the low and high dose adapted EV71 vaccine groups. Fewer subjects in both placebo groups experienced muscle pain and tiredness compared to the No formal statistical analyses of adverse events frequencies or severity were performed for the small numbers in the study groups. There were no reported deaths or SAEs during this study.

Evaluation of Laboratory Parameters

Toxicity grades for each laboratory parameter were determined using either the Common Terminology Criteria for Adverse Events (CTCAE) Version 4, 2009 or the Food and Drug Administration (FDA) Guidance for Industry: Toxicity Grading Scale for Healthy Adult and Adolescent Volunteers Enrolled in Preventive Vaccine Clinical Trials, September 2007. All toxicity grades post Day 0 were compared to baseline grades and any change or shift in the toxicity grade were analyzed.

For serum chemistry, frequent values changes from baseline were experienced by subjects in the low dose adapted EV71 vaccine group compared to the high dose adapted EV71 vaccine group. In the low dose group, increases in glucose were the most frequently reported event, followed by decreases in potassium, increases in sodium and decreases in glucose. In the high dose group, increases and decreases in glucose were the most frequently reported values shifts. The majority of changes were 1 grade or 2 grades.

Only one 4 grade change was reported in this study: increases in glucose. This subject was randomized to low dose adapted EV71 vaccine group. For this subject at Day 0, glucose levels were low, 3.5 mmol/L (normal ranges 4-7.8 mmol/L) and returned to within normal limits between Days 7 and 35, and dropped again below normal ranges to 3.4 mmol/L. At Day 56, glucose levels significantly increased to 8.8 mmol/L. The overall change at Day 56 compared to Day 0 resulted in a shift of 4 grades over this time period. This event was not reported as an adverse event and was not considered clinically significant by the Investigator.

The most notable changes in hematology were decreases in hemoglobin. A similar frequency of values shifts in hemoglobin (mainly 1 Grade) was observed in both the high and low dose groups. The most commonly reported changes in values for urinalysis were changes to the presence of urinary red blood cells. These 1 grade changes were noted in both the high adapted EV71 vaccine dose group and placebo dose group and adapted EV71 vaccine low dose group. A summary of the most frequently reported value shifts from baseline for serum chemistry, hematology and urinalysis are presented in Table 24 [these shifts are reported for both vaccine (V) and placebo (P) groups].

TABLE 24

Summary of Frequently Reported Values Shifts from Baseline

| | Low Dose (Vaccine N = 12) (Placebo N = 6) Change in Grade from Baseline N (%) of Subjects | | | | | | | | High Dose (Vaccine N = 12) (Placebo N = 6) Change in Grade from Baseline N (%) of Subjects | | | | | | | |
|---|---|---|---|---|---|---|---|---|---|---|---|---|---|---|---|---|
| | 1 Grade | | 2 Grades | | 3 Grades | | 4 Grades | | 1 Grade | | 2 Grades | | 3 Grades | | 4 Grades | |
| Lab Result | V | P | V | P | V | P | V | P | V | P | V | P | V | P | V | P |
| Serum Chemistry* | | | | | | | | | | | | | | | | |
| Glucose (inc) | 7 (58%) | 3 (50%) | 2 (17%) | 1 (17%) | — | — | 1 (8%) | — | 3 (25%) | 1 (17%) | 1 (8%) | 1 (17%) | — | — | — | — |
| Glucose (dec) | 1 (8%) | 1 (17%) | 2 (17%) | 1 (17%) | | | | | 2 (17%) | 1 (17%) | 3 (25%) | 1 (17%) | | | | |
| Potassium (dec) | 4 (33%) | 1 (17%) | — | — | — | — | — | — | — | | 1 (8%) | — | — | — | — | — |
| Sodium (inc) | 3 (25%) | 3 (50%) | — | — | — | — | — | — | 1 (8%) | 1 (17%) | — | — | — | — | — | — |
| Hematology* | | | | | | | | | | | | | | | | |
| Haemoglobin (dec) | 10 (83%) | 6 (100%) | — | — | 1 (8%) | — | — | — | 9 (75%) | 4 (67%) | 1 (8%) | — | — | — | — | — |
| Urinalysis* | | | | | | | | | | | | | | | | |
| Urine Red Blood Cells | 3 (25%) | — | — | 1 (17%) | — | — | — | — | 4 (33%) | 4 (67%) | — | — | 1 (8%) | — | — | — |

*laboratory results where value was noted for greater than 20% of subjects in any dose group Vital signs, including temperature, pulse rate, respiratory rate and blood pressure (systolic and diastolic) were assessed throughout the study until Day 196. There were no clinically significant findings for any of the vital signs recorded. Pulse rate, respiratory rate and blood pressure remained relatively constant over time and there were no observed differences between treatment groups. Review of changes from baseline in temperature over time demonstrated that slightly greater increases (ie. greater than 0.5° C.) were observed at Day 0; 5 and 30 minutes post dose for the adapted EV71 vaccine high dose group (mean change of 0.53° C. and 0.55° C. respectively), compared to mean increases in the low dose group of 0.29° C. and 0.24° C., the placebo low dose group of 0.25° C. and 0.37° C. and the placebo high dose group of 0.25° C. and 0.48° C. at the same time points.

A complete physical examination was done by the Investigator or his designee for each subject at screening, prior to vaccine administration on Days 0 and 28, and on Day 56. There was only one abnormal physical finding (ear, nose, throat and neck) that was subsequently reported as an adverse event, tonsillitis, for a subject at Day 56 in the adapted EV71 vaccine low dose group. No other significant physical findings were reported for any of the subjects at any time point.

Safety Conclusions

A total of 42 AEs were reported by 23 of the 36 subjects across the two dose group up to Day 56. In the low dose group, 12 of the 18 subjects reported a total of 22 AEs. In the high dose group, 11 of the 18 subjects reported a total of 20 AEs.

All AEs were considered to be mild in severity with the exception of one event that was of moderate severity. Only two events were deemed to be associated with investigational product, both occurring in the low dose group. One subject experienced musculoskeletal stiffness, and another subject experienced headache. Both subjects were randomized to the placebo group. The most frequently reported AEs were cough, rhinorrhea, pyrexia and oropharyngeal pain.

The incidence of injection site reactions was low with at most 17% of subjects at any one time point experiencing a reaction. Injection site reactions were most commonly seen within the 60 minutes following the vaccination for both the prime and the booster dose (at Day 0 and Day 28). There was no difference in the frequency of reactions between the adapted EV71 vaccine group and placebo group or between the low dose and the high dose groups or between the prime and the booster dose.

Shifts in values from baseline were experienced by more subjects in the low dose group compared to the high dose group. Increases in glucose were the most frequently reported changes for serum chemistry. Values changes were also observed for hematology and urinalysis parameters. The incidence was similar between the low dose and high dose groups. None of the values changes were reported as adverse events or deemed to be clinically significant.

There was only one abnormal physical finding (ear, nose, throat and neck) that was subsequently reported as the adverse event, tonsillitis, at Day 56 (low dose adapted EV71 vaccine group). No other significant physical findings were reported for any of the subjects at any time point. In summary, adapted EV71 vaccine at both the low and high dose levels was deemed to be safe and well tolerated.

Overall Conclusions

This was a first in human study for the adapted EV71 vaccine. One objective of this study was to assess the safety and tolerability of adapted EV71 vaccine in healthy adults. The composition of the low dose was intended to provide initial assessments of the safety of the adapted EV71 vaccine.

Review of AEs demonstrated that the incidence of AEs was similar between the treatment groups, between the dose groups and between first and second dose. All AEs were considered to be mild in severity with the exception of one event that was of moderate severity. Only two events were deemed to be associated with investigational product. The events, musculoskeletal stiffness and headache, both mild in severity occurred in the low dose group and were reported in two subjects, both of whom received placebo.

The incidence of injection site reactions was similar across all dose and treatment groups and was minimal with only 17% of subjects at any one time point experiencing a reaction. The majority of injection site reactions occurred within the 60 minutes following the vaccination for both the prime and the booster dose (at Day 0 and Day 28). None of the observed changes in values for laboratory parameters were reported as adverse events or deemed to be clinically significant by the investigator.

Another objective of this study was to assess immunogenicity of the adapted EV71 vaccine by measuring the levels of EV71 neutralizing antibodies in the serum collected at various times during the study. Higher GMTs were observed in the high dose group compared to the low dose group. The immune response observed in terms of neutralizing titers followed a similar pattern in both the low dose and high dose groups. Highest GMTs were observed at Day 42 in both dose groups. All subjects in the low dose and high dose groups seroconverted at Day 42 (14 days after the second dose) and seroconversion rates were similar between the high and low dose groups. The GMTs declined slightly over time from Day 56 to Day 196 in both dose groups; however, they remained well above baseline values during this time.

In summary, the adapted EV71 vaccine at both the low and high dose levels was deemed to be safe and well tolerated. Good immune responses in terms of EV71 neutralizing titers and seroconversion were observed following administration of one and two doses of adapted EV71 vaccine at both the low dose and high dose levels which persisted to Day 196.

Example 9: Adaptation of CVA6 in Vero Cells

Adaptation of CVA6 was performed by subjecting the source virus to 11 passages in Vero cells. Similar to the adaptation protocol described in Example 1, two rounds of transfection was used for CVA6. However, as CVA6 does not form plaques in Vero cells, following the two rounds of transfection two rounds of cloning by limiting dilution was performed.

Results of a TCID50 neutralization assay on adapted virus at different passage numbers are shown in Table 25.

TABLE 25

Adaptation of CVA6

| Viruses propagated in Vero Cells | Harvest (cells and supernatant) | RC cell titration TCID50/ml | Vero cell titration TCID50/ml |
|---|---|---|---|
| CVA6 P-1 | Day 14 | 1e3 | N/A |
| CVA6 P-11 | Day 10 | 2.4e7 | N/A |

The CVA6 P-11 virus causes widespread cell rounding throughout the monolayer but does not exhibit overt CPE in Vero cells. The CVA6 P-11 is being used for future rederivation and clonal selection.

Sequencing of Full Length Genome of Adapted CVA6

Figure 6:
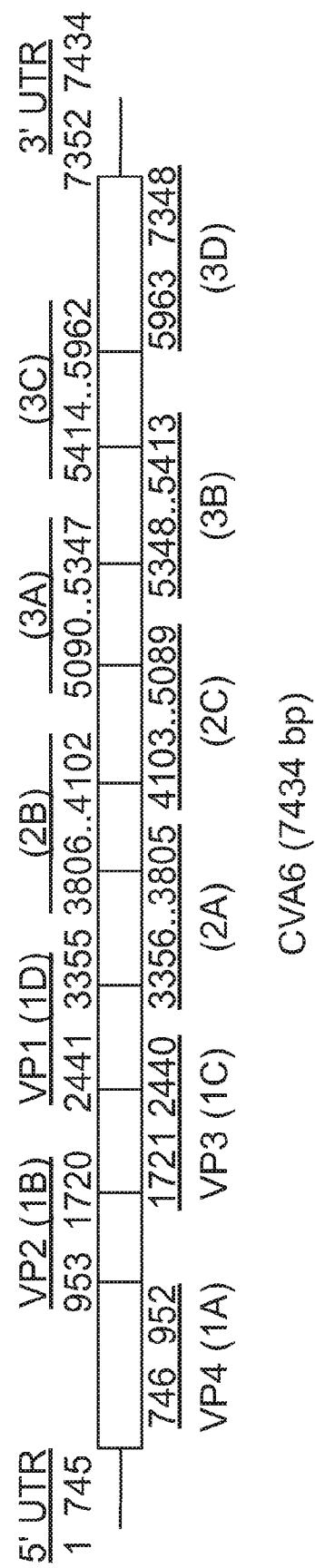
FIG. 6 shows a diagram of the CVA6 genome.

RNA was purified from clarified harvest following one freeze-thaw cycle. 4 DNA fragments covering the full length genome (FIG. 6) were amplified from the RNA by RT-PCR.

Sequencing was performed at UW-Biotech Center by Sanger's cycle sequencing method. Sequences were assembled using the DNAstar (Laser gene) software and compared using the BLAST program at PubMed. A total of 21 nucleotide changes were seen between CVA6 P-0 and CVA6 P-11 (FIG. 7).

TABLE 26

Sequencing of full length genome of CVA6: P-0 vs P-11

| | Nucleotide sequence | | Amino acid sequence | |
|---|---|---|---|---|
| | CVA6 P-0 | CVA6 P-11 | CVA6 P-0 | CVA6 P-11 |
| 5'UTR | 1-T | 1-G | — | — |
| | 13-G | 13-A | | |
| | 14-T | 14-G | | |
| | 15-G | 15-C | | |
| | 16-G | 16-A | | |
| | 21-C | 21-T | | |
| | 23-C | 23-T | | |
| | 34-G | 34-T | | |
| | 40-C | 40-G | | |
| VP4 | No Change | No Change | No Change | No Change |
| VP2 | 1216-C | 1216-C | 88-D | 88-D |
| | 1382-C | 1382-A | 144-Q | 144-K |
| VP3 | 1753-C | 1753-T | 11-N | 11-N |
| | 2024-A | 2024-G | 92-I | 92-V |
| | 2275-T | 2275-C | 175-D | 175-D |
| VP1 | 2577-C | 2577-T | 46-A | 46-V |
| | 2708-G | 2708-A | 90-E | 90-K |
| | 2726-A | 2726-G | 96-T | 96-A |
| | 3022-A | 3022-T | 194-S | 194-S |
| | 3242-G | 3242-A | 268-V | 268-I |
| 2A | 3691-C | 3691-T | 112-G | 112-G |
| 3'UTR | 7395-G | 7395-T | — | — |

A higher number of changes (9 nucleotides) were clustered in the 5'UTR region (Table 26). The nine nucleic acid substitutions identified in the adapted CVA6 strain were located at positions 1, 13, 14, 15, 16, 21, 23, 34, and 40 of the 5' untranslated region (UTR). The highest number of amino acid mutations (4) was observed in the VP1 protein. The four amino acid substitutions and their respective positions within SEQ ID NO: 2 are shown in Table 26 above. Based upon the sequencing results, all amino acid mutations (46A-V, 90E-K, 96T-A, 268V-I) in the VP1 protein of CVA6 P-11 were unique and not seen in any circulating strains (FIG. 7). One mutation was observed in each of the VP2 and VP3 proteins. All field isolates tested and the CVA6 strain have complete conservation of these amino acids. Thus adaptation in Vero cells resulted in these mutations. At positions 5, 10, 14, 33, 98, 160, 174, 194, 261, 279, 283, 305, the CVA6 P-0, and P-11 have the same sequence but differ from the field isolates. Field isolates n28297 and n40428 have similar sequences to CVA6 P-0, and P-11 at positions: 98, 160, 174 and 194.

Example 10: Adaptation of CVA16 in Vero Cells

Adaptation of CVA16 was performed by subjecting the source virus to 3 passages in Vero cells. Similar to the adaptation protocol described in Example 1, following adaptation in Vero cells, RNA was extracted and the virus was re-derived by transfecting the RNA into Vero cells two consecutive times. Single viral clones were then isolated through two rounds of plaque purification. Results of a TCID50 neutralization assay on adapted virus at different passage numbers are shown in Table 27. The adapted CVA16 P-3 virus exhibits extensive CPE in Vero cells, similar to the adapted EV71 virus. CVA16 P-3 is being used for future rederivation and clonal selection.

TABLE 27

Adaptation of CVA16 strain in Vero Cells

| Viruses propagated in Vero Cells | Harvest (cells and supernatant) | RC cell titration TCID50/ml | Vero cell titration TCID50/ml |
|---|---|---|---|
| CVA16 P-1 | Day 7 | 2.14e6 | N/A |
| CVA16 P-3 | Day 4 | 1.5e7 | 4.2e7 |

Sequencing of Full Length Genome of Adapted CVA16

Figure 9:
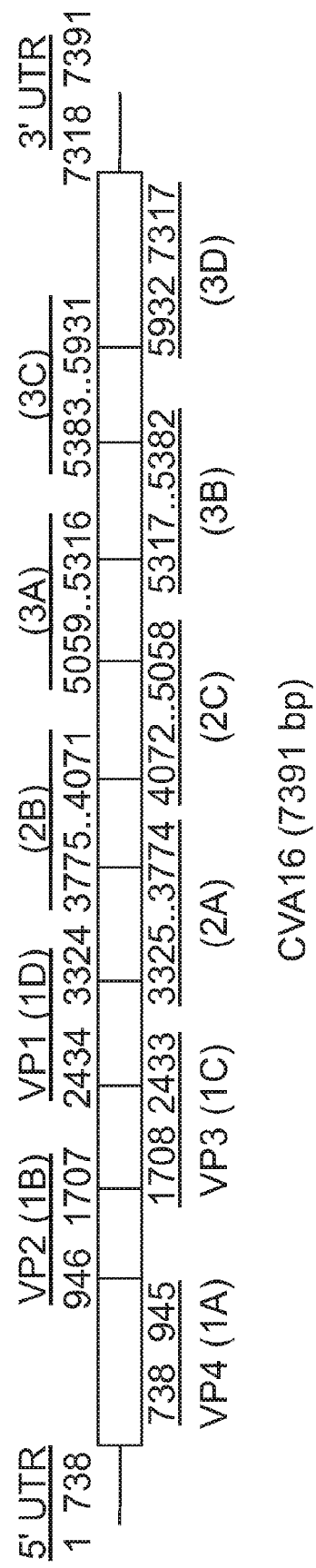
FIG. 9 shows a diagram of the CVA16 genome.

Primers used for sequencing of the adapted CVA16 genome are shown in FIG. 8. DNA fragments covering the full length genome (FIG. 9) were amplified by RT-PCR. A total of 6 nucleotide changes were seen between CVA16 P-0 and CVA16 P-3. The four amino acid substitutions and their respective positions within SEQ ID NOs: 5-7 (2A corresponds to SEQ ID NO: 5, VP2 corresponds to SEQ ID NO: 6, and VP1 corresponds to SEQ ID NO: 7) are shown in Table 28 below.

TABLE 28

Sequencing of full length genome of CVA16: P-0 vs P-3

|  | Nucleotide sequence | | Amino acid sequence | |
|---|---|---|---|---|
|  | CVA16 P-0 | CVA16 P-3 | CVA16 P-0 | CVA16 P-3 |
| 5'UTR | 6-G | 6-A | | |
|  | 33-G | 33-C | | |

TABLE 28-continued

Sequencing of full length genome of CVA16: P-0 vs P-3

|  | Nucleotide sequence | | Amino acid sequence | |
|---|---|---|---|---|
|  | CVA16 P-0 | CVA16 P-3 | CVA16 P-0 | CVA16 P-3 |
| VP2 | 1427-T | 1427-C | 161-M | 161-T |
| VP1 | 2729-A | 2729-G | 99-D | 99-G |
|  | 2867-T | 2867-A | 145-V | 145-E |
| 2A | 3328-A | 3328-G | 2-K | 2-E |

Figure 11:
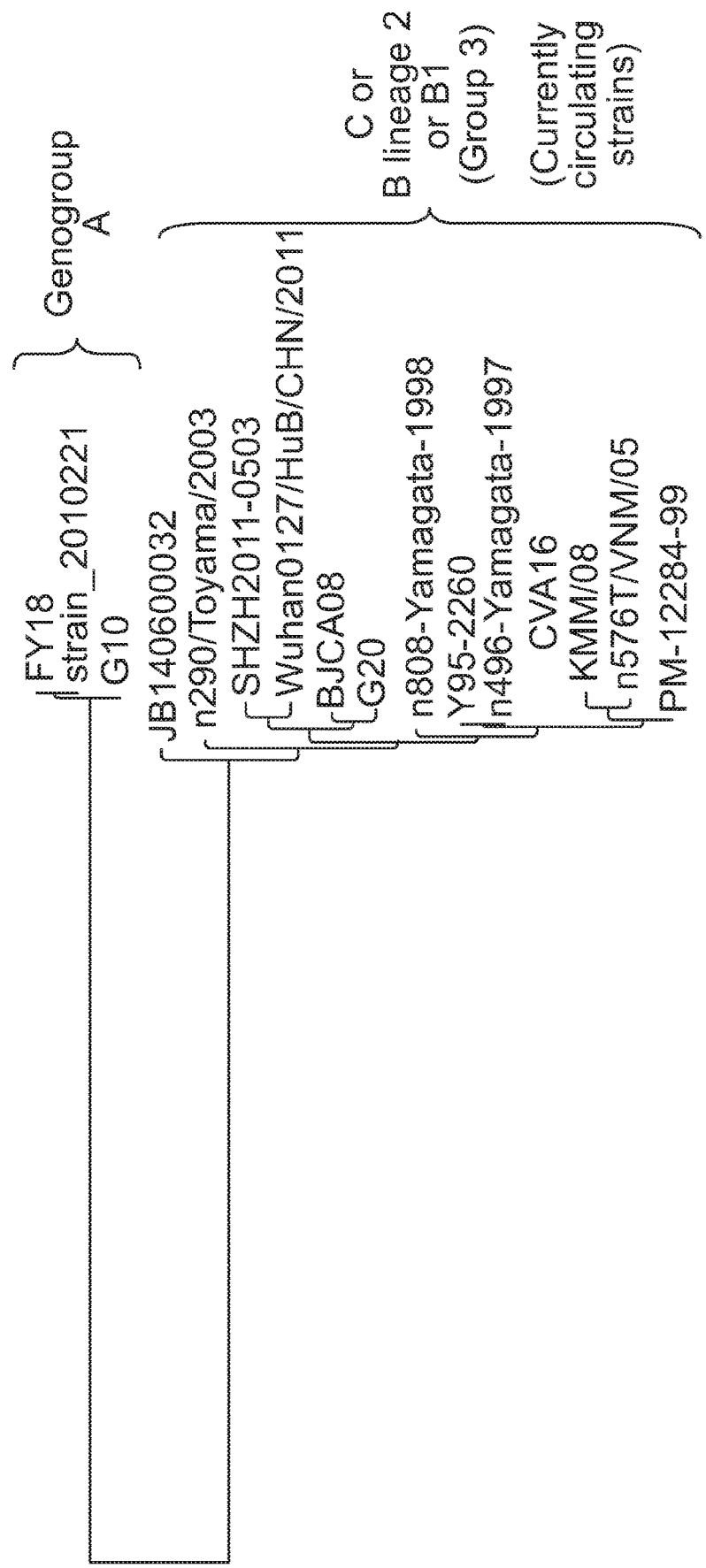
FIG. 11 shows a phylogenic classification of the CVA16 based on the VP1 gene.

Two nucleic acid substitutions were identified in the 5' UTR region of the adapted CVA16 virus at positions 6 and 33 (Table 28). Additionally, two amino acid substations were identified in the VP1 protein at positions 99 and 145, one amino acid substation was identified in the VP2 protein at position 161, and one amino acid substation was identified in the 2A protein at position 2 (Table 28). The two mutations in the VP1 protein of the P3 virus acquired are present in circulating strains, while the mutations in the VP2 and 2A polypeptides are unique and not present in circulating strains (FIG. 10). The CVA16 strain was classified as genogroup C, based upon phylogenic classification of the VP1 gene (FIG. 11).

Example 11: Cross-Reactivity of Anti-CVA16 Antibodies Against Other CVA16 Isolates Serum samples collected on day 42 post-vaccination with inactivated CVA16 were pooled and tested by microneutralization assay. Antibodies raised against CVA16 efficiently neutralized other CVA16 isolates (Table 29).

TABLE 29

Cross-reactivity of anti-CVA16/P-0 antibodies against other CVA16 isolates.

| Virus | Neutralizing titer |
|---|---|
| CVA16 P-0 | ≥5120 |
| CVA16/737 | 2560 |
| CVA16/721 | 2560 |
| CVA16/494 | 1280 |
| CVA16/1160 | 2560 |

Example 12: Antigenic Stability of Vero-Adapted Viruses

Mice were vaccinated with inactivated CVA16 (P-0) or CVA6 (P-0) along with alum. Serum samples collected after two immunizations (day 0,28) were pooled and tested for neutralization antibody titers using a conventional TCID50-based assay (Table 30). No significant differences in neutralizing titers were observed between adapted and unadapted viruses, indicating no effect on antigenicity.

TABLE 30

Antigenic stability of vero-adapted viruses.

| Assay virus | Neutralizing titer of pooled antisera |
|---|---|
| CVA16 | |
| CVA16 p0 (RD cell) | 320 |
| CVA16 p3 (Vero cell) | 320 |

TABLE 30-continued

Antigenic stability of vero-adapted viruses.

| Assay virus | Neutralizing titer of pooled antisera |
|---|---|
| CVA6 | |
| CVA6 p0 (RD cell) | 2560 |
| CVA6 p11 (Vero cell) | 1280 |

Example 13: Re-Derivation and Cloning of Adapted CVA6 and CVA16 Strains

Adapted CVA6 and CVA16 strains were rederived from purified viral RNA via two rounds of transfection. Cells transfected with adapted CVA6 (P11) and CVA16 (P3) were frozen at −80° C. on day of harvest, thawed, clarified and aliquoted. One aliquot was thawed and titrated for virus titer. Viral titer results are shown in Table 31. Cytopathic effects manifested by CVA6 and CVA16 in Vero cells transfected with viral RNA are shown in FIG. 12.

TABLE 31

Rederivation of CVA6 and CVA16 from purified RNA

| | Round 1 transfection | | | Round 2 transfection | | |
|---|---|---|---|---|---|---|
| Virus | Amount of Viral RNA | Day of harvest | Virus titer TCID 50/ml | Amount of Viral RNA | Day of harvest | Virus titer TCID 50/ml |
| CVA16 P-3 | 100 ng | 4 | 1.78E+05 | 90_ng | 6 | 3.16E+05 |
| CVA6 P-11 | 2000 ng | 4 | 3.16E+05 | 270_ng | 8 | 1.00E+04 |

Cloning of CVA6 by Limiting Dilution

Figure 13A:
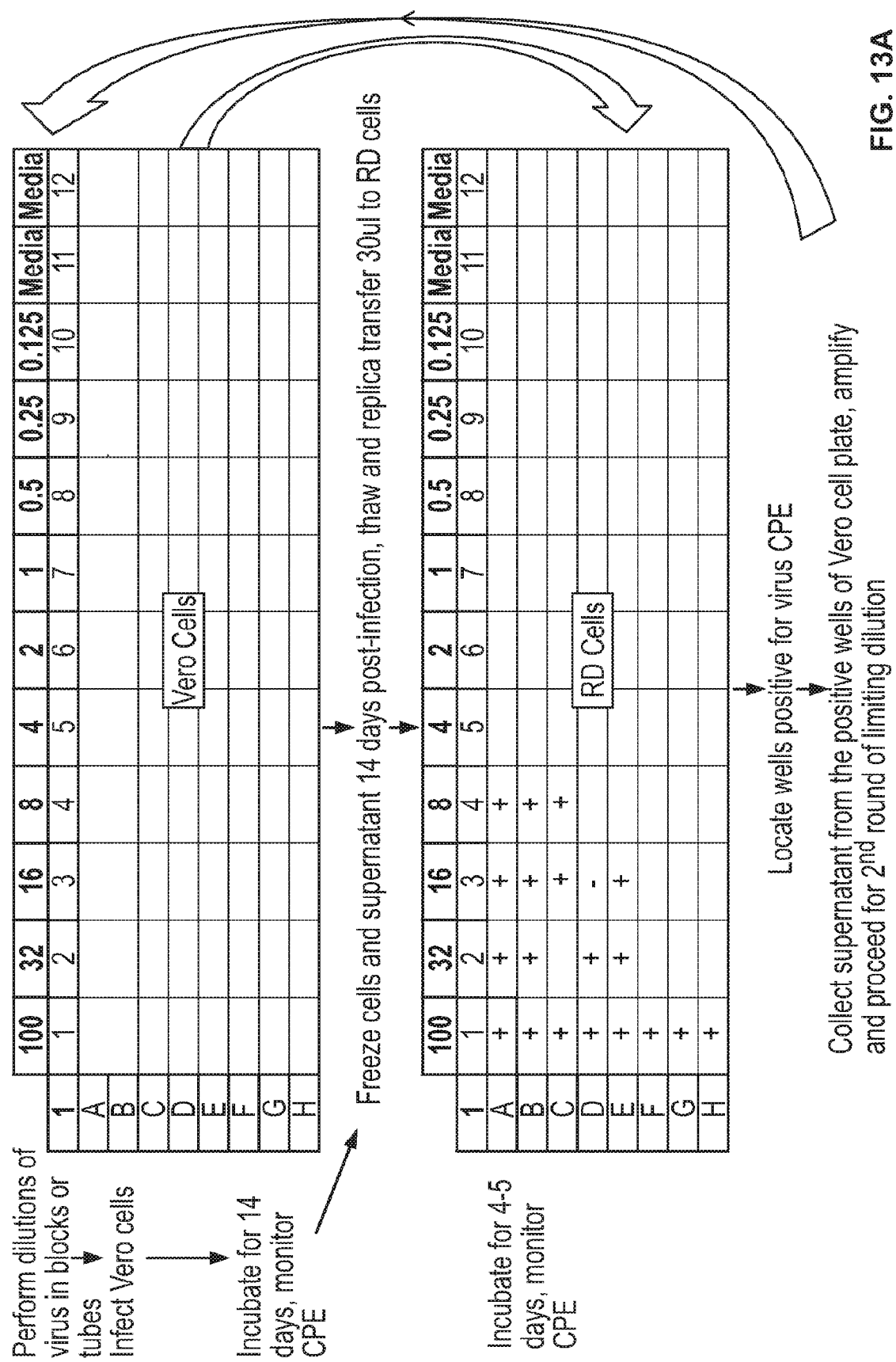
FIG. 13A shows a diagram of a protocol for clonal isolation of CVA6 by limiting dilution.

A limiting dilution technique was used for preparation of the adapted CVA6 premaster viral seed. Serial dilutions of the virus were made and the last well that supports virus growth was identified. After incubation for 14 days in Vero cells, cells and supernatant were frozen. Positive wells were identified by transferring the cell lysate to RD cells, incubating for 4-5 days, and subsequently amplifying virus from wells positive for virus CPE in Vero cells. Clones 1B7, 1C3, 1G3, and 2D6 were selected for a second round of limiting dilution after quantitation of viral titers. Clones 1B7F3 and 2D6G4 were selected for a third round of limiting dilution. Virus from these clones will be amplified, quantified, and further cloned by a third round of limiting dilution. Diagrammatic representation of the limiting dilution technique is shown in FIG. 13A-13C. A comparison of titers of RNA-re-derived CVA6 in Vero and RD cells is shown in FIG. 14. The virus titer calculated in RD cells and Vero cells differed. The limiting dilution was repeated with known $TCID_5$ values calculated by viral titration in Vero cells. Two rounds of limiting dilution have been completed. After amplification, a clone will be selected on the basis of viral titer and grown to prepare a stock for characterization.

Cloning of CVA16 by Plaque Purification

Figure 15A:
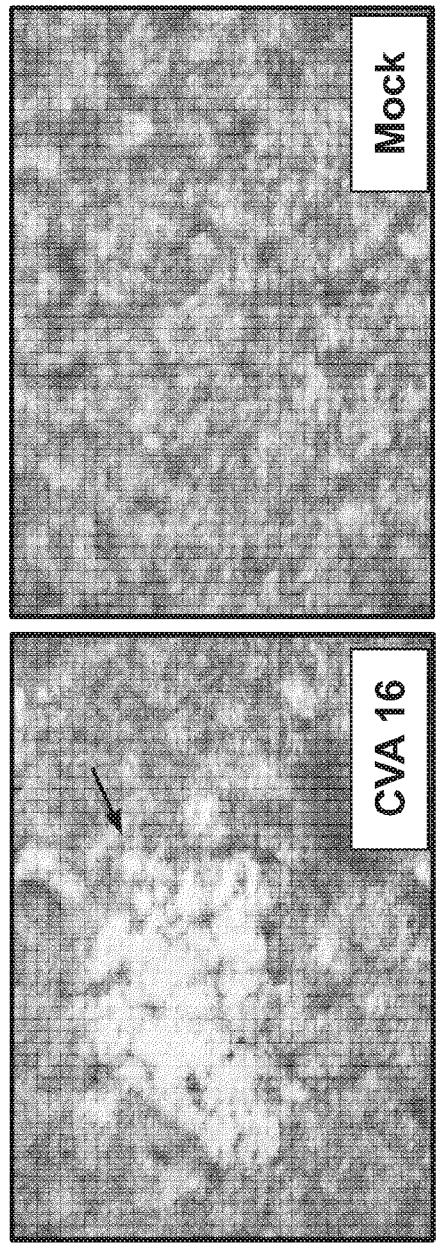
FIG. 15A shows the first round plaque purification of CVA16.
Figure 15B:
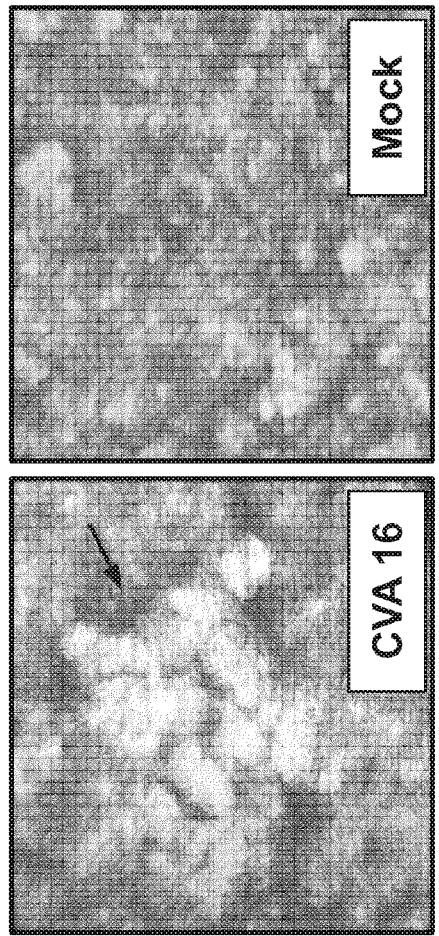
FIG. 15B shows the second round plaque purification of CVA16.

Vero cells were infected with 10-fold dilutions of adapted CVA16 virus and overlayed with 0.5% sea plaque agarose in serum free medium. Plaque were picked up on day 4-5 post-infection and incubated at 37 degrees Celsius for 24 hours. Virus was amplified by inoculating Vero cells with 250/750 µl amounts and harvested when the CPE was 90-100%. After overnight benzonase treatment at 4 degrees Celsius, virus was aliquoted and stored at −85 degrees Celsius. Two rounds of plaque purification were performed, as shown in FIG. 15A-15B. The cloned CVA16 (Clone 1-250) did not show any amino acid changed in the VP1 protein when compared to the P-3 virus described above, as shown in FIG. 16. The adapted CVA16 virus will be further characterized and used to prepare the pre-MVS as described for the adapted EV71 virus in Example 1.

Example 14: Immunogenicity of Trivalent HFMD Vaccine

The following Example demonstrates the efficacy of an inactivated EV71, CVA6, and CVA16 trivalent HFMD vaccine in adult mice. Both active immunization and passive transfer studies were performed using adult mice.

The inactivated monovalent EV71, CA6, and CA16 vaccines were formulated as described in Examples 1-14. The three monovalent vaccines were combined at a ratio of 1:1:1 to produce the inactivated trivalent vaccine. Each of the inactivated monovalent vaccines were used as controls. Adult A129 (α/β interferon (IFN) receptor deficient) and AG129 (α/β, γ IFN receptor deficient) mice were used for the studies described in this Example.

Cross-neutralizing Potential of Sera After Immunization with Monovalent Vaccines Groups of AG129 mice were vaccinated with 1.5 µg of the EV71, CVA16, or CVA6 monovalent vaccine on day 0 and day 28. Serum collected on day 42 post-vaccination was pooled per group and tested by microneutralization assay against each virus. The results are depicted in Table 32.

TABLE 32

| | Neutralizing titer | | |
|---|---|---|---|
| Anti-serum | EV71 | CVA16 | CVA6 |
| Anti-EV71 | 2280 | <40 | <40 |
| Anti-CVA16 | <40 | ≥5120 | <40 |
| Anti-CVA6 | <40 | <40 | ≥5120 |

The results in Table 32 indicate that no cross-neutralization was observed between the viruses tested.

Immunogenicity of HFMD Vaccines

Figure 17:
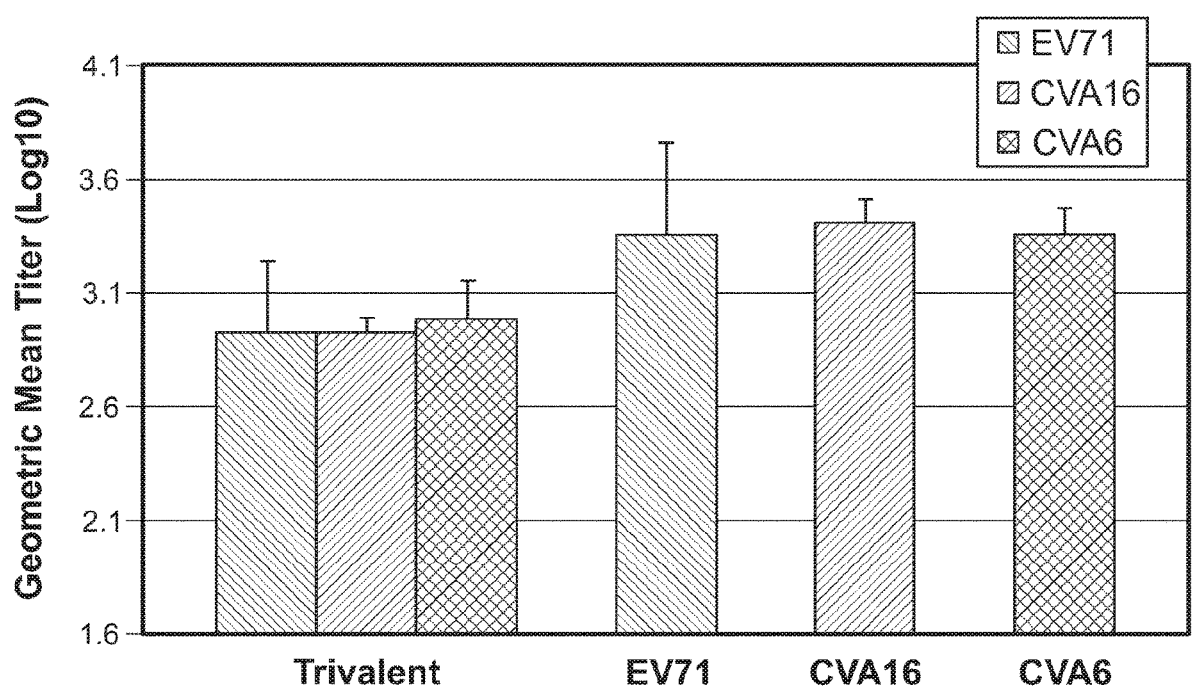
FIG. 17 shows the geometric mean titer of antibodies to EV71, CVA16, and CVA6.

AG129 mice were vaccinated either with 1.5 µg of one of the monovalent vaccine or a trivalent mixture of 1.5 µg of each of EV71, CVA6, and CVA16 on day 0 and day 28. Serum samples were collected from mice on day 42. The trivalent immune serum was tested against EV71, CVA16, and CVA6. Each monovalent immune serum was tested against its homologous virus. The geometric mean titer for each vaccine is depicted in FIG. 17.

Vaccine Efficacy Against EV71 and CVA16 in Mouse Model

Figure 18:
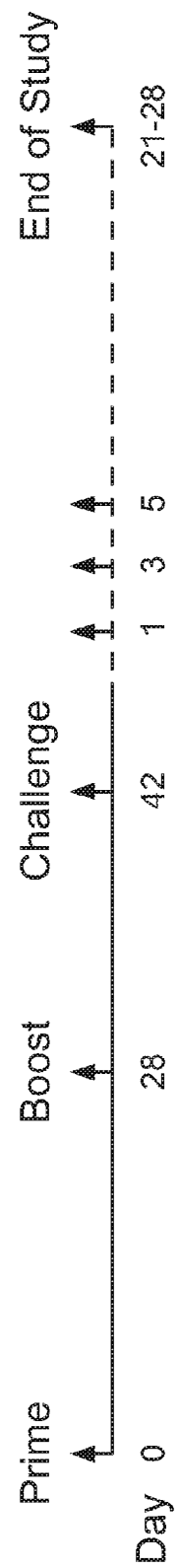
FIG. 18 shows the treatment protocol for immunization and challenge with EV71 and CVA16 in mice.

The efficacy of the trivalent vaccine was then tested in a murine model of EV71 and CVA16 infection. Groups (n=5-6) of four-week old AG129 mice were vaccinated intramuscularly (IM). The monovalent and trivalent vaccines described above were adjuvanted with equal volume of alum (Alhydrogel 85) by mixing on a rotator for 4 hrs at 4° C. as described in Example 2. Mice were vaccinated with a monovalent vaccine at a dosage of 1.5 µg per animal, the trivalent vaccine mixture at a total dosage of 4.5 µg per animal (1.5 µg per animal of each monovalent vaccine), or alum adjuvant as a control. The mice were challenged with virus via intraperitoneal (IP) injection at a challenge dosage of $9.8 \times 10^5$ $TCID_{50}$/400 µl virus. The treatment and challenge for each mouse group, as well as the schedule of treatment and challenge is depicted in FIG. 18.

Figure 19:
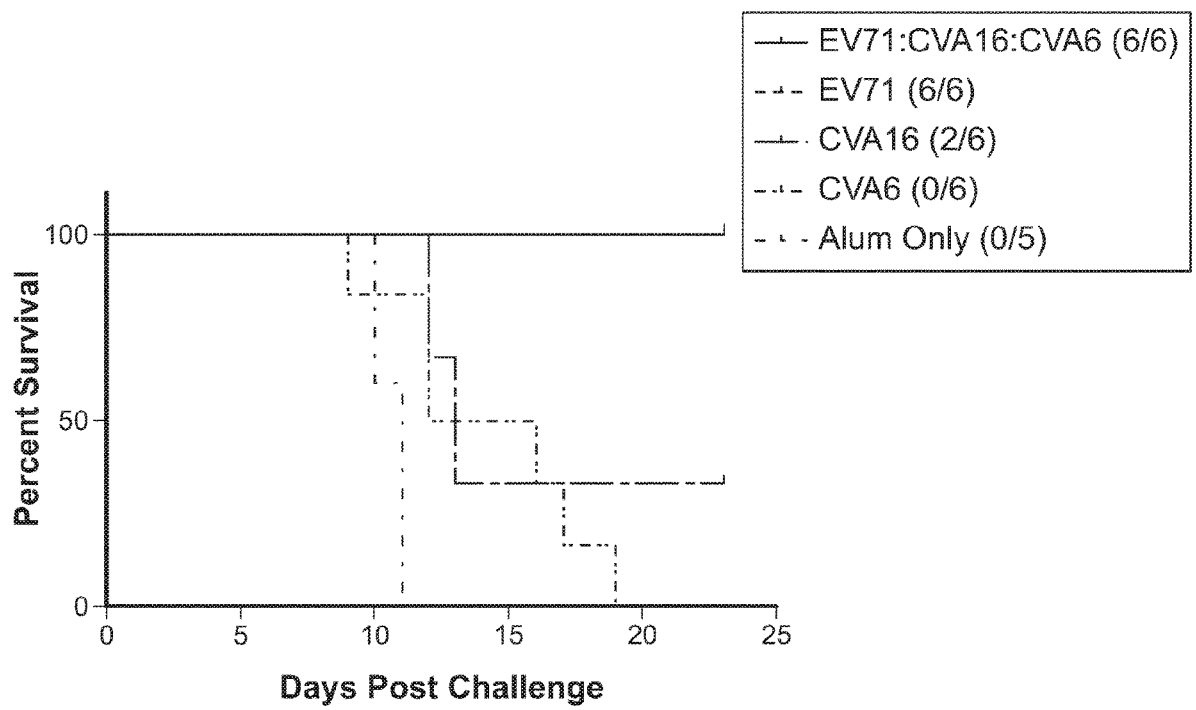
FIG. 19 shows survival rate of mice challenged with EV71.

As shown in FIG. 19, six out of six mice vaccinated with either the EV71 monovalent vaccine or the trivalent vaccine survived at least 25 days post-challenge with mouse-adapted EV71. However, only two out of six mice vaccinated with the CVA16 vaccine and no mice vaccinated with the CVA6 vaccine survived 20 days post-challenge with EV71, indicating that no cross-protection was observed.

Figure 20:
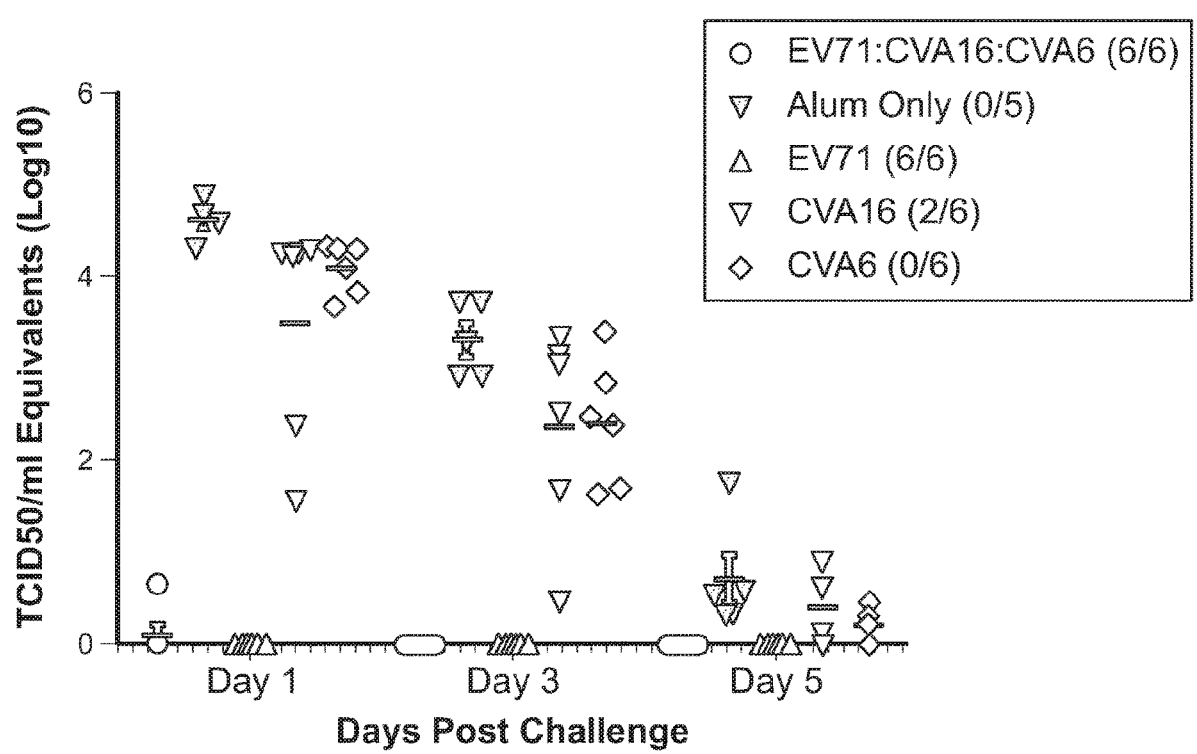
FIG. 20 shows the serum EV71 viral titer in immunized mice.

The vaccines were also tested for their ability to inhibit EV71 viremia. Viral titers were measured at days 1, 3, and 5 post-challenge with EV71 (FIG. 20). Serum samples from the vaccinated mice were collected on days 1, 3, and 5 post-challenge with EV71 and viral titer was determined by Real Time RT-PCR using a SYBR Green Kit (Qiagen). A standard curve was generated from serially diluted mouse adapted virus stock. Normal mouse serum was used as a negative control and to determine cut off values. The results indicate that both the EV71 monovalent vaccine and the trivalent vaccine were able to reduce viral titer in serum to approximately zero, as measured by $TCID_{50}$/ml equivalents (FIG. 20).

Figure 21:
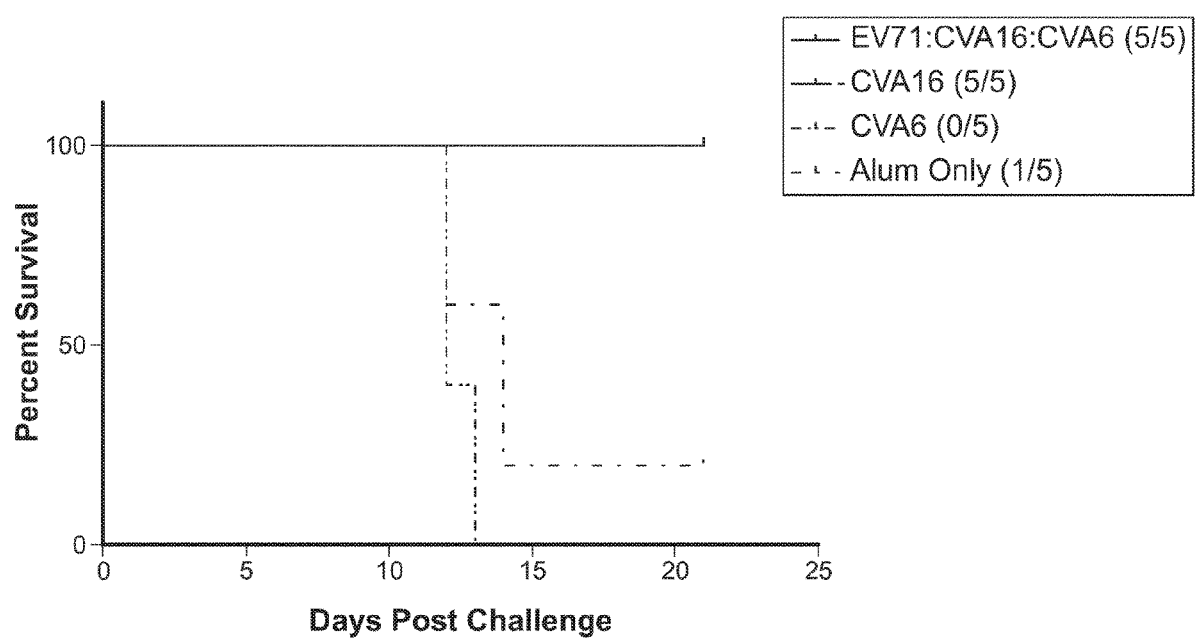
FIG. 21 shows survival rate of mice challenged with CVA16.

As shown in FIG. 21, five out of five mice vaccinated with either the CVA16 monovalent vaccine or the trivalent vaccine survived at least 20 days post-challenge with mouse-adapted CVA16. However, no mice vaccinated with the CVA6 vaccine survived 15 days post-challenge with EV71, indicating that no cross-protection was observed.

Figure 22:
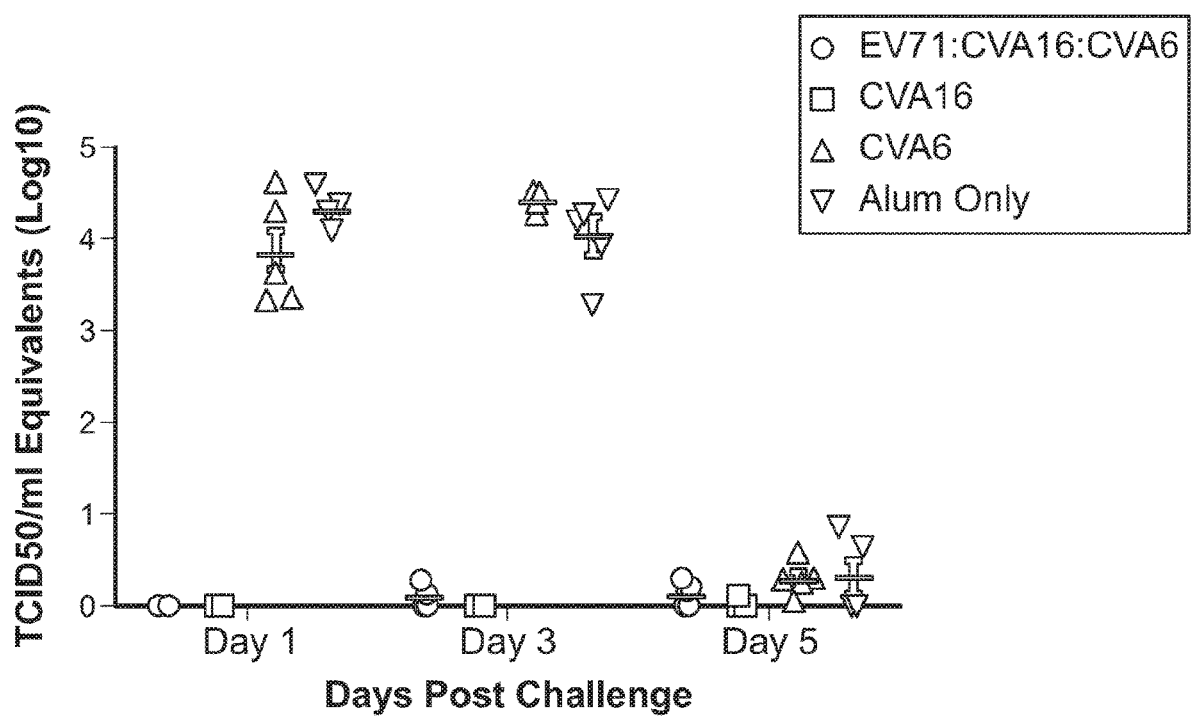
FIG. 22 shows the serum CVA16 viral titer in immunized mice.

The vaccines were also tested for their ability to inhibit CVA16 viremia. Viral titers were measured at days 1, 3, and 5 post-challenge with CVA16 (FIG. 22). Serum samples from the vaccinated mice were collected on days 1, 3, and 5 post-challenge with CVA16 and viral titer was determined by Real Time RT-PCR using a SYBR Green Kit (Qiagen). A standard curve was generated from serially diluted mouse adapted virus stock. Normal mouse serum was used as a negative control and to determine cut off values. The results indicate that both the CVA16 monovalent vaccine and the trivalent vaccine were able to reduce viral titer in serum to approximately zero, as measured by $TCID_{50}$/ml equivalents (FIG. 22).

Vaccine Efficacy Against CVA6 Utilizing Passive Transfer

Figure 23:
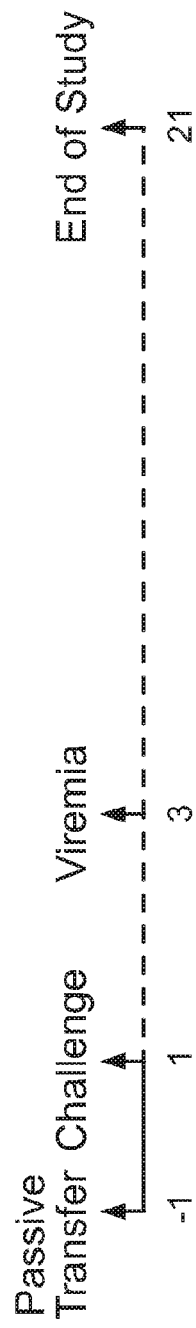
FIG. 23 shows the treatment protocol for passive immunization and challenge with CVA6 in mice.

The efficacy of the trivalent vaccine was then tested in a murine model of CVA6 infection. Groups (n=5-6) of three-week old A129 mice were passively immunized via intraperitoneal (IP) injection with neutralizing antibody serum. Neutralizing antibody serum was raised in mice by vaccinating mice with the CVA6 monovalent vaccine at a dosage of 1.5 µg per animal or with the trivalent vaccine mixture at a total dosage of 4.5 µg per animal (1.5 µg per animal of each monovalent vaccine). Serum samples containing neutralizing antibodies were then collected from each group at day 42 post vaccination and pooled per group and tested by microneutralization test. For the trivalent serum, the geometric mean antibody titer for EV71 was 640, the geometric mean antibody titer for CVA16 was 1280, and the geometric mean antibody titer for CVA6 was 1280. For the CVA6 monovalent serum, the geometric mean antibody titer for CVA6 was 5120. The mice were challenged with mouse-adapted CVA6 virus via intraperitoneal (IP) injection at a challenge dosage of $2.31 \times 10^4$ $TCID_{50}$/200 µl CVA6. The passive transfer and challenge for each mouse group, as well as the schedule of treatment and challenge is depicted in FIG. 23.

Figure 24:
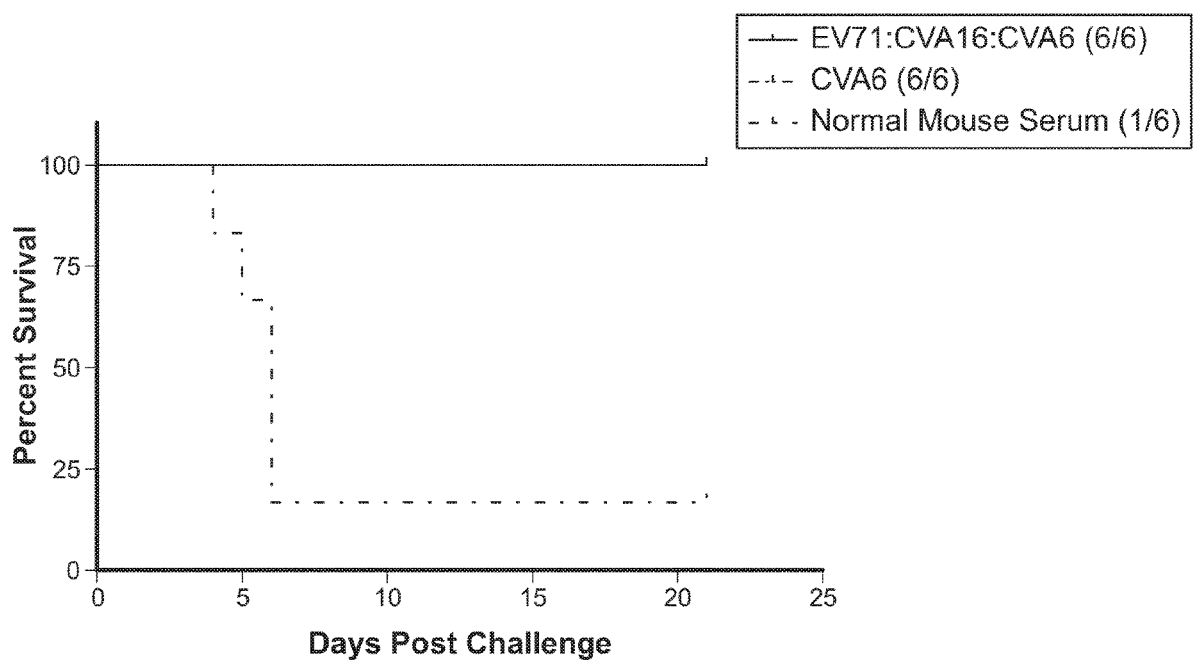
FIG. 24 shows survival rate of mice challenged with CVA6.

FIG. 24 depicts the results of passive immunization with the trivalent serum or the CVA6 monovalent serum. Six out of six mice immunized with either the trivalent serum or the CVA6 monovalent serum survived 20 days post-challenge with CVA6, while only one mouse out of six immunized with control serum from normal mouse survived 20 days post-challenge with CVA6 (FIG. 24). The results indicate that passive transfer of serum from mice vaccinated with the trivalent vaccine was protective against homologous viral challenge with CVA6.

Figure 25:
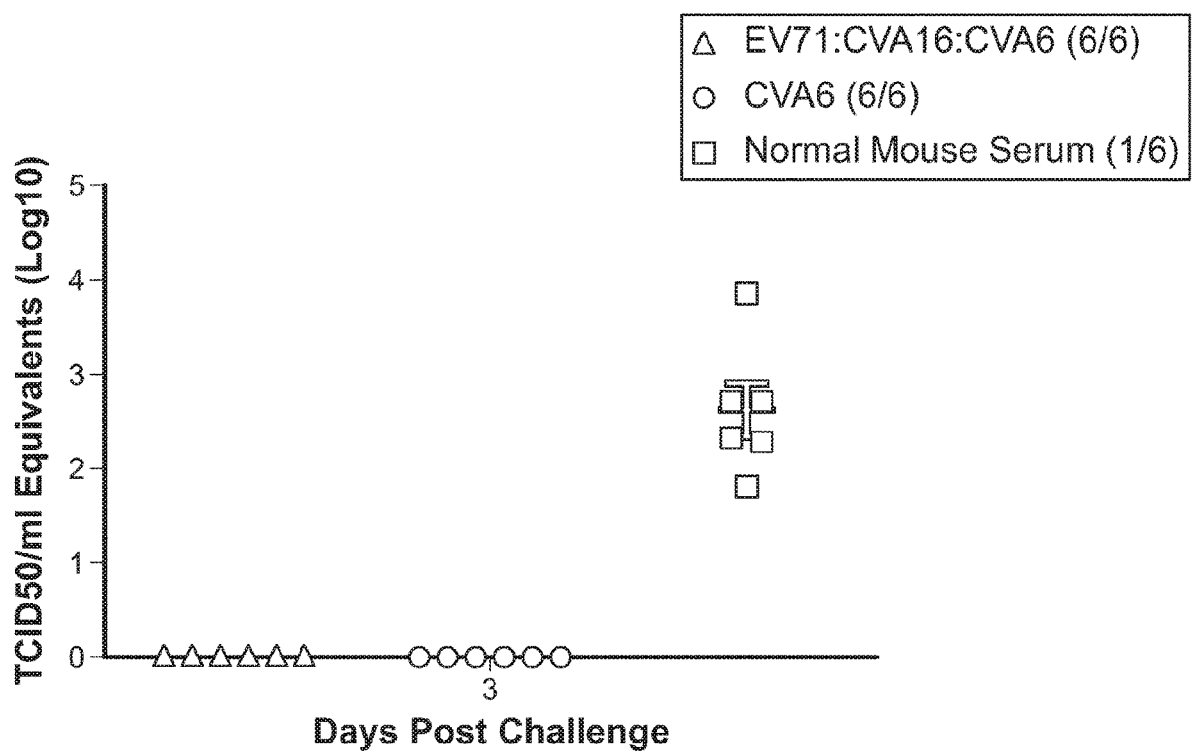
FIG. 25 shows the serum CVA6 viral titer in immunized mice.

The protective sera were also tested for their ability to inhibit CVA6 viremia. Viral titers were measured at days 1, 3, and 5 post-challenge with CVA6 (FIG. 25). Serum samples from the vaccinated mice were collected on days 1, 3, and 5 post-challenge with CVA6 and viral titer was determined by Real Time RT-PCR using a SYBR Green Kit (Qiagen). A standard curve generated from serially diluted mouse adapted virus stock. Normal mouse serum was used as a negative control and to determine cut off values. The results indicate that serum from mice vaccinated with either the CVA6 monovalent vaccine or the trivalent vaccine was able to reduce viral titer in serum to approximately zero, as measured by $TCID_{50}$/ml equivalents (FIG. 25).

CONCLUSIONS

The results demonstrate that antibodies to the HFMD viruses EV71, CVA16, or CVA6 did not cross-neutralize in vitro or cross-protect mice from lethal challenge, and that inactivated preparations of EV71, CVA16, and CVA6 are immunogenic in mice when administered as monovalent or multivalent vaccine formulations. The results also indicate that inactivated preparations of EV71, CVA16, and CVA6 are 100% effective against homologous challenge in the AG129 mouse model for EV71 and CVA16, and in the A129 mouse model for CVA6.

What is claimed is:

1. A hand, foot, and mouth immunogenic composition comprising one or more antigens from a chemically-inactivated enterovirus 71 (EV71), wherein the one or more antigens comprise the VP1 polypeptide of EV71, wherein the VP1 polypeptide comprises four mutations comprising:

(i) a valine to methionine substitution at position 7 of SEQ ID NO: 1, or at a position corresponding to position 7 of SEQ ID NO: 1 when aligned to SEQ ID NO: 1 using a pairwise alignment algorithm;

(ii) an aspartic acid to asparagine substitution at position 14 of SEQ ID NO: 1, or at a position corresponding to position 14 of SEQ ID NO: 1 when aligned to SEQ ID NO: 1 using a pairwise alignment algorithm;

(iii) a glutamic acid to glutamine substitution at position 145 of SEQ ID NO: 1, or at a position corresponding to position 145 of SEQ ID NO: 1 when aligned to SEQ ID NO: 1 using a pairwise alignment algorithm; and (iv) an asparagine to aspartic acid substitution at a position corresponding to position 282 of SEQ ID NO: 1 when aligned to SEQ ID NO: 1 using a pairwise alignment algorithm.

2. The immunogenic composition of claim 1, wherein the chemically-inactivated EV71 was chemically inactivated with one or more of:

a. beta-propiolactone (BPL);

b. formalin;

c. a combination of BPL and formalin; or d. binary ethylenimine (BEI).

3. The immunogenic composition of claim 2, wherein the BPL-inactivated virus comprises one or more modifications, wherein:

a. the one or more modifications comprise a modified nucleic acid, wherein the modified nucleic acid is an alkylated nucleic acid; and/or b. the one or more modifications comprise a modified polypeptide, wherein the modified polypeptide comprises a modified amino acid residue comprising one or more of cysteine, methionine, histidine, aspartic acid, glutamic acid, tyrosine, lysine, serine, and threonine.

4. The immunogenic composition of claim 2, wherein the formalin-inactivated virus comprises one or more modifications, wherein the one or more modifications comprise a cross-linked polypeptide.

5. The immunogenic composition of claim 4, wherein the immunogenic composition further comprises formalin.

6. The immunogenic composition of claim 2, wherein the BEI-inactivated virus comprises one or more modifications, wherein the one or more modifications comprise a modified nucleic acid, wherein the modified nucleic acid is an alkylated nucleic acid.

7. The immunogenic composition of claim 6, wherein any unreacted BEI was hydrolyzed with sodium thiosulfate.

8. The immunogenic composition of claim 2, wherein the immunogenic composition further comprising an adjuvant, wherein the adjuvant is selected from the group consisting of aluminum salts, toll-like receptor (TLR) agonists, monophosphoryl lipid A (MLA), synthetic lipid A, lipid A mimetics or analogs, MLA derivatives, cytokines, saponins, muramyl dipeptide (MDP) derivatives, CpG oligos, lipopolysaccharide (LPS) of gram-negative bacteria, polyphosphazenes, emulsions, virosomes, cochleates, poly(lactide-co-glycolides) (PLG) microparticles, poloxamer particles, microparticles, liposomes, Complete Freund's Adjuvant (CFA), and Incomplete Freund's Adjuvant (IFA).

9. The immunogenic composition of claim 2, wherein the immunogenic composition further comprises an aluminum salt adjuvant, wherein at least 75% of the antigen is adsorbed to aluminum salt adjuvant.

10. The immunogenic composition of claim 9, wherein the aluminum salt adjuvant is selected from alum, aluminum phosphate, aluminum hydroxide, potassium aluminum sulfate, and combinations thereof.

11. The immunogenic composition of claim 2, wherein the one or more antigens were produced by culturing a non-human cell in serum-free media.

12. The immunogenic composition of claim 11, wherein the non-human cell is a Vero cell line.

13. The immunogenic composition of claim 12, wherein the Vero cell line is selected from WHO Vero 10-87, ATCC No. CCL-81, Vero 76 (ATCC No. CRL-1587), and Vero C1008 (ATCC No. CRL-1586).

14. The immunogenic composition of claim 2, characterized in that the immunogenic composition is a vaccine, and wherein the vaccine is a purified antigen vaccine, a subunit vaccine, or an inactivated whole virus vaccine.

* * * * *

SEQUENCE LISTING

```
<160> NUMBER OF SEQ ID NOS: 44

<210> SEQ ID NO 1
<211> LENGTH: 297
<212> TYPE: PRT
<213> ORGANISM: Enterovirus 71

<400> SEQUENCE: 1

Gly Asp Arg Val Ala Asp Val Ile Glu Ser Ser Ile Gly Asp Ser Val
1               5                   10                  15

Ser Arg Ala Leu Thr Gln Ala Leu Pro Ala Pro Thr Gly Gln Asn Thr
            20                  25                  30
```

```
Gln Val Ser Ser His Arg Leu Asp Thr Gly Glu Val Pro Ala Leu Gln
        35                  40                  45

Ala Ala Glu Ile Gly Ala Ser Ser Asn Thr Ser Asp Glu Ser Met Ile
    50                  55                  60

Glu Thr Arg Cys Val Leu Asn Ser His Ser Thr Ala Glu Thr Thr Leu
65                  70                  75                  80

Asp Ser Phe Phe Ser Arg Ala Gly Leu Val Gly Glu Ile Asp Leu Pro
                85                  90                  95

Leu Glu Gly Thr Thr Asn Pro Asn Gly Tyr Ala Asn Trp Asp Ile Asp
            100                 105                 110

Ile Thr Gly Tyr Ala Gln Met Arg Arg Lys Val Glu Leu Phe Thr Tyr
        115                 120                 125

Met Arg Phe Asp Ala Glu Phe Thr Phe Val Ala Cys Thr Pro Thr Gly
    130                 135                 140

Glu Val Val Pro Gln Leu Leu Gln Tyr Met Phe Val Pro Pro Gly Ala
145                 150                 155                 160

Pro Lys Pro Glu Ser Arg Glu Ser Leu Ala Trp Gln Thr Ala Thr Asn
                165                 170                 175

Pro Ser Val Phe Val Lys Leu Thr Asp Pro Pro Ala Gln Val Ser Val
            180                 185                 190

Pro Phe Met Ser Pro Ala Ser Ala Tyr Gln Trp Phe Tyr Asp Gly Tyr
        195                 200                 205

Pro Thr Phe Gly Glu His Lys Gln Glu Lys Asp Leu Glu Tyr Gly Ala
    210                 215                 220

Cys Pro Asn Asn Met Met Gly Thr Phe Ser Val Arg Thr Val Gly Ser
225                 230                 235                 240

Ser Lys Ser Lys Tyr Pro Leu Val Val Arg Ile Tyr Met Arg Met Lys
                245                 250                 255

His Val Arg Ala Trp Ile Pro Arg Pro Met Arg Asn Gln Asn Tyr Leu
            260                 265                 270

Phe Lys Ala Asn Pro Asn Tyr Ala Gly Asn Ser Ile Lys Pro Thr Gly
        275                 280                 285

Thr Ser Arg Asn Ala Ile Thr Thr Leu
    290                 295

<210> SEQ ID NO 2
<211> LENGTH: 305
<212> TYPE: PRT
<213> ORGANISM: Coxsackievirus A6

<400> SEQUENCE: 2

Asn Asp Pro Ile Ser Asn Ala Ile Glu Asn Ala Val Ser Thr Leu Ala
1               5                   10                  15

Asp Thr Thr Ile Ser Arg Val Thr Ala Ala Asn Thr Ala Ala Ser Ser
            20                  25                  30

His Ser Leu Gly Thr Gly Arg Val Pro Ala Leu Gln Ala Ala Glu Thr
        35                  40                  45

Gly Ala Ser Ser Asn Ala Ser Asp Glu Asn Leu Ile Glu Thr Arg Cys
    50                  55                  60

Val Met Asn Arg Asn Gly Val Asn Glu Ala Ser Val Glu His Phe Tyr
65                  70                  75                  80

Ser Arg Ala Gly Leu Val Gly Val Val Glu Val Lys Asp Ser Gly Thr
                85                  90                  95

Ser Gln Asp Gly Tyr Thr Val Trp Pro Ile Asp Val Met Gly Phe Val
            100                 105                 110
```

```
Gln Gln Arg Arg Lys Leu Glu Leu Ser Thr Tyr Met Arg Phe Asp Ala
            115                 120                 125

Glu Phe Thr Phe Val Ser Asn Leu Asn Asp Ser Thr Thr Pro Gly Met
130                 135                 140

Leu Leu Gln Tyr Met Tyr Val Pro Pro Gly Ala Pro Lys Pro Asp Gly
145                 150                 155                 160

Arg Lys Ser Tyr Gln Trp Gln Thr Ala Thr Asn Pro Ser Ile Phe Ala
                165                 170                 175

Lys Leu Ser Asp Pro Pro Gln Val Ser Val Pro Phe Met Ser Pro
            180                 185                 190

Ala Ser Ala Tyr Gln Trp Phe Tyr Asp Gly Tyr Pro Thr Phe Gly Glu
            195                 200                 205

His Lys Gln Ala Thr Asn Leu Gln Tyr Gly Gln Cys Pro Asn Asn Met
        210                 215                 220

Met Gly His Phe Ala Ile Arg Thr Val Ser Glu Ser Thr Thr Gly Lys
225                 230                 235                 240

Asn Val His Val Arg Val Tyr Met Arg Ile Lys His Val Arg Ala Trp
                245                 250                 255

Val Pro Arg Pro Phe Arg Ser Gln Ala Tyr Met Val Lys Asn Tyr Pro
            260                 265                 270

Thr Tyr Ser Gln Thr Ile Ser Asn Thr Ala Ala Asp Arg Ala Ser Ile
            275                 280                 285

Thr Thr Thr Asp Tyr Glu Gly Gly Val Pro Ala Asn Pro Gln Arg Thr
        290                 295                 300

Phe
305

<210> SEQ ID NO 3
<211> LENGTH: 256
<212> TYPE: PRT
<213> ORGANISM: Coxsackievirus A6

<400> SEQUENCE: 3

Ser Pro Ser Val Glu Ala Cys Gly Tyr Ser Asp Arg Val Ala Gln Leu
1               5                   10                  15

Thr Val Gly Asn Ser Thr Ile Thr Thr Gln Glu Ala Ala Asn Ile Val
            20                  25                  30

Leu Ser Tyr Gly Glu Trp Pro Gly Tyr Cys Pro Ser Thr Asp Ala Thr
        35                  40                  45

Ala Val Asp Lys Pro Thr Arg Pro Asp Val Ser Val Asn Arg Phe Tyr
50                  55                  60

Thr Leu Ser Thr Lys Ser Trp Lys Thr Glu Ser Thr Gly Trp Tyr Trp
65                  70                  75                  80

Lys Phe Pro Asp Val Leu Asn Asp Thr Gly Val Phe Gly Gln Asn Ala
                85                  90                  95

Gln Phe His Tyr Leu Tyr Arg Ser Gly Phe Cys Met His Val Gln Cys
            100                 105                 110

Asn Ala Ser Lys Phe His Gln Gly Ala Leu Leu Val Val Val Ile Pro
        115                 120                 125

Glu Phe Val Val Ala Ala Ser Ser Pro Ala Met Lys Pro Asn Gly Gln
130                 135                 140

Gly Leu Tyr Pro Asp Phe Ala His Thr Asn Pro Gly Lys Glu Gly Gln
145                 150                 155                 160

Val Phe Arg Asp Pro Tyr Val Leu Asp Ala Gly Ile Pro Leu Ser Gln
```

```
                165                 170                 175
Ala Leu Val Phe Pro His Gln Trp Ile Asn Leu Arg Thr Asn Asn Cys
            180                 185                 190

Ala Thr Ile Ile Met Pro Tyr Val Asn Ala Leu Pro Phe Asp Ser Ala
            195                 200                 205

Leu Asn His Ser Asn Phe Gly Leu Ala Val Ile Pro Ile Ser Pro Leu
            210                 215                 220

Lys Tyr Cys Asn Gly Ala Thr Thr Glu Val Pro Ile Thr Leu Thr Ile
225                 230                 235                 240

Ala Pro Leu Asn Ser Glu Phe Ser Gly Leu Arg Gln Ala Ile Lys Gln
            245                 250                 255

<210> SEQ ID NO 4
<211> LENGTH: 240
<212> TYPE: PRT
<213> ORGANISM: Coxsackievirus A6

<400> SEQUENCE: 4

Gly Leu Pro Thr Glu Leu Lys Pro Gly Thr Asn Gln Phe Leu Thr Thr
1               5                   10                  15

Asp Asp Gly Thr Ser Pro Pro Ile Leu Pro Gly Phe Glu Pro Thr Pro
            20                  25                  30

Leu Ile His Ile Pro Gly Glu Phe Thr Ser Leu Leu Asp Leu Cys Arg
        35                  40                  45

Ile Glu Thr Ile Leu Glu Val Asn Asn Thr Gly Thr Thr Gly Val
    50                  55                  60

Asn Arg Leu Leu Ile Pro Val Arg Ala Gln Asn Asn Val Asp Gln Leu
65                  70                  75                  80

Cys Ala Ser Phe Gln Val Asp Pro Gly Arg Asn Gly Pro Trp Gln Ser
                85                  90                  95

Thr Met Val Gly Gln Ile Cys Arg Tyr Tyr Thr Gln Trp Ser Gly Ser
            100                 105                 110

Leu Lys Val Thr Phe Met Phe Thr Gly Ser Phe Met Ala Thr Gly Lys
        115                 120                 125

Met Leu Ile Ala Tyr Thr Pro Pro Gly Ser Ala Gln Pro Thr Thr Arg
    130                 135                 140

Glu Ala Ala Met Leu Gly Thr His Ile Val Trp Asp Phe Gly Leu Gln
145                 150                 155                 160

Ser Ser Val Thr Leu Val Ile Pro Trp Ile Ser Asn Thr His Phe Arg
                165                 170                 175

Ala Val Lys Thr Gly Gly Val Tyr Asp Tyr Tyr Ala Thr Gly Ile Val
            180                 185                 190

Thr Ile Trp Tyr Gln Thr Asn Phe Val Val Pro Pro Asp Thr Pro Ser
        195                 200                 205

Glu Ala Asn Ile Ile Ala Leu Gly Ala Ala Gln Glu Asn Phe Thr Leu
    210                 215                 220

Lys Leu Cys Lys Asp Thr Asp Glu Ile Arg Gln Thr Ala Glu Tyr Gln
225                 230                 235                 240

<210> SEQ ID NO 5
<211> LENGTH: 150
<212> TYPE: PRT
<213> ORGANISM: Coxsackievirus A16

<400> SEQUENCE: 5

Gly Lys Phe Gly Gln Gln Ser Gly Ala Ile Tyr

-continued

```
1               5                   10                  15

Val Val Asn Arg His Leu Ala Thr His Asn Asp Trp Ala Asn Leu Val
            20                  25                  30

Trp Glu Asp Ser Ser Arg Asp Leu Leu Val Ser Ser Thr Thr Ala Gln
        35                  40                  45

Gly Cys Asp Thr Ile Ala Arg Cys Asp Cys Gln Thr Gly Ile Tyr Tyr
    50                  55                  60

Cys Ser Ser Lys Arg Lys His Tyr Pro Val Ser Phe Thr Lys Pro Ser
65                  70                  75                  80

Leu Ile Phe Val Glu Ala Ser Glu Tyr Tyr Pro Ala Arg Tyr Gln Ser
                85                  90                  95

His Leu Met Leu Ala Val Gly His Ser Glu Pro Gly Asp Cys Gly Gly
            100                 105                 110

Ile Leu Arg Cys Gln His Gly Val Val Gly Ile Val Ser Thr Gly Gly
        115                 120                 125

Asn Gly Leu Val Gly Phe Ala Asp Val Arg Asp Leu Leu Trp Leu Asp
    130                 135                 140

Glu Glu Ala Met Glu Gln
145                 150

<210> SEQ ID NO 6
<211> LENGTH: 254
<212> TYPE: PRT
<213> ORGANISM: Coxsackievirus A16

<400> SEQUENCE: 6

Ser Pro Ser Ala Glu Ala Cys Gly Tyr Ser Asp Arg Val Ala Gln Leu
1               5                   10                  15

Thr Ile Gly Asn Ser Thr Ile Thr Thr Gln Glu Ala Ala Asn Ile Val
            20                  25                  30

Ile Ala Tyr Gly Glu Trp Pro Glu Tyr Cys Pro Asp Thr Asp Ala Thr
        35                  40                  45

Ala Val Asp Lys Pro Thr Arg Pro Asp Val Ser Val Asn Arg Phe Phe
    50                  55                  60

Thr Leu Asp Thr Lys Ser Trp Ala Lys Asp Ser Lys Gly Trp Tyr Trp
65                  70                  75                  80

Lys Phe Pro Asp Val Leu Thr Glu Val Gly Val Phe Gly Gln Asn Ala
                85                  90                  95

Gln Phe His Tyr Leu Tyr Arg Ser Gly Phe Cys Val His Val Gln Cys
            100                 105                 110

Asn Ala Ser Lys Phe His Gln Gly Ala Leu Leu Val Ala Val Leu Pro
        115                 120                 125

Glu Tyr Val Leu Gly Thr Ile Ala Gly Gly Thr Gly Asn Glu Asn Ser
    130                 135                 140

His Pro Pro Tyr Ala Thr Thr Gln Pro Gly Gln Val Gly Ala Val Leu
145                 150                 155                 160

Met His Pro Tyr Val Leu Asp Ala Gly Ile Pro Leu Ser Gln Leu Thr
                165                 170                 175

Val Cys Pro His Gln Trp Ile Asn Leu Arg Thr Asn Asn Cys Ala Thr
            180                 185                 190

Ile Ile Val Pro Tyr Met Asn Thr Val Pro Phe Asp Ser Ala Leu Asn
        195                 200                 205

His Cys Asn Phe Gly Leu Leu Val Ile Pro Val Val Pro Leu Asp Phe
    210                 215                 220
```

```
Asn Ala Gly Ala Thr Ser Glu Ile Pro Ile Thr Val Thr Ile Ala Pro
225                 230                 235                 240

Met Cys Ala Glu Phe Ala Gly Leu Arg Gln Ala Val Lys Gln
                245                 250
```

<210> SEQ ID NO 7
<211> LENGTH: 297
<212> TYPE: PRT
<213> ORGANISM: Coxsackievirus A16

<400> SEQUENCE: 7

```
Gly Asp Pro Ile Ala Asp Met Ile Asp Gln Thr Val Asn Asn Gln Val
1               5                   10                  15

Asn Arg Ser Leu Thr Ala Leu Gln Val Leu Pro Thr Ala Ala Asn Thr
                20                  25                  30

Glu Ala Ser Ser His Arg Leu Gly Thr Gly Val Val Pro Ala Leu Gln
            35                  40                  45

Ala Ala Glu Thr Gly Ala Ser Ser Asn Ala Ser Asp Lys Asn Leu Ile
        50                  55                  60

Glu Thr Arg Cys Val Leu Asn His His Ser Thr Gln Glu Thr Ala Ile
65                  70                  75                  80

Gly Asn Phe Phe Ser Arg Ala Gly Leu Val Ser Ile Ile Thr Met Pro
                85                  90                  95

Thr Thr Asp Thr Gln Asn Thr Asp Gly Tyr Val Asn Trp Asp Ile Asp
            100                 105                 110

Leu Met Gly Tyr Ala Gln Leu Arg Arg Lys Cys Glu Leu Phe Thr Tyr
        115                 120                 125

Met Arg Phe Asp Ala Glu Phe Thr Phe Val Val Ala Lys Pro Asn Gly
130                 135                 140

Val Leu Val Pro Gln Leu Leu Gln Tyr Met Tyr Val Pro Pro Gly Ala
145                 150                 155                 160

Pro Lys Pro Thr Ser Arg Asp Ser Phe Ala Trp Gln Thr Ala Thr Asn
                165                 170                 175

Pro Ser Val Phe Val Lys Met Thr Asp Pro Pro Ala Gln Val Ser Val
            180                 185                 190

Pro Phe Met Ser Pro Ala Ser Ala Tyr Gln Trp Phe Tyr Asp Gly Tyr
        195                 200                 205

Pro Thr Phe Gly Glu His Leu Gln Ala Asn Asp Leu Asp Tyr Gly Gln
210                 215                 220

Cys Pro Asn Asn Met Met Gly Thr Phe Ser Ile Arg Thr Val Gly Thr
225                 230                 235                 240

Glu Lys Ser Pro His Ser Ile Thr Leu Arg Val Tyr Met Arg Ile Lys
                245                 250                 255

His Val Arg Ala Trp Ile Pro Arg Pro Leu Arg Asn Gln Pro Tyr Leu
            260                 265                 270

Phe Lys Thr Asn Pro Asn Tyr Lys Gly Asn Asp Ile Lys Cys Thr Ser
        275                 280                 285

Thr Ser Arg Asp Lys Ile Thr Thr Leu
290                 295
```

<210> SEQ ID NO 8
<211> LENGTH: 745
<212> TYPE: DNA
<213> ORGANISM: Coxsackievirus A6

<400> SEQUENCE: 8
ttaaaacagc tagtgggttg cacccactca cagggcccac tgggcgctag cacactgatt 60
tcccggaatc cttgtgcgcc tgttttatat cccctccccc atgcgcaact tagaagcaat 120
ctacaccttc gatcaatagc aggcgtggcg cgccagccat gtctagatca agcacttctg 180
tttccccgga ctgagtatca ataaactgct cacgcggttg aaggagaaaa tgttcgttac 240
ccggctaact acttcgagaa acctagtagc accatgaaaa ttgcagagcg tttcgctcag 300
cgcttccccc gcgtagatca ggctgatgag tcactgcatt cctcacgggc gaccgtggca 360
gtggctgcgt tggcggcctg cccatggggt aacccatggg acgctctaat atggacatgg 420
tgtgaagagt ctattgagct agttagtagt cctccggccc ctgaatgcgg ctaatcctaa 480
ctgcggagca catacccca aaccaggggg cggtgtgtcg taacgggcaa ctctgcagcg 540
gaaccgacta ctttgggtgt ccgtgtttcc ttttattctt atattggctg cttatggtga 600
caattgaaag attgttacca tatagctatt ggattggcca tccggtgaat aacagagcct 660
tgatatacct ttttgtaggg tttataccac ttactcttcg cgttgttgag actctaaagt 720
acattctaat cttgaacact agaaa 745

<210> SEQ ID NO 9
<211> LENGTH: 739
<212> TYPE: DNA
<213> ORGANISM: Coxsackievirus A16

<400> SEQUENCE: 9
agcctgtggg ttgttcccac ccacagggcc cagtgggcgc tagcacactg attctgcggg 60
atctttgtgc gcctgtttta taacccccttc cctaagcagc aacttagaag tttcacacaa 120
tcacgaccag tagtgggcgt ggcgcgccag tcacgtcttg gtcaagcact tctgttcccc 180
cggactgagt atcaatagac tgctcacgcg gttgaaggag aaaacgttcg ttatccggct 240
aactacttcg agaaacctag tagcaccgtg aaagttgcgg agtgtttcgc tcagcacttc 300
ccccgtgtag atcaggtcga tgagtcactg taaaccccac gggcgaccgt gacagtggct 360
gcgttggcgg cctgcccatg ggtaacccca tgggacgctc taatacagac atggtgtgaa 420
gagtctattg agctagttag tagtcctccg gcccctgaat gcggctaatc ctaactgcgg 480
agcacgcacc ctcaacccag gggcggcgt gtcgtaatgg gtaactctgc agcggaaccg 540
actactttgg gtgtccgtgt ttccttttat tccttattgg ctgcttatgg tgacaattga 600
aaagttgtta ccatatagct attggattgg ccatccggtg tctaacagag ctattgttta 660
cctatttatt ggatacgtcc ctcttaatct caaggccatt caaactcttg attatatatt 720
gctccttaac tgtaagaaa 739

<210> SEQ ID NO 10
<211> LENGTH: 20
<212> TYPE: DNA
<213> ORGANISM: unknown
<220> FEATURE:
<223> OTHER INFORMATION: synthetic construct

<400> SEQUENCE: 10
tccatgacgt tcctgacgtt 20

<210> SEQ ID NO 11
<211> LENGTH: 18
<212> TYPE: DNA
<213> ORGANISM: unknown
<220> FEATURE:
<223> OTHER INFORMATION: synthetic construct

<400> SEQUENCE: 11
tctcccagcg tgcgccat                                                    18

<210> SEQ ID NO 12
<211> LENGTH: 30
<212> TYPE: DNA
<213> ORGANISM: unknown
<220> FEATURE:
<223> OTHER INFORMATION: synthetic construct

<400> SEQUENCE: 12
accgatgacg tcgccggtga cggcaccacg                                        30

<210> SEQ ID NO 13
<211> LENGTH: 24
<212> TYPE: DNA
<213> ORGANISM: unknown
<220> FEATURE:
<223> OTHER INFORMATION: synthetic construct

<400> SEQUENCE: 13
tcgtcgtttt gtcgttttgt cgtt                                              24

<210> SEQ ID NO 14
<211> LENGTH: 20
<212> TYPE: DNA
<213> ORGANISM: unknown
<220> FEATURE:
<223> OTHER INFORMATION: synthetic construct

<400> SEQUENCE: 14
tccatgacgt tcctgatgct                                                   20

<210> SEQ ID NO 15
<211> LENGTH: 291
<212> TYPE: PRT
<213> ORGANISM: Coxsackievirus A6

<400> SEQUENCE: 15

Asn Asp Pro Ile Ala Ser Ala Val Glu Ser Ala Val Asn Ala Phe Ala
1               5                   10                  15

Asp Thr Thr Ile Ser Arg Val Thr Ala Ala Asn Thr Ala Ala Ser Thr
            20                  25                  30

His Ser Leu Gly Thr Gly Arg Val Pro Ala Leu Gln Ala Ala Glu Thr
        35                  40                  45

Gly Ala Ser Ser Asn Ala Ser Asp Glu Asn Leu Ile Glu Thr Arg Cys
    50                  55                  60

Val Met Asn Arg Asn Gly Ile Asn Glu Ala Ser Val Glu His Phe Tyr
65                  70                  75                  80

Ser Arg Ala Gly Leu Val Gly Val Val Glu Val Lys Asp Ser Gly Thr
                85                  90                  95

Asn Gln Asp Gly Tyr Thr Val Trp Pro Ile Asp Val Met Gly Phe Val
            100                 105                 110

Gln Gln Arg Arg Lys Leu Glu Leu Ser Thr Tyr Met Arg Phe Asp Ala
        115                 120                 125

Glu Phe Thr Phe Val Ser Asn Leu Asn Asp Ser Thr Thr Pro Gly Met
    130                 135                 140

Leu Leu Gln Tyr Met Tyr Val Pro Pro Gly Ala Pro Lys Pro Asp Gly
145                 150                 155                 160

```
Arg Lys Ser Tyr Gln Trp Gln Thr Ala Thr Asn Pro Ser Ile Phe Ala
            165                 170                 175

Lys Leu Ser Asp Pro Pro Gln Val Tyr Val Pro Phe Met Ser Pro
        180                 185                 190

Ala Ser Ala Tyr Gln Trp Phe Tyr Asp Gly Tyr Pro Thr Phe Gly Glu
            195                 200                 205

His Lys Gln Ala Thr Asn Leu Gln Tyr Gly Gln Cys Pro Asn Asn Met
        210                 215                 220

Met Gly His Phe Ala Ile Arg Thr Val Ser Glu Ser Thr Thr Gly Lys
225                 230                 235                 240

Asn Ile His Val Arg Val Tyr Met Arg Ile Lys His Val Arg Ala Trp
            245                 250                 255

Val Pro Arg Pro Leu Arg Ser Gln Ala Tyr Met Val Lys Asn Tyr Pro
        260                 265                 270

Thr Tyr Asn Gln Thr Ile Thr Asn Ser Ala Thr Asp Arg Ala Ser Ile
            275                 280                 285

Thr Thr Thr
        290

<210> SEQ ID NO 16
<211> LENGTH: 291
<212> TYPE: PRT
<213> ORGANISM: Coxsackievirus A6

<400> SEQUENCE: 16

Asn Asp Pro Ile Ala Asn Ala Val Glu Gly Ala Val Gly Thr Leu Ala
1               5                   10                  15

Asp Ala Thr Ile Ser Arg Val Thr Ala Ala Asn Thr Ile Ala Ser Thr
            20                  25                  30

His Ser Leu Gly Thr Gly Arg Val Pro Ala Leu Gln Ala Ala Glu Thr
        35                  40                  45

Gly Ala Ser Ser Asn Ala Ser Asp Glu Asn Leu Ile Glu Thr Arg Cys
    50                  55                  60

Val Met Asn Arg Asn Gly Ile Asn Glu Ala Ser Val Glu His Phe Tyr
65                  70                  75                  80

Ser Arg Ala Gly Leu Val Gly Val Val Glu Val Lys Asp Ser Gly Thr
            85                  90                  95

Ser Gln Asp Gly Tyr Thr Val Trp Pro Ile Asp Val Met Gly Phe Val
        100                 105                 110

Gln Gln Arg Arg Lys Leu Glu Leu Ser Thr Tyr Met Arg Phe Asp Ala
    115                 120                 125

Glu Phe Thr Phe Val Ser Asn Leu Asn Asp Ser Thr Thr Pro Gly Met
130                 135                 140

Leu Leu Gln Tyr Met Tyr Val Pro Pro Gly Ala Pro Lys Pro Asp Gly
145                 150                 155                 160

Arg Lys Ser Tyr Gln Trp Gln Thr Ala Thr Asn Pro Ser Ile Phe Ala
            165                 170                 175

Lys Leu Ser Asp Pro Pro Gln Val Ser Val Pro Phe Met Ser Pro
        180                 185                 190

Ala Ser Ala Tyr Gln Trp Phe Tyr Asp Gly Tyr Pro Thr Phe Gly Glu
            195                 200                 205

His Lys Gln Ala Thr Asn Leu Gln Tyr Gly Gln Cys Pro Asn Asn Met
        210                 215                 220

Met Gly His Phe Ala Ile Arg Thr Val Ser Glu Ser Thr Thr Gly Lys
225                 230                 235                 240
```

```
Asn Ile His Val Arg Val Tyr Met Arg Ile Lys His Val Arg Ala Trp
            245                 250                 255

Val Pro Arg Pro Phe Arg Ser Gln Ala Tyr Met Val Lys Asn Tyr Pro
            260                 265                 270

Thr Tyr Asn Gln Thr Ile Thr Asn Ser Ala Thr Asp Arg Ala Asn Ile
        275                 280                 285

Thr Thr Thr
    290

<210> SEQ ID NO 17
<211> LENGTH: 305
<212> TYPE: PRT
<213> ORGANISM: Coxsackievirus A6

<400> SEQUENCE: 17

Asn Asp Pro Ile Ser Asn Ala Ile Glu Asn Ala Val Ser Thr Leu Ala
1               5                   10                  15

Asp Thr Thr Ile Ser Arg Val Thr Ala Ala Asn Thr Ala Ala Ser Ser
            20                  25                  30

His Ser Leu Gly Thr Gly Arg Val Pro Ala Leu Gln Ala Ala Glu Thr
        35                  40                  45

Gly Ala Ser Ser Asn Ala Ser Asp Glu Asn Leu Ile Glu Thr Arg Cys
    50                  55                  60

Val Met Asn Arg Asn Gly Val Asn Glu Ala Ser Val Glu His Phe Tyr
65                  70                  75                  80

Ser Arg Ala Gly Leu Val Gly Val Val Glu Val Lys Asp Ser Gly Thr
                85                  90                  95

Ser Gln Asp Gly Tyr Thr Val Trp Pro Ile Asp Val Met Gly Phe Val
            100                 105                 110

Gln Gln Arg Arg Lys Leu Glu Leu Ser Thr Tyr Met Arg Phe Asp Ala
        115                 120                 125

Glu Phe Thr Phe Val Ser Asn Leu Asn Asp Ser Thr Thr Pro Gly Met
    130                 135                 140

Leu Leu Gln Tyr Met Tyr Val Pro Pro Gly Ala Pro Lys Pro Asp Gly
145                 150                 155                 160

Arg Lys Ser Tyr Gln Trp Gln Thr Ala Thr Asn Pro Ser Ile Phe Ala
                165                 170                 175

Lys Leu Ser Asp Pro Pro Pro Gln Val Ser Val Pro Phe Met Ser Pro
            180                 185                 190

Ala Ser Ala Tyr Gln Trp Phe Tyr Asp Gly Tyr Pro Thr Phe Gly Glu
        195                 200                 205

His Lys Gln Ala Thr Asn Leu Gln Tyr Gly Gln Cys Pro Asn Asn Met
    210                 215                 220

Met Gly His Phe Ala Ile Arg Thr Val Ser Glu Ser Thr Thr Gly Lys
225                 230                 235                 240

Asn Val His Val Arg Val Tyr Met Arg Ile Lys His Val Arg Ala Trp
                245                 250                 255

Val Pro Arg Pro Phe Arg Ser Gln Ala Tyr Met Val Lys Asn Tyr Pro
            260                 265                 270

Thr Tyr Ser Gln Thr Ile Ser Asn Thr Ala Ala Asp Arg Ala Ser Ile
        275                 280                 285

Thr Thr Thr Asp Tyr Glu Gly Gly Val Pro Ala Asn Pro Gln Arg Thr
    290                 295                 300

Phe
```

-continued

```
<210> SEQ ID NO 18
<211> LENGTH: 305
<212> TYPE: PRT
<213> ORGANISM: Coxsackievirus A6

<400> SEQUENCE: 18

Asn Asp Pro Ile Ser Asn Ala Ile Glu Asn Ala Val Ser Thr Leu Ala
1

```
                1               5                      10                      15
            Asp Thr Thr Ile Ser Arg Val Thr Ala Ala Asn Thr Ala Ala Ser Ser
                            20                      25                      30

His Ser Leu Gly Thr Gly Arg Val Pro Ala Leu Gln Ala Val Glu Thr
                            35                      40                      45

Gly Ala Ser Ser Asn Ala Ser Asp Glu Asn Leu Ile Glu Thr Arg Cys
                            50                      55                      60

Val Met Asn Arg Asn Gly Val Asn Glu Ala Ser Val Glu His Phe Tyr
            65                      70                      75                      80

Ser Arg Ala Gly Leu Val Gly Val Lys Val Lys Asp Ser Gly Ala
                                    85                      90                      95

Ser Gln Asp Gly Tyr Thr Val Trp Pro Ile Asp Val Met Gly Phe Val
                                    100                     105                     110

Gln Gln Arg Arg Lys Leu Glu Leu Ser Thr Tyr Met Arg Phe Asp Ala
                                    115                     120                     125

Glu Phe Thr Phe Val Ser Asn Leu Asn Asp Ser Thr Thr Pro Gly Met
                            130                     135                     140

Leu Leu Gln Tyr Met Tyr Val Pro Pro Gly Ala Pro Lys Pro Asp Gly
            145                     150                     155                     160

Arg Lys Ser Tyr Gln Trp Gln Thr Ala Thr Asn Pro Ser Ile Phe Ala
                                    165                     170                     175

Lys Leu Ser Asp Pro Pro Pro Gln Val Ser Val Pro Phe Met Ser Pro
                            180                     185                     190

Ala Ser Ala Tyr Gln Trp Phe Tyr Asp Gly Tyr Pro Thr Phe Gly Glu
                                    195                     200                     205

His Lys Gln Ala Thr Asn Leu Gln Tyr Gly Gln Cys Pro Asn Asn Met
                            210                     215                     220

Met Gly His Phe Ala Ile Arg Thr Val Ser Glu Ser Thr Thr Gly Lys
            225                     230                     235                     240

Asn Val His Val Arg Val Tyr Met Arg Ile Lys His Val Arg Ala Trp
                                    245                     250                     255

Val Pro Arg Pro Phe Arg Ser Gln Ala Tyr Met Ile Lys Asn Tyr Pro
                            260                     265                     270

Thr Tyr Ser Gln Thr Ile Ser Asn Thr Ala Ala Asp Arg Ala Ser Ile
                            275                     280                     285

Thr Thr Thr Asp Tyr Glu Gly Gly Val Pro Ala Asn Pro Gln Arg Thr
                            290                     295                     300

Phe
            305

<210> SEQ ID NO 20
            <211> LENGTH: 305
            <212> TYPE: PRT
            <213> ORGANISM: Coxsackievirus A6

<400> SEQUENCE: 20

Asn Asp Pro Ile Ala Asn Ala Val Glu Ser Ala Val Ser Ala Leu Ala
            1               5                       10                      15

Asp Thr Thr Ile Tyr Arg Val Thr Ala Ala Ser Thr Ala Ala Ser Thr
                            20                      25                      30

His Ser Leu Gly Thr Gly Arg Val Pro Ala Leu Gln Ala Ala Glu Thr
                            35                      40                      45

Gly Ala Ser Ser Asn Ala Ser Asp Glu Asn Leu Ile Glu Thr Arg Cys
                            50                      55                      60
```

```
Val Met Asn Arg Asn Gly Val Asn Glu Ala Ser Val Glu His Phe Tyr
 65                  70                  75                  80

Ser Arg Ala Gly Leu Val Gly Val Val Glu Val Lys Asp Ser Gly Thr
                 85                  90                  95

Ser Leu Asp Gly Tyr Thr Val Trp Pro Ile Asp Val Met Gly Phe Val
                100                 105                 110

Gln Gln Arg Arg Lys Leu Glu Leu Ser Thr Tyr Met Arg Phe Asp Ala
                115                 120                 125

Glu Phe Thr Phe Val Ser Asn Leu Asn Asp Ser Thr Thr Pro Gly Met
130                 135                 140

Leu Leu Gln Tyr Met Tyr Val Pro Pro Gly Ala Pro Lys Pro Asp Ser
145                 150                 155                 160

Arg Lys Ser Tyr Gln Trp Gln Thr Ala Thr Asn Pro Ser Val Phe Ala
                165                 170                 175

Lys Leu Ser Asp Pro Pro Gln Val Ser Val Pro Phe Met Ser Pro
                180                 185                 190

Ala Thr Ala Tyr Gln Trp Phe Tyr Asp Gly Tyr Pro Thr Phe Gly Glu
                195                 200                 205

His Lys Gln Ala Thr Asn Leu Gln Tyr Gly Gln Cys Pro Asn Asn Met
210                 215                 220

Met Gly His Phe Ala Ile Arg Thr Val Ser Glu Ser Thr Thr Gly Lys
225                 230                 235                 240

Asn Val His Val Arg Val Tyr Met Arg Ile Lys His Val Arg Ala Trp
                245                 250                 255

Val Pro Arg Pro Leu Arg Ser Gln Ala Tyr Met Val Lys Asn Tyr Pro
                260                 265                 270

Thr Tyr Ser Gln Thr Ile Thr Asn Thr Ala Thr Asp Arg Ala Ser Ile
                275                 280                 285

Thr Thr Thr Asp Tyr Glu Gly Gly Val Pro Ala Asn Ser Gln Arg Thr
290                 295                 300

Ser
305

<210> SEQ ID NO 21
<211> LENGTH: 291
<212> TYPE: PRT
<213> ORGANISM: Coxsackievirus A6

<400> SEQUENCE: 21

Asn Asp Pro Ile Thr Asn Ala Val Glu Ser Ala Val Ser Ala Leu Ala
  1               5                  10                  15

Asp Thr Thr Ile Ser Arg Val Thr Ala Ala Asn Thr Ala Val Ser Thr
                 20                  25                  30

His Ser Leu Gly Thr Gly Arg Val Pro Ala Leu Gln Ala Ala Glu Thr
                 35                  40                  45

Gly Ala Ser Ser Asn Ala Ser Asp Glu Asn Leu Ile Glu Thr Arg Cys
             50                  55                  60

Val Met Asn Arg Asn Gly Val Asn Glu Ala Ser Val Glu His Phe Tyr
 65                  70                  75                  80

Ser Arg Ala Gly Leu Val Gly Val Val Glu Val Lys Asp Ser Gly Thr
                 85                  90                  95

Ser Leu Asp Gly Tyr Thr Val Trp Pro Ile Asp Val Met Gly Phe Val
                100                 105                 110

Gln Gln Arg Arg Lys Leu Glu Leu Ser Thr Tyr Met Arg Phe Asp Ala
                115                 120                 125
```

```
Glu Phe Thr Phe Val Ser Asn Leu Asn Asp Ser Thr Thr Pro Gly Met
    130                 135                 140

Leu Leu Gln Tyr Met Tyr Val Pro Pro Gly Ala Pro Lys Pro Asp Ser
145                 150                 155                 160

Arg Lys Ser Tyr Gln Trp Gln Thr Ala Thr Asn Pro Ser Val Phe Ala
                165                 170                 175

Lys Leu Ser Asp Pro Pro Gln Val Ser Val Pro Phe Met Ser Pro
                180                 185                 190

Ala Thr Ala Tyr Gln Trp Phe Tyr Asp Gly Tyr Pro Thr Phe Gly Glu
                195                 200                 205

His Lys Gln Ala Thr Asn Leu Gln Tyr Gly Gln Cys Pro Asn Asn Met
    210                 215                 220

Met Gly His Phe Ala Ile Arg Thr Val Ser Glu Ser Thr Thr Gly Lys
225                 230                 235                 240

Asn Val His Val Arg Val Tyr Met Arg Ile Lys His Val Arg Ala Trp
                245                 250                 255

Val Pro Arg Pro Leu Arg Ser Gln Ala Tyr Met Val Lys Asn Tyr Pro
                260                 265                 270

Thr Tyr Ser Gln Thr Ile Thr Asn Thr Ala Thr Asp Arg Ala Ser Ile
                275                 280                 285

Thr Ile Thr
    290

<210> SEQ ID NO 22
<211> LENGTH: 305
<212> TYPE: PRT
<213> ORGANISM: Coxsackievirus A6

<400> SEQUENCE: 22

Asn Asp Pro Ile Thr Asn Ala Val Glu Ser Ala Val Ser Ala Leu Ala
1               5                   10                  15

Asp Thr Thr Ile Ser Arg Val Thr Ala Ala Asn Thr Ala Ala Ser Thr
                20                  25                  30

His Ser Leu Gly Thr Gly Arg Val Pro Ala Leu Gln Ala Ala Glu Thr
            35                  40                  45

Gly Ala Ser Ser Asn Ser Ser Asp Glu Asn Leu Ile Glu Thr Arg Cys
    50                  55                  60

Val Met Asn Arg Asn Gly Val Asn Glu Ala Ser Val Glu His Phe Tyr
65                  70                  75                  80

Ser Arg Ala Gly Leu Val Gly Val Val Glu Val Lys Asp Ser Gly Thr
                85                  90                  95

Ser Leu Asp Gly Tyr Thr Val Trp Pro Ile Asp Val Met Gly Phe Val
                100                 105                 110

Gln Gln Arg Arg Lys Leu Glu Leu Ser Thr Tyr Met Arg Phe Asp Ala
            115                 120                 125

Glu Phe Thr Phe Val Ser Asn Leu Asn Asp Ser Thr Thr Pro Gly Met
    130                 135                 140

Leu Leu Gln Tyr Met Tyr Val Pro Pro Gly Ala Pro Lys Pro Asp Ser
145                 150                 155                 160

Arg Lys Ser Tyr Gln Trp Gln Thr Ala Thr Asn Pro Ser Val Phe Ala
                165                 170                 175

Lys Leu Ser Asp Pro Pro Gln Val Ser Val Pro Phe Met Ser Pro
                180                 185                 190

Ala Thr Ala Tyr Gln Trp Phe Tyr Asp Gly Tyr Pro Thr Phe Gly Glu
```

```
                195                 200                 205
His Lys Gln Ala Thr Asn Leu Gln Tyr Gly Gln Cys Pro Asn Asn Met
    210                 215                 220

Met Gly His Phe Ala Ile Arg Thr Val Ser Glu Ser Thr Thr Gly Lys
225                 230                 235                 240

Asn Ile His Val Arg Val Tyr Met Arg Ile Lys His Val Arg Ala Trp
                245                 250                 255

Val Pro Arg Pro Leu Arg Ser Gln Ala Tyr Met Val Lys Asn Tyr Pro
                260                 265                 270

Thr Tyr Ser Gln Thr Ile Thr Asn Thr Ala Thr Asp Arg Ala Ser Ile
                275                 280                 285

Thr Thr Thr Asp Tyr Glu Gly Gly Val Pro Ala Asn Pro Gln Arg Thr
                290                 295                 300

Ser
305

<210> SEQ ID NO 23
<211> LENGTH: 305
<212> TYPE: PRT
<213> ORGANISM: Coxsackievirus A6

<400> SEQUENCE: 23

Asn Asp Pro Ile Thr Asn Ala Val Glu Ser Ala Val Ser Ala Leu Ala
1               5                   10                  15

Asp Thr Thr Ile Ser Arg Val Thr Ala Ala Asn Thr Ala Ala Ser Thr
                20                  25                  30

His Ser Leu Gly Thr Gly Arg Val Pro Ala Leu Gln Ala Ala Glu Thr
            35                  40                  45

Gly Ala Ser Ser Asn Ala Ser Asp Glu Asn Leu Ile Glu Thr Arg Cys
    50                  55                  60

Val Met Asn Arg Asn Gly Val Asn Glu Ala Ser Val Glu His Phe Tyr
65                  70                  75                  80

Ser Arg Ala Gly Leu Val Gly Val Val Glu Val Lys Asp Ser Gly Thr
                85                  90                  95

Ser Leu Asp Gly Tyr Thr Val Trp Pro Ile Asp Val Met Gly Phe Val
            100                 105                 110

Gln Gln Arg Arg Lys Leu Glu Leu Ser Thr Tyr Met Arg Phe Asp Ala
        115                 120                 125

Glu Phe Thr Phe Val Ser Asn Leu Asn Asn Ser Thr Thr Pro Gly Met
130                 135                 140

Leu Leu Gln Tyr Met Tyr Val Pro Pro Gly Ala Pro Lys Pro Asp Ser
145                 150                 155                 160

Arg Lys Ser Tyr Gln Trp Gln Thr Ala Thr Asn Pro Ser Val Phe Ala
                165                 170                 175

Lys Leu Ser Asp Pro Pro Pro Gln Val Ser Val Pro Phe Met Ser Pro
                180                 185                 190

Ala Thr Ala Tyr Gln Trp Phe Tyr Asp Gly Tyr Pro Thr Phe Gly Glu
            195                 200                 205

His Lys Gln Ala Thr Asn Leu Gln Tyr Gly Gln Cys Pro Asn Asn Met
    210                 215                 220

Met Gly His Phe Ala Ile Arg Thr Val Ser Glu Ser Thr Thr Gly Lys
225                 230                 235                 240

Asn Val His Val Arg Val Tyr Met Arg Ile Lys His Val Arg Ala Trp
                245                 250                 255
```

```
Val Pro Arg Pro Leu Arg Ser Gln Ala Tyr Met Val Lys Asn Tyr Pro
            260                 265                 270

Thr Tyr Ser Gln Thr Ile Thr Asn Thr Ala Thr Asp Arg Ala Ser Ile
        275                 280                 285

Thr Thr Thr Asp Tyr Glu Gly Gly Val Pro Ala Ser Pro Gln Arg Thr
    290                 295                 300

Ser
305

<210> SEQ ID NO 24
<211> LENGTH: 305
<212> TYPE: PRT
<213> ORGANISM: Coxsackievirus A6

<400> SEQUENCE: 24

Asn Asp Pro Ile Thr Asn Ala Val Glu Ser Ala Val Ser Ala Leu Ala
1               5                   10                  15

Asp Thr Thr Ile Ser Arg Val Thr Ala Ala Asn Thr Ala Ala Ser Thr
            20                  25                  30

His Ser Leu Gly Thr Gly Arg Val Pro Ala Leu Gln Ala Ala Glu Thr
        35                  40                  45

Gly Ala Ser Ser Asn Ala Ser Asp Glu Asn Leu Ile Glu Thr Arg Cys
    50                  55                  60

Val Met Asn Arg Asn Gly Val Asn Glu Ala Ser Val Glu His Phe Tyr
65                  70                  75                  80

Ser Arg Ala Gly Leu Val Gly Val Val Glu Val Lys Asp Ser Gly Thr
                85                  90                  95

Ser Leu Asp Gly Tyr Thr Val Trp Pro Ile Asp Val Met Gly Phe Val
            100                 105                 110

Gln Gln Arg Arg Lys Leu Glu Leu Ser Thr Tyr Met Arg Phe Asp Ala
        115                 120                 125

Glu Phe Thr Phe Val Ser Asn Leu Asn Asp Ser Thr Thr Pro Gly Met
130                 135                 140

Leu Leu Gln Tyr Met Tyr Val Pro Pro Gly Ala Pro Lys Pro Asp Ser
145                 150                 155                 160

Arg Lys Ser Tyr Gln Trp Gln Thr Ala Thr Asn Pro Ser Val Phe Ala
                165                 170                 175

Lys Leu Ser Asp Pro Pro Gln Val Ser Val Pro Phe Met Ser Pro
            180                 185                 190

Ala Thr Ala Tyr Gln Trp Phe Tyr Asp Gly Tyr Pro Thr Phe Gly Glu
        195                 200                 205

His Lys Gln Ala Thr Asn Leu Gln Tyr Gly Gln Cys Pro Asn Asn Met
210                 215                 220

Met Gly His Phe Ala Ile Arg Thr Val Ser Glu Ser Thr Thr Gly Lys
225                 230                 235                 240

Asn Val His Val Arg Val Tyr Met Arg Ile Lys His Val Arg Ala Trp
                245                 250                 255

Val Pro Arg Pro Leu Arg Ser Gln Ala Tyr Met Val Lys Asn Tyr Pro
            260                 265                 270

Thr Tyr Ser Gln Thr Ile Thr Asn Thr Ala Thr Asp Arg Ala Ser Ile
        275                 280                 285

Thr Thr Thr Asp Tyr Glu Gly Gly Val Pro Ala Asn Pro Gln Arg Thr
    290                 295                 300

Ser
305
```

<210> SEQ ID NO 25
<211> LENGTH: 262
<212> TYPE: PRT
<213> ORGANISM: Coxsackievirus A16

<400> SEQUENCE: 25

Gly Asp Ser Ile Ala Asp Met Ile Asp Gln Thr Val Asn Asn Gln Val
1               5                   10                  15

Asn Arg Ser Leu Thr Ala Leu Gln Val Leu Pro Thr Ala Ala Asn Thr
            20                  25                  30

Glu Ala Ser Ser His Arg Leu Gly Thr Gly Val Val Pro Ala Leu Gln
        35                  40                  45

Ala Ala Glu Thr Gly Ala Ser Ser Asn Ala Ser Asp Lys Asn Leu Ile
    50                  55                  60

Glu Thr Arg Cys Val Leu Asn His His Ser Thr Gln Glu Thr Ala Ile
65                  70                  75                  80

Gly Asn Phe Phe Ser Arg Ala Gly Leu Val Ser Ile Ile Thr Met Pro
                85                  90                  95

Thr Thr Gly Thr Gln Asn Thr Asp Gly Tyr Val Asn Trp Asp Ile Asp
            100                 105                 110

Leu Met Gly Tyr Ala Gln Leu Arg Arg Lys Cys Glu Leu Phe Thr Tyr
        115                 120                 125

Met Arg Phe Asp Ala Glu Phe Thr Phe Val Val Ala Lys Pro Asn Gly
    130                 135                 140

Glu Leu Val Pro Gln Leu Leu Gln Tyr Met Tyr Val Pro Pro Gly Ala
145                 150                 155                 160

Pro Lys Pro Thr Ser Arg Asp Ser Phe Ala Trp Gln Thr Ala Thr Asn
                165                 170                 175

Leu Ser Val Phe Val Lys Met Thr Asp Pro Pro Ala Gln Ala Ser Val
            180                 185                 190

Pro Phe Met Ser Pro Ala Ser Ala Tyr Gln Trp Phe Tyr Asp Gly Tyr
        195                 200                 205

Pro Thr Phe Gly Glu His Leu Gln Ala Asn Asp Leu Asp Tyr Gly Gln
    210                 215                 220

Cys Pro Asn Asn Met Met Gly Thr Phe Ser Val Arg Thr Val Gly Ala
225                 230                 235                 240

Glu Lys Ser Pro His Ser Ile Thr Leu Arg Val Tyr Met Arg Ile Lys
                245                 250                 255

His Val Arg Ala Trp Ile
            260

<210> SEQ ID NO 26
<211> LENGTH: 297
<212> TYPE: PRT
<213> ORGANISM: Coxsackievirus A16

<400> SEQUENCE: 26

Gly Asp Ser Ile Ala Asp Met Ile Asp Gln Thr Val Asn Asn Gln Val
1               5                   10                  15

Asn Arg Ser Leu Thr Ala Leu Gln Val Met Pro Thr Ser Ala Asn Thr
            20                  25                  30

Glu Ala Ser Ser His Arg Leu Gly Thr Gly Val Val Pro Ala Leu Gln
        35                  40                  45

Ala Ala Glu Thr Gly Ala Ser Ser Asn Ala Ser Asp Lys Asn Leu Ile
    50                  55                  60

```
Glu Thr Arg Cys Val Leu Asn His His Ser Thr Gln Glu Thr Ala Ile
 65                  70                  75                  80

Gly Asn Phe Phe Ser Arg Ala Gly Leu Val Ser Ile Ile Thr Met Pro
                 85                  90                  95

Thr Thr Gly Thr Gln Asn Thr Asp Gly Tyr Val Asn Trp Asp Ile Asp
            100                 105                 110

Leu Met Gly Tyr Ala Gln Leu Arg Arg Lys Cys Glu Leu Phe Thr Tyr
        115                 120                 125

Met Arg Phe Asp Ala Glu Phe Thr Phe Val Val Ala Lys Pro Asn Gly
    130                 135                 140

Glu Leu Val Pro Gln Leu Leu Gln Tyr Met Tyr Val Pro Pro Gly Ala
145                 150                 155                 160

Pro Lys Pro Thr Ser Arg Asp Ser Phe Ala Trp Gln Thr Ala Thr Asn
                165                 170                 175

Pro Ser Val Phe Val Lys Met Thr Asp Pro Pro Ala Gln Val Ser Val
            180                 185                 190

Pro Phe Met Ser Pro Ala Ser Ala Tyr Gln Trp Phe Tyr Asp Gly Tyr
        195                 200                 205

Pro Thr Phe Gly Glu His Leu Gln Ala Asn Asp Leu Asp Tyr Gly Gln
    210                 215                 220

Cys Pro Asn Asn Met Met Gly Thr Phe Ser Val Arg Thr Val Gly Ala
225                 230                 235                 240

Glu Lys Ser Pro His Ser Ile Thr Leu Arg Val Tyr Met Arg Ile Lys
                245                 250                 255

His Val Arg Ala Trp Ile Pro Arg Pro Leu Arg Asn Gln Pro Tyr Leu
            260                 265                 270

Phe Lys Thr Asn Pro Asn Tyr Lys Gly Asn Asp Ile Lys Cys Thr Ser
        275                 280                 285

Thr Ser Arg Asp Lys Ile Thr Thr Leu
    290                 295

<210> SEQ ID NO 27
<211> LENGTH: 297
<212> TYPE: PRT
<213> ORGANISM: Coxsackievirus A16

<400> SEQUENCE: 27

Gly As

```
         130                 135                 140
Glu Leu Val Pro Gln Leu Leu Gln Tyr Met Tyr Val Pro Pro Gly Ala
145                 150                 155                 160

Pro Lys Pro Thr Ser Arg Asp Ser Phe Ala Trp Gln Thr Ala Thr Asn
                165                 170                 175

Pro Ser Val Phe Val Lys Met Thr Asp Pro Pro Ala Gln Val Ser Val
            180                 185                 190

Pro Phe Met Ser Pro Ala Ser Ala Tyr Gln Trp Phe Tyr Asp Gly Tyr
        195                 200                 205

Pro Thr Phe Gly Glu His Leu Gln Ala Asn Asp Leu Asp Tyr Gly Gln
    210                 215                 220

Cys Pro Asn Asn Met Met Gly Thr Phe Ser Val Arg Thr Val Gly Thr
225                 230                 235                 240

Glu Lys Ser Pro His Ser Ile Thr Leu Arg Val Tyr Met Arg Ile Lys
                245                 250                 255

His Val Arg Ala Trp Ile Pro Arg Pro Leu Arg Asn Gln Pro Tyr Leu
            260                 265                 270

Phe Lys Thr Asn Pro Asn Tyr Lys Gly Asn Asp Ile Lys Cys Thr Ser
        275                 280                 285

Thr Ser Arg Asp Lys Ile Thr Thr Leu
    290                 295

<210> SEQ ID NO 28
<211> LENGTH: 297
<212> TYPE: PRT
<213> ORGANISM: Coxsackievirus A16

<400> SEQUENCE: 28

Gly Asp Pro Ile Ala Asp Met Ile Asp Gln Thr Val Asn Asn Gln Val
1               5                   10                  15

Asn Arg Ser Leu Thr Ala Leu Gln Val Leu Pro Thr Ala Ala Asn Thr
                20                  25                  30

Glu Ala Ser Ser His Arg Leu Gly Thr Gly Val Val Pro Ala Leu Gln
            35                  40                  45

Ala Ala Glu Thr Gly Ala Ser Ser Asn Ala Ser Asp Lys Asn Leu Ile
        50                  55                  60

Glu Thr Arg Cys Val Leu Asn His His Ser Thr Gln Glu Thr Ala Ile
65                  70                  75                  80

Gly Asn Phe Phe Ser Arg Ala Gly Leu Val Ser Ile Ile Thr Met Pro
                85                  90                  95

Thr Thr Asp Thr Gln Asn Thr Asp Gly Tyr Val Asn Trp Asp Ile Asp
            100                 105                 110

Leu Met Gly Tyr Ala Gln Leu Arg Arg Lys Cys Glu Leu Phe Thr Tyr
        115                 120                 125

Met Arg Phe Asp Ala Glu Phe Thr Phe Val Val Ala Lys Pro Asn Gly
    130                 135                 140

Val Leu Val Pro Gln Leu Leu Gln Tyr Met Tyr Val Pro Pro Gly Ala
145                 150                 155                 160

Pro Lys Pro Thr Ser Arg Asp Ser Phe Ala Trp Gln Thr Ala Thr Asn
                165                 170                 175

Pro Ser Val Phe Val Lys Met Thr Asp Pro Pro Ala Gln Val Ser Val
            180                 185                 190

Pro Phe Met Ser Pro Ala Ser Ala Tyr Gln Trp Phe Tyr Asp Gly Tyr
        195                 200                 205
```

```
Pro Thr Phe Gly Glu His Leu Gln Ala Asn Asp Leu Asp Tyr Gly Gln
    210                 215                 220

Cys Pro Asn Asn Met Met Gly Thr Phe Ser Ile Arg Thr Val Gly Thr
225                 230                 235                 240

Glu Lys Ser Pro His Ser Ile Thr Leu Arg Val Tyr Met Arg Ile Lys
                245                 250                 255

His Val Arg Ala Trp Ile Pro Arg Pro Leu Arg Asn Gln Pro Tyr Leu
                260                 265                 270

Phe Lys Thr Asn Pro Asn Tyr Lys Gly Asn Asp Ile Lys Cys Thr Ser
            275                 280                 285

Thr Ser Arg Asp Lys Ile Thr Thr Leu
    290                 295
```

<210> SEQ ID NO 29
<211> LENGTH: 277
<212> TYPE: PRT
<213> ORGANISM: Coxsackievirus A16

<400> SEQUENCE: 29

```
Gly Asp Pro Ile Ala Asp Met Ile Asp Gln Thr Val Asn

<210> SEQ ID NO 30
<211> LENGTH: 283
<212> TYPE: PRT
<213> ORGANISM: Coxsackievirus A16

<400> SEQUENCE: 30

Gly Asp Ser Ile Ala Asp Met Ile Asp Gln Thr Val Asn Asn Gln Val
1               5                   10                  15

Asn Arg Ser Leu Thr Ala Met Gln Val Leu Pro Thr Ala Ala Asn Thr
            20                  25                  30

Glu Ala Ser Ser His Arg Leu Gly Thr Gly Val Val Pro Ala Leu Gln
        35                  40                  45

Ala Ala Glu Thr Gly Ala Ser Ser Asn Ala Ser Asp Lys Asn Leu Ile
    50                  55                  60

Glu Thr Arg Cys Val Leu Asn His His Ser Thr Gln Glu Thr Ala Ile
65                  70                  75                  80

Gly Asn Phe Phe Ser Arg Ala Gly Leu Val Ser Ile Ile Thr Met Pro
                85                  90                  95

Thr Thr Gly Thr Gln Asn Thr Asp Gly Tyr Val Asn Trp Asp Ile Asp
            100                 105                 110

Leu Met Gly Tyr Ala Gln Leu Arg Arg Lys Cys Glu Leu Phe Thr Tyr
        115                 120                 125

Met Arg Phe Asp Ala Glu Phe Thr Phe Val Val Ala Lys Pro Asn Gly
    130                 135                 140

Glu Leu Val Pro Gln Leu Leu Gln Tyr Met Tyr Val Pro Pro Gly Ala
145                 150                 155                 160

Pro Lys Pro Thr Ser Arg Asp Ser Phe Ala Trp Gln Thr Ala Thr Asn
                165                 170                 175

Pro Ser Val Phe Val Lys Met Thr Asp Pro Pro Ala Gln Val Ser Val
            180                 185                 190

Pro Phe Met Ser Pro Ala Ser Ala Tyr Gln Trp Phe Tyr Asp Gly Tyr
        195                 200                 205

Pro Thr Phe Gly Glu His Leu Gln Ala Asn Asp Leu Asp Tyr Gly Gln
    210                 215                 220

Cys Pro Asn Asn Met Met Gly Thr Phe Ser Ile Arg Thr Val Gly Thr
225                 230                 235                 240

Glu Lys Ser Pro His Ser Ile Thr Leu Arg Val Tyr Met Arg Ile Lys
                245                 250                 255

His Val Arg Ala Trp Ile Pro Arg Pro Leu Arg Asn Gln Pro Tyr Leu
            260                 265                 270

Phe Lys Thr Asn Pro Asn Tyr Lys Gly Asn Asp
        275                 280

<210> SEQ ID NO 31
<211> LENGTH: 297
<212> TYPE: PRT
<213> ORGANISM: Coxsackievirus A16

<400> SEQUENCE: 31

Gly Asp Pro Ile Ala Asp Met Ile Asp Gln Thr Val Asn Asn Gln Val
1               5                   10                  15

Asn Arg Ser Leu Thr Ala Leu Gln Val Leu Pro Thr Ala Ala Asn Thr
            20                  25                  30

Glu Ala Ser Ser His Arg Leu Gly Thr Gly Val Val Pro Ala Leu Gln
        35                  40                  45

```
Ala Ala Glu Thr Gly Ala Ser Ser Asn Ala Ser Asp Lys Asn Leu Ile
            50                  55                  60

Glu Thr Arg Cys Val Leu Asn His His Ser Thr Gln Glu Thr Ala Ile
 65                  70                  75                  80

Gly Asn Phe Phe Ser Arg Ala Gly Leu Val Ser Ile Ile Thr Met Pro
                    85                  90                  95

Thr Thr Gly Thr Gln Asn Ala Asp Gly Tyr Val Asn Trp Asp Ile Asp
                100                 105                 110

Leu Met Gly Tyr Ala Gln Leu Arg Arg Lys Cys Glu Leu Phe Thr Tyr
            115                 120                 125

Met Arg Phe Asp Ala Glu Phe Thr Phe Val Val Ala Lys Pro Asn Gly
    130                 135                 140

Glu Leu Val Pro Gln Leu Leu Gln Tyr Met Tyr Val Pro Pro Gly Ala
145                 150                 155                 160

Pro Lys Pro Thr Ser Arg Asp Ser Phe Ala Trp Gln Thr Ala Thr Asn
                165                 170                 175

Pro Ser Val Phe Val Lys Met Thr Asp Pro Pro Ala Gln Val Ser Val
                180                 185                 190

Pro Phe Met Ser Pro Ala Ser Ala Tyr Gln Trp Phe Tyr Asp Gly Tyr
            195                 200                 205

Pro Thr Phe Gly Glu His Leu Gln Ala Asn Asp Leu Asp Tyr Gly Gln
    210                 215                 220

Cys Pro Asn Asn Met Met Gly Thr Phe Ser Ile Arg Thr Val Gly Thr
225                 230                 235                 240

Glu Lys Ser Pro His Ser Ile Thr Leu Arg Val Tyr Met Arg Ile Lys
                245                 250                 255

His Val Arg Ala Trp Ile Pro Arg Pro Leu Arg Asn Gln Pro Tyr Leu
            260                 265                 270

Phe Lys Thr Asn Pro Asn Tyr Lys Gly Asn Asp Ile Lys Cys Thr Ser
    275                 280                 285

Thr Ser Arg Asp Lys Ile Thr Thr Leu
            290                 295

<210> SEQ ID NO 32
<211> LENGTH: 297
<212> TYPE: PRT
<213> ORGANISM: Coxsackievirus A16

<400> SEQUENCE: 32

Gly Asp Ser Ile Ala Asp Met Ile Asp Gln Thr Val Asn Asn Gln Val
1               5                   10                  15

Asn Arg Ser Leu Thr Ala Leu Gln Val Leu Pro Thr Ala Ala Asn Thr
            20                  25                  30

Glu Ala Ser Ser His Arg Leu Gly Thr Gly Val Val Pro Ala Leu Gln
        35                  40                  45

Ala Ala Glu Thr Gly Ala Ser Ser Asn Ala Ser Asp Lys Asn Leu Ile
            50                  55                  60

Glu Thr Arg Cys Val Leu Asn His His Ser Thr Gln Glu Thr Ala Ile
 65                  70                  75                  80

Gly Asn Phe Phe Ser Arg Ala Gly Leu Val Ser Ile Ile Thr Met Pro
                    85                  90                  95

Thr Thr Gly Thr Gln Asn Thr Asp Gly Tyr Val Asn Trp Asp Ile Asp
                100                 105                 110

Leu Met Gly Tyr Ala Gln Leu Arg Arg Lys Cys Glu Leu Phe Thr Tyr
```

Met Arg Phe Asp Ala Glu Phe Thr Phe Val Val Ala Lys Pro Asn Gly
130                 135                 140

Glu Leu Val Pro Gln Leu Leu Gln Tyr Met Tyr Val Pro Pro Gly Ala
145                 150                 155                 160

Pro Lys Pro Thr Ser Arg Asp Ser Phe Ala Trp Gln Thr Ala Thr Asn
                165                 170                 175

Pro Ser Val Phe Val Lys Met Thr Asp Pro Pro Ala Gln Val Ser Val
            180                 185                 190

Pro Phe Met Ser Pro Ala Ser Ala Tyr Gln Trp Phe Tyr Asp Gly Tyr
        195                 200                 205

Pro Thr Phe Gly Glu His Leu Gln Ala Asn Asp Leu Asp Tyr Gly Gln
    210                 215                 220

Cys Pro Asn Asn Met Met Gly Thr Phe Ser Ile Arg Thr Val Gly Thr
225                 230                 235                 240

Glu Lys Ser Pro His Ser Ile Thr Leu Arg Val Tyr Met Arg Ile Lys
                245                 250                 255

His Val Arg Ala Trp Ile Pro Arg Pro Leu Arg Asn Gln Pro Tyr Leu
            260                 265                 270

Phe Lys Thr Asn Pro Asn Tyr Lys Gly Asn Asp Ile Lys Cys Thr Ser
                275                 280                 285

Thr Ser Arg Asp Lys Ile Thr Thr Leu
                290                 295

<210> SEQ ID NO 33
<211> LENGTH: 297
<212> TYPE: PRT
<213> ORGANISM: Coxsackievirus A16

<400> SEQUENCE: 33

Gly Asp Pro Ile Ala Asp Met Ile Asp Gln Thr Val Asn Asn Gln Val
1               5                   10                  15

Asn Arg Ser Leu Thr Ala Leu Gln Val Leu Pro Thr Ala Ala Asn Thr
            20                  25                  30

Glu Ala Ser Ser His Arg Leu Gly Thr Gly Val Val Pro Ala Leu Gln
        35                  40                  45

Ala Ala Glu Thr Gly Ala Ser Ser Asn Ala Ser Asp Lys Asn Leu Ile
    50                  55                  60

Glu Thr Arg Cys Val Leu Asn His His Ser Thr Gln Glu Thr Ala Ile
65                  70                  75                  80

Gly Asn Phe Phe Ser Arg Ala Gly Leu Val Ser Ile Ile Thr Met Pro
                85                  90                  95

Thr Thr Gly Thr Gln Asn Thr Asp Gly Tyr Val Asn Trp Asp Ile Asp
            100                 105                 110

Leu Met Gly Tyr Ala Gln Leu Arg Arg Lys Cys Glu Leu Phe Thr Tyr
        115                 120                 125

Met Arg Phe Asp Ala Glu Phe Thr Phe Val Val Ala Lys Pro Asn Gly
130                 135                 140

Glu Leu Val Pro Gln Leu Leu Gln Tyr Met Tyr Val Pro Pro Gly Ala
145                 150                 155                 160

Pro Lys Pro Thr Ser Arg Asp Ser Phe Ala Trp Gln Thr Ala Thr Asn
                165                 170                 175

Pro Ser Val Phe Val Lys Met Thr Asp Pro Pro Ala Gln Val Ser Val
            180                 185                 190

```
Pro Phe Met Ser Pro Ala Ser Ala Tyr Gln Trp Phe Tyr Asp Gly Tyr
            195                 200                 205

Pro Thr Phe Gly Glu His Leu Gln Ala Asn Asp Leu Asp Tyr Gly Gln
        210                 215                 220

Cys Pro Asn Asn Met Met Gly Thr Phe Ser Ile Arg Thr Val Gly Thr
225                 230                 235                 240

Lys Lys Ser Pro His Ser Ile Thr Leu Arg Val Tyr Met Arg Ile Lys
                245                 250                 255

His Val Arg Ala Trp Ile Pro Arg Pro Leu Arg Asn Gln Pro Tyr Leu
            260                 265                 270

Phe Lys Thr Asn Pro Asn Tyr Lys Gly Asn Asp Ile Lys Cys Thr Ser
        275                 280                 285

Thr Ser Arg Asp Lys Ile Thr Thr Leu
        290                 295

<210> SEQ ID NO 34
<211> LENGTH: 297
<212> TYPE: PRT
<213> ORGANISM: Coxsackievirus A16

<400> SEQUENCE: 34

Gly Asp Pro Ile Ala Asp Met Ile Asp Gln Thr Val Asn Asn Gln Val
1               5                   10                  15

Asn Arg Ser Leu Thr Ala Leu Gln Val Leu Pro Thr Ala Ala Asn Thr
            20                  25                  30

Glu Ala Ser Ser His Arg Leu Gly Thr Gly Val Val Pro Ala Leu Gln
        35                  40                  45

Ala Ala Glu Thr Gly Ala Ser Ser Asn Ala Ser Asp Lys Asn Leu Ile
    50                  55                  60

Glu Thr Arg Cys Val Leu Asn His His Ser Thr Gln Glu Thr Ala Ile
65                  70                  75                  80

Gly Asn Phe Phe Ser Arg Ala Gly Leu Val Ser Ile Ile Thr Met Pro
            85                  90                  95

Thr Ala Gly Thr Gln Asn Thr Asp Gly Tyr Val Asn Trp Asp Ile Asp
            100                 105                 110

Leu Met Gly Tyr Ala Gln Leu Arg Arg Lys Cys Glu Leu Phe Thr Tyr
        115                 120                 125

Met Arg Phe Asp Ala Glu Phe Thr Phe Val Val Ala Lys Pro Asn Gly
    130                 135                 140

Glu Leu Val Pro Gln Leu Leu Gln Tyr Met Tyr Val Pro Pro Gly Ala
145                 150                 155                 160

Pro Lys Pro Thr Ser Arg Asp Ser Phe Ala Trp Gln Thr Ala Thr Asn
                165                 170                 175

Pro Ser Val Phe Val Lys Met Thr Asp Pro Pro Ala Gln Val Ser Val
            180                 185                 190

Pro Phe Met Ser Pro Ala Ser Ala Tyr Gln Trp Phe Tyr Asp Gly Tyr
        195                 200                 205

Pro Thr Phe Gly Glu His Leu Gln Ala Asn Asp Leu Asp Tyr Gly Gln
        210                 215                 220

Cys Pro Asn Asn Met Met Gly Thr Phe Ser Ile Arg Thr Val Gly Thr
225                 230                 235                 240

Glu Lys Ser Pro His Ser Ile Thr Leu Arg Val Tyr Met Arg Ile Lys
                245                 250                 255

His Val Arg Ala Trp Ile Pro Arg Pro Leu Arg Asn Gln Pro Tyr Leu
            260                 265                 270
```

```
Phe Lys Thr Asn Pro Asn Tyr Lys Gly Asn Asp Ile Lys Cys Thr Ser
        275                 280                 285

Thr Ser Arg Asp Lys Ile Thr Thr Leu
        290                 295

<210> SEQ ID NO 35
<211> LENGTH: 297
<212> TYPE: PRT
<213> ORGANISM: Coxsackievirus A16

<400> SEQUENCE: 35

Gly Asp Pro Ile Ala Asp Met Ile Asp Gln Thr Val Asn Asn Gln Val
1               5                   10                  15

Asn Arg Ser Leu Thr Ala Leu Gln Val Leu Pro Thr Ala Ala Asn Thr
            20                  25                  30

Glu Ala Ser Ser His Arg Leu Gly Thr Gly Val Val Pro Ala Leu Gln
        35                  40                  45

Ala Ala Glu Thr Gly Ala Ser Ser Asn Ala Ser Asp Lys Asn Leu Ile
    50                  55                  60

Glu Thr Arg Cys Val Leu Asn His His Ser Thr Gln Glu Thr Ala Ile
65                  70                  75                  80

Gly Asn Phe Phe Ser Arg Ala Gly Leu Val Ser Ile Ile Thr Met Pro
                85                  90                  95

Thr Ala Gly Thr Gln Asn Thr Asp Gly Tyr Val Asn Trp Asp Ile Asp
            100                 105                 110

Leu Met Gly Tyr Ala Gln Leu Arg Arg Lys Cys Glu Leu Phe Thr Tyr
        115                 120                 125

Met Arg Phe Asp Ala Glu Phe Thr Phe Val Val Ala Lys Pro Asn Gly
    130                 135                 140

Glu Leu Val Pro Gln Leu Leu Gln Tyr Met Tyr Val Pro Pro Gly Ala
145                 150                 155                 160

Pro Lys Pro Thr Ser Arg Asp Ser Phe Ala Trp Gln Thr Ala Thr Asn
                165                 170                 175

Pro Ser Val Phe Val Lys Met Thr Asp Pro Pro Ala Gln Val Ser Val
            180                 185                 190

Pro Phe Met Ser Pro Ala Ser Ala Tyr Gln Trp Phe Tyr Asp Gly Tyr
        195                 200                 205

Pro Thr Phe Gly Glu His Leu Gln Ala Asn Asp Leu Asp Tyr Gly Gln
    210                 215                 220

Cys Pro Asn Asn Met Met Gly Thr Phe Ser Ile Arg Thr Val Gly Thr
225                 230                 235                 240

Glu Lys Ser Pro His Ser Ile Thr Leu Arg Val Tyr Met Arg Ile Lys
                245                 250                 255

His Val Arg Ala Trp Ile Pro Arg Pro Leu Arg Asn Gln Pro Tyr Leu
            260                 265                 270

Phe Lys Thr Asn Pro Asn Tyr Lys Gly Asn Asp Ile Lys Cys Thr Ser
        275                 280                 285

Thr Ser Arg Asp Lys Ile Thr Thr Leu
        290                 295

<210> SEQ ID NO 36
<211> LENGTH: 297
<212> TYPE: PRT
<213> ORGANISM: Coxsackievirus A16

<400> SEQUENCE: 36
```

Gly Asp Pro Ile Ala Asp Met Ile Asp Gln Thr Val Asn Asn Gln Val
1               5                   10                  15

Asn Arg Ser Leu Thr Ala Leu Gln Val Leu Pro Thr Ala Ala Asn Thr
            20                  25                  30

Glu Ala Ser Ser His Arg Leu Gly Thr Gly Val Val Pro Ala Leu Gln
        35                  40                  45

Ala Ala Glu Thr Gly Ala Ser Ser Asn Ala Ser Asp Lys Asn Leu Ile
50                  55                  60

Glu Thr Arg Cys Val Leu Asn His His Ser Thr Gln Glu Thr Ala Ile
65                  70                  75                  80

Gly Asn Phe Phe Ser Arg Ala Gly Leu Val Ser Ile Ile Thr Met Pro
                85                  90                  95

Thr Thr Gly Thr Gln Asn Thr Asp Gly Tyr Val Asn Trp Asp Ile Asp
                100                 105                 110

Leu Met Gly Tyr Ala Gln Leu Arg Arg Lys Cys Glu Leu Phe Thr Tyr
            115                 120                 125

Met Arg Phe Asp Ala Glu Phe Thr Phe Val Val Ala Lys Pro Asn Gly
    130                 135                 140

Glu Leu Val Pro Gln Leu Leu Gln Tyr Met Tyr Val Pro Pro Gly Ala
145                 150                 155                 160

Pro Lys Pro Thr Ser Arg Asp Ser Phe Ala Trp Gln Thr Ala Thr Asn
                165                 170                 175

Pro Ser Val Phe Val Lys Met Thr Asp Pro Pro Ala Gln Val Ser Val
                180                 185                 190

Pro Phe Met Ser Pro Ala Ser Ala Tyr Gln Trp Phe Tyr Asp Gly Tyr
            195                 200                 205

Pro Thr Phe Gly Glu His Leu Gln Ala Asn Asp Leu Asp Tyr Gly Gln
    210                 215                 220

Cys Pro Asn Asn Met Met Gly Thr Phe Ser Ile Arg Thr Val Gly Thr
225                 230                 235                 240

Glu Lys Ser Pro His Ser Ile Thr Leu Arg Val Tyr Met Arg Ile Lys
                245                 250                 255

His Val Arg Ala Trp Ile Pro Arg Pro Leu Arg Asn Gln Pro Tyr Leu
            260                 265                 270

Phe Lys Thr Asn Pro Asn Tyr Lys Gly Asn Asp Ile Lys Cys Thr Ser
    275                 280                 285

Thr Ser Arg Asp Lys Ile Thr Thr Leu
    290                 295

<210> SEQ ID NO 37
<211> LENGTH: 297
<212> TYPE: PRT
<213> ORGANISM: Coxsackievirus A16

<400> SEQUENCE: 37

Gly Asp Pro Ile Ala Asp Met Ile Asp Gln Thr Val Asn Asn Gln Val
1               5                   10                  15

Asn Arg Ser Leu Thr Ala Leu Gln Val Leu Pro Thr Ala Ala Asn Thr
            20                  25                  30

Glu Ala Ser Ser His Arg Leu Gly Thr Gly Val Val Pro Ala Leu Gln
        35                  40                  45

Ala Ala Glu Thr Gly Ala Ser Ser Asn Ala Ser Asp Lys Asn Leu Ile
50                  55                  60

Glu Thr Arg Cys Val Leu Asn His His Ser Thr Gln Glu Thr Ala Ile

```
                 65                  70                  75                  80
Gly Asn Phe Phe Ser Arg Ala Gly Leu Val Ser Ile Ile Thr Met Pro
                    85                  90                  95

Thr Thr Gly Thr Gln Asn Thr Asp Gly Tyr Val Asn Trp Asp Ile Asp
                100                 105                 110

Leu Met Gly Tyr Ala Gln Leu Arg Arg Lys Cys Glu Leu Phe Thr Tyr
                115                 120                 125

Met Arg Phe Asp Ala Glu Phe Thr Phe Val Val Ala Lys Pro Asn Gly
            130                 135                 140

Glu Leu Val Pro Gln Leu Leu Gln Tyr Met Tyr Val Pro Pro Gly Ala
145                 150                 155                 160

Pro Lys Pro Thr Ser Arg Asp Ser Phe Ala Trp Gln Thr Ala Thr Asn
                165                 170                 175

Pro Ser Val Phe Val Lys Met Thr Asp Pro Pro Ala Gln Val Ser Val
                180                 185                 190

Pro Phe Met Ser Pro Ala Ser Ala Tyr Gln Trp Phe Tyr Asp Gly Tyr
                195                 200                 205

Pro Thr Phe Gly Glu His Leu Gln Ala Asn Asp Leu Asp Tyr Gly Gln
            210                 215                 220

Cys Pro Asn Asn Met Met Gly Thr Phe Ser Ile Arg Thr Val Gly Thr
225                 230                 235                 240

Glu Lys Ser Pro His Ser Ile Thr Leu Arg Val Tyr Met Arg Ile Lys
                245                 250                 255

His Val Arg Ala Trp Ile Pro Arg Pro Leu Arg Asn Gln Pro Tyr Leu
                260                 265                 270

Phe Lys Thr Asn Pro Asn Tyr Lys Gly Asn Asp Ile Lys Cys Thr Ser
            275                 280                 285

Thr Ser Arg Asp Lys Ile Thr Thr Leu
290                 295

<210> SEQ ID NO 38
<211> LENGTH: 297
<212> TYPE: PRT
<213> ORGANISM: Coxsackievirus A16

<400> SEQUENCE: 38

Gly Asp Pro Ile Ala Asp Met Ile Asp Gln Thr Val As

-continued

```
Glu Leu Val Pro Gln Leu Leu Gln Tyr Met Tyr Val Pro Pro Gly Ala
145                 150                 155                 160

Pro Lys Pro Thr Ser Arg Asp Ser Phe Ala Trp Gln Thr Ala Thr Asn
            165                 170                 175

Pro Ser Val Phe Val Lys Met Thr Asp Pro Pro Ala Gln Val Ser Val
            180                 185                 190

Pro Phe Met Ser Pro Ala Ser Ala Tyr Gln Trp Phe Tyr Asp Gly Tyr
            195                 200                 205

Pro Thr Phe Gly Glu His Leu Gln Ala Asn Asp Leu Asp Tyr Gly Gln
            210                 215                 220

Cys Pro Asn Asn Met Met Gly Thr Phe Ser Ile Arg Thr Val Gly Thr
225                 230                 235                 240

Glu Lys Ser Pro His Ser Ile Thr Leu Arg Val Tyr Met Arg Ile Lys
            245                 250                 255

His Val Arg Ala Trp Ile Pro Arg Pro Leu Arg Asn Gln Pro Tyr Leu
            260                 265                 270

Phe Lys Thr Asn Pro Asn Tyr Lys Gly Asn Asp Ile Lys Cys Thr Ser
            275                 280                 285

Thr Ser Arg Asp Lys Ile Thr Thr Leu
290                 295
```

<210> SEQ ID NO 39
<211> LENGTH: 297
<212> TYPE: PRT
<213> ORGANISM: Coxsackievirus A16

<400> SEQUENCE: 39

```
Gly Asp Pro Ile Ala Asp Met Ile Asp Gln Thr Val Asn Asn Gln Val
1               5                   10                  15

Asn Arg Ser Leu Thr Ala Leu Gln Val Leu Pro Thr Ala Ala Asn Thr
            20                  25                  30

Glu Ala Ser Ser His Arg Leu Gly Thr Gly Val Val Pro Ala Leu Gln
        35                  40                  45

Ala Ala Glu Thr Gly Ala Ser Ser Asn Ala Ser Asp Lys Asn Leu Ile
    50                  55                  60

Glu Thr Arg Cys Val Leu Asn His His Ser Thr Gln Glu Thr Ala Ile
65                  70                  75                  80

Gly Asn Phe Phe Ser Arg Ala Gly Leu Val Ser Ile Ile Thr Met Pro
                85                  90                  95

Thr Thr Gly Thr Gln Asn Thr Asp Gly Tyr Val Asn Trp Asp Ile Asp
            100                 105                 110

Leu Met Gly Tyr Ala Gln Leu Arg Arg Lys Cys Glu Leu Phe Thr Tyr
        115                 120                 125

Met Arg Phe Asp Ala Glu Phe Thr Phe Val Val Ala Lys Pro Asn Gly
    130                 135                 140

Glu Leu Val Pro Gln Leu Leu Gln Tyr Met Tyr Val Pro Pro Gly Ala
145                 150                 155                 160

Pro Lys Pro Thr Ser Arg Asp Ser Phe Ala Trp Gln Thr Ala Thr Asn
            165                 170                 175

Pro Ser Val Phe Val Lys Met Thr Asp Pro Pro Ala Gln Val Ser Val
            180                 185                 190

Pro Phe Met Ser Pro Ala Ser Ala Tyr Gln Trp Phe Tyr Asp Gly Tyr
            195                 200                 205

Pro Thr Phe Gly Glu His Leu Gln Ala Asn Asp Leu Asp Tyr Gly Gln
            210                 215                 220
```

```
Cys Pro Asn Asn Met Met Gly Thr Phe Ser Ile Arg Thr Val Gly Thr
225                 230                 235                 240

Glu Lys Ser Pro His Ser Ile Thr Leu Arg Val Tyr Met Arg Ile Lys
            245                 250                 255

His Val Arg Ala Trp Ile Pro Arg Pro Leu Arg Asn Gln Pro Tyr Leu
                260                 265                 270

Phe Lys Thr Asn Pro Asn Tyr Lys Gly Asn Asp Ile Lys Cys Thr Ser
            275                 280                 285

Thr Ser Arg Asp Lys Ile Thr Thr Leu
        290                 295

<210> SEQ ID NO 40
<211> LENGTH: 297
<212> TYPE: PRT
<213> ORGANISM: Coxsackievirus A16

<400> SEQUENCE: 40

Gly Asp Pro Ile Ala Asp Met Ile Asp Gln Thr Val Asn Asn Gln Val
1               5                   10                  15

Asn Arg Ser Leu Thr Ala Leu Gln Val Leu Pro Thr Ala Ala Asn Thr
            20                  25                  30

Glu Ala Ser Ser His Arg Leu Gly Thr Gly Val Val Pro Ala Leu Gln
        35                  40                  45

Ala Ala Glu Thr Gly Ala Ser Ser Asn Ala Ser Asp Lys Asn Leu Ile
    50                  55                  60

Glu Thr Arg Cys Val Leu Asn His His Ser Thr Gln Glu Thr Ala Ile
65                  70                  75                  80

Gly Asn Phe Phe Ser Arg Ala Gly Leu Val Ser Ile Ile Thr Met Pro
                85                  90                  95

Thr Thr Gly Thr Gln Asn Thr Asp Gly Tyr Val Asn Trp Asp Ile Asp
            100                 105                 110

Leu Met Gly Tyr Ala Gln Leu Arg Arg Lys Cys Glu Leu Phe Thr Tyr
        115                 120                 125

Met Arg Phe Asp Ala Glu Phe Thr Phe Val Val Ala Lys Pro Asn Gly
130                 135                 140

Glu Leu Val Pro Gln Leu Leu Gln Tyr Met Tyr Val Pro Pro Gly Ala
145                 150                 155                 160

Pro Lys Pro Thr Ser Arg Asp Ser Phe Ala Trp Gln Thr Ala Thr Asn
                165                 170                 175

Pro Ser Val Phe Val Lys Met Thr Asp Pro Pro Ala Gln Val Ser Val
            180                 185                 190

Pro Phe Met Ser Pro Ala Ser Ala Tyr Gln Trp Phe Tyr Asp Gly Tyr
        195                 200                 205

Pro Thr Phe Gly Glu His Leu Gln Ala Asn Asp Leu Asp Tyr Gly Gln
    210                 215                 220

Cys Pro Asn Asn Met Met Gly Thr Phe Ser Ile Arg Thr Val Gly Thr
225                 230                 235                 240

Glu Lys Ser Pro His Ser Ile Thr Leu Arg Val Tyr Met Arg Ile Lys
            245                 250                 255

His Val Arg Ala Trp Ile Pro Arg Pro Leu Arg Asn Gln Pro Tyr Leu
                260                 265                 270

Phe Lys Thr Asn Pro Asn Tyr Lys Gly Asn Asp Ile Lys Cys Thr Ser
            275                 280                 285

Thr Ser Arg Asp Lys Ile Thr Thr Leu
```

<210> SEQ ID NO 41
<211> LENGTH: 297
<212> TYPE: PRT
<213> ORGANISM: Coxsackievirus A16

<400> SEQUENCE: 41

Gly Asp Pro Ile Ala Asp Met Ile Asp Gln Thr Val Asn Asn Gln Val
1               5                   10                  15

Asn Arg Ser Leu Thr Ala Leu Gln Val Leu Pro Thr Ala Ala Asn Thr
            20                  25                  30

Glu Ala Ser Ser His Arg Leu Gly Thr Gly Val Val Pro Ala Leu Gln
        35                  40                  45

Ala Ala Glu Thr Gly Ala Ser Ser Asn Ala Ser Asp Lys Asn Leu Ile
    50                  55                  60

Glu Thr Arg Cys Val Leu Asn His His Ser Thr Gln Glu Thr Ala Ile
65                  70                  75                  80

Gly Asn Phe Phe Ser Arg Ala Gly Leu Val Ser Ile Ile Thr Met Pro
                85                  90                  95

Thr Thr Gly Thr Gln Asn Thr Asp Gly Tyr Val Asn Trp Asp Ile Asp
            100                 105                 110

Leu Met Gly Tyr Ala Gln Leu Arg Arg Lys Cys Glu Leu Phe Thr Tyr
        115                 120                 125

Met Arg Phe Asp Ala Glu Phe Thr Phe Val Val Ala Lys Pro Asn Gly
    130                 135                 140

Glu Leu Val Pro Gln Leu Leu Gln Tyr Met Tyr Val Pro Pro Gly Ala
145                 150                 155                 160

Pro Lys Pro Thr Ser Arg Asp Ser Phe Ala Trp Gln Thr Ala Thr Asn
                165                 170                 175

Pro Ser Val Phe Val Lys Met Thr Asp Pro Pro Ala Gln Val Ser Val
            180                 185                 190

Pro Phe Met Ser Pro Ala Ser Ala Tyr Gln Trp Phe Tyr Asp Gly Tyr
        195                 200                 205

Pro Thr Phe Gly Glu His Leu Gln Ala Asn Asp Leu Asp Tyr Gly Gln
    210                 215                 220

Cys Pro Asn Asn Met Met Gly Thr Phe Ser Ile Arg Thr Val Gly Thr
225                 230                 235                 240

Glu Lys Ser Pro His Ser Ile Thr Leu Arg Val Tyr Met Arg Ile Lys
                245                 250                 255

His Val Arg Ala Trp Ile Pro Arg Pro Leu Arg Asn Gln Pro Tyr Leu
            260                 265                 270

Phe Lys Thr Asn Pro Asn Tyr Lys Gly Asn Asp Ile Lys Cys Thr Ser
        275                 280                 285

Thr Ser Arg Asp Lys Ile Thr Thr Leu
    290                 295

<210> SEQ ID NO 42
<211> LENGTH: 297
<212> TYPE: PRT
<213> ORGANISM: Coxsackievirus A16

<400> SEQUENCE: 42

Gly Asp Pro Ile Ala Asp Met Ile Asp Gln Thr Val Asn Asn Gln Val
1               5                   10                  15

Asn Arg Ser Leu Thr Ala Leu Gln Val Leu Pro Thr Ala Ala Asn Thr

```
                    20                  25                  30
Glu Ala Ser Ser His Arg Leu Gly Thr Gly Val Val Pro Ala Leu Gln
                35                  40                  45
Ala Ala Glu Thr Gly Ala Ser Ser Asn Ala Ser Asp Lys Asn Leu Ile
 50                  55                  60
Glu Thr Arg Cys Val Leu Asn His His Ser Thr Gln Glu Thr Ala Ile
 65                  70                  75                  80
Gly Asn Phe Phe Ser Arg Ala Gly Leu Val Ser Ile Ile Thr Met Pro
                85                  90                  95
Thr Thr Gly Thr Gln Asn Thr Asp Gly Tyr Val Asn Trp Asp Ile Asp
                100                 105                 110
Leu Met Gly Tyr Ala Gln Leu Arg Arg Lys Cys Glu Leu Phe Thr Tyr
                115                 120                 125
Met Arg Phe Asp Ala Glu Phe Thr Phe Val Val Ala Lys Pro Asn Gly
                130                 135                 140
Glu Leu Val Pro Gln Leu Leu Gln Tyr Met Tyr Val Pro Pro Gly Ala
145                 150                 155                 160
Pro Lys Pro Thr Ser Arg Asp Ser Phe Ala Trp Gln Thr Ala Thr Asn
                165                 170                 175
Pro Ser Val Phe Val Lys Met Thr Asp Pro Pro Ala Gln Val Ser Val
                180                 185                 190
Pro Phe Met Ser Pro Ala Ser Ala Tyr Gln Trp Phe Tyr Asp Gly Tyr
                195                 200                 205
Pro Thr Phe Gly Glu His Leu Gln Ala Asn Asp Leu Asp Tyr Gly Gln
                210                 215                 220
Cys Pro Asn Asn Met Met Gly Thr Phe Ser Ile Arg Thr Val Gly Thr
225                 230                 235                 240
Glu Lys Ser Pro His Ser Ile Thr Leu Arg Val Tyr Met Arg Ile Lys
                245                 250                 255
His Val Arg Ala Trp Ile Pro Arg Pro Leu Arg Asn Gln Pro Tyr Leu
                260                 265                 270
Phe Lys Thr Asn Pro Asn Tyr Lys Gly Asn Asp Ile Lys Cys Thr Ser
                275                 280                 285
Thr Ser Arg Asp Lys Ile Thr Thr Leu
                290                 295

<210> SEQ ID NO 43
<211> LENGTH: 297
<212> TYPE: PRT
<213> ORGANISM: Coxsackievirus A16

<400> SEQUENCE: 43

Gly Asp Pro Ile Ala Asp Met Ile Asp Gln Thr Val Ser Asn Gln Val
1               5                   10                  15
Asn Arg Ser Leu Thr Ala Leu Gln Val Leu Pro Thr Ala Ala Asn Thr
                20                  25                  30
Glu Ala Ser Ser His Arg Leu Gly Thr Gly Val Val Pro Ala Leu Gln
                35                  40                  45
Ala Ala Glu Thr Gly Ala Ser Ser Asn Ala Ser Asp Lys Asn Leu Ile
 50                  55                  60
Glu Thr Arg Cys Val Leu Asn His His Ser Thr Gln Glu Thr Ala Ile
 65                  70                  75                  80
Gly Asn Phe Phe Ser Arg Ala Gly Leu Val Ser Ile Ile Thr Met Pro
                85                  90                  95
```

```
Thr Thr Gly Thr Gln Asn Thr Asp Gly Tyr Val Asn Trp Asp Ile Asp
            100                 105                 110

Leu Met Gly Tyr Ala Gln Leu Arg Arg Lys Cys Glu Leu Phe Thr Tyr
        115                 120                 125

Met Arg Phe Asp Ala Glu Phe Thr Phe Val Val Ala Lys Pro Asn Gly
    130                 135                 140

Glu Leu Val Pro Gln Leu Leu Gln Tyr Met Tyr Val Pro Pro Gly Ala
145                 150                 155                 160

Pro Lys Pro Thr Ser Arg Asp Ser Phe Ala Trp Gln Thr Ala Thr Asn
                165                 170                 175

Pro Ser Val Phe Val Lys Met Thr Asp Pro Pro Ala Gln Val Ser Val
                180                 185                 190

Pro Phe Met Ser Pro Ala Ser Ala Tyr Gln Trp Phe Tyr Asp Gly Tyr
            195                 200                 205

Pro Thr Phe Gly Glu His Leu Gln Ala Asn Asp Leu Asp Tyr Gly Gln
        210                 215                 220

Cys Pro Asn Asn Met Met Gly Thr Phe Ser Ile Arg Thr Val Gly Thr
225                 230                 235                 240

Glu Lys Ser Pro His Ser Ile Thr Leu Arg Val Tyr Met Arg Ile Lys
                245                 250                 255

His Val Arg Ala Trp Ile Pro Arg Pro Leu Arg Asn Gln Pro Tyr Leu
                260                 265                 270

Phe Lys Thr Asn Pro Asn Tyr Lys Gly Asn Asp Ile Lys Cys Thr Ser
            275                 280                 285

Thr Ser Arg Asp Lys Ile Thr Thr Leu
290                 295

<210> SEQ ID NO 44
<211> LENGTH: 297
<212> TYPE: PRT
<213> ORGANISM: Coxsackievirus A16

<400> SEQUENCE: 44

Gly Asp Pro Ile Ala Asp Met Ile Asp Gln Thr Val Asn Asn Gln Val
1               5                   10                  15

Asn Arg Ser Leu Thr Ala Leu Gln Val Leu Pro Thr Ala Ala Asn Thr
            20                  25                  30

Glu Ala Ser Ser His Arg Leu Gly Thr Gly Val Val Pro Ala Leu Gln
        35                  40                  45

Ala Ala Glu Thr Gly Ala Ser Ser Asn Ala Ser Asp Lys Asn Leu Ile
50                  55                  60

Glu Thr Arg Cys Val Leu Asn His His Ser Thr Gln Glu Thr Ala Ile
65                  70                  75                  80

Gly Asn Phe Phe Ser Arg Ala Gly Leu Val Ser Ile Ile Thr Met Pro
                85                  90                  95

Thr Thr Gly Thr Gln Asn Thr Asp Gly Tyr Val Asn Trp Asp Ile Asp
            100                 105                 110

Leu Met Gly Tyr Ala Gln Leu Arg Arg Lys Cys Glu Leu Phe Thr Tyr
        115                 120                 125

Met Arg Phe Asp Ala Glu Phe Thr Phe Val Val Ala Lys Pro Asn Gly
    130                 135                 140

Glu Leu Val Pro Gln Leu Leu Gln Tyr Met Tyr Val Pro Pro Gly Ala
145                 150                 155                 160

Pro Lys Pro Thr Ser Arg Asp Ser Phe Ala Trp Gln Thr Ala Thr Asn
                165                 170                 175
```

-continued

```
Pro Ser Val Phe Val Lys Met Thr Asp Pro Pro Ala Gln Val Ser Val
            180                 185                 190

Pro Phe Met Ser Pro Ala Ser Ala Tyr Gln Trp Phe Tyr Asp Gly Tyr
        195                 200                 205

Pro Thr Phe Gly Glu His Leu Gln Ala Asn Asp Leu Asp Tyr Gly Gln
    210                 215                 220

Cys Pro Asn Asn Met Met Gly Thr Phe Ser Ile Arg Thr Val Gly Thr
225                 230                 235                 240

Glu Lys Ser Pro His Ser Ile Thr Leu Arg Val Tyr Met Arg Ile Lys
                245                 250                 255

His Val Arg Ala Trp Ile Pro Arg Pro Leu Arg Asn Gln Pro Tyr Leu
            260                 265                 270

Phe Lys Thr Asn Pro Asn Tyr Lys Gly Asn Asp Ile Lys Cys Thr Ser
        275                 280                 285

Thr Ser Arg Asp Lys Ile Thr Thr Leu
    290                 295
```